(12) United States Patent
Hammock et al.

(10) Patent No.: US 8,476,043 B2
(45) Date of Patent: *Jul. 2, 2013

(54) INHIBITORS FOR THE SOLUBLE EPOXIDE HYDROLASE

(75) Inventors: Bruce D. Hammock, Davis, CA (US); In-Hae Kim, Davis, CA (US); Christophe Morisseau, West Sacramento, CA (US); Takaho Watanabe, Kanagawa-ken (JP); John W. Newman, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 237 days.

This patent is subject to a terminal disclaimer.

(21) Appl. No.: 12/631,577

(22) Filed: Dec. 4, 2009

(65) Prior Publication Data

US 2011/0021448 A1 Jan. 27, 2011

Related U.S. Application Data

(63) Continuation of application No. 11/256,685, filed on Oct. 20, 2005, now Pat. No. 7,662,910.

(60) Provisional application No. 60/651,487, filed on Oct. 20, 2004.

(51) Int. Cl.
*C12P 19/48* (2006.01)
*C07C 211/16* (2006.01)
*C12Q 1/34* (2006.01)

(52) U.S. Cl.
USPC ............................. 435/80; 435/18; 564/462

(58) Field of Classification Search
None
See application file for complete search history.

(56) References Cited

U.S. PATENT DOCUMENTS

| | | | |
|---|---|---|---|
| 3,539,626 A | 11/1970 | Gagneux | |
| 3,587,060 A | 6/1971 | Quinn et al. | |
| 3,703,537 A | 11/1972 | Richter et al. | |
| 3,755,415 A | 8/1973 | Richter et al. | |
| 4,252,954 A | 2/1981 | Abdulla et al. | |
| 5,037,826 A | 8/1991 | Blythin et al. | |
| 5,142,017 A | 8/1992 | Sugimoto et al. | |
| 5,231,216 A | 7/1993 | Pecar et al. | |
| 5,273,982 A | 12/1993 | Alig et al. | |
| 5,314,902 A | 5/1994 | Tjoeng et al. | |
| 5,389,682 A | 2/1995 | Tait et al. | |
| 5,445,956 A | 8/1995 | Hammock et al. | |
| 5,576,335 A | 11/1996 | Sueda et al. | |
| 5,614,498 A | 3/1997 | Ishikawa et al. | |
| 5,637,113 A | 6/1997 | Tartaglia et al. | |
| 5,877,224 A | 3/1999 | Brocchini et al. | |
| 5,886,044 A | 3/1999 | Widdowson et al. | |
| 5,962,455 A | 10/1999 | Blum et al. | |
| 6,150,415 A | 11/2000 | Hammock et al. | |
| 6,287,285 B1 | 9/2001 | Michal et al. | |
| 6,290,722 B1 | 9/2001 | Wang | |
| 6,299,604 B1 | 10/2001 | Ragheb et al. | |
| 6,322,847 B1 | 11/2001 | Zhong et al. | |
| 6,329,395 B1 | 12/2001 | Dugar et al. | |
| 6,335,029 B1 | 1/2002 | Kamath et al. | |
| 6,344,358 B1 | 2/2002 | Matsuoka et al. | |
| 6,351,506 B1 | 2/2002 | Lewicki | |
| 6,444,686 B1 | 9/2002 | Ko et al. | |
| 6,444,691 B1 | 9/2002 | Oremus et al. | |
| 6,531,506 B1 | 3/2003 | Kroetz et al. | |
| 6,562,849 B1 | 5/2003 | Fujita et al. | |
| 6,586,446 B1 | 7/2003 | Durcia et al. | |
| 6,613,572 B2 | 9/2003 | Matsuoka et al. | |
| 6,710,043 B1 | 3/2004 | Yamada et al. | |
| 7,176,201 B2 | 2/2007 | Piomelli et al. | |
| 7,662,910 B2 * | 2/2010 | Hammock et al. | 530/300 |
| 2002/0045548 A1 | 4/2002 | Saito | |
| 2002/0090732 A1 | 7/2002 | Matsuoka et al. | |
| 2003/0078426 A1 | 4/2003 | Fujita et al. | |
| 2004/0014745 A1 | 1/2004 | Yamada et al. | |
| 2004/0014754 A1 | 1/2004 | Crooks et al. | |
| 2004/0054187 A1 | 3/2004 | Mammen et al. | |
| 2004/0092487 A1 | 5/2004 | Kroetz et al. | |
| 2005/0026844 A1 | 2/2005 | Hammock et al. | |
| 2005/0164951 A1 | 7/2005 | Hammock et al. | |
| 2005/0203135 A1 | 9/2005 | Burdick et al. | |
| 2007/0054904 A1 | 3/2007 | Knolle et al. | |
| 2007/0225283 A1 | 9/2007 | Hammock et al. | |
| 2011/0021448 A1 | 1/2011 | Hammock et al. | |

FOREIGN PATENT DOCUMENTS

| | | |
|---|---|---|
| CA | 2 360 360 A1 | 7/2000 |
| DD | 123 466 A | 12/1976 |
| DE | 3540919 A1 | 5/1987 |
| EP | 0 503 627 A1 | 9/1992 |
| EP | 1 031 564 A1 | 8/2000 |
| EP | 1167366 | 1/2002 |
| JP | 49-116004 A | 11/1974 |
| JP | 49-048548 B | 12/1974 |

(Continued)

OTHER PUBLICATIONS

AN 2000: 473143, CAPLUS abstract of Jefferson et al., "Solid-phase synthesis of a heterocyclic ethylenediamine-derivatized library," J. Comb. Chem., 2(5):441-444 (2000) abstract only.

Argiriadi, M.A. et al., "Binding of alkylurea inhibitors to epoxide hydrolase implicates active site tyrosines in substrate activation" J. Biol. Chem., 275:15265-15270 (2000).

Argiriadi, M.A. et al., "Detoxification of encironmental mutagens and carcinogens: structure, mechanism, and evolution of liver epoxide hydrolase" Proc. Natl. Acad. Sci. USA, 96:10637-10642 (1999).

Bardin, C. W. (ed.), Current Therapy in Endocrinology and Metabolism, 6th Edition, Mosby—Year Book, Inc., St. Louis, MO 1997.

Beetham, J. et al., "cDNA cloning and expression of a soluble epoxide hydrolase from human liver" Arch. Biochem. Biophys., 305(1):197-201 (1993).

(Continued)

Primary Examiner — Satyanarayana R Gudibande
(74) Attorney, Agent, or Firm — Kilpatrick Townsend & Stockton LLP.

(57) ABSTRACT

Inhibitors of the soluble epoxide hydrolase (sEH) are provided that incorporate multiple pharmacophores and are useful in the treatment of diseases.

9 Claims, 14 Drawing Sheets

FOREIGN PATENT DOCUMENTS

| | | |
|---|---|---|
| JP | 63-159382 A | 7/1988 |
| JP | 4-13666 A | 1/1992 |
| JP | 7-133224 A | 5/1995 |
| JP | 07-258199 A | 10/1995 |
| JP | 9160300 A | 6/1997 |
| JP | 2001-158789 A | 6/2001 |
| JP | 2002-059655 A | 2/2002 |
| JP | 2002-506058 A | 2/2002 |
| JP | 2002-509881 A | 4/2002 |
| JP | 2002179568 | 6/2002 |
| JP | 2002-532427 A | 10/2002 |
| JP | 2003-501473 A | 1/2003 |
| JP | 2003-512355 A | 4/2003 |
| JP | 2003-522120 T | 7/2003 |
| JP | 2004-002414 A | 1/2004 |
| JP | 2005-539072 A | 12/2005 |
| JP | 2006-511484 A | 4/2006 |
| JP | 2007-503393 A | 2/2007 |
| JP | 2010-500959 A | 1/2010 |
| JP | 2011-509838 A | 3/2011 |
| RU | 2 208 608 C2 | 7/2003 |
| WO | WO 95/33729 A1 | 12/1995 |
| WO | WO 96/40258 A1 | 12/1996 |
| WO | WO 98/06261 A1 | 2/1998 |
| WO | WO 99/07700 A1 | 2/1999 |
| WO | WO 99/09024 A1 | 2/1999 |
| WO | 99/15164 | 4/1999 |
| WO | WO 99/32437 A1 | 7/1999 |
| WO | WO 99/46244 A1 | 9/1999 |
| WO | WO 00/42011 A1 | 7/2000 |
| WO | WO 00/48593 A1 | 8/2000 |
| WO | WO 00/61581 A1 | 10/2000 |
| WO | WO 00/72834 A2 | 12/2000 |
| WO | WO 00/72834 A3 | 12/2000 |
| WO | WO 00/76457 A2 | 12/2000 |
| WO | WO 00/76457 A3 | 12/2000 |
| WO | 01/28987 | 4/2001 |
| WO | WO 01/42212 A1 | 6/2001 |
| WO | WO 02/14311 A2 | 2/2002 |
| WO | WO 02/14311 A3 | 2/2002 |
| WO | WO 03/002555 A1 | 1/2003 |
| WO | WO 03/009845 A1 | 2/2003 |
| WO | WO 03/061597 A2 | 7/2003 |
| WO | WO 03/061597 A3 | 7/2003 |
| WO | WO 03/070242 A1 | 8/2003 |
| WO | WO 03/070691 * | 8/2003 |
| WO | WO 03/070691 A1 | 8/2003 |
| WO | WO 03/070727 A1 | 8/2003 |
| WO | WO 03/076426 A2 | 9/2003 |
| WO | WO 03/076426 A3 | 9/2003 |
| WO | WO 03/077907 A1 | 9/2003 |
| WO | WO 03/082861 A2 | 10/2003 |
| WO | WO 03/082861 A3 | 10/2003 |
| WO | WO 03/097586 A1 | 11/2003 |
| WO | WO 03/097618 A1 | 11/2003 |
| WO | 03/099805 | 12/2003 |
| WO | WO 2004/007459 A2 | 1/2004 |
| WO | WO 2004/007459 A3 | 1/2004 |
| WO | WO 2004/026836 A2 | 4/2004 |
| WO | WO 2004/026836 A3 | 4/2004 |
| WO | WO 2004/063181 A1 | 7/2004 |
| WO | WO 2004/064730 A2 | 8/2004 |
| WO | WO 2004/064730 A3 | 8/2004 |
| WO | WO 2004/089296 A2 | 10/2004 |
| WO | WO 2004/094381 A1 | 11/2004 |
| WO | WO 2004/111009 A1 | 12/2004 |
| WO | WO 2004/111031 A1 | 12/2004 |
| WO | WO 2005/014580 A1 | 2/2005 |
| WO | WO 2005/018624 A2 | 3/2005 |
| WO | WO 2005/030209 A1 | 4/2005 |
| WO | WO 2005/037199 A2 | 4/2005 |
| WO | WO 2005/037199 A3 | 4/2005 |
| WO | WO 2005/089763 A1 | 9/2005 |
| WO | 2005/105802 | 11/2005 |
| WO | WO 2005/113511 A1 | 12/2005 |
| WO | WO 2006/009741 A1 | 1/2006 |
| WO | WO 2006/014136 A1 | 2/2006 |
| WO | WO 2006/014359 A2 | 2/2006 |
| WO | WO 2006/014359 A3 | 2/2006 |
| WO | WO 2006/016039 A1 | 2/2006 |
| WO | WO 2006/045119 A2 | 4/2006 |
| WO | WO 2009/077907 A2 | 6/2009 |

OTHER PUBLICATIONS

Beetham, J. et al., "Gene evolution of epoxide hydrolases and recommended nomenclature" DNA Cell Biol., 14(1):61-71 (1995).

Campbell, W.B., "New role for epoxyeicosatrienoic acids as anti-inflammatory mediators" Trends Pharmacol. Sci., 21:125-127 (2000).

Capdevila, J.H. et al., "Cytochrome P450 and arachidonic acid bioactivation: molecular and functional properties of the arachidonate monooxygenase" J. Lipid. Res., 41:163-181 (2000).

Carroll, M.A. et al., "A new class of lipid mediators: cytochrome P450 arachidonate metabolites" Thorax, 55:S13-16 (2000).

CAS Accession No. 71:18417; Accessed Dec. 12, 2006.

Chiasson, J. et al., "The efficacy of acarbose in the treatment of patients with non-insulin-dependent diabetes mellitus" Ann. Intern. Med., 121:928-935 (1994).

Coniff, R. et al., "Acarbose: a review of US clinical experience" Clin. Ther., 19:16-26 (1997).

Coniff, R. et al., "Multicenter, placebo-controlled trial comparing acarbose (BAY g5421) with placebo, tolbutamide, and tolbutamide-plus-acarbose in non-insulin-dependent diabetes mellitus" Am. J. Med., 98:443-451 (1995).

Defronzo, R. et al. (eds.), "Introduction" Diabetes Reviews, 5(4):293 (1997).

Dudda, A. et al., "Lipid oxidation products in ischemic porcine heart tissue" Chem. Phys. Lipids, 82:39-51 (1996).

Fang, X., et al., "Effect of soluble epoxide hydrolase inhibition on epoxyeicosatrienoic acid metabolism in human blood vessels" Am. J. Physiol. Heart Circ. Physiol. 287:H2412-H2420 (2004).

Fisslthaler, B. et al., "Cytochrome P450 2C is an EDHF synthase in coronary arteries" Nature, 401:493-497 (1999).

Fretland, A.J. et al., "Epoxide hyrolases: biochemistry and molecular biology" Chem. Biol. Intereract., 129:41-59 (2000).

Fukushima, A. et al., "Cardiovascular effects of leukotoxin (9,10-epoxy-12-octadecenoate) and free fatty acids in dogs" Cardiovasc. Res., 22:213-218 (1988).

Gibson, G.G. and Skett, P., *Introduction to Drug Metabolism*, Second Ed., Chapman and Hall, New York pp. 199-210 (1994).

Grant, D. et al., "Molecular cloning and expression of murine liver soluble epoxide hydrolase" J. Biol. Chem., 268(23):17628-17633 (1993).

Haffner, S., "Management of dyslipidemia in adults with diabetes" Diabetes Care, 21:160-178 (1998).

Hammock, B.D. et al., "Chapter 3.18: Epoxide Hyrolases" in *Comprehensive Toxicology*. Oxford: Pergamon Press pp. 283-305 (1977).

Honig and Ingram, "Chronic Bronchitis, Emphysema, and Airways Obstruction" in *Harrison's Principles of Internal Medicine*, (Fauci et al., Eds.), 14th Ed., McGraw-Hill, New York, pp. 1451-1460 (1998).

Hwang, S. et al., "Orally Bioavailable Potent Soluble Epoxide Hydrolase Inhibitors" J. Medicinal Chemistry, pp. A-P (2007).

Ishizaki, T. et al., "Endothelin-1 potentiates leukotoxin-induced edematous lung injury" J. Appl. Physiol., 79:1106-1611 (1995).

Ishizaki, T. et al., "Leukotoxin, 9,10-epoxy-12-octadecenoate causes pulmonary vasodilation in rats" Am. J. Physiol., 268:L123-128 (1995).

Ishizaki, T. et al., "Leukotoxin, 9,10-epoxy-12-octadecenoate causes edematous lung injury via activation of vascular nitric oxide synthase" Am. J. Physiol., 269:L65-70 (1995).

Iwamoto, Y. et al., "Effect of combination therapy of troglitazone and sulphonylureas in patients with type 2 diabetes who were poorly controlled by sulphonylurea therapy alone" Diabet. Med., 13:365-370 (1996).

Jefferson, Elizabeth A. et al.; "Solid-Phase Synthesis of a Heterocyclic Ethylenediamine-derivatized Library"; 2000, J. Comb. Chem., vol. 2, No. 5, pp. 441-444 (abstract only).

Kim, I., et al., "Design, synthesis, and biological activity of 1,3-disubstituted ureas as potent inhibitors of the soluble epoxide hydrolase of increased water solubility" J. Med. Chem. 47:2110-2122 (2004).

Kricheldorf, H.R. et al. "Polykondensation von N-Aryloxycarbonyl-w-aminocarbonsäuren und N-Phenoxycarbonyldipeptiden," Die Angewandte Makromolekulare Chemie 45:119-137 (1975).

Kwiterovich, P., "State-of-the-art update and review: clinical trials of lipid-lowering agents" Am. J. Cardiol., 82(12A):3U-17U (1998).

Mahler, R. et al., "Type 2 diabetes mellitus: update on diagnosis, pathophysiology, and treatment" J. Clin. Endocrinol. Metab., 84:1165-71 (1999).

McElroy, N.R, et al., "QSAR and classification of murine and human soluble epoxide hydrolase inhibition by urea-like compounds" J. Med. CHem. 46:1066-1080 (2003).

Moghaddam, M.F. et al., "Bioactivation of leukotoxins to their toxic diols by epoxide hydrolase" Nat. Med., 3:562-567 (1997).

Morisseau, C., et al., "Inhibition of microsomal epoxide hydrolases by ureas, amides, and amines" Chem. Res. Toxicol. 14:409-415 (2001).

Morisseau, C., et al., "Potent urea and carbamate inhibitors of soluble epoxide hydrolases" Proc. Natl. Acad. Sci. USA, 96:8849-8854 (1999).

Morisseau, et al., "Structural refinement of inhibitors of urea-based soluble epoxide hydrolases" Biochem. Pharm., 63:1599-1608 (2002).

Nakagawa, Y., et al., "3-D QSAR analysis of inhibition of murine soluble epoxide hydrolase (MsEH) by benzoylureas, arylureas, and their analogues" Bioorg. Med. Chem. 8:2663-2673 (2000).

Newman, J.W. et al., "Evaluation of fish models of soluble epoxide hydrolase inhibition" Environ. Health Perspect., 109:61-66 (2001).

Node, K. et al., "Anti-inflammatory properties of cytochrome P450 epoxygenase-derived eicosanoids" Science, 285:1276-1279 (1999).

Oesch, F. et al., "Mammalian epoxide hydrases: inducible enzymes catalyzing the inactivation of carcinogenic and cytotoxic metabolites derived from aromatic and olefinic compounds" Xenobiotica, 3:305-340 (1973).

Oltman, C.L. et al., "Epoxyeicosatrienoic acids and dihydroxyeicosatrienoic acids are potent vasodilators in the canine coronary microcirculation" Circ Res., 83:932-939 (1998).

Ozawa, T. et al., "Existence of leukotoxin 9,10-epoxy-12-octadecenoate in lung lavages from rats breathing pure oxygen and from patients with the adult respiratory distress syndrome" Am. Rev. Respir. Dis., 137:535-540 (1988).

Reynolds, H.Y., "Interstitial lung diseases" in *Harrison's Principles of Internal Medicine*, (Fauci et al., Eds.), 14th Ed., McGraw-Hill, New York, pp. 1460-1466 (1998).

Sakai, T. et al., "Leukotoxin, 9,10-epoxy-12-octadecenoate inhibits mitochondrial respiration of isolated perfused rat lung" Am. J. Physiol., 269:L326-331 (1995).

Sinal, C.J. et al., "Targeted disruption of soluble epoxide hydrolase reveals a role in blood pressure regulation" J. Biol. Chem., 275:40504-405010 (2000).

Speizer, "Environmental Lung Diseases," *Harrison's Principles of Internal Medicine*, (Fauci et al., Eds.), 14th Ed., 1998, McGraw-Hill, New York, pp. 1429-1436.

Turner, N. et al., "Insulin resistance, impaired glucose tolerance and non-insulin-dependent diabetes, pathologic mechanisms and treatment: Current status and therapeutics possibilities" Prog. Drug Res., 51:33-94 (1998).

United Kingdom Prospective Diabetes Study Group, "UKPDS 28: a randomized trial of efficacy of early addition of metformin in sulfonylurea-treated type 2 diabetes", Diabetes Care, 21: 87-92 (1998).

Walter, E. et al., "Transepithelial transport properties of peptidomimetic thrombin inhibitors in monolayers of a human intestinal cell line (Caco-2) and their correlation to in vivo data" Pharm. Res., 12: 360-365 (1995).

Watanabe, K. et al., "Studies on intestinal absorption of sulpiride (2): transepithelial transport of sulpiride across the human intestinal cell line caco-2" Biol. Pharm. Bull., 25:1345-1350 (2002).

Watanabe, T., et al., "In vitro metabolism of the mammalian soluble epoxide hydrolase inhibitor, 1-cyclohexyl-3-dodecyl-urea" Drug Metab. Dispos. 31(7):846-853 (2003).

Watanabe, T., et al., "Rapid Determination of Soluble Epoxide Hydrolase Inhibitors in Rat Hepatic Microsomes by High-Performance Liquid Chromatography with Electrospray Tandem Mass Spectrometry" Anal. Biochem., 299:227-234 (2001).

Weintraub, N.L. et al., "Epoxide hydrolases regulate epoxyeicosatrienoic acid incorporation into coronary endothelial phospholipids" Am. J. Physiol., 277:H2098-2108 (1992).

Yamada, T. et al. "Biochemical Evidence for the Involvement of Tyrosine in Epoxide Activation During the Catalytic Cycle of Epoxide Hydrolase," J. Biol. Chem., 275(30):23082-23088 (Jul. 2000).

Yu, Z. et al., "Soluble epoxide hydrolase regulates hydrolysis of vasoactive epoxyeicosatrienoic acids" Circ. Res., 87:992-998 (2000).

Zeldin, D.C., et al., "Regio- and enantiofacial selectivity of epoxyeicosatrienoic acid hydration by cytosolic epoxide hydrolase" J. Biol. Chem., 268:6402-6407 (1993).

Zhao, X., et al., "Soluble epoxide hydrolase inhibition protects the kidney from hypertension-induced damage" J. Am. Soc. Nephrol. 15:1244-1253 (2004).

Zheng, J. et al., "Leukotoxin-Diol: a putative toxic mediator involved in acute respiratory distress syndrome" Am. J. Respir. Cell Mol. Biol., 25:434-438 (2001).

Canadian Office Action Dated Apr. 13, 2012, issued in related Canadian Application No. 2,584,342.

Arand, M., et al., "Sequence similarity of mammalian epoxide hydrolases to the bacterial haloalkane dehalogenase and other related proteins," *FEBS Lett.*, vol. 338, pp. 251-256.

Translation of Notice of Reasons for Rejection issued Jan. 12, 2011, for Japanese Application No. 2007-538151, 8 pgs.

Davis, B., et al., "Inhibitors of soluble epoxide hydrolase attenuate vascular smooth muscle cell proliferation," *Proceedings of the National Academy of Sciences*, vol. 99(4), pp. 2222-2227 (Feb. 19, 2002).

Lin, WK, et al., "Effect of 14, 15-epoxyeicosatrienoic acid infusion on blood pressure in normal and hypertensive rats," *Biochemical and Biophysical Research Communications*, vol. 167(3), pp. 977-981 (Mar. 30, 1990).

Severson, TF, et al., "Urea and amide-based inhibitors of the juvenile hormone epoxide hyrolase of the tobacco hornworm (Manduca sexta: Sphingidae)," *Insect Biochemistry and Molecular Biology*, vol. 32(12), pp. 1741-1756 (Dec 2002).

White, RW, et al., "Aliphatic hydroxylation by cytochrome P-450. Evidence for rapid hydrolysis of an intermediate iron-nitrene complex," *J. Am. Chem.*, vol. 106(17), pp. 4922- 4926 (1984).

* cited by examiner

FIG. 1
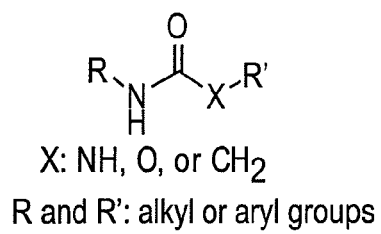
X: NH, O, or CH₂
R and R': alkyl or aryl groups
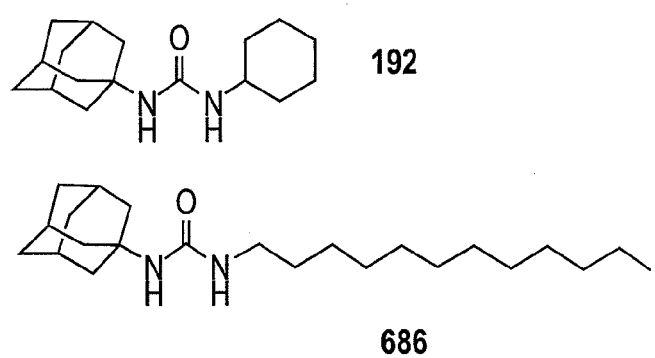
FIG. 2
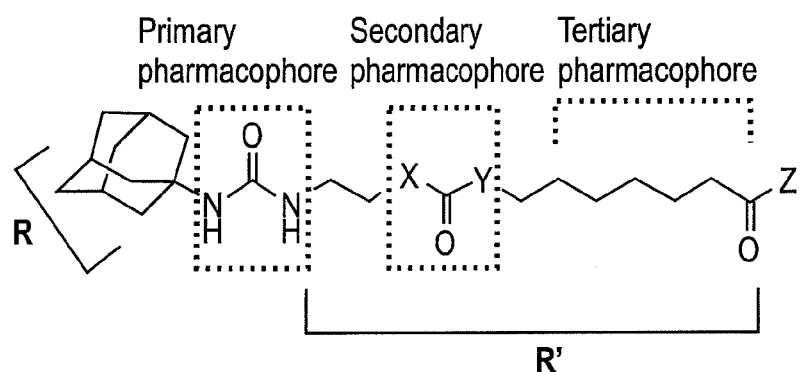

FIG. 4

```
Human sEH (JC4711)          MTLRAAVFDLDGVLALPAVFGVLGRTEEALALPRGLLNDA   40
Rat sEH (P80299)            MALRVAAFDLDGVLALPSIAGVLRHTEEALALPRDFLLGA   40
Mouse liver sEH (AAA37555)  MALRVAAFDLDGVLALPSIAGAFRRSEFALALPRDFLLGA   40
Mouse ovary sEH (AAM28238)  M-----------------RFAAMAAFSVFFVSKGLLMNS    22

Human sEH (JC4711)          FQKGGPEGATTRLMKGEITLSQWIPLMEENCRKCSETAKV   80
Rat sEH (P80299)            FQMKFPEGPTEQLMKGKITFSQWVPLMDESCRKSSKACGA   80
Mouse liver sEH (AAA37555)  YQTEFPEGPTEQLMKGKITFSQWVPLMDESYRKSSKACGA   80
Mouse ovary sEH (AAM28238)  NIWCVGQEGPSQEDTDTIHTSEWVPLMDESYRKSSKACGA   62

Human sEH (JC4711)          CLPKNFSIKEIFDKAISARKINRPMLQAALMLRKKGFTTA  120
Rat sEH (P80299)            SLPENFSISEIFSQANAAKSINRPMLQAAAALKKKGFTTC  120
Mouse liver sEH (AAA37555)  NLPENFSISQIFSQANAAKSINRPMLQAAIALKKKGFTTC  120
Mouse ovary sEH (AAM28238)  NLPENFSISQIFSQAMAAKSINRPMLQAAIALKKKGFTTC  102

Human sEH (JC4711)          IVTNTWLDDRAERDGLAQLMCELKMHFDFLIESCQVGMVK  160
Rat sEH (P80299)            IVTNNWLDDSDKRDILAQMMCELSQHFDFLIESCQVGMIK  160
Mouse liver sEH (AAA37555)  IVTNNWLDDGDKRDSLAQMMCELSQHFDFLIESCQVGMIK  160
Mouse ovary sEH (AAM28238)  IVTNNWLDDGDKRDSLAQMMCELSQHFDFLIESCQVGMIK  142

Human sEH (JC4711)          PEPQIYKFLLDTLKASPSEVVFLDDIGANLKPARDLGMVT  200
Rat sEH (P80299)            PEPQIYKFVLDTLKAKPNEVVFLDDFGSNLKPARDMGMVT  200
Mouse liver sEH (AAA37555)  PEPQIYNFLLDTLKAKPNEVVFLDDFGSNLKPARDMGMVT  200
Mouse ovary sEH (AAM28238)  PEPQIYNFLLDTLKAKPNEVVFLDDFGSNLKPARDMGMVT  182

Human sEH (JC4711)          ILVQDTDTALKELEKVTGIQLLNTPAPLPTSCNPSDMSHG  240
Rat sEH (P80299)            ILVRDTASALRELEKVTGTQFPEAPLPVPCSPN--DVSHG  238
Mouse liver sEH (AAA37555)  ILVHNTASALRELEKVTGTQFPEAPLPVPCNPN--DVSHG  238
Mouse ovary sEH (AAM28238)  ILVHNTASALRELEKVTGTQFPEAPLPVPCNPN--DVSHG  220

Human sEH (JC4711)          YVTVKPRVRLHFVELGSGPAVCLCHGFPESWYSWRYQIPA  279
Rat sEH (P80299)            YVTVKPGIRLHFVEMGSGPALCLCHGFPESWFSWRYQIPA  278
Mouse liver sEH (AAA37555)  YVTVKPGIRLHFVEMGSGPALCLCHGFPESWFSWRYQIPA  278
Mouse ovary sEH (AAM28238)  YVTVKPGIRLHFVEMGSGPALCLCHGFPESWFSWRYQIPA  260

Human sEH (JC4711)          LAQAGYRVLAMDMKGYGESSAPPEIEEYCMEVLCKEMVTF  319
Rat sEH (P80299)            LAQAGFRVLAIDMKGYGDSSSPPEIEEYAMFLLCEEMVTF  318
Mouse liver sEH (AAA37555)  LAQAGFRVLAIDMKGYGDSSSPPEIEEYAMELLCKEMVTF  318
Mouse ovary sEH (AAM28238)  LAQAGFRVLAIDMKGYGDSSSPPEIEEYAMELLCKEMVTF  300
                                             † ‡
Human sEH (JC4711)          LDKLGLSQAVFIGHDWGGMLVWYMALFYPERVRAVASLNT  359
Rat sEH (P80299)            LNKLGIPQAVFIGHDWAGVLVWNMALFHPERVRAVASLNT  358
Mouse liver sEH (AAA37555)  LDKLGIPQAVFIGHDWAGVNVWNMALFYPERVRAVASLNT  358
Mouse ovary sEH (AAM28238)  LDKLGIPQAVFIGHDWAGVMVWNMALFYPERVRAVASLNT  340
```

Protein sequences obtained from the NCBI database (accession numbers) showing identical (bold) and homologous (boxed) residues in the mammalian proteins. Sites for interaction with the primary (†), secondary (‡) and tertiary (°) pharmacophores are indicated above each sequence.

FIG. 5

```
                              † ‡
Human sEH (JC4711)       PFIPANPNMSPLESIKANPVFDYQLYFQEPGVAEAELEQN  399
Rat sEH (P80299)         PLNPPNPEVSPMEVIRSIPVFNYQLYFQEPGVAEAELEKN  398
Mouse liver sEH (AAA37555)  PFMPPDPDVSPMKVIRSIPVFNYQLYFQEPGVAEAELEKN  398
Mouse ovary sEH (AAM28238)  PFMPPDPDVSPMKVIRSIPVFNYQLYFQEPGVAEAELEKN  380

Human sEH (JC4711)       LSRTFKSLFRASDESVLSM-HKVCEAGGLFVNSPEEPSLS  439
Rat sEH (P80299)         MSRTFKSFFRTSDDMGLLTVNKATEMGGILVGTPEDPKVS  438
Mouse liver sEH (AAA37555)  MSRTFKSFFRASDETGFIAVHKATEIGGILVNTPEDPNLS  438
Mouse ovary sEH (AAM28238)  MSRTFKSFFRASDETGFIAVHKATEIGGILVNTPEDPNLS  420
                                      †            °
Human sEH (JC4711)       RMVTEEEIQFYVQQFKKSGFRGPLNWYRNMERNWKWACKS  479
Rat sEH (P80299)         KITTEEEIEYYIQQFKKSGFRGPLMWYRNTERNWKWSCKA  478
Mouse liver sEH (AAA37555)  KITTEEEIEFYIQQFKKTGFRGPLMWYRNTERNWKWSCKG  478
Mouse ovary sEH (AAM28238)  KITTEEEISFYIQQFKKTGFRGPLNWYRNTERNWKWSCKG  460

Human sEH (JC4711)       LGRKILIPALMVTAEKDFVLVPQMSQHMEDWIPHLKRGHI  519
Rat sEH (P80299)         LGRKILVPALMVTAEKDIVLRPEMSKNMENWIPFLKRGHI  518
Mouse liver sEH (AAA37555)  LGRKILVPALMVTAEKDIVLRPEMSKNMEKWIPFLKRGHI  518
Mouse ovary sEH (AAM28238)  LGRKILVPALMVTAEKDIVLRPEMSKNMEKWIPFLKRGHI  500

Human sEH (JC4711)       EDCGHWTQMDKPTEVNQILIKWLDSDARNPPVVSKM     555
Rat sEH (P80299)         EDCGHWTQIEKPAEVNQILIKWLKTEIQNPSVTSKI     554
Mouse liver sEH (AAA37555)  EDCGHWTQIEKPTEVNQILIKWLQTEVQNPSVTSKI     554
Mouse ovary sEH (AAM28238)  EDCGHWTQIEKPTEVNQILIKWLQTEVQNPSVTSKI     536
```

Protein sequences obtained from the NCBI database (accession numbers) showing identical (bold) and homologous (boxed) residues in the mammalian proteins. Sites for the interaction with the primary (†), secondary (‡) and tertiary (°) pharmacophores are indicated above each sequence.

Urinary Octadecanoids

Urinary Eicosanoids

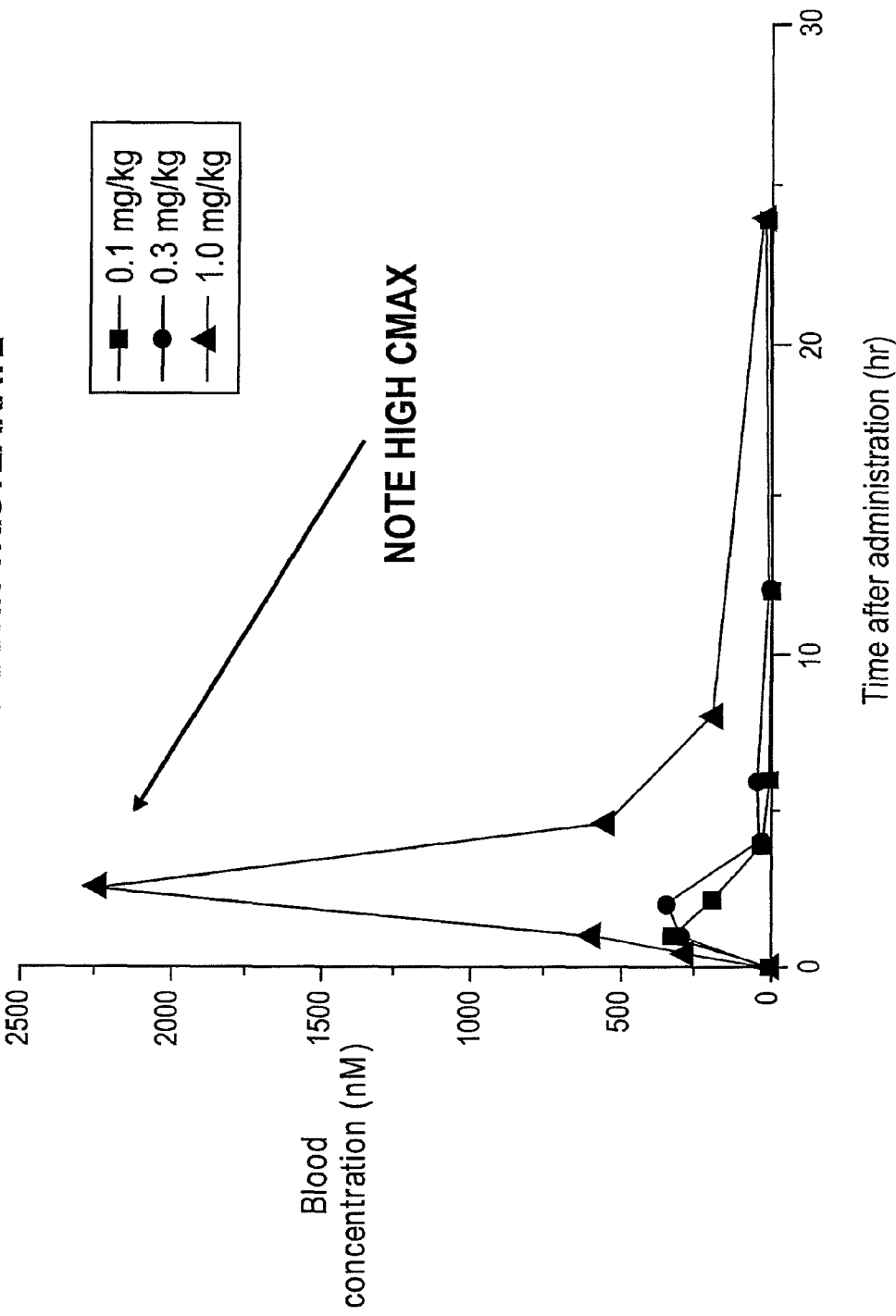

950

| Mp (°C) | 74-75 |
|---|---|
| Ms | 396.30 |
| Murine sEH IC$_{50}$ (µM) | 0.10 ± 0.01 |
| Murine IC$_{90}$ (µM) | 2.00 ± 0.20 |
| Water Solubility (µg/mL) | 120 ± 7.91 |
| Log $P$ | 1.86 |

In vitro metabolic stability of 950 without NADPH

Metabolic Stability of #950 in S9 fraction

950 Metabolic Stability in Microsome (ng/mL)

INHIBITORS FOR THE SOLUBLE EPOXIDE HYDROLASE

CROSS-REFERENCE TO RELATED APPLICATION

This application is a continuation of U.S. patent application Ser. No. 11/256,685, filed Oct. 20, 2005, which claims the benefit of U.S. Patent Application No. 60/651,487, filed Oct. 20, 2004, the contents of which are herein incorporated by reference.

STATEMENT AS TO RIGHTS TO INVENTIONS MADE UNDER FEDERALLY SPONSORED RESEARCH OR DEVELOPMENT

The U.S. Government has certain rights to the invention pursuant to contract ES02710 awarded by the National Institutes of Health.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Epoxide hydrolases (EHs, EC 3.3.2.3) catalyze the hydrolysis of epoxides or arene oxides to their corresponding diols by the addition of water (see, Oesch, F., et al., *Xenobiotica* 1973, 3, 305-340). Some EHs play an important role in the metabolism of a variety of compounds including hormones, chemotherapeutic drugs, carcinogens, environmental pollutants, mycotoxins, and other harmful foreign compounds.

There are two well-studied EHs, microsomal epoxide hydrolase (mEH) and soluble epoxide hydrolase (sEH). These enzymes are very distantly related, have different subcellular localization, and have different but partially overlapping substrate selectivities. The soluble and microsomal EH forms are known to complement each other in degrading some plant natural products (see, Hammock, B. D., et al., COMPREHENSIVE TOXICOLOGY. Oxford: Pergamon Press 1977, 283-305 and Fretland, A. J., et al., *Chem. Biol. Intereract* 2000, 129, 41-59).

The major role of the sEH is in the metabolism of lipid epoxides including the metabolism of arachidonic acid (see, Zeldin, D. C., et al., *J. Biol. Chem.* 1993, 268, 6402-6407), linoleic (see, Moghaddam, M. F., et al., *Nat. Med.* 1997, 3, 562-567) acid, some of which are endogenous chemical mediators (see, Carroll, M. A., et al., *Thorax* 2000, 55, S13-16). Epoxides of arachidonic acid (epoxyeicosatrienoic acids or EETs) and other lipid epoxides and diols are known effectors of blood pressure (see, Capdevila, J. H., et al., *J. Lipid. Res.* 2000, 41, 163-181), and modulators of vascular permeability (see, Oltman, C. L., et al., *Circ Res.* 1998, 83, 932-939). The vasodilatory properties of EETs are associated with an increased open-state probability of calcium-activated potassium channels leading to hyperpolarization of the vascular smooth muscle (see Fisslthaler, B., et al., *Nature* 1999, 401, 493-497). Hydrolysis of the arachidonate epoxides by sEH diminishes this activity (see, Capdevila, J. H., et al., *J. Lipid. Res.* 2000, 41, 163-181). sEH hydrolysis of EETs also regulates their incorporation into coronary endothelial phospholipids, suggesting a regulation of endothelial function by sEH (see, Weintraub, N. L., et al., *Am. J. Physiol.* 1992, 277, H2098-2108). It has recently been shown that treatment of spontaneous hypertensive rats (SHRs) with selective sEH inhibitors significantly reduces their blood pressure (see, Yu, Z., et al., *Circ. Res.* 2000, 87, 992-998). In addition, male knockout sEH mice have significantly lower blood pressure than wild-type mice (see Sinal, C. J., et al., *J. Biol. Chem.* 2000, 275, 40504-405010), further supporting the role of sEH in blood pressure regulation.

The EETs have also demonstrated anti-inflammatory properties in endothelial cells (see, Node, K., et al., *Science* 1999, 285, 1276-1279 and Campbell, W. B. *Trends Pharmacol. Sci.* 2000, 21, 125-127). In contrast, diols derived from epoxy-linoleate (leukotoxin) perturb membrane permeability and calcium homeostasis (see, Moghaddam, M. F., et al., *Nat. Med.* 1997, 3, 562-567), which results in inflammation that is modulated by nitric oxide synthase and endothelin-1 (see, Ishizaki, T., et al., *Am. J. Physiol.* 1995, 269, L65-70 and Ishizaki, T., et al., *J. Appl. Physiol.* 1995, 79, 1106-1611). Micromolar concentrations of leukotoxin reported in association with inflammation and hypoxia (see, Dudda, A., et al., *Chem. Phys. Lipids* 1996, 82, 39-51), depress mitochondrial respiration in vitro (see, Sakai, T., et al., *Am. J. Physiol.* 1995, 269, L326-331), and cause mammalian cardiopulmonary toxicity in vivo (see, Ishizaki, T., et al., *Am. J. Physiol.* 1995, 269, L65-70; Fukushima, A., et al., *Cardiovasc. Res.* 1988, 22, 213-218; and Ishizaki, T., et al., *Am. J. Physiol.* 1995, 268, L123-128). Leukotoxin toxicity presents symptoms suggestive of multiple organ failure and acute respiratory distress syndrome (ARDS) (see, Ozawa, T. et al., *Am. Rev. Respir. Dis.* 1988, 137, 535-540). In both cellular and organismal models, leukotoxin-mediated toxicity is dependent upon epoxide hydrolysis (see, Moghaddam, M. F., et al., *Nat. Med.* 1997, 3, 562-567; Morisseau, C., et al., *Proc. Natl. Acad. Sci. USA* 1999, 96, 8849-8854; and Zheng, J., et al., *Am. J. Respir. Cell Mol. Biol.* 2001, 25, 434-438), suggesting a role for sEH in the regulation of inflammation and vascular permeability. The bioactivity of these epoxy-fatty acids suggests that inhibition of vicinal-dihydroxy-lipid biosynthesis may have therapeutic value, making sEH a promising pharmacological target.

Recently, 1,3-disubstituted ureas, carbamates, and amides have been reported as new potent and stable inhibitors of sEH (FIG. 1). See, U.S. Pat. No. 6,150,415. Compounds 192 and 686 are representative structures for this type of inhibitors (FIG. 1). These compounds are competitive tight-binding inhibitors with nanomolar $K_I$ values that interact stoichiometrically with purified recombinant sEH (see, Morisseau, C., et al., *Proc. Natl. Acad. Sci. USA* 1999, 96, 8849-8854). Based on the X-ray crystal structure, the urea inhibitors were shown to establish hydrogen bonds and to form salt bridges between the urea function of the inhibitor and residues of the sEH active site, mimicking features encountered in the reaction coordinate of epoxide ring opening by this enzyme (see, Argiriadi, M. A., et al., *Proc. Natl. Acad. Sci. USA* 1999, 96, 10637-10642 and Argiriadi, M. A., et al., *J. Biol. Chem.* 2000, 275, 15265-15270). These inhibitors efficiently reduced epoxide hydrolysis in several in vitro and in vivo models (see, Yu, Z., et al., *Circ. Res.* 2000, 87, 992-998; Morisseau, C., et al., *Proc. Natl. Acad. Sci. USA* 1999, 96, 8849-8854; and Newman, J. W., et al., *Environ. Health Perspect.* 2001, 109, 61-66). Despite the high activity associated with these inhibitors, there exists a need for compounds possessing similar or increased activities, with improved solubility and pharmacokinetic properties to facilitate formulation and delivery.

Surprisingly, the present invention provides such compounds along with methods for their use and compositions that contain them.

BRIEF SUMMARY OF THE INVENTION

In one aspect, the present invention provides a method for inhibiting a soluble epoxide hydrolase, comprising contacting the soluble epoxide hydrolase with an inhibiting amount of a compound having a formula selected from the group consisting of:

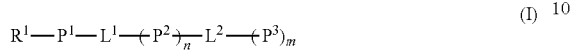
(I)

and their pharmaceutically acceptable salts, wherein the symbol; $R^1$ is a member selected from the group consisting of substituted or unsubstituted alkyl, substituted or unsubstituted heteroalkyl, substituted or unsubstituted cycloalkylalkyl, substituted or unsubstituted cycloalkylheteroalkyl, substituted or unsubstituted arylalkyl, substituted or unsubstituted arylheteroalkyl, substituted or unsubstituted $C_5$-$C_{12}$ cycloalkyl, substituted or unsubstituted aryl, substituted or unsubstituted heteroaryl and combinations thereof, wherein said cycloalkyl portions are monocyclic or polycyclic; $P^1$ is a primary pharmacophore selected from the group consisting of —OC(O)O—, —OC(O)CH$_2$—, —CH$_2$C(O)O—, —OC(O)—, —C(O)O—, —NHC(NH)NH—, —NHC(NH)CH$_2$—, —CH$_2$C(NH)NH—, —NHC(NH)—, —C(NH)NH—, —NHC(O)NH—, —OC(O)NH—, —NHC(O)O—, —NHC(S)NH—, —NHC(S)CH$_2$—, CH$_2$C(S)NH—, —SC(O)CH$_2$—, —CH$_2$C(O)S—, —SC(NH)CH$_2$—, —CH$_2$C(NH)S—, —N=C=N—, —CH$_2$C(O)NH—, —NHC(O)CH$_2$—, —C(O)NH—, —NHC(O)—,

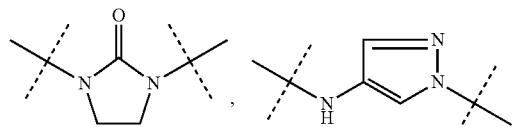

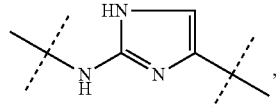

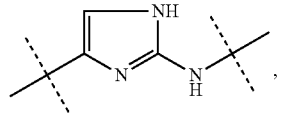

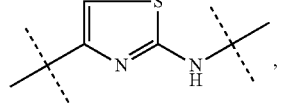

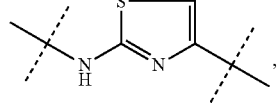

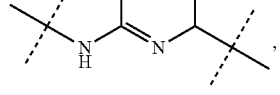

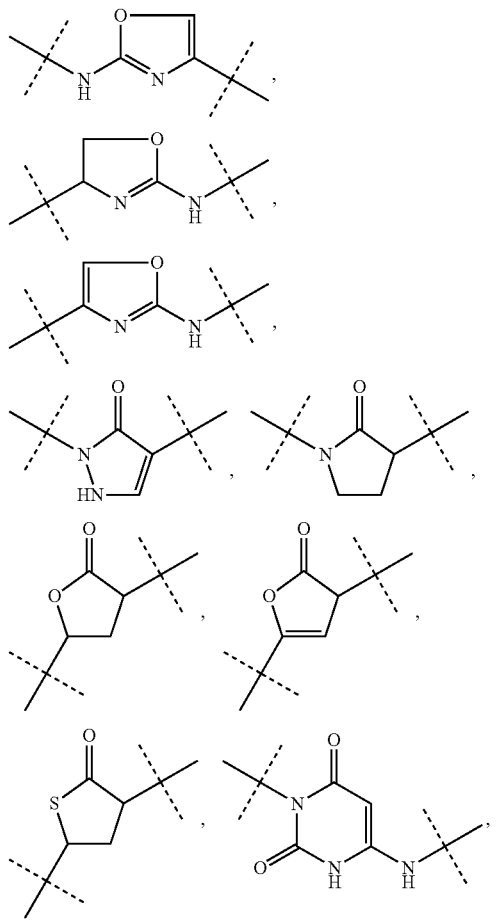

and

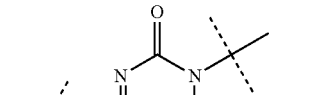

;

$P^2$ is a secondary pharmacophore selected from the group consisting of —NH—, —OC(O)O—, —C(O)—, —CH(OH)—, —O(CH$_2$CH$_2$O)$_q$—, —C(O)O—, —OC(O)—, —NHC(NH)NH—, —NHC(NH)CH$_2$—, —CH$_2$C(NH)NH—, —NHC(O)NH—, —OC(O)NH—, —NHC(O)O—, —C(O)NH—, —NHC(O)—; —NHC(S)NH—, —NHC(S)CH$_2$—, CH$_2$C(S)NH—, —SC(O)CH$_2$—, —CH$_2$C(O)S—, —SC(NH)CH$_2$—, —CH$_2$C(NH)S—, —N=C=N—,

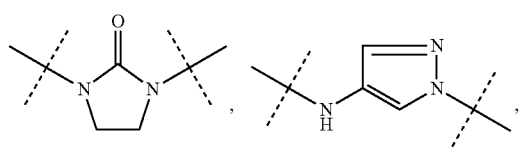

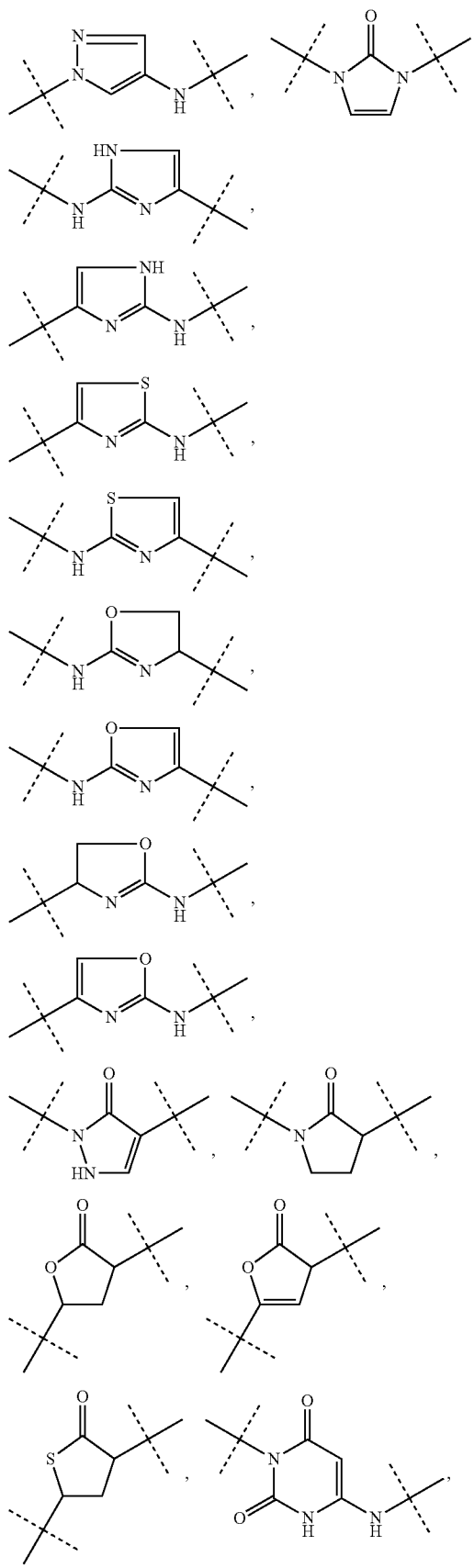

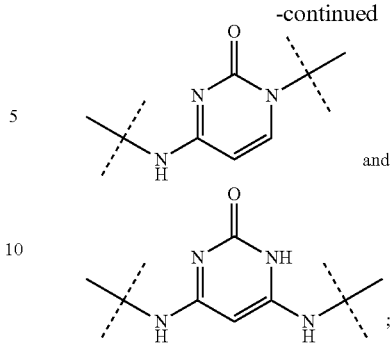

P³ is a tertiary pharmacophore selected from the group consisting of $C_2$-$C_6$ alkenyl, $C_2$-$C_6$ alkynyl, $C_1$-$C_6$ haloalkyl, aryl, heteroaryl, heterocyclyl, —O(CH$_2$CH$_2$O)$_q$—R², —OR², —C(O)NHR², —C(O)NHS(O)$_2$R², —NHS(O)$_2$R², —OC$_2$—C$_4$alkyl-C(O)OR², —C(O)R², —C(O)OR² and carboxylic acid analogs, wherein R² is a member selected from the group consisting of hydrogen, substituted or unsubstituted $C_1$-$C_4$ alkyl, substituted or unsubstituted $C_3$-$C_8$ cycloalkyl, substituted or unsubstituted heterocyclyl; substituted or unsubstituted aryl and substituted or unsubstituted aryl $C_1$-$C_4$ alkyl; L¹ is a first linker selected from the group consisting of substituted or unsubstituted $C_1$-$C_6$ alkylene, substituted or unsubstituted $C_3$-$C_6$ cycloalkylene, substituted or unsubstituted arylene and substituted or unsubstituted heteroarylene; L² is a second linker selected from the group consisting of substituted or unsubstituted $C_1$-$C_{12}$ alkylene, substituted or unsubstituted $C_3$-$C_6$ cycloalkylene, substituted or unsubstituted arylene, substituted or unsubstituted heteroarylene; an amino acid, a dipeptide and a dipeptide analog; and combinations thereof; or is selected from the group consisting of H and CH$_3$ when m is 0. In the above formulae, the subscripts n and m are each independently 0 or 1, and at least one of n or m is 1, and the subscript q is 0 to 6. When n is 0, then L¹ and L² are combined. When m is 0, then L² can also be H.

Turning next to the linking groups, the symbol L¹ represents a first linker that is a substituted or unsubstituted $C_1$-$C_6$ alkylene, $C_3$-$C_6$-cycloalkylene, or an arylene or heteroarylene group; the symbol L² represents a second linker selected from substituted or unsubstituted $C_1$-$C_{12}$ alkylene, substituted or unsubstituted arylene, an amino acid, a dipeptide, a dipeptide analog, and combinations thereof; or is H when m is 0.

In a related aspect, the present invention provides methods of treating diseases modulated by soluble epoxide hydrolases, the method comprising administering to a subject in need of such treatment an effective amount of a compound having a formula selected from formula (I), above.

In other aspects, the present invention provides methods of reducing renal deterioration in a subject, the method comprising administering to the subject an effective amount of a compound of formula (I), above.

In a related aspect, the present invention provides methods method for inhibiting progression of nephropathy in a subject, the method comprising administering to the subject an effective amount of a compound of formula (I), above.

In another aspect, the present invention provides for reducing blood pressure in a subject, the method comprising administering to the subject an effective amount of a compound of formula (I), above.

In a related aspect, the present invention provides methods of inhibiting the proliferation of vascular smooth muscle cells in a subject, the method comprising administering to the subject an effective amount of a compound of formula (I), above.

In another aspect, the present invention provides methods of inhibiting the progression of an obstructive pulmonary disease, an interstitial lung disease, or asthma in a subject, the method comprising administering to the subject an effective amount of a compound of formula (I), above. The obstructive pulmonary disease can be, for example, chronic obstructive pulmonary disease ("COPD"), emphysema, or chronic bronchitis. The interstitial lung disease can be, for example, idiopathic pulmonary fibrosis, or one associated with occupational exposure to a dust.

In yet another aspect, the present invention provides compounds having a formula (I) above, as well as pharmaceutical compositions containing one or more of the subject compounds.

BRIEF DESCRIPTION OF THE DRAWINGS

FIG. 1 provides structures of known sEH inhibitors having only a primary pharmacophore: 1-adamantyl-3-cyclohexylurea (192), 1-adamantyl-3-dodecylurea (686).

FIG. 2 provides a structural diagram defining the sEH inhibitors primary, secondary, and tertiary pharmacophores. The nomenclature used refers to the three pharmacophores and two substituents (R and R' groups). The secondary and tertiary pharmacophores located in the R' area are illustrated linearly from the primary pharmacophore. The secondary pharmacophore generally consists of a polar carbonyl group or a polar ether group. When the secondary pharmacophore is a carbonyl group, it is located about 7.5±1 Å from the carbonyl of the primary pharmacophore, with either side of the carbonyl (X and Y) being a $CH_2$, O or NH. When the secondary pharmacophore is a ether group it is preferably located about 1 carbon unit further from the carbonyl of the primary pharmacophore. The tertiary pharmacophore is also a polar group located approximately 11 carbon units (17±1 Å) from the carbonyl of the primary pharmacophore with the Z group as an OH, or a substituted amine or alcohol or a heterocyclic or acyclic structure mimicking the terminal ester or acid.

FIG. 4 provides mammalian soluble epoxide hydrolase protein sequence alignments (residue 1-340).

FIG. 5 provides mammalian soluble epoxide hydrolase protein sequence alignments (residue 341-554).

FIG. 14 is a graph showing blood concentration vs. time profiles of 950 after single oral administration of 0.1 to 1.0 mg/kg of 950 to 70 kg rats. The presence of the polyether secondary pharmacophore increases the maximum circulating concentration of 950 observed. This translates into a longer half-life for the inhibitor.

DETAILED DESCRIPTION OF THE INVENTION

Abbreviations and Definitions

Figure 3:
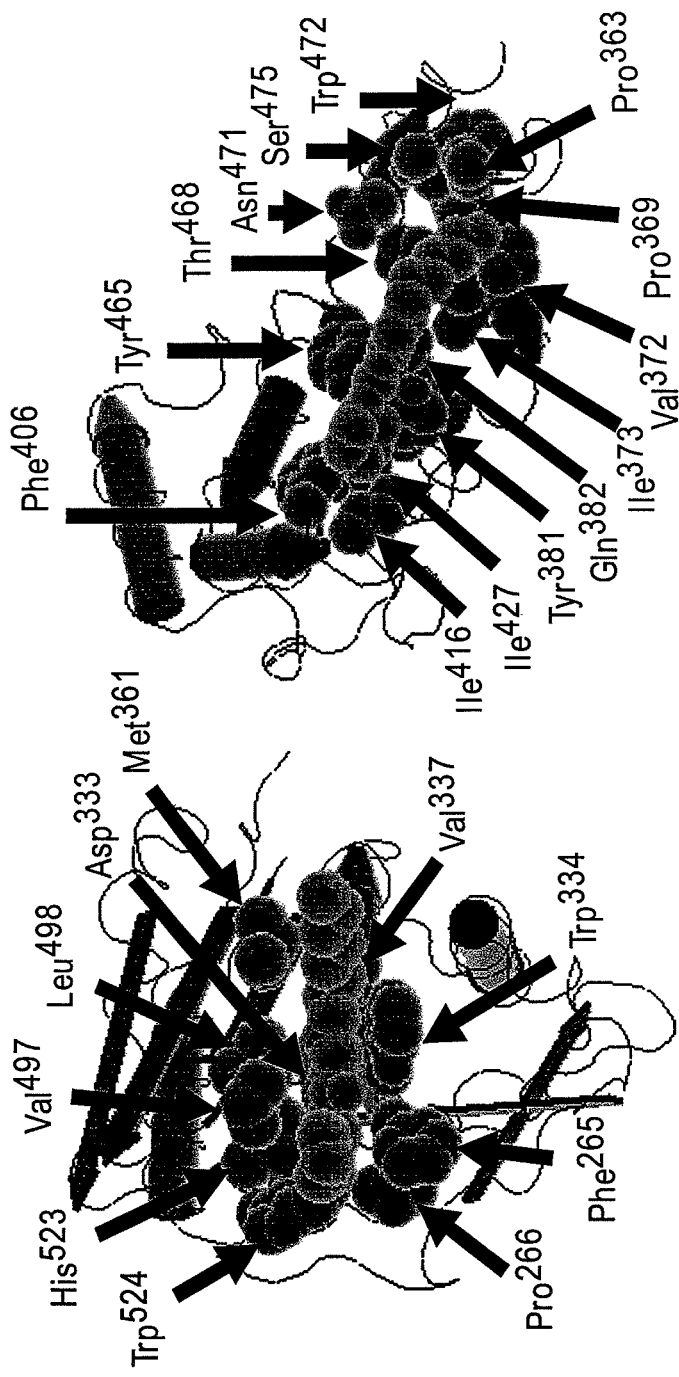
FIG. 3 provides a hydrophobicity map of the mouse sEH substrate binding pocket co-crystallized with the inhibitor 1-cyclohexyl-3-dodecyl urea. A shading gradient indicates degrees of hydrophobicity. A series of hydrophilic residues were observed on the "top" side of the channel, while the "bottom" of the channel was very hydrophobic, with the exception of the catalytic aspartate ($Asp^{333}$). This structural analysis indicated that a number of potential hydrogen bonding sites are observed in the substrate binding pocket of the soluble epoxide hydrolase, primarily located on the surface opposite $Asp^{333}$ (the catalytic nucleophile which reacts with the substrate or binds to the primary pharmacophores).

"cis-Epoxyeicosatrienoic acids" ("EETs") are biomediators synthesized by cytochrome P450 epoxygenases.

"Epoxide hydrolases" ("EH;" EC 3.3.2.3) are enzymes in the alpha/beta hydrolase fold family that add water to 3 membered cyclic ethers termed epoxides.

"Soluble epoxide hydrolase" ("sEH") is an enzyme which in endothelial, smooth muscle and other cell types converts EETs to dihydroxy derivatives called dihydroxyeicosatrienoic acids ("DHETs"). The cloning and sequence of the murine sEH is set forth in Grant et al., *J. Biol. Chem.* 268(23): 17628-17633 (1993). The cloning, sequence, and accession numbers of the human sEH sequence are set forth in Beetham et al., *Arch. Biochem. Biophys.* 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., *DNA Cell Biol.* 14(1):61-71 (1995). Soluble epoxide hydrolase represents a single highly conserved gene product with over 90% homology between rodent and human (Arand et al., *FEBS Lett.*, 338:251-256 (1994)).

The terms "treat", "treating" and "treatment" refer to any method of alleviating or abrogating a disease or its attendant symptoms.

The term "therapeutically effective amount" refers to that amount of the compound being administered sufficient to prevent or decrease the development of one or more of the symptoms of the disease, condition or disorder being treated.

The term "modulate" refers to the ability of a compound to increase or decrease the function, or activity, of the associated activity (e.g., soluble epoxide hydrolase). "Modulation", as used herein in its various forms, is meant to include antagonism and partial antagonism of the activity associated with sEH. Inhibitors of sEH are compounds that, e.g., bind to, partially or totally block the enzyme's activity.

The term "compound" as used herein is intended to encompass not only the specified molecular entity but also its pharmaceutically acceptable, pharmacologically active derivatives, including, but not limited to, salts, prodrug conjugates such as esters and amides, metabolites and the like.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In some embodiments, the subject is a human.

As used herein, the term "sEH-mediated disease or condition" and the like refers to a disease or condition characterized by less than or greater than normal, sEH activity. A sEH-mediated disease or condition is one in which modulation of sEH results in some effect on the underlying condition or disease (e.g., a sEH inhibitor or antagonist results in some improvement in patient well-being in at least some patients).

"Parenchyma" refers to the tissue characteristic of an organ, as distinguished from associated connective or supporting tissues.

"Chronic Obstructive Pulmonary Disease" or "COPD" is also sometimes known as "chronic obstructive airway disease", "chronic obstructive lung disease", and "chronic airways disease." COPD is generally defined as a disorder characterized by reduced maximal expiratory flow and slow forced emptying of the lungs. COPD is considered to encompass two related conditions, emphysema and chronic bronchitis. COPD can be diagnosed by the general practitioner using art recognized techniques, such as the patient's forced vital capacity ("FVC"), the maximum volume of air that can be forceably expelled after a maximal inhalation. In the offices of general practitioners, the FVC is typically approximated by a 6 second maximal exhalation through a spirometer. The definition, diagnosis and treatment of COPD, emphysema, and chronic bronchitis are well known in the art and discussed in detail by, for example, Honig and Ingram, in Harrison's Principles of Internal Medicine, (Fauci et al., Eds.), 14th Ed., 1998, McGraw-Hill, New York, pp. 1451-1460 (hereafter, "Harrison's Principles of Internal Medicine").

"Emphysema" is a disease of the lungs characterized by permanent destructive enlargement of the airspaces distal to the terminal bronchioles without obvious fibrosis.

"Chronic bronchitis" is a disease of the lungs characterized by chronic bronchial secretions which last for most days of a month, for three months a year, for two years.

As the names imply, "obstructive pulmonary disease" and "obstructive lung disease" refer to obstructive diseases, as opposed to restrictive diseases. These diseases particularly include COPD, bronchial asthma and small airway disease.

"Small airway disease." There is a distinct minority of patients whose airflow obstruction is due, solely or predominantly to involvement of the small airways. These are defined as airways less than 2 mm in diameter and correspond to small cartilaginous bronchi, terminal bronchioles and respiratory bronchioles. Small airway disease (SAD) represents luminal obstruction by inflammatory and fibrotic changes that increase airway resistance. The obstruction may be transient or permanent.

The "interstitial lung diseases (ILDs)" are a group of conditions involving the alveolar walls, perialveolar tissues, and contiguous supporting structures. As discussed on the website of the American Lung Association, the tissue between the air sacs of the lung is the interstitium, and this is the tissue affected by fibrosis in the disease. Persons with the disease have difficulty breathing in because of the stiffness of the lung tissue but, in contrast to persons with obstructive lung disease, have no difficulty breathing out. The definition, diagnosis and treatment of interstitial lung diseases are well known in the art and discussed in detail by, for example, Reynolds, H. Y., in Harrison's Principles of Internal Medicine, supra, at pp. 1460-1466. Reynolds notes that, while ILDs have various initiating events, the immunopathological responses of lung tissue are limited and the ILDs therefore have common features.

"Idiopathic pulmonary fibrosis," or "IPF," is considered the prototype ILD. Although it is idiopathic in that the cause is not known, Reynolds, supra, notes that the term refers to a well defined clinical entity.

"Bronchoalveolar lavage," or "BAL," is a test which permits removal and examination of cells from the lower respiratory tract and is used in humans as a diagnostic procedure for pulmonary disorders such as IPF. In human patients, it is usually performed during bronchoscopy.

As used herein, the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "aralkyl," "alkylamino" and similar terms. In some embodiments, alkyl groups are those containing 1 to 24 carbon atoms. All numerical ranges in this specification and claims are intended to be inclusive of their upper and lower limits. Lower alkyl refers to those alkyl groups having 1 to 4 carbon atoms. Additionally, the alkyl and heteroalkyl groups may be attached to other moieties at any position on the alkyl or heteroalkyl radical which would otherwise be occupied by a hydrogen atom (such as, for example, 2-pentyl, 2-methylpent-1-yl and 2-propyloxy). Divalent alkyl groups may be referred to as "alkylene", and divalent heteroalkyl groups may be referred to as "heteroalkylene" such as those groups used as linkers in the present invention. The alkyl, alkylene, and heteroalkyl moieties may also be optionally substituted with halogen atoms, or other groups such as oxo, cyano, nitro, alkyl, alkylamino, carboxyl, hydroxyl, alkoxy, aryloxy, and the like.

The terms "cycloalkyl" and "cycloalkylene" refer to a saturated hydrocarbon ring and includes bicyclic and polycyclic rings. Similarly, cycloalkyl and cycloalkylene groups having a heteroatom (e.g., N, O, or S) in place of a carbon ring atom may be referred to as "heterocycloalkyl" and "heterocycloalkylene," respectively. Examples of cycloalkyl and heteroaryl groups are, for example, cyclohexyl, norbornyl, adamantyl, morpholinyl, thiomorpholinyl, dioxothiomorpholinyl, and the like. The cycloalkyl and heterocycloalkyl moieties may also be optionally substituted with halogen atoms, or other groups such as nitro, alkyl, alkylamino, carboxyl, alkoxy, aryloxy and the like. In some embodiments, cycloalkyl and cycloalkylene moieties are those having 3 to 12 carbon atoms in the ring (e.g., cyclohexyl, cyclooctyl, norbornyl, adamantyl, and the like). In some embodiments, heterocycloalkyl and heterocycloalkylene moieties are those having 1 to 3 hetero atoms in the ring (e.g., morpholinyl, thiomorpholinyl, dioxothiomorpholinyl, piperidinyl, and the like). Additionally, the term "(cycloalkyl) alkyl" refers to a group having a cycloalkyl moiety attached to an alkyl moiety. Examples are cyclohexylmethyl, cyclohexylethyl, and cyclopentylpropyl.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon radical (such as, for example, methoxy, ethoxy, aryloxy and t-butoxy).

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g. N, O or S) in place of a carbon ring atom are referred to as "heteroaryl". Examples of aryl and heteroaryl groups are, for example, phenyl, naphthyl, biphenyl, diphenylmethyl, 2,2-diphenyl-1-ethyl, thienyl, pyridyl and quinoxalyl. The aryl and heteroaryl moieties may also be optionally substituted with halogen atoms, or other groups such as nitro, alkyl, alkylamino, carboxyl, alkoxy, phenoxy and the like. Additionally, the aryl and heteroaryl groups may be attached to other moieties at any position on the aryl or heteroaryl radical which would otherwise be occupied by a hydrogen atom (such as, for example, 2-pyridyl, 3-pyridyl and 4-pyridyl). Divalent aryl groups are "arylene", and divalent heteroaryl groups are referred to as "heteroarylene" such as those groups used as linkers in the present invention.

The terms "arylalkyl", "arylalkenyl" and "aryloxyalkyl" refer to an aryl radical attached directly to an alkyl group, an alkenyl group, or an oxygen which is attached to an alkyl group, respectively. For brevity, aryl as part of a combined term as above, is meant to include heteroaryl as well.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_1$-$C_6$ haloalkyl" is mean to include trifluoromethyl, 2,2,2-trifluoroethyl, 4-chlorobutyl, 3-bromopropyl, and the like.

The term "hetero" as used in a "heteroatom-containing alkyl group" (a "heteroalkyl" group) or a "heteroatom-containing aryl group" (a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur or more that none non-carbon atom (e.g., sulfonamide). Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrophobic radical" or "hydrophobic group" refers to a group which lowers the water solubility of a molecule. In some embodiments, hydrophobic radicals are groups containing at least 3 carbon atoms.

The term "carboxylic acid analog" refers to a variety of groups having an acidic moiety that are capable of mimicking a carboxylic acid residue. Examples of such groups are sulfonic acids, sulfinic acids, phosphoric acids, phosphonic acids, phosphinic acids, sulfonamides, and heterocyclic moieties such as, for example, imidazoles, triazoles and tetrazoles.

The term "substituted" refers to the replacement of an atom or a group of atoms of a compound with another atom or group of atoms. For example, an atom or a group of atoms may be substituted with one or more of the following substituents or groups: halo, cyano, nitro, alkyl, alkylamino, hydroxyalkyl, haloalkyl, carboxyl, hydroxyl, alkoxy, alkoxyalkoxy, haloalkoxy, thioalkyl, aryl, aryloxy, cycloalkyl, cycloalkylalkyl, aryl, heteroaryl optionally substituted with 1 or more, preferably 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, cyano, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl. When the term "substituted" appears prior to a list of possible substituted groups, it is intended that the term apply to every member of that group.

The term "unsubstituted" refers to a native compound that lacks replacement of an atom or a group of atoms.

General:

The present invention derives from the discovery that 1,3-disubstituted ureas (or the corresponding amides or carbamates, also referred to as the primary pharmacophore) can be further functionalized to provide more potent sEH inhibitors with improved physical properties. As described herein, the introduction of secondary and/or tertiary pharmacophores can increase water solubility and oral availability of sEH inhibitors (see FIG. 2). The combination of the three pharmacophores (see the compounds of Table 18) provides a variety of compounds of increased water solubility.

The discovery of the secondary and tertiary pharmacophores has also led to the employment of combinatorial chemistry approaches for establishing a wide spectrum of compounds having sEH inhibitory activity. The polar pharmacophores divide the molecule into domains each of which can be easily manipulated by common chemical approaches in a combinatorial manner, leading to the design and confirmation of novel orally available therapeutic agents for the treatment of diseases such as hypertension and vascular inflammation. The agents of the present invention treat such diseases while simultaneously increasing sodium excretion, reducing vascular and renal inflammation, and reducing male erectile dysfunction As shown below (see Example 51 and FIG. 13), alterations in solubility, bioavailability and pharmacological properties leads to compounds that can alter the regulatory lipids of experimental animals increasing the relative amounts of epoxy arachidonate derivatives when compared either to their diol products or to the proinflammatory and hypertensive hydroxyeicosatetraenoic acids (HETEs). Since epoxy arachidonates are anti-hypertensive and anti-inflammatory, altering the lipid ratios can lead to reduced blood pressure and reduced vascular and renal inflammation. This approach has been validated in a patient approaching end stage renal disease (ESRD) where even a brief oral treatment with low doses compound 800 altered the serum profile of regulatory lipids in a positive manner. This resulted in reduced systolic and diastolic blood pressure, a dramatic reduction in blood urea nitrogen (an indicator of renal inflammation) and dramatically reduced serum levels of C reactive protein (a common indicator of vascular inflammation).

Without intending to be bound by theory, and with reference to FIGS. 2, 3, 4 and 5, it is believed that the left side of the primary pharmacophore or R (in FIG. 2) can be varied to obtain optimal properties as can the primary pharmacophore, which contains groups able to hydrogen bond to the catalytic aspartic acid on one side and the catalytic tyrosines on the other (see FIG. 3). The right side of the primary pharmacophore is effectively divided into 4 segments: a spacer separating the primary and secondary pharmacophore (termed $L^1$ in the present invention), the secondary pharmacophore (termed $P^2$ in the present invention) and a tertiary pharmacophore ($P^3$) flanked by a spacer ($L^2$) and finally a terminating group Z (collectively provided with the tertiary pharmacophore as $P^3$). The spacer between the primary and secondary pharmacophores, is optimally 3 atom units in length, while the secondary pharmacophore can be, for example, a ketone, carbonate, amide, carbamate, urea, ether/polyether, ester or other functionality able to form a hydrogen bond with the enzyme approximately 7.5 angstroms from the carbonyl of the primary pharmacophore. The identified tertiary pharmacophore consists of a polar group located approximately six to eleven carbon units from the primary pharmacophore (see FIG. 2). A conserved asparagine residue ($Asn^{471}$, see FIGS. 4 and 5) is thought to provide the site of interaction between the protein and the polar functionality located at this tertiary site. While, in the rodent a threonine ($Thr^{468}$) is also in an appropriate position for hydrogen bonding, residue 468 is a methionine in the human enzyme (FIG. 5). As with the secondary pharmacophore, this group improves water solubility of sEH inhibitors as well as the specificity for the sEH, and a wide diversity of functionalities such as an ester, amide, carbamate, or similar functionalities capable of donating or accepting a hydrogen bond similarly can contribute to this polar group. For example, in pharmaceutical chemistry heterocyclic groups are commonly used to mimic carbonyls as hydrogen bond donors and acceptors. Of course the primary, secondary and tertiary pharmacophore groups can be combined in a single molecule with suitable spacers to improve activity or present the inhibitor as a prodrug.

Figure 11:
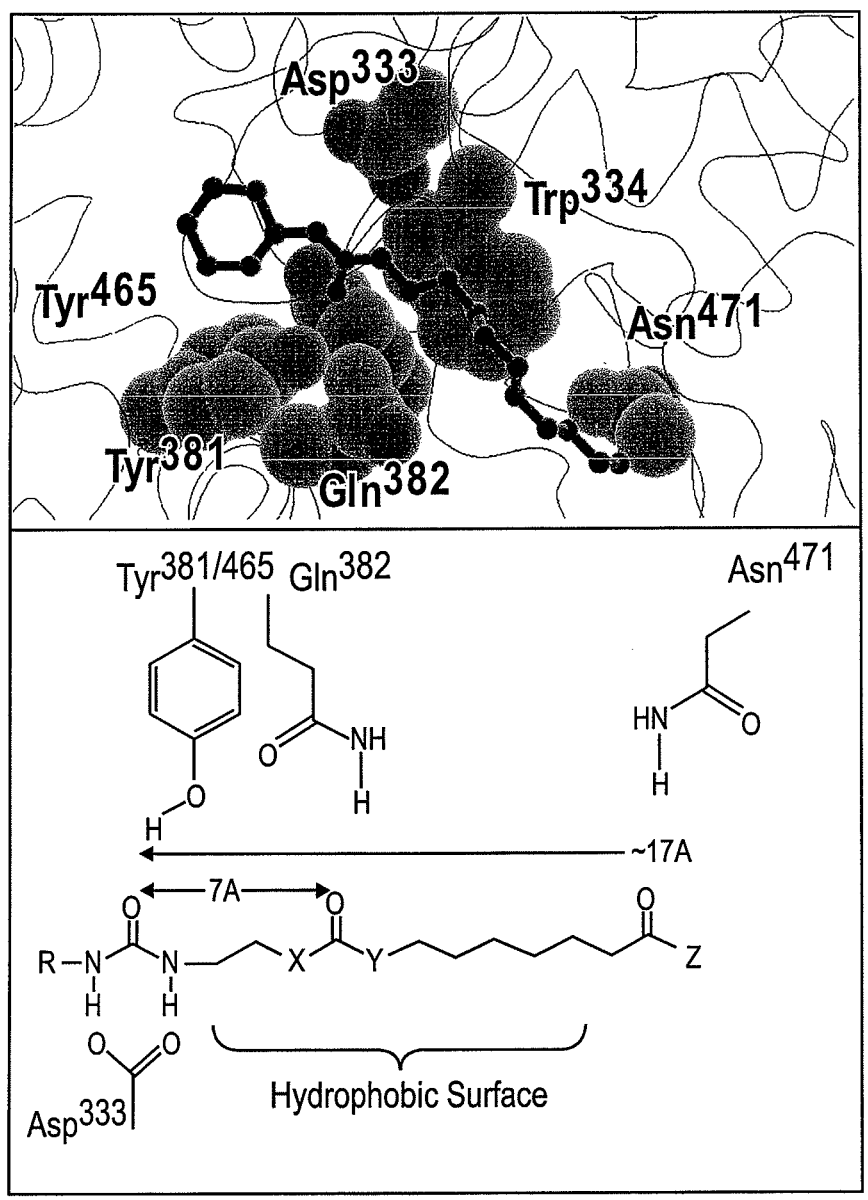
FIG. 11 provides a structural evaluation of conserved hydrogen bond donors in the sEH substrate binding pocket with linear distances to the primary pharmacophore noted and further illustrating the effect of functional group distances on interactions with the mammalian soluble epoxide hydrolases.

FIG. 11 illustrates the binding interaction for structural evaluation of conserved hydrogen bond donors in the sEH substrate binding pocket with linear distances to the primary pharmacophore noted. The table below provides specific distances to residues provided in FIGS. 4 and 5.

TABLE

Linear distances of hydrophylic residues to the carbonyl carbon of the bound urea

| Residue | Distance from Urea Carbon | Conserved |
|---|---|---|
| $Asp^{333}$ | 4.7 Å | + |
| $Tyr^{465}$ O | 4.5 Å | + |
| $Tyr^{381}$ O | 4.6 Å | + |
| $Trp^{334} N_{Ring}$ | 7.1 Å | + |
| $Gln^{382}$ N | 8.2 Å | + |
| $Tyr^{465} N_{Back Bone}$ | 10.5 Å | + |
| $Thr^{468}$ | 14.9 Å | Met in Human |
| $Asn^{471}$ N | 15.2 Å | + |
| $Asn^{471}$ O | 16.7 Å | + |

*Note FIG. 11 distances are measured linearly from the carbonyl oxygen to the alternate pharmacophores.
This Table measures 3 dimensional distances from carbonyl carbon of the primary pharmacophore to amino acids which could hydrogen bond with the inhibitor.

Methods of Inhibiting Soluble Epoxide Hydrolases:

In view of the above, the present invention provides, in one aspect, a method for inhibiting a soluble epoxide hydrolase, comprising contacting the soluble epoxide hydrolase with an inhibiting amount of a compound having a formula selected from the group consisting of:

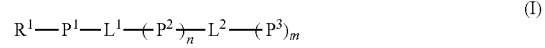

(I)

and their pharmaceutically acceptable salts, wherein the symbol $R^1$ is a member selected from the group consisting of substituted or unsubstituted alkyl, substituted or unsubstituted heteroalkyl, substituted or unsubstituted cycloalkylalkyl, substituted or unsubstituted cycloalkylheteroalkyl, substituted or unsubstituted arylalkyl, substituted or unsubstituted arylheteroalkyl, substituted or unsubstituted $C_5$-$C_{12}$ cycloalkyl, substituted or unsubstituted aryl, substituted or unsubstituted heteroaryl and combinations thereof, wherein said cycloalkyl portions are monocyclic or polycyclic; $P^1$ is a primary pharmacophore selected from the group consisting of —OC(O)O—, —OC(O)CH$_2$—, CH$_2$C(O)O—, —OC(O)—, —C(O)O—, —NHC(NH)NH—, —NHC(NH)CH$_2$—, —CH$_2$C(NH)NH—, —NHC(NH)—, —C(NH)NH—, —NHC(O)NH—, —OC(O)NH—, —NHC(O)O—, —NHC(S)NH—, —NHC(S)CH$_2$—, CH$_2$C(S)NH—, —SC(O)CH$_2$—, —CH$_2$C(O)S—, —SC(NH)CH$_2$—, —CH$_2$C(NH)S—, —N=C=N—, —CH$_2$C(O)NH—, —NHC(O)CH$_2$—, —C(O)NH—, —NHC(O)—,

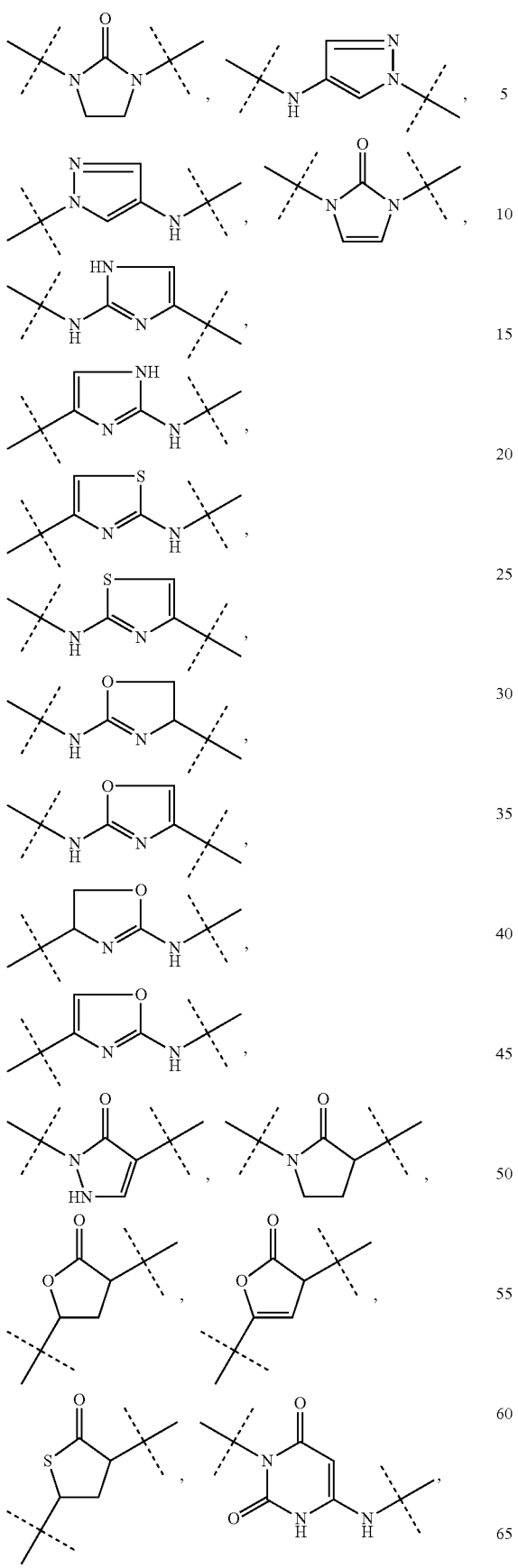
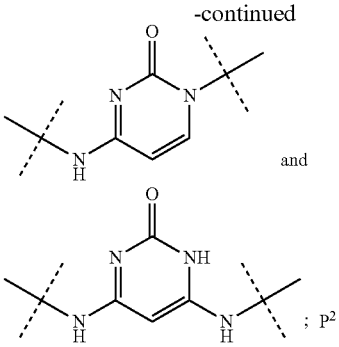
-continued
and
; P[2] is a secondary pharmacophore selected from the group consisting of —NH—, —OC(O)O—, —C(O)—, —CH(OH)—, —O(CH$_2$CH$_2$O)$_q$—, —C(O)O—, —OC(O)—, —NHC(NH)NH—, —NHC(NH)CH$_2$—, —CH$_2$C(NH)NH—, —NHC(O)NH—, —OC(O)NH—, —NHC(O)O—, —C(O)NH—, —NHC(O)—; —NHC(S)NH—, —NHC(S)CH$_2$—, CH$_2$C(S)NH—, —SC(O)CH$_2$—, —CH$_2$C(O)S—, —SC(NH)CH$_2$—, —CH$_2$C(NH)S—, —N=C=N—,
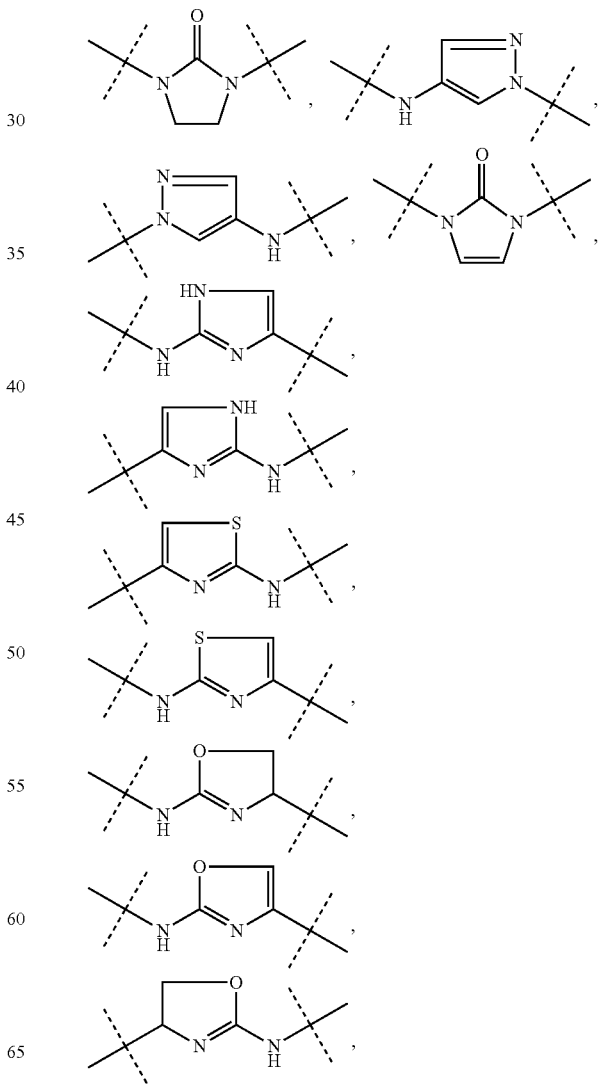

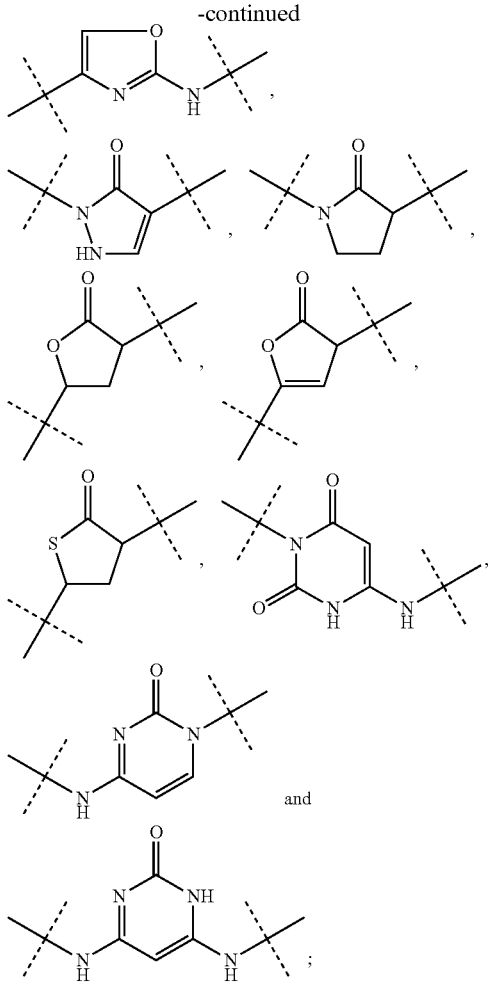

P³ is a tertiary pharmacophore selected from the group consisting of $C_2$-$C_6$ alkenyl, $C_2$-$C_6$ alkynyl, $C_1$-$C_6$ haloalkyl, aryl, heteroaryl, heterocyclyl, —O(CH₂CH₂O)$_q$—R², —OR², —C(O)NHR², —C(O)NHS(O)₂R², —NHS(O)₂R², —OC₂—C₄alkyl-C(O)OR², —C(O)R², —C(O)OR² and carboxylic acid analogs, wherein R² is a member selected from the group consisting of hydrogen, substituted or unsubstituted $C_1$-$C_4$ alkyl, substituted or unsubstituted $C_3$-$C_8$ cycloalkyl, substituted or unsubstituted heterocyclyl; substituted or unsubstituted aryl and substituted or unsubstituted aryl $C_1$-$C_4$ alkyl. In the above formula, the subscripts n and m are each independently 0 or 1, and at least one of n or m is 1, and the subscript q is 0 to 6.

Turning next to the linking groups, the symbol L¹ represents a first linker that is selected from the group consisting of substituted or unsubstituted $C_1$-$C_6$ alkylene, substituted or unsubstituted $C_3$-$C_6$ cycloalkylene, substituted or unsubstituted arylene and substituted or unsubstituted heteroarylene; the symbol L² represents a second linker selected from the group consisting of substituted or unsubstituted $C_1$-$C_{12}$ alkylene, substituted or unsubstituted $C_3$-$C_6$ cycloalkylene, substituted or unsubstituted arylene, substituted or unsubstituted heteroarylene; an amino acid, a dipeptide and a dipeptide analog; and combinations thereof; or is H when m is 0. Preferably, the compounds are other than 11-(3-cyclohexylureido)-undecanoic acid, 11-(3-cyclohexylureido)-undecanoic acid methyl ester, 11-(3-cyclohexylureido)-undecanoic acid amide, 12-(3-cyclohexylureido)-dodecanoic acid and 12-(3-adamantan-1-yl-ureido)-dodecanoic acid.

In a first group of embodiments, R¹ is selected from the group consisting of substituted or unsubstituted alkyl, substituted or unsubstituted heteroalkyl, substituted or unsubstituted cycloalkylalkyl, substituted or unsubstituted cycloalkylheteroalkyl, substituted or unsubstituted arylalkyl and substituted or unsubstituted arylheteroalkyl. In another group of embodiments, R¹ is selected from $C_5$-$C_{12}$ cycloalkyl, phenyl and naphthyl. More preferably, R¹ is selected from $C_6$-$C_{10}$ cycloalkyl and phenyl. In some embodiments, are those embodiments in which R¹ is cyclohexyl, cycloheptyl, cyclooctyl, norbornyl, adamantyl, noradamantyl, and phenyl, wherein the phenyl group is either unsubstituted or substituted with from one to three substituents selected from halogen, lower alkyl, lower halo alkyl, lower alkoxy, $C_3$-$C_5$ cycloalkyl and cyano.

Returning to formula (I), P¹ is preferably selected from —NHC(O)NH—, —OC(O)NH— and —NHC(O)O—. Most preferably, P¹ is —NHC(O)NH—. In other embodiments, P¹ is selected from the group consisting of —OC(O)O—, —OC(O)CH₂—, CH₂C(O)O—, —OC(O)—, —C(O)O—, —NHC(NH)NH—, —NHC(NH)CH₂—, —CH₂C(NH)NH—, —NHC(NH)—, —C(NH)NH—, —NHC(S)NH—, —NHC(S)CH₂—, CH₂C(S)NH—, —SC(O)CH₂—, —CH₂C(O)S—, —SC(NH)CH₂—, —CH₂C(NH)S—, —N═C═N—, —NHC(O)CH₂—,

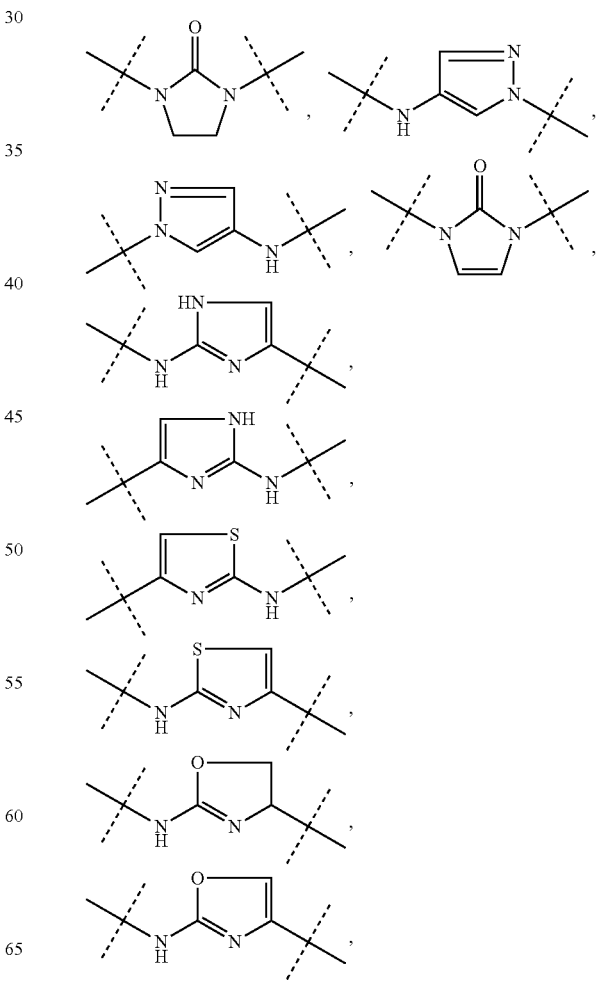

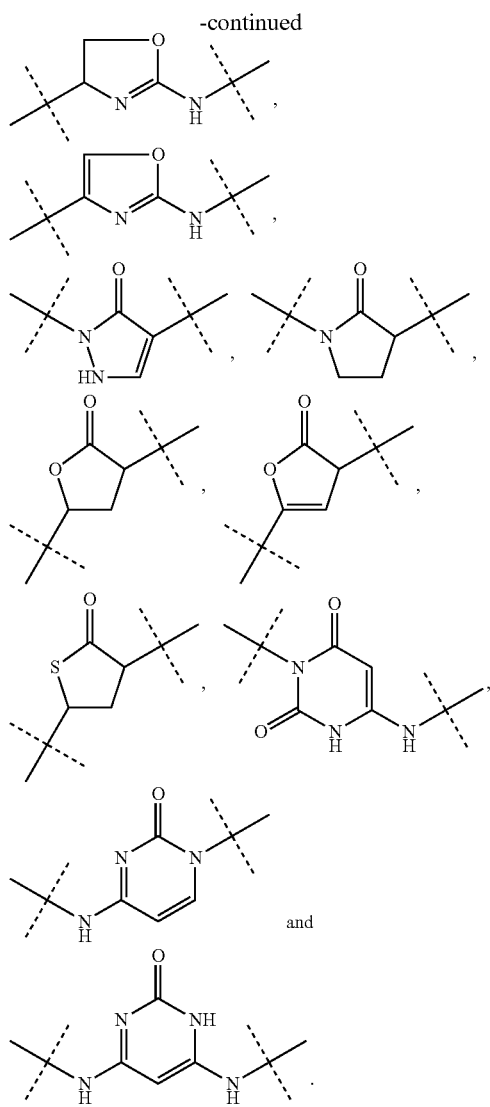

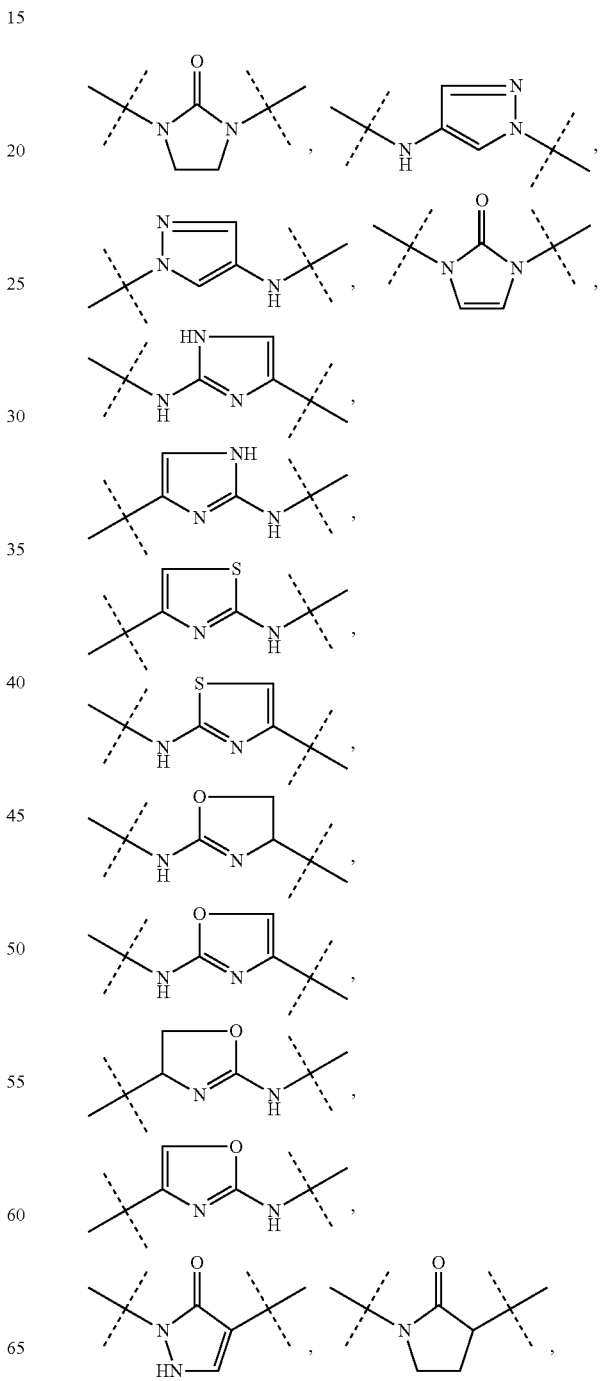

selected to provide spacing between the first pharmacophore carbonyl moiety (in P$^1$) and the second pharmacophore carbonyl moiety (in P$^2$) of about 7.5±2 angstroms and more preferably, about 7.5±1 angstroms.

The secondary pharmacophore, P$^2$, when present (n is 1) is selected from the group consisting of —NH—, —OC(O)O—, —C(O)—, —CH(OH)—, —O(CH$_2$CH$_2$O)$_q$—, —C(O)O—, —OC(O)—, —NHC(NH)NH—, —NHC(NH)CH$_2$—, —CH$_2$C(NH)NH—, —NHC(O)NH—, —OC(O)NH—, —NHC(O)O—, —C(O)NH—, —NHC(O)—; —NHC(S)NH—, —NHC(S)CH$_2$—, CH$_2$C(S)NH—, —SC(O)CH$_2$—, —CH$_2$C(O)S—, —SC(NH)CH$_2$—, —CH$_2$C(NH)S—, —N=C=N—, Turning next to the first linking group, L$^1$ is preferably selected from substituted or unsubstituted C$_1$-C$_6$ alkylene, wherein the substituents are selected to impart desired properties to the overall composition. For example, in some embodiments in which R$^1$ is a particularly hydrophobic residue, L$^1$ may preferably have substituents that are hydrophilic to offset to some degree the lack of aqueous solubility normally associated with very hydrophobic compounds. As a result, in some embodiments, L$^1$ will have one or two hydroxy moieties as substituents, preferably only one hydroxy moiety substituents. In other embodiments, L$^1$ will be an alkylene, arylene or cycloalkylene linker having the length indicated above, wherein one or more of the hydrogen atoms are replaced with fluorine atoms to impart other attractive properties, such as facilitating the compound's use in stents so that it is slowly released from the stent to then inhibit the soluble epoxide hydrolase. Other examples of substituents, include but are not limited to, halo, cyano, nitro, alkyl, alkylamino, carboxyl, hydroxyl, alkoxy, aryloxy, and the like. Further are embodiments in which L$^1$ is C$_2$-C$_5$ alkylene, more preferably C$_2$-C$_4$ alkylene, still more preferably C$_2$-C$_3$ alkylene, and most preferably an ethylene linkage. Where L$^1$ is C$_3$-C$_6$ cycloalkylene, it is more preferably cyclohexyl that can be linked in a 1, 3 or 1,4 manner. In certain embodiments, L$^1$ is

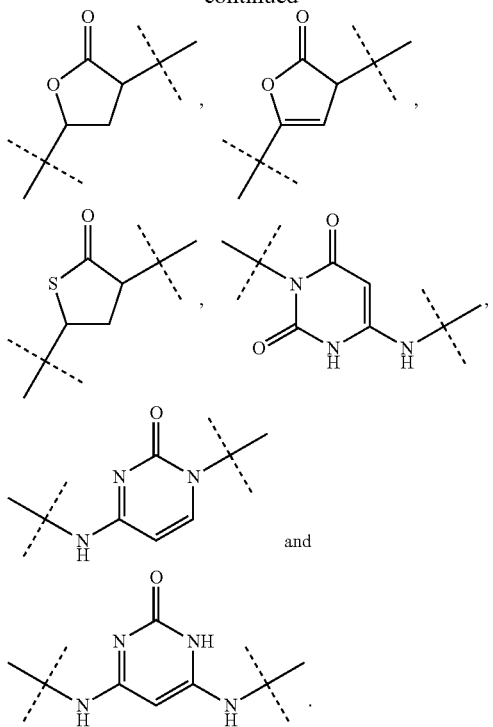

More preferably, $P^2$ is selected from —C(O)—, —O(CH$_2$CH$_2$O)$_q$—, —C(O)O—, —OC(O)—, —OC(O)O—, —OC(O)NH— and —C(O)NH—. Most preferably, $P^2$ is selected from —C(O)—, —O(CH$_2$CH$_2$O)$_q$—, and —C(O)O—. In another embodiment, $P^2$ is preferably selected from the group consisting of —NH—, —OC(O)O—, —NHC(NH)NH—, —NHC(NH)CH$_2$—, —CH$_2$C(NH)NH—, —NHC(S)NH—, —NHC(S)CH$_2$—, CH$_2$C(S)NH—, —SC(O)CH$_2$—, —CH$_2$C(O)S—, —SC(NH)CH$_2$—, —CH$_2$C(NH)S—, —N=C=N—,

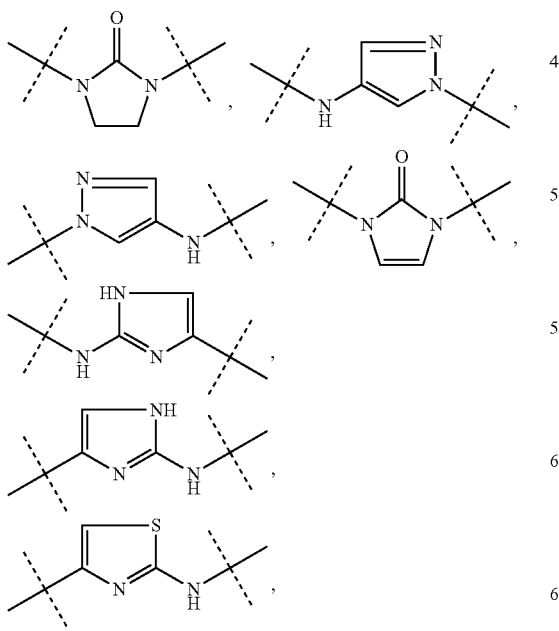

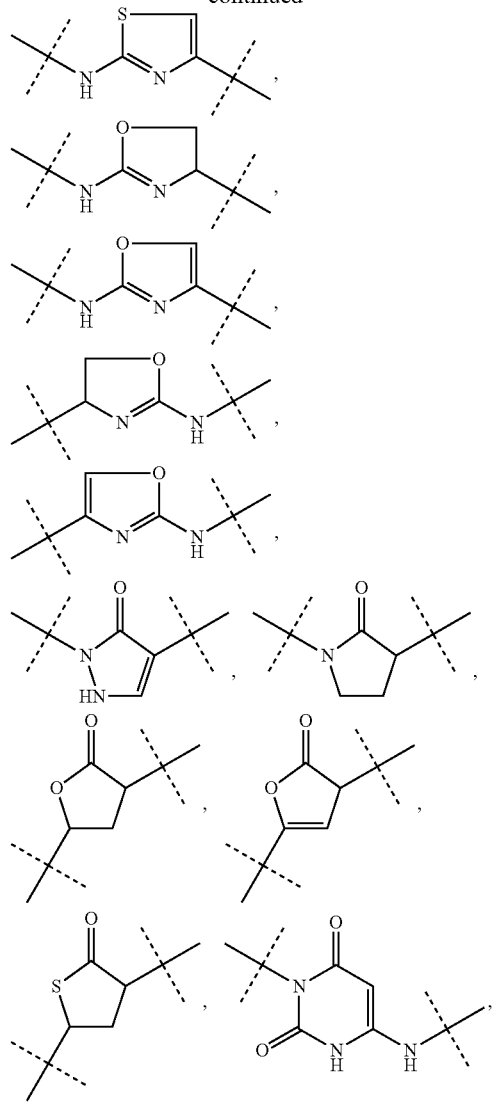

The second linking group, $L^2$ is selected from substituted or unsubstituted $C_1$-$C_{12}$ alkylene, substituted or unsubstituted arylene, and combinations thereof. For those embodiments in which a secondary pharmacophore ($P^2$) is not present, the linking group $L^2$ will be combined with $L^1$ to provide spacing between the primary pharmacophore and the tertiary pharmacophore preferably of about $\geq 2$, and $\leq 12$ carbon atoms. Accordingly, when $L^1$ is an alkylene or part of a cycloalkylene linkage of from 1 to 4 carbon atoms, and $P^2$ is not present, $L^2$ will preferably be an alkylene linkage of from 1 to 8 carbon atoms, more preferably, 4 to 8 carbon atoms, and most preferably 5, 6, 7 or 8 carbon atoms. For those embodiments in which a tertiary pharmacophore (P³) is not present, the linking group L² may be H or will terminate with hydrogen or a substituent selected as described for L¹ above. In such embodiments, the arylene group need not be divalent. In some embodiments, L² will comprise an arylene group, preferably a phenylene group that can be linked in a 1,2 or 1,3 or 1,4 manner, preferably in a 1, 3 or 1,4 manner. As with L¹, the alkylene portions of L² can be substituted or unsubstituted. The substituents are selected as described for L¹ above.

The tertiary pharmacophore, P³, is a tertiary pharmacophore selected from the group consisting of $C_2$-$C_6$ alkenyl, $C_2$-$C_6$ alkynyl, $C_1$-$C_6$ haloalkyl, aryl, heteroaryl, heterocyclyl, —O(CH$_2$CH$_2$O)$_q$—R², —OR², —C(O)NHR², —C(O)NHS(O)$_2$R², —NHS(O)$_2$R², —OC$_2$—C$_4$alkyl-C(O)OR², —C(O)R², —C(O)OR² and carboxylic acid analogs, wherein R² is a member selected from the group consisting of hydrogen, substituted or unsubstituted $C_1$-$C_4$ alkyl, substituted or unsubstituted $C_3$-$C_8$ cycloalkyl, substituted or unsubstituted heterocyclyl; substituted or unsubstituted aryl and substituted or unsubstituted aryl $C_1$-$C_4$ alkyl. In certain embodiments, R² is H, methyl, ethyl, propyl, allyl, 3-propynyl, butyl, 2-propyl, 1,1-dimethylethyl, 2-butyl, 2-methyl-1-propyl, adamantylmethyl, benzyl, 2-chlorobenzyl and naphthylmethyl. In one group of embodiments, P³ is —C(O)NHR², —C(O)NHS(O)$_2$R², —NHS(O)$_2$R², —C(O)OR² and carboxylic acid analogs, wherein R² is selected from hydrogen, unsubstituted $C_1$-$C_4$ alkyl, and unsubstituted $C_3$-$C_8$ cycloalkyl. Still more preferably, R² is H, Me or Et. In some embodiments, P³ is —C(O)OR² and carboxylic acid analogs, wherein R² is selected from hydrogen, Me or Et. In other embodiments, P³ is preferably selected from the group consisting of is selected from the group consisting of $C_2$-$C_6$ alkenyl, heterocyclyl, OR², —OC$_2$—C$_4$alkyl-C(O)OR² and —C(O)R², wherein R² is a member selected from the group consisting of hydrogen, substituted or unsubstituted $C_1$-$C_4$ alkyl, substituted or unsubstituted $C_3$-$C_8$ cycloalkyl, substituted or unsubstituted heterocyclyl; substituted or unsubstituted aryl and substituted or unsubstituted aryl $C_1$-$C_4$ alkyl.

With the embodiments provided above, certain combinations of embodiments represent particular embodiments. While all combinations of the groups represent additional embodiments of the invention, particular embodiments include those wherein P¹ is selected from —NHC(O)NH—, —OC(O)NH— and —NHC(O)O—; P² is selected from —C(O)O—, —OC(O)—, —O(CH$_2$CH$_2$O)$_q$—, —C(O)NH— and —NHC(O)—; m is 0 and L¹ is selected from unsubstituted $C_1$-$C_6$ alkylene. In another group of particular embodiments, P¹ is selected from —NHC(O)NH—, —OC(O)NH— and —NHC(O)O—; P² is selected from —C(O)O—, —OC(O)—, —O(CH$_2$CH$_2$O)$_q$—, —C(O)NH— and —NHC(O)—; n and m are each 1; L¹ is selected from unsubstituted $C_1$-$C_6$ alkylene; L² is selected from substituted or unsubstituted $C_1$-$C_6$ alkylene; and P³ is selected from —C(O)NHR², —C(O)NHS(O)$_2$R², —NHS(O)$_2$R², and —C(O)OR², wherein R² is a member selected from the group consisting of hydrogen, substituted or unsubstituted $C_1$-$C_4$ alkyl, substituted or unsubstituted $C_3$-$C_8$ cycloalkyl, substituted or unsubstituted heterocyclyl; substituted or unsubstituted aryl and substituted or unsubstituted aryl $C_1$-$C_4$ alkyl. Still other particular embodiments are those in which the compound has formula (I), wherein P¹ is selected from —NHC(O)NH—, —OC(O)NH— and —NHC(O)O—; n is 0; m is 1; L¹ is selected from unsubstituted $C_1$-$C_6$ alkylene; L² is selected from substituted or unsubstituted $C_1$-$C_6$ alkylene; and P³ is selected from —C(O)NHR², —C(O)NHS(O)$_2$R², —NHS(O)$_2$R², and —C(O)OR², wherein R² is a member selected from the group consisting of hydrogen, substituted or unsubstituted $C_1$-$C_4$ alkyl, substituted or unsubstituted $C_3$-$C_8$ cycloalkyl, substituted or unsubstituted heterocyclyl; substituted or unsubstituted aryl and substituted or unsubstituted aryl $C_1$-$C_4$ alkyl.

In one embodiment, the compound has the formula:

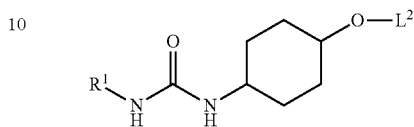

wherein R¹ is a member selected from the group consisting of alkyl, aryl, alkylaryl, cycloalkyl, cycloalkylaryl, optionally substituted with from 1 to 2 substituents each independently selected from the group consisting of alkyl, halo, haloalkyl, alkoxy, nitro, haloalkoxy, thioalkyl and phenyl; and L² is selected from the group consisting of phenylene or methylenephenylene, heteroarylene, optionally substituted with from 1 to 2 substituents each independently selected from the group consisting of halo and haloalkyl. Within this embodiment, the compound has the formula:

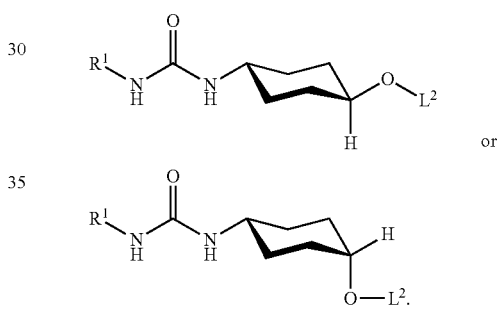

In other embodiments, the compound has the formula:

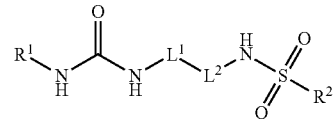

wherein R² is selected from the group consisting of substituted or unsubstituted $C_3$-$C_8$ cycloalkyl, substituted or unsubstituted heterocyclyl; substituted or unsubstituted aryl and substituted or unsubstituted aryl $C_1$-$C_4$ alkyl. Within this embodiment, the compound preferably has the formula:

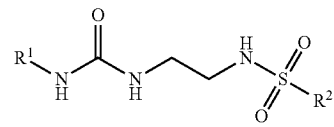

wherein R² is substituted or unsubstituted aryl; and more preferably has the formula:

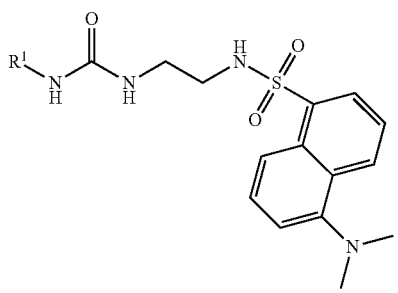

wherein R¹ is a member selected from the group consisting of alkyl, aryl, alkylaryl, cycloalkyl, cycloalkylaryl, optionally substituted with from 1 to 2 substituents each independently selected from the group consisting of alkyl, halo, haloalkyl, alkoxy, nitro, haloalkoxy, thioalkyl and phenyl.

In one embodiment, compounds for use in this aspect of the invention are those compounds provided in the Tables below, particularly Tables 5, 8-10 and 18.

In another group of embodiments the compounds of formula (I), as noted above, contain an amino acid or dipeptide component which can be a dipeptide analog. The amino acid residues, by themselves or as part of a dipeptide, are denoted by single-letter or three-letter designations following conventional practices. The designations for gene-encoded amino acids are as follows (amino acid, one letter symbol, three letter symbol): Alanine, A, Ala; Arginine, R, Arg; Asparagine, N, Asn; Aspartic acid, D, Asp; Cysteine, C, Cys; Glutamine, Q, Gln; Glutamic acid, E, Glu; Glycine, G, Gly; Histidine, H, His; Isoleucine, I, Ile; Leucine, L, Leu; Lysine, K, Lys; Methionine, M, Met; Phenylalanine, F, Phe; Proline, P, Pro; Serine, S, Ser; Threonine, T, Thr; Tryptophan, W, Trp; Tyrosine, Y, Tyr; and Valine, V, Val. Commonly encountered amino acids which are not gene-encoded may also be used in the present invention. These amino acids and their abbreviations include ornithine (Orn); t-butylglycine (t-BuG); phenylglycine (PhG); cyclohexylalanine (Cha); norleucine (Nle); 2-naphthylalanine (2-Nal); 1-naphthylalanine (1-Nal); 2-thienylaniline (2-Thi); N-methylisoleucine (N-MeIle), homoarginine (Har), Nα-methylarginine (N-MeArg) and sarcosine (Sar). All of the amino acids used in the present invention may be either the D- or L-isomer.

In one embodiment, compounds of the invention are those in which $L^2$ is selected from the group consisting of substituted or unsubstituted $C_3$-$C_6$ cycloalkylene, substituted or unsubstituted arylene, substituted or unsubstituted heteroarylene. In other embodiments, $L^2$ is preferably an amino acid or a dipeptide. Preferably, the dipeptide has a Tyr, His, Lys, Phe or Trp residue directly attached to $P^2$.

Other compounds for use in the present invention are those in which $R^1$, $P^1$ and $L^1$ are selected from the groupings as described above for formula (I). Particular compounds of formula (I) are those in which $R^1$ is selected from $C_5$-$C_{12}$ cycloalkyl and phenyl. More particularly, $R^1$ is selected from $C_6$-$C_{10}$ cycloalkyl and phenyl. Other embodiments are those embodiments in which $R^1$ is cyclohexyl, cycloheptyl, cyclooctyl, norbornyl, adamantly or noradamantyl. $P^1$ is preferably a urea (—NHC(O)NH—) or carbamate (—OC(O)NH—), more preferably a urea. $L^1$ is preferably a substituted or unsubstituted $C_2$-$C_5$ alkylene, more preferably $C_2$-$C_4$ alkylene, still more preferably an ethylene or propylene linkage.

For those embodiments in which $L^2$ is a single amino acid, $L^2$ is preferably selected from Ala, Arg, Asp, Cys, Glu, Gly, His, Ile, Leu, Lys, Met, Phe, Pro, Ser, Thr, Trp, Tyr and Val. More preferably, $L^2$ is selected from His, Ile, Lys, Phe, Trp and Tyr in which the amino acid is linked to $P^2$ in a manner to afford an amide linkage and terminal carboxylic acid group. Of course, one of skill in the art will appreciate that these amino acids are meant to refer to their corresponding methyl or ethyl esters, as well as their carboxamide derivatives (e.g., terminal —C(O)NH₂). Most preferably, the compounds are those provided in Table 11.

For those embodiments in which $L^1$ is a dipeptide, $P^2$ is preferably attached to a Tyr, His, Lys, Phe or Trp residue, with the remaining amino acid being selected from the gene-encoded amino acids, their D-isomers or analogs thereof (e.g., hydroxy acids such as lactic acid and the like). Still more preferably, $L^2$ is selected from TyrAla, TyrArg, TyrAsp, TyrGly, TyrIle, TyrLeu, TyrLys, TyrMet, TyrPhe, TyrPro, TyrSer, TyrThr, TyrTrp, TyrTyr and TyrVal. More preferably, $L^2$ is selected from TyrArg, TyrAsp, TyrMet, TyrPhe, TyrSer, TyrTrp, TyrTyr and TyrVal. in which the Tyr amino acid is linked to $P^2$ in a manner to afford an amide linkage. As above, these dipeptides are also meant to refer to their corresponding methyl or ethyl esters, as well as their carboxamide derivatives (e.g., terminal —C(O)NH₂). Most preferably, the compounds are those provided in Table 12.

Assays to Monitor Soluble Epoxide Hydrolase Activity:

Additionally, the present invention provides a variety of assays and associated methods for monitoring soluble epoxide hydrolase activity, particularly the activity that has been modulated by the administration of one or more of the compounds provided above.

In one group of embodiments, the invention provides methods for reducing the formation of a biologically active diol produced by the action of a soluble epoxide hydrolase, the method comprising contacting the soluble epoxide hydrolase with an amount of a compound of formula (I) above, sufficient to inhibit the activity of the soluble epoxide hydrolase and reduce the formation of the biologically active diol.

In another group of embodiments, the invention provides methods for stabilizing biologically active epoxides in the presence of a soluble epoxide hydrolase, the method comprising contacting the soluble epoxide hydrolase with an amount of a compound of formula (I), sufficient to inhibit the activity of the soluble epoxide hydrolase and stabilize the biologically active epoxide.

In each of these groups of embodiments, the methods can be carried out as part of an in vitro assay or the methods can be carried out in vivo by monitoring blood titers of the respective biologically active epoxide or diol.

Epoxides and diols of some fatty acids are biologically important chemical mediators and are involved in several biological processes. The strongest biological data support the action of oxylipins as chemical mediators between the vascular endothelium and vascular smooth muscle. Accordingly, the epoxy lipids are anti-inflammatory and anti-hypertensive. Additionally, the lipids are thought to be metabolized by beta-oxidation, as well as by epoxide hydration. The soluble epoxide hydrolase is considered to be the major enzyme involved in the hydrolytic metabolism of these oxylipins. The compounds of formula (I) can inhibit the epoxide hydrolase and stabilize the epoxy lipids both in vitro and in vivo. This activity results in a reduction of hypertension in four separate rodent models. Moreover, the inhibitors show a reduction in renal inflammation associated with and independent of the hypertensive models.

More particularly, the present invention provides methods for monitoring a variety of lipids in both the arachidonate and linoleate cascade simultaneously in order to address the biology of the system. A GLC-MS system or a LC-MS method can be used to monitor over 740 analytes in a highly quantitative fashion in a single injection. The analytes include the regioisomers of the arachidonate epoxides (EETs), the diols (DHETs), as well as other P450 products including HETEs. Characteristic products of the cyclooxygenase, lipoxygenase, and peroxidase pathways in both the arachidonate and linoleate series can also be monitored. Such methods are particularly useful as being predictive of certain disease states. The oxylipins can be monitored in mammals following the administration of inhibitors of epoxide hydrolase. Generally, EH inhibitors increase epoxy lipid concentrations at the expense of diol concentrations in body fluids and tissues.

Other compounds for use in this aspect of the invention are those inhibitors of formula (I) in which the primary pharmacophore is separated from a tertiary pharmacophore by a distance that approximates the distance between the terminal carboxylic acid and an epoxide functional group in the natural substrate.

Methods of Treating Diseases Modulated by Soluble Epoxide Hydrolases:

In another aspect, the present invention provides methods of treating diseases, especially those modulated by soluble epoxide hydrolases (sEH). The methods generally involve administering to a subject in need of such treatment an effective amount of a compound having a formula (I) above. The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the invention and the pharmaceutically acceptable salts thereof are administered via oral, parenteral, subcutaneous, intramuscular, intravenous or topical routes. Generally, the compounds are administered in dosages ranging from about 2 mg up to about 2,000 mg per day, although variations will necessarily occur depending, as noted above, on the disease target, the patient, and the route of administration. Dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated.

It has previously been shown that inhibitors of soluble epoxide hydrolase ("sEH") can reduce hypertension. See, e.g., U.S. Pat. No. 6,351,506. Such inhibitors can be useful in controlling the blood pressure of persons with undesirably high blood pressure, including those who suffer from diabetes.

In some embodiments, compounds of formula (I) are administered to a subject in need of treatment for hypertension, specifically renal, hepatic, or pulmonary hypertension; inflammation, specifically renal inflammation, vascular inflammation, and lung inflammation; adult respiratory distress syndrome; diabetic complications; end stage renal disease; Raynaud syndrome and arthritis.

Methods for Inhibiting Progression of Kidney Deterioration (Nephropathy) and Reducing Blood Pressure:

In another aspect of the invention, the compounds of the invention can reduce damage to the kidney, and especially damage to kidneys from diabetes, as measured by albuminuria. The compounds of the invention can reduce kidney deterioration (nephropathy) from diabetes even in individuals who do not have high blood pressure. The conditions of therapeutic administration are as described above.

cis-Epoxyeicosantrienoic acids ("EETs") can be used in conjunction with the compounds of the invention to further reduce kidney damage. EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into DHETs is reduced. Without wishing to be bound by theory, it is believed that raising the level of EETs interferes with damage to kidney cells by the microvasculature changes and other pathologic effects of diabetic hyperglycemia. Therefore, raising the EET level in the kidney is believed to protect the kidney from progression from microalbuminuria to end stage renal disease.

EETs are well known in the art. EETs useful in the methods of the present invention include 14,15-EET, 8,9-EET and 11,12-EET, and 5,6 EETs, in that order of preference. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

EETs produced by the endothelium have anti-hypertensive properties and the EETs 11,12-EET and 14,15-EET may be endothelium-derived hyperpolarizing factors (EDHFs). Additionally, EETs such as 11,12-EET have profibrinolytic effects, anti-inflammatory actions and inhibit smooth muscle cell proliferation and migration. In the context of the present invention, these favorable properties are believed to protect the vasculature and organs during renal and cardiovascular disease states.

It is now believed that sEH activity can be inhibited sufficiently to increase the levels of EETs and thus augment the effects of administering sEH inhibitors by themselves. This permits EETs to be used in conjunction with one or more sEH inhibitors to reduce nephropathy in the methods of the invention. It further permits EETs to be used in conjunction with one or more sEH inhibitors to reduce hypertension, or inflammation, or both. Thus, medicaments of EETs can be made which can be administered in conjunction with one or more sEH inhibitors, or a medicament containing one or more sEH inhibitors can optionally contain one or more EETs.

The EETs can be administered concurrently with the sEH inhibitor, or following administration of the sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs are administered after the inhibitor is administered, therefore, it is desirable that the EETs be administered during the period during which the inhibitor will be present in amounts to be effective to delay hydrolysis of the EETs. Typically, the EET or EETs will be administered within 48 hours of administering an sEH inhibitor. Preferably, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor.

In some embodiments, the EETs, the compound of the invention, or both, are provided in a material that permits them to be released over time to provide a longer duration of action. Slow release coatings are well known in the pharmaceutical art; the choice of the particular slow release coating is not critical to the practice of the present invention.

EETs are subject to degradation under acidic conditions. Thus, if the EETs are to be administered orally, it is desirable that they are protected from degradation in the stomach. Conveniently, EETs for oral administration may be coated to permit them to passage the acidic environment of the stomach into the basic environment of the intestines. Such coatings are well known in the art. For example, aspirin coated with so-called "enteric coatings" is widely available commercially. Such enteric coatings may be used to protect EETs during passage through the stomach. An exemplary coating is set forth in the Examples.

While the anti-hypertensive effects of EETs have been recognized, EETs have not been administered to treat hypertension because it was thought endogenous sEH would hydrolyse the EETs too quickly for them to have any useful effect. Surprisingly, it was found during the course of the studies underlying the present invention that exogenously administered inhibitors of sEH succeeded in inhibiting sEH sufficiently that levels of EETs could be further raised by the administration of exogenous EETs. These findings underlie the co-administration of sEH inhibitors and of EETs described above with respect to inhibiting the development and progression of nephropathy. This is an important improvement in augmenting treatment. While levels of endogenous EETs are expected to rise with the inhibition of sEH activity caused by the action of the sEH inhibitor, and therefore to result in at least some improvement in symptoms or pathology, it may not be sufficient in all cases to inhibit progression of kidney damage fully or to the extent intended. This is particularly true where the diseases or other factors have reduced the endogenous concentrations of EETs below those normally present in healthy individuals. Administration of exogenous EETs in conjunction with a sEH inhibitor is therefore expected to be beneficial and to augment the effects of the sEH inhibitor in reducing the progression of diabetic nephropathy.

The present invention can be used with regard to any and all forms of diabetes to the extent that they are associated with progressive damage to the kidney or kidney function. The chronic hyperglycemia of diabetes is associated with long-term damage, dysfunction, and failure of various organs, especially the eyes, kidneys, nerves, heart, and blood vessels. The long-term complications of diabetes include retinopathy with potential loss of vision; nephropathy leading to renal failure; peripheral neuropathy with risk of foot ulcers, amputation, and Charcot joints.

In addition, persons with metabolic syndrome are at high risk of progression to type 2 diabetes, and therefore at higher risk than average for diabetic nephropathy. It is therefore desirable to monitor such individuals for microalbuminuria, and to administer a sEH inhibitor and, optionally, one or more EETs, as an intervention to reduce the development of nephropathy. The practitioner may wait until microalbuminuria is seen before beginning the intervention. As noted above, a person can be diagnosed with metabolic syndrome without having a blood pressure of 130/85 or higher. Both persons with blood pressure of 130/85 or higher and persons with blood pressure below 130/85 can benefit from the administration of sEH inhibitors and, optionally, of one or more EETs, to slow the progression of damage to their kidneys. In some embodiments, the person has metabolic syndrome and blood pressure below 130/85.

Dyslipidemia or disorders of lipid metabolism is another risk factor for heart disease. Such disorders include an increased level of LDL cholesterol, a reduced level of HDL cholesterol, and an increased level of triglycerides. An increased level of serum cholesterol, and especially of LDL cholesterol, is associated with an increased risk of heart disease. The kidneys are also damaged by such high levels. It is believed that high levels of triglycerides are associated with kidney damage. In particular, levels of cholesterol over 200 mg/dL, and especially levels over 225 mg/dL, would suggest that sEH inhibitors and, optionally, EETs, should be administered. Similarly, triglyceride levels of more than 215 mg/dL, and especially of 250 mg/dL or higher, would indicate that administration of sEH inhibitors and, optionally, of EETs, would be desirable. The administration of compounds of the present invention with or without the EETs, can reduce the need to administer statin drugs (HMG-CoA reductase inhibitors) to the patients, or reduce the amount of the statins needed. In some embodiments, candidates for the methods, uses and compositions of the invention have triglyceride levels over 215 mg/dL and blood pressure below 130/85. In some embodiments, the candidates have triglyceride levels over 250 mg/dL and blood pressure below 130/85. In some embodiments, candidates for the methods, uses and compositions of the invention have cholesterol levels over 200 mg/dL and blood pressure below 130/85. In some embodiments, the candidates have cholesterol levels over 225 mg/dL and blood pressure below 130/85.

Methods of Inhibiting the Proliferation of Vascular Smooth Muscle Cells:

In other embodiments, compounds of formula (I) inhibit proliferation of vascular smooth muscle (VSM) cells without significant cell toxicity, (e.g. specific to VSM cells). Because VSM cell proliferation is an integral process in the pathophysiology of atherosclerosis, these compounds are suitable for slowing or inhibition atherosclerosis. These compounds are useful to subjects at risk for atherosclerosis, such as individuals who have had a heart attack or a test result showing decreased blood circulation to the heart. The conditions of therapeutic administration are as described above.

The methods of the invention are particularly useful for patients who have had percutaneous intervention, such as angioplasty to reopen a narrowed artery, to reduce or to slow the narrowing of the reopened passage by restenosis. In some embodiments, the artery is a coronary artery. The compounds of the invention can be placed on stents in polymeric coatings to provide a controlled localized release to reduce restenosis. Polymer compositions for implantable medical devices, such as stents, and methods for embedding agents in the polymer for controlled release, are known in the art and taught, for example, in U.S. Pat. Nos. 6,335,029; 6,322,847; 6,299,604; 6,290,722; 6,287,285; and 5,637,113. In some embodiments, the coating releases the inhibitor over a period of time, preferably over a period of days, weeks, or months. The particular polymer or other coating chosen is not a critical part of the present invention.

The methods of the invention are useful for slowing or inhibiting the stenosis or restenosis of natural and synthetic vascular grafts. As noted above in connection with stents, desirably, the synthetic vascular graft comprises a material which releases a compound of the invention over time to slow or inhibit VSM proliferation and the consequent stenosis of the graft. Hemodialysis grafts are a particular embodiment.

In addition to these uses, the methods of the invention can be used to slow or to inhibit stenosis or restenosis of blood vessels of persons who have had a heart attack, or whose test results indicate that they are at risk of a heart attack.

In one group of embodiments, compounds of the invention are administered to reduce proliferation of VSM cells in persons who do not have hypertension. In another group of embodiments, compounds of the invention are used to reduce proliferation of VSM cells in persons who are being treated for hypertension, but with an agent that is not an sEH inhibitor.

The compounds of the invention can be used to interfere with the proliferation of cells which exhibit inappropriate cell cycle regulation. In one important set of embodiments, the cells are cells of a cancer. The proliferation of such cells can be slowed or inhibited by contacting the cells with a compound of the invention. The determination of whether a particular compound of the invention can slow or inhibit the proliferation of cells of any particular type of cancer can be determined using assays routine in the art.

In addition to the use of the compounds of the invention, the levels of EETs can be raised by adding EETs. VSM cells contacted with both an EET and a compound of the invention exhibited slower proliferation than cells exposed to either the EET alone or to the a compound of the invention alone. Accordingly, if desired, the slowing or inhibition of VSM cells of a compound of the invention can be enhanced by adding an EET along with a compound of the invention. In the case of stents or vascular grafts, for example, this can conveniently be accomplished by embedding the EET in a coating along with a compound of the invention so that both are released once the stent or graft is in position.

Methods of Inhibiting the Progression of Obstructive Pulmonary Disease, Interstitial Lung Disease, or Asthma:

Chronic obstructive pulmonary disease, or COPD, encompasses two conditions, emphysema and chronic bronchitis, which relate to damage caused to the lung by air pollution, chronic exposure to chemicals, and tobacco smoke. Emphysema as a disease relates to damage to the alveoli of the lung, which results in loss of the separation between alveoli and a consequent reduction in the overall surface area available for gas exchange. Chronic bronchitis relates to irritation of the bronchioles, resulting in excess production of mucin, and the consequent blocking by mucin of the airways leading to the alveoli. While persons with emphysema do not necessarily have chronic bronchitis or vice versa, it is common for persons with one of the conditions to also have the other, as well as other lung disorders.

Some of the damage to the lungs due to COPD, emphysema, chronic bronchitis, and other obstructive lung disorders can be inhibited or reversed by administering inhibitors of the enzyme known as soluble epoxide hydrolase, or "sEH". The effects of sEH inhibitors can be increased by also administering EETs. The effect is at least additive over administering the two agents separately, and may indeed be synergistic.

The studies reported herein show that EETs can be used in conjunction with sEH inhibitors to reduce damage to the lungs by tobacco smoke or, by extension, by occupational or environmental irritants. These findings indicate that the co-administration of sEH inhibitors and of EETs can be used to inhibit or slow the development or progression of COPD, emphysema, chronic bronchitis, or other chronic obstructive lung diseases which cause irritation to the lungs.

Animal models of COPD and humans with COPD have elevated levels of immunomodulatory lymphocytes and neutrophils. Neutrophils release agents that cause tissue damage and, if not regulated, will over time have a destructive effect. Without wishing to be bound by theory, it is believed that reducing levels of neutrophils reduces tissue damage contributing to obstructive lung diseases such as COPD, emphysema, and chronic bronchitis. Administration of sEH inhibitors to rats in an animal model of COPD resulted in a reduction in the number of neutrophils found in the lungs. Administration of EETs in addition to the sEH inhibitors also reduced neutrophil levels. The reduction in neutrophil levels in the presence of sEH inhibitor and EETs was greater than in the presence of the sEH inhibitor alone.

While levels of endogenous EETs are expected to rise with the inhibition of sEH activity caused by the action of the sEH inhibitor, and therefore to result in at least some improvement in symptoms or pathology, it may not be sufficient in all cases to inhibit progression of COPD or other pulmonary diseases. This is particularly true where the diseases or other factors have reduced the endogenous concentrations of EETs below those normally present in healthy individuals. Administration of exogenous EETs in conjunction with an sEH inhibitor is therefore expected to augment the effects of the sEH inhibitor in inhibiting or reducing the progression of COPD or other pulmonary diseases.

In addition to inhibiting or reducing the progression of chronic obstructive airway conditions, the invention also provides new ways of reducing the severity or progression of chronic restrictive airway diseases. While obstructive airway diseases tend to result from the destruction of the lung parenchyma, and especially of the alveoli, restrictive diseases tend to arise from the deposition of excess collagen in the parenchyma. These restrictive diseases are commonly referred to as "interstitial lung diseases", or "ILDs", and include conditions such as idiopathic pulmonary fibrosis. The methods, compositions and uses of the invention are useful for reducing the severity or progression of ILDs, such as idiopathic pulmonary fibrosis. Macrophages play a significant role in stimulating interstitial cells, particularly fibroblasts, to lay down collagen. Without wishing to be bound by theory, it is believed that neutrophils are involved in activating macrophages, and that the reduction of neutrophil levels found in the studies reported herein demonstrate that the methods and uses of the invention will also be applicable to reducing the severity and progression of ILDs.

In some embodiments, the ILD is idiopathic pulmonary fibrosis. In other embodiments, the ILD is one associated with an occupational or environmental exposure. Exemplars of such ILDs, are asbestosis, silicosis, coal worker's pneumoconiosis, and berylliosis. Further, occupational exposure to any of a number of inorganic dusts and organic dusts is believed to be associated with mucus hypersecretion and respiratory disease, including cement dust, coke oven emissions, mica, rock dusts, cotton dust, and grain dust (for a more complete list of occupational dusts associated with these conditions, see Table 254-1 of Speizer, "Environmental Lung Diseases," Harrison's Principles of Internal Medicine, infra, at pp. 1429-1436). In other embodiments, the ILD is sarcoidosis of the lungs. ILDs can also result from radiation in medical treatment, particularly for breast cancer, and from connective tissue or collagen diseases such as rheumatoid arthritis and systemic sclerosis. It is believed that the methods, uses and compositions of the invention can be useful in each of these interstitial lung diseases.

In another set of embodiments, the invention is used to reduce the severity or progression of asthma. Asthma typically results in mucin hypersecretion, resulting in partial airway obstruction. Additionally, irritation of the airway results in the release of mediators which result in airway obstruction. While the lymphocytes and other immunomodulatory cells recruited to the lungs in asthma may differ from those recruited as a result of COPD or an ILD, it is expected that the invention will reduce the influx of immunomodulatory cells, such as neutrophils and eosinophils, and ameliorate the extent of obstruction. Thus, it is expected that the administration of sEH inhibitors, and the administration of sEH inhibitors in combination with EETs, will be useful in reducing airway obstruction due to asthma.

In each of these diseases and conditions, it is believed that at least some of the damage to the lungs is due to agents released by neutrophils which infiltrate into the lungs. The presence of neutrophils in the airways is thus indicative of continuing damage from the disease or condition, while a reduction in the number of neutrophils is indicative of reduced damage or disease progression. Thus, a reduction in the number of neutrophils in the airways in the presence of an agent is a marker that the agent is reducing damage due to the disease or condition, and is slowing the further development of the disease or condition. The number of neutrophils present in the lungs can be determined by, for example, bronchioalveolar lavage.

Prophylatic and Therapeutic Methods to Reduce Stroke Damage

Inhibitors of soluble epoxide hydrolase ("sEH") and EETs administered in conjunction with inhibitors of sEH have been shown to reduce brain damage from strokes. Based on these results, we expect that inhibitors of sEH taken prior to an ischemic stroke will reduce the area of brain damage and will likely reduce the consequent degree of impairment. The reduced area of damage should also be associated with a faster recovery from the effects of the stroke.

While the pathophysiologies of different subtypes of stroke differ, they all cause brain damage. Hemorrhagic stroke differs from ischemic stroke in that the damage is largely due to compression of tissue as blood builds up in the confined space within the skull after a blood vessel ruptures, whereas in ischemic stroke, the damage is largely due to loss of oxygen supply to tissues downstream of the blockage of a blood vessel by a clot. Ischemic strokes are divided into thrombotic strokes, in which a clot blocks a blood vessel in the brain, and embolic strokes, in which a clot formed elsewhere in the body is carried through the blood stream and blocks a vessel there. But, in both hemorrhagic stroke and ischemic stroke, the damage is due to the death of brain cells. Based on the results observed in our studies, however, we would expect at least some reduction in brain damage in all types of stroke and in all subtypes.

A number of factors associated with an increased risk of stroke. Given the results of the studies underlying the present invention, sEH inhibitors administered to persons with any one or more of the following conditions or risk factors: high blood pressure, tobacco use, diabetes, carotid artery disease, peripheral artery disease, atrial fibrillation, transient ischemic attacks (TIAs), blood disorders such as high red blood cell counts and sickle cell disease, high blood cholesterol, obesity, alcohol use of more than one drink a day for women or two drinks a day for men, use of cocaine, a family history of stroke, a previous stroke or heart attack, or being elderly, will reduce the area of brain damaged of a stroke. With respect to being elderly, the risk of stroke increases for every 10 years. Thus, as an individual reaches 60, 70, or 80, administration of sEH inhibitors has an increasingly larger potential benefit. As noted in the next section, the administration of EETs in combination with one or more sEH inhibitors can be beneficial in further reducing the brain damage.

In some uses and methods, the sEH inhibitors and, optionally, EETs, are administered to persons who use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

Clot dissolving agents, such as tissue plasminogen activator (tPA), have been shown to reduce the extent of damage from ischemic strokes if administered in the hours shortly after a stroke. tPA, for example, is approved by the FDA for use in the first three hours after a stroke. Thus, at least some of the brain damage from a stoke is not instantaneous, but occurs over a period of time or after a period of time has elapsed after the stroke. It is therefore believed that administration of sEH inhibitors, optionally with EETs, can also reduce brain damage if administered within 6 hours after a stroke has occurred, more preferably within 5, 4, 3, or 2 hours after a stroke has occurred, with each successive shorter interval being more preferable. Even more preferably, the inhibitor or inhibitors are administered 2 hours or less or even 1 hour or less after the stroke, to maximize the reduction in brain damage. Persons of skill are well aware of how to make a diagnosis of whether or not a patient has had a stroke. Such determinations are typically made in hospital emergency rooms, following standard differential diagnosis protocols and imaging procedures.

In some uses and methods, the sEH inhibitors and, optionally, EETs, are administered to persons who have had a stroke within the last 6 hours who: use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

The conditions of therapeutic administration for all of these indications are as described above.

Combination Therapy

As noted above, the compounds of the present invention will, in some instances, be used in combination with other therapeutic agents to bring about a desired effect. Selection of additional agents will, in large part, depend on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W., (ed.), Current Therapy In Endocrinology And Metabolism, 6th Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. *Am. J. Cardiol* (1998) 82(12A): 3U-17U). Combination therapy includes administration of a single pharmaceutical dosage formulation which contains a compound having the general structure of formula 1 and one or more additional active agents, as well as administration of a compound of formula 1 and each active agent in its own separate pharmaceutical dosage formulation. For example, a compound of formula 1 and one or more angiotensin receptor blockers, angiotensin converting enzyme inhibitors, calcium channel blockers, diuretics, alpha blockers, beta blockers, centrally acting agents, vasopeptidase inhibitors, renin inhibitors, endothelin receptor agonists, AGE crosslink breakers, sodium/potassium ATPase inhibitors, endothelin receptor agonists, endothelin receptor antagonists, angiotensin vaccine, and the like; can be administered to the human subject together in a single oral dosage composition, such as a tablet or capsule, or each agent can be administered in separate oral dosage formulations. Where separate dosage formulations are used, a compound of formula 1 and one or more additional active agents can be administered at essentially the same time (i.e., concurrently), or at separately staggered times (i.e., sequentially). Combination therapy is understood to include all these regimens.

Compounds for Inhibiting Soluble Epoxide Hydrolases:

In addition to the methods provided above, the present invention provides in another aspect, compounds that can inhibit the activity of soluble epoxide hydrolases. In particular, the present invention provides compounds having a formula selected from formula (I) above. Preferably, the compounds are other than 11-(3-cyclohexylureido)-undecanoic acid, 11-(3-cyclohexylureido)-undecanoic acid methyl ester, 11-(3-cyclohexylureido)-undecanoic acid amide, 12-(3-cyclohexylureido)-dodecanoic acid and 12-(3-adamantan-1-yl-ureido)-dodecanoic acid.

In one embodiment, compounds are those compounds described above as for the recited uses.

Methods of Preparation

The compounds of the present invention can be prepared by a variety of methods as outlined generally in the schemes below.

Scheme 1—Introduction of a Secondary Pharmacophore (Ketone)

Scheme 1 illustrates general methods that can be used for preparation of compounds of the invention having a secondary pharmacophore that is a ketone functional group. While the scheme is provided for the synthesis of 1-(3-chlorophenyl)-3-(4-oxodecyl)urea, one of skill in the art will understand that a number of commercially available isocyanates could be used in place of 3-chlorophenyl isocyanate, and that shorter or longer analogs of ethyl 4-aminobutyric acid or hexylbromide could also be employed.

Scheme 1: Synthesis of 1-(3-chlorophenyl)-3-(4-oxodecyl)urea (794).

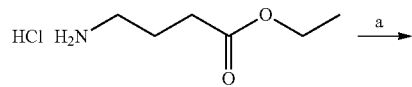

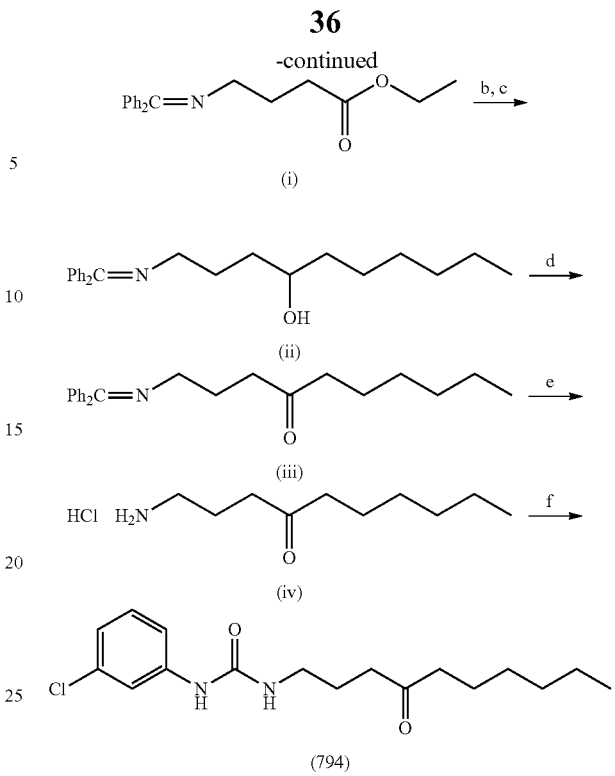

Scheme 1: Synthesis of 1-(3-chlorophenyl)-3-(4-oxodecyl)urea (794):
(a) Benzophenone imine, CH$_2$Cl$_2$, rt;
(b) DIBAL, THF, -78° C.;
(c) Mg/I$_2$, hexylbromide, THF, rt;
(d) acetic anhydride, DMSO, rt;
(e) 1 N HCl/dioxane, rt;
(f) 3-chlorophenyl isocyanate, TEA, DMF, rt.

As shown in Scheme 1, ethyl 4-aminobutyrate hydrochloride (available from Aldrich Chemical Co., Milwaukee, Wis., USA) is combined with benzophenone imine at room temperature to provide intermediate (i). DIBAL reduction of the ester group provides an unisolated aldehyde moiety that is then reacted with a suitable Grignard reagent (prepared in situ) to provide intermediate alcohol (ii). Oxidation of the alcohol moiety to a ketone provides (iii) which can then be deprotected to form the amino-ketone (iv). Reaction of (iv) with a suitable isocyanate provides the target compound (794). Substitution of 3-chlorophenyl isocyanate with, for example, adamantyl isocyanate or cyclohexyl isocyanate (also available from Aldrich Chemical Co.) provides other compounds of the invention.

Scheme 2 - Introduction of a secondary pharmacophore (ester or amide)

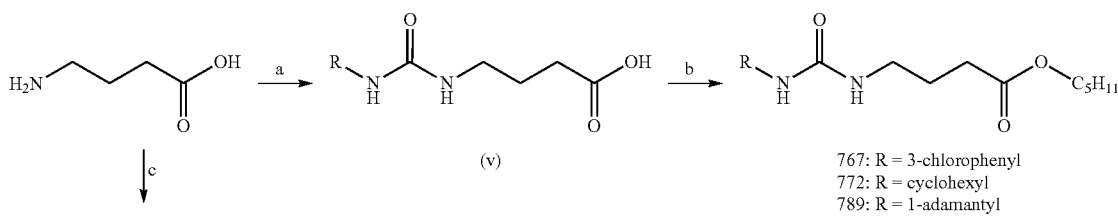

767: R = 3-chlorophenyl
772: R = cyclohexyl
789: R = 1-adamantyl

-continued

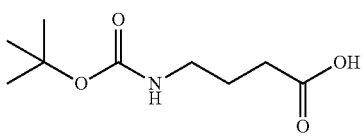

(vi)

↓ d

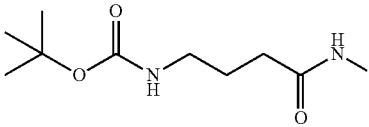

(vii) → (768)

Scheme 2: Syntheses of 1-(aryl or alkyl)-3-(3-alkylated proply(ureas:
(a) aryl or alkyl isocyanate, DMF, rt;
(b) bromopentane, $K_2CO_3$, NaI, acetonitrile, reflux;
(c) di-t-butyl dicarbonate, dioxane, 50° C.;
(d) pentylamine, isobutyl chloroformate, NMM, DMF, rt;
(e) 4 M hydrochloric acid, dioxane;
(f) 3-chlorophenyl isocyanate, TEA, DMF, rt.

As shown in Scheme 2, a variety of compounds having a secondary pharmacophore that is either an ester or amide functional group can be prepared. Beginning with 4-aminobutyric acid, treatment with a suitable cycloalkyl or aryl isocyanate provides the urea intermediates shown as (v), wherein R is 3-chlorophenyl, cyclohexyl or 1-adamantyl. Of course other suitable isocyanates can also be employed to provide desired urea intermediates. Esterification via alkylation of the carboxylic acid present in (v) with, for example, pentyl bromide provides the target compounds 767, 772 and 789. A variety of suitable alkyl halides can be used to prepare other compounds of the invention. The second path illustrated in Scheme 2 can be used to prepare compounds such as 768, as well as those compounds having a primary pharmacophore that is a carbamate. Accordingly, treatment of 4-aminobutyric acid with di-t-butyl dicarbonate provides the t-butyl carbamate acid (vi) that is converted to a desired amide (vii) using pentylamine, for example, in a mild procedure employing isobutyl chloroformate, and N-methyl morpholine (NMM). Removal of the carbamate protecting group (as it is used in this instance) followed by formation of a urea with a suitable isocyanate (shown here as 3-chlorophenyl isocyanate) provides the target compounds (e.g., 768).

Scheme 3-Introduction of a secondary pharmacophore (ester, carbonate, carbamate, amide and urea)

A

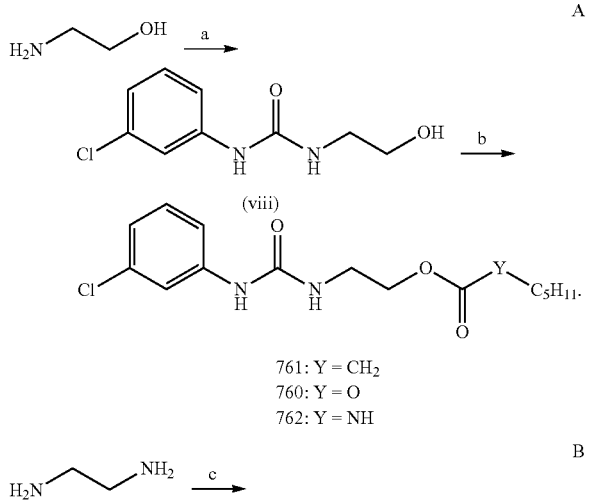

761: Y = $CH_2$
760: Y = O
762: Y = NH

B

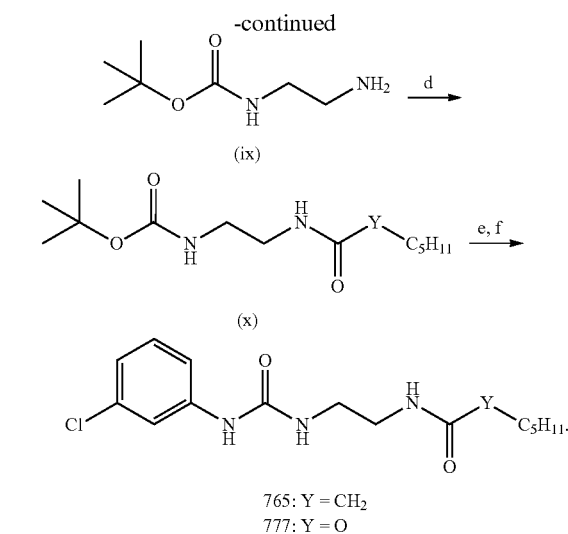

765: Y = $CH_2$
777: Y = O
766: Y = NH

Scheme 3: Syntheses of 1-(3-chlorophenyl)-3-(2-alkylatedethyl)ureas:
(a) 3-chlorophenyl isocyanate, DMF, rt;
(b) heptanoic anhydride (761), chloroformic acid pentyl ester (760), or pentyl isocyanate (762), TEA, DMF, rt;
(c) di-t-butyl dicarbonate, dioxane, rt;
(d) heptanoic anhydride (765), chloroformic acid pentyl ester (777), or pentyl isocyanate (766), DMF, rt;
(e) 4 M HCl, dioxane;
(f) 3-chlorophenyl isocyanate, TEA, DMF, rt.

Scheme 3 illustrates a variety of methods for introducing secondary pharmacophores that are esters, amide, ureas, carbonates and carbamates, from readily accessible starting materials. In A, ethanolamine is treated with a suitable isocyanate to introduce a primary pharmacophore that is a urea and form intermediate (viii). Treatment of (viii) with an anhydride, a chloro formic acid ester or an isocyanate provides compounds such as 761, 760 and 762, respectively. Similar methodology in employed in B, with the addition of protection/deprotection steps. Accordingly, ethylenediamine is monoprotected as a t-butyl carbamate. The free amine is then converted to a secondary pharmacophore that is an amide, carbamate or urea using reactants and conditions similar to those employed in "A" to provide intermediates (x). Deprotection of (x) and reaction with a suitable isocyanate provides the target compounds 765, 777 and 766. Again, use of isocyanates other than 3-chlorophenyl isocyanate leads to other compounds of the invention, while substitution of certain reactants used, for example, in the conversion of (ix) to (x) can provide still other compounds of the invention.

an amide moiety following standard procedures to provide, for example, 780-785, 788 and 800-804 (as esters) and 786, 787, 792 and 793 (as esters and amides).

Scheme 5 illustrates pathways for the synthesis of cis- or trans-phenoxy or benzyloxy-cyclohexyl compounds. In each case, trans-4-aminocyclohexanol hydrochloride is converted to the desired isomer of the phenoxy or benzyloxy derivative.

Scheme 4 - Introduction of a tertiary pharmacophore (ester and amide)

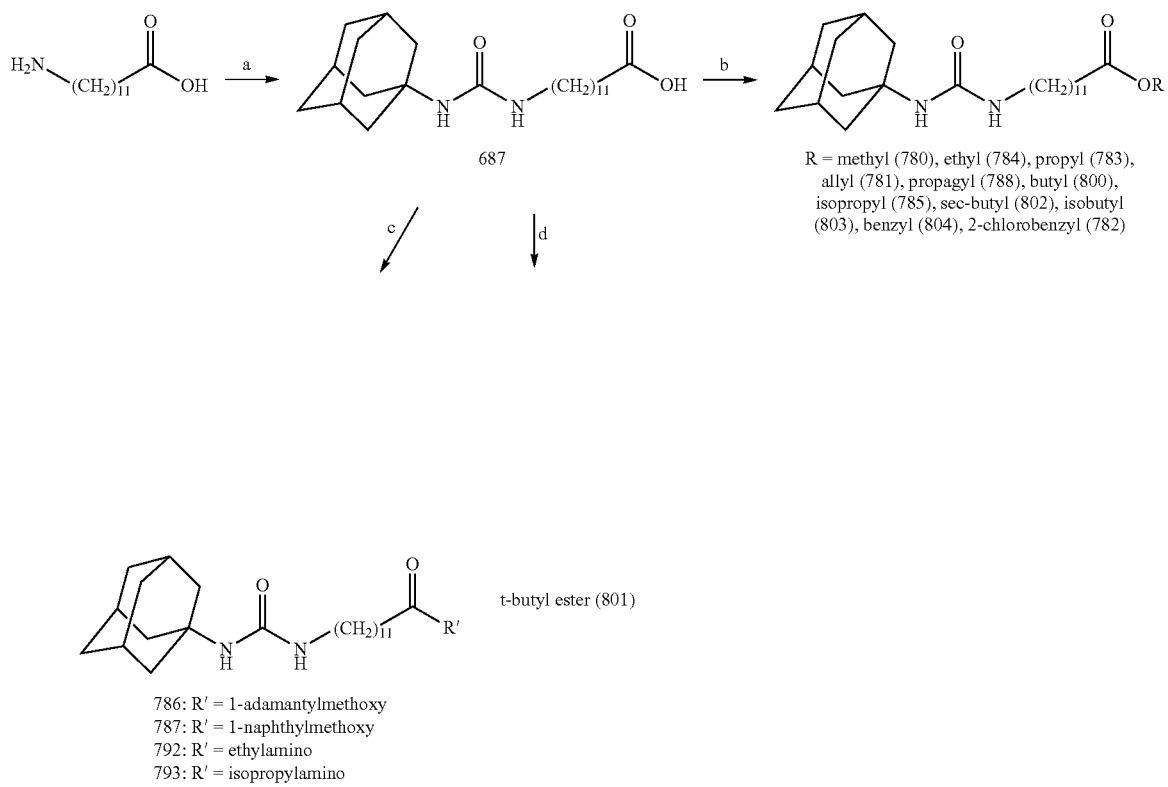

786: R' = 1-adamantylmethoxy
787: R' = 1-naphthylmethoxy
792: R' = ethylamino
793: R' = isopropylamino Scheme 4: Syntheses of 1-(1-adamantyl)-3-(11-alkylated undecyl)ureas:
(a) adamantyl isocyanate, chloroform, reflux;
(b) alkyl or aryl halide, $K_2CO_3$, NaI, acetonitrile, reflux;
(c) alcohol or amine, isobutyl chloroformate, TEA, DMF, rt;
(d) t-butanol, EDCI, DMAP, methylene chloride, rt.

Scheme 4 illustrates pathways for the introduction of a tertiary pharmacophore that is an ester or an amide functional group. In each case, a carboxylic acid group is converted to the desired ester or amide. As shown in Scheme 4, 12-aminododecanoic acid (Aldrich Chemical Co.) is converted to urea (687) upon treatment with adamantyl isocyanate. One of skill in the art will appreciate that a variety of alkyl, aryl and cycloalkyl isocyanates can be similarly employed to form other ureas as the primary pharmacophore. Similarly, 11-aminoundecanoic acid or another long chain amino fatty acid could be used in place of 12-aminododecanoic acid. The carboxylic acid moiety can then be esterified or converted to The alcohol moiety can be alkylated with an appropriately substituted benzyl halide following standard procedures to provide, the corresponding benzyl ether. Likewise, the alcohol moiety can be alkylated with an appropriately substituted phenol in the presence of triphenylphosphine following standard procedures to provide, the corresponding phenyl ether. As shown in Scheme 5, each isomer can be converted to the corresponding urea upon treatment with an appropriately substituted isocyanate, e.g. adamantyl isocyanate. One of skill in the art will appreciate that a variety of alkyl, aryl and cycloalkyl isocyanates can be similarly employed to form other ureas as the primary pharmacophore.

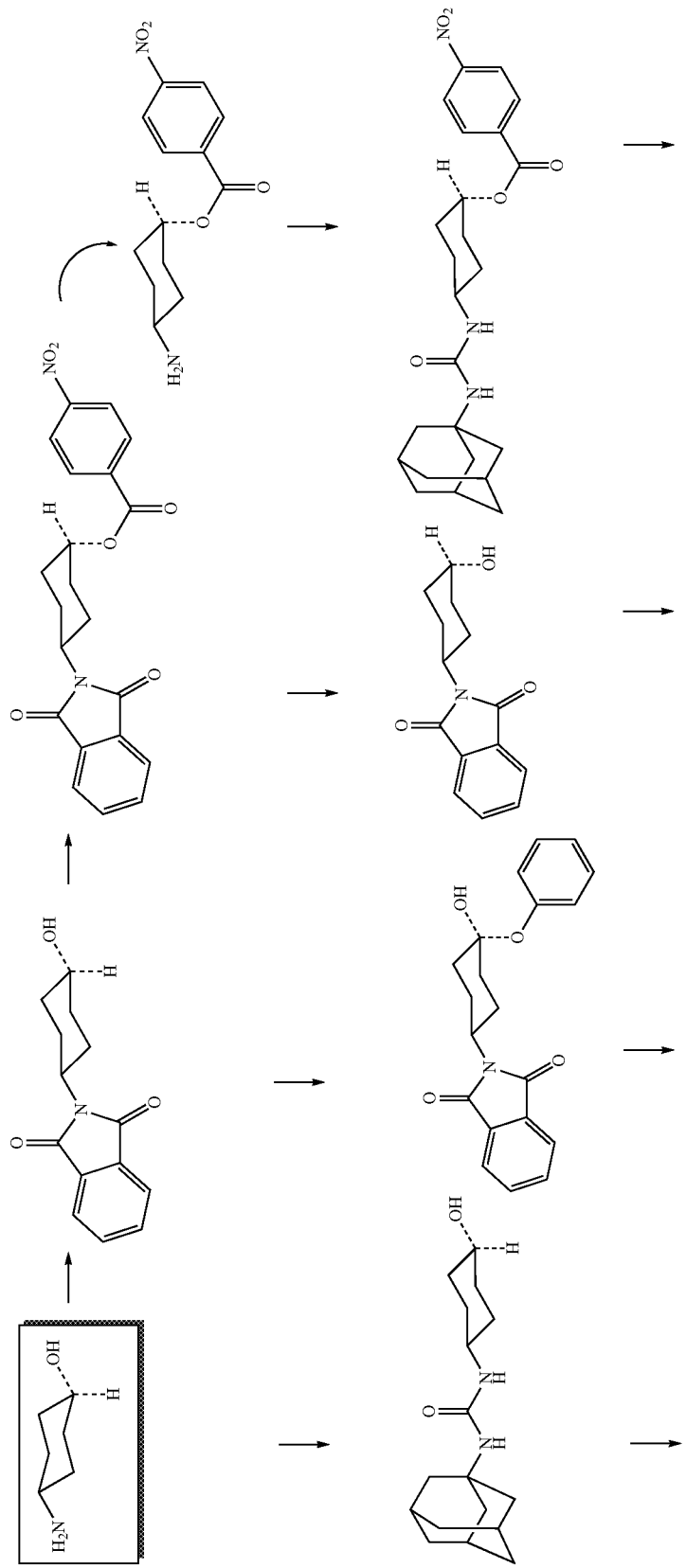
Scheme 5: Syntheses of cis and trans-phenoxy- and benzyloxy-cyclohexyl compounds.

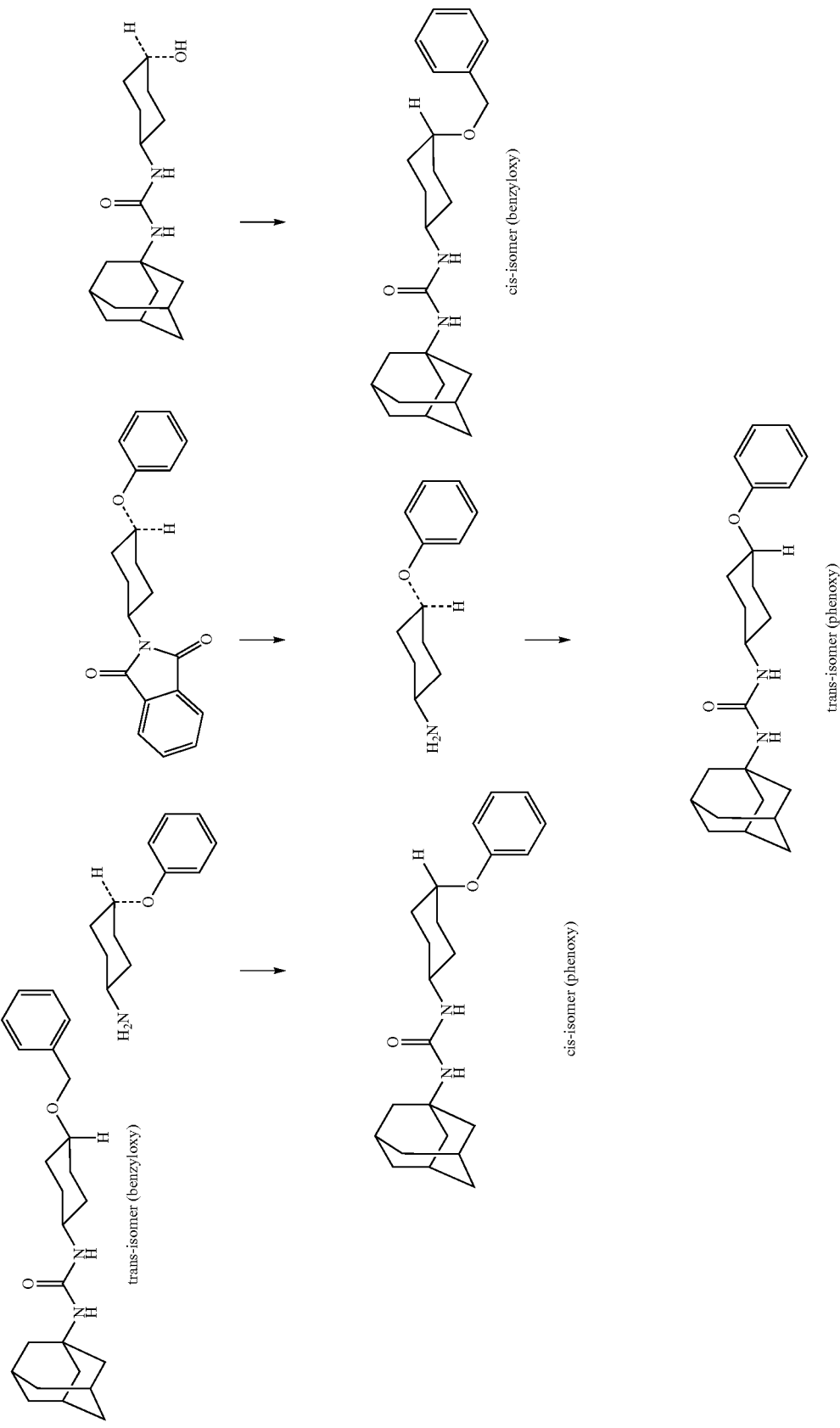

Combinatorial Library Synthesis

A 192-member urea library has been constructed by a known two-step solid-phase synthesis (*Tetrahedron Letters* 2003, 44, 6099-6102), which employs a PS-Indole-CHO resin. As shown in Scheme 6, four amines and 48 isocyanates have been used as building blocks to find the optimal left side of urea for sEH inhibitors. Resin-bound secondary amines can be obtained by a reductive amination with amines using sodium cyanoborohydride in the presence of triethylorthoformate. The reaction with isocyanates gives the desired resin-bound ureas, which can be cleaved from the resin by very mild acidic condition by using 1% TFA in dichloromethane at room temperature. The 192 urea compounds were prepared in 20-50% overall yields from the indole aldehyde resin. The identification and purity of the library could be determined by LC-MS. Purities were above 80%. Compounds with purities below this level were removed from the library.

Scheme 6: Combinatorial syntheses of urea inhibitors.

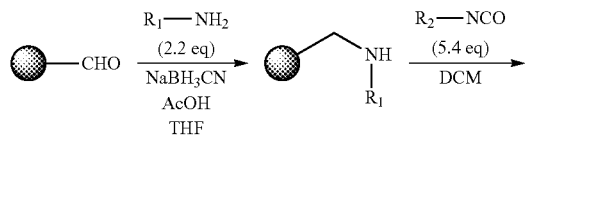

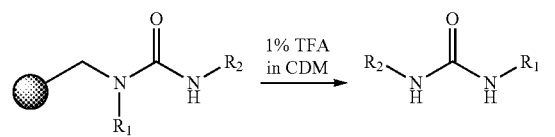

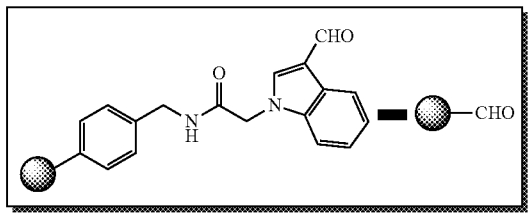

48 x 4 = 192 member-urea library for example:

one of
48 isocyanates

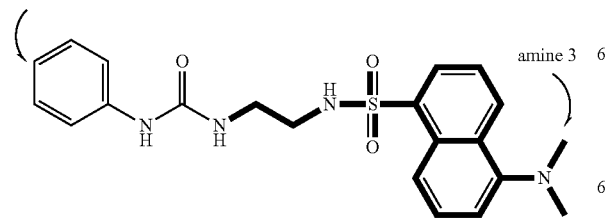

$R_3$—NCO: 48 different isocyanates $R_1$—$NH_2$:

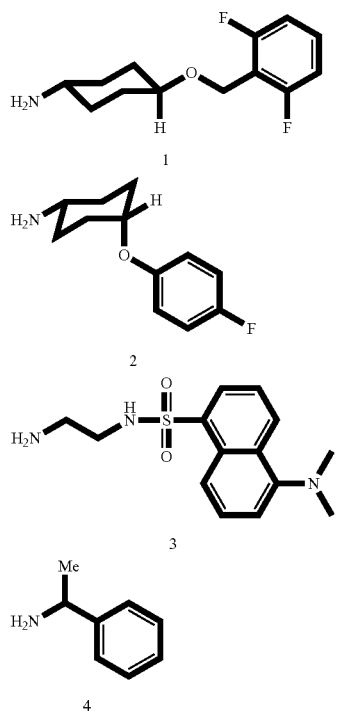

As the polyether compounds of the invention increase the ease of formulation, oral availability and serum half life of the compounds, another aspect of the present invention is to provide a method of increasing ease of formulation, oral availability, or serum half-life of a compound comprising covalently attaching a polyether substituent to a compound.

The following examples are provided to illustrate the invention and are not intended to limit any aspect of the invention as set forth above or in the claims below.

EXAMPLES

All melting points were determined with a Thomas-Hoover apparatus (A.H. Thomas Co.) and are uncorrected. Mass spectra were measured by LC-MS (Waters 2790). $^1$H-NMR spectra were recorded on QE-300 spectrometer, using tetramethylsilane as an internal standard. Signal multiplicities are represented as singlet (s), doublet (d), double doublet (dd), triplet (t), quartet (q), quintet (quint), multiplet (m), broad (br) and broad singlet (brs). Synthetic methods are described for representative compounds.

Lower case bolded Roman numerals in the examples below refer to the corresponding intermediates in Schemes 1-4 above. Compounds numbers are also used as provided in the Schemes as well as in the Tables below.

Example 1

Synthesis of 1-(3-chlorophenyl)-3-(4-oxodecyl)urea (794)

1.00 g (5.52 mmol) of benzophenone imine, 0.94 g (5.52 mmol) of ethyl 4-aminobutyrate hydrochloride, and 20 mL of methylene chloride were stirred at room temperature for 24 hr. The reaction mixture was filtered to remove $NH_4Cl$ and evaporated to dryness. The benzophenone Schiff base of ethyl 4-aminobutyrate (i) was extracted with ether (20 mL), and the ether solution was washed with water (20 mL), dried over sodium sulfate ($Na_2SO_4$), and concentrated. The residue was purified by column chromatography on silica gel eluting with hexane and ethyl acetate (5:1) to give i (1.00 g, 61%) as an oil. To the solution of the benzophenone Schiff base (i) in 20 mL of tetrahydrofuran (THF) was added 3.7 mL of 1M diisobutylaluminum hydride (DIBAL) solution in pentane (3.73 mmol) at −78° C. under nitrogen, and the reaction was stirred for 2 hr at the temperature. To 0.10 g of magnesium turning (4.07 mmol) and $I_2$ (catalytic amount) in THF (10 mL) was added 0.48 mL of hexylbromide (3.39 mmol) at room temperature under nitrogen. After stirring for 1 hr, this reaction solution was added dropwise to the above reaction mixture at −78° C., and the solution was allowed to warm to room temperature with stirring. After stirring for 5 hr at room temperature, 10 mL of $NaHCO_3$ aqueous solution was added to the reaction, then the alkylated alcohol (ii) was extracted with ether (20 mL), and the ether solution was washed with water (20 mL), dried over $Na_2SO_4$, and concentrated to give 0.26 g (60%) of the alcohol product (ii).

Acetic anhydride (2 mL) was added to a solution of ii (0.77 mmol) in 5 mL of dimethyl sulfoxide (DMSO). The mixture was allowed to stand at room temperature for 12 hr and concentrated. The residue was extracted with ether (20 mL), and the ether was washed with water (20 mL), dried over $Na_2SO_4$, and evaporated to provide 0.26 g (100%) of the ketone compound (iii). To a solution of iii in dioxane (5 mL) was added 1 mL of 1N HCl in dioxane at room temperature. The reaction mixture was stirred for 2 hr and concentrated to give keto amine hydrochloride (iv). Then iv was dissolved in 5 mL of dimethylformamide (DMF) and treated with triethylamine (TEA, 0.27 mL, 1.95 mmol) and a solution of 3-chlorophenyl isocyanate (0.10 mL, 0.78 mmol) in DMF (3 mL) at room temperature. After stirring for 5 hr, the product was extracted with ether (30 mL), and the ether was washed with water (30 mL), dried over $Na_2SO_4$, and evaporated to dryness. The residue was purified by column chromatography on silica gel eluting hexane and ethyl acetate (3:1) to afford 75 mg (30%) of 794. $\delta(CDCl_3)$: 0.88 (3H, t, J=6.9 Hz), 1.21-1.29 (6H, m), 1.53-1.58 (2H, m), 1.81 (2H, quint, J=6.9 Hz), 2.43 (2H, t, J=6.9 Hz), 2.49 (2H, t, J=6.9 Hz), 3.23 (2H, t, J=6.9 Hz), 5.10 (1H, s), 6.93 (1H, s), 6.98-7.02 (1H, m), 7.10-7.23 (2H, m), 7.49 (1H, s), [M+H]$^+$ 325.21

Example 2

Synthesis of 1-(3-chlorophenyl)-3-(3-pentoxycarbonylpropyl)urea (767)

To a suspension of 4-aminobutyric acid (1.41 g, 13.7 mol) in DMF (25 mL) was added 3-chlorophenyl isocyanate (0.70 g, 4.56 mmol; cyclohexyl isocyanate for 772 and 1-adamantyl isocyanate for 789) at room temperature. The reaction mixture was stirred for 24 hr. Then ethyl acetate (30 mL) and 1N HCl aqueous solution (30 mL) were added into the reaction, and the ethyl acetate layer dissolving the acid product was collected. The product was extracted with ethyl acetate (20 mL) two more times from the aqueous layer. The combined organic solution was dried over $Na_2SO_4$, and evaporated. The residue was purified using column chromatography on silica gel eluting hexane and ethyl acetate (1:1) to give 0.88 g (75%) of urea acid (v). A mixture of v (0.50 g, 1.95 mmol), potassium carbonate ($K_2CO_3$, 0.54 g, 3.90 mmol), bromopentane (0.37 mL, 2.92 mmol), and sodium iodide (60 mg, 0.39 mmol) in DMF (20 mL) was stirred at room temperature for 20 hr. Then the product was extracted with ether (20 mL), and the ether was washed with 1N NaOH aqueous solution (20 mL) and brine (20 mL), dried over $Na_2SO_4$, and evaporated to afford 0.59 g (92%) of 767. $\delta(CDCl_3)$: 0.90 (3H, t, J=6.9 Hz), 1.26-1.34 (4H, m), 1.62-1.65 (2H, m), 1.88 (2H, quint, J=6.9 Hz), 2.41 (2H, t, J=6.9 Hz), 3.30 (2H, t, J=6.9 Hz), 4.08 (2H, t, J=6.9 Hz), 4.96 (1H, s), 6.62 (1H, s), 7.01-7.04 (1H, m), 7.18-7.22 (2H, m), 7.47 (1H, s), [M+H]$^+$ 326.90

The following compounds were prepared in a similar manner:

1-Cyclohexyl-3-(3-pentoxycarbonylpropyl)urea
(772)

$\delta(CDCl_3)$: 0.89 (3H, t, J=6.9 Hz), 1.04-1.21 (2H, m), 1.29-1.43 (4H, m), 1.58-1.74 (6H, m), 1.82 (2H, quint, J=6.9 Hz), 2.37 (2H, t, J=6.9 Hz), 3.17-3.24 (2H, m), 3.46-3.48 (1H, m), 4.07 (2H, t, J=6.9 Hz), 4.29 (1H, s), 4.47 (1H, s), [M+H]$^+$ 299.24

1-(1-Adamantyl)-3-(3-pentoxycarbonylpropyl)urea
(789)

$\delta(CDCl_3)$: 0.92 (3H, t, J=6.9 Hz), 1.29-1.43 (4H, m), 1.64-1.69 (m, 10H), 1.83 (2H, quint, J=6.9 Hz), 1.94-1.98 (6H, m), 2.06-2.09 (3H, m), 2.37 (2H, t, J=6.9 Hz), 3.20 (2H, t, J=6.9 Hz), 4.06-4.14 (3H, m), 4.30 (1H, s), [M+H]$^+$ 251.26.

Example 3

Synthesis of 1-(3-chlorophenyl)-3-(3-pentylaminocarbonylpropyl)urea (768)

To a suspension of 4-aminobutyric acid (2.84 g, 27.5 mmol) in DMF (30 mL) was added TEA (3.86 mL, 27.5 mmol). To this mixture, di-t-butyl dicarbonate (2.00 g, 9.17 mmol) was added with stirring. The reaction mixture was heated to 50° C. for 12 hr, and then stirred with ice-cold dilute hydrochloric acid (15 mL) for 10 min. The t-butoxycarbonylated amino acid (vi) was immediately extracted with ether (2×30 mL). The organic extract was dried over $Na_2SO_4$ and evaporated to give 1.00 g (54%) of vi as an oil.

A solution of vi and 4-methyl morpholine (NMM, 0.54 mL, 4.92 mmol) in DMF (10 mL) was treated at room temperature with isobutyl chloroformate (0.64 mL, 4.92 mmol). After 30 min, pentylamine (0.57 mL, 4.92 mmol) was added. The reaction mixture was stirred for 12 hr. The solvent was evaporated, and the residue was partitioned between ethyl acetate (25 mL) and water (25 mL). The ethyl acetate layer was washed with 5% $NaHCO_3$ (10 mL) and brine (20 mL) and dried over $Na_2SO_4$, and evaporated. The residue was chromatographed on silica gel eluting hexane and ethyl acetate (2:1) to give 0.33 g (33%) of t-butoxycarbonylated amino amide (vii). To a solution of vii in dioxane (10 mL) was treated with 4M hydrochloric acid (2 mL) in dioxane, and the mixture was stirred for 1 hr at room temperature. Then the solvent was evaporated to dryness, and the residual solid was dissolved in DMF (10 mL) and treated with TEA (0.51 mL, 3.63 mmol) and 3-chlorophenyl isocyanate (0.15 mL, 1.21 mmol) at room temperature. After stirring for 5 hr, the product was extracted with ether (30 mL), and the ether was washed with water (30 mL), dried over $Na_2SO_4$, and evaporated to dryness. The residue was purified by column chromatography on silica gel eluting hexane and ethyl acetate (3:1) to afford 0.39 g (100%) of 768. $\delta(CDCl_3)$: 0.89 (t, 3H, J=6.9 Hz), 1.26-1.28 (4H, m), 1.46-1.50 (2H, m), 1.86 (2H, quint, J=6.9 Hz), 2.30 (t, 2H, J=6.9 Hz), 3.23 (t, 2H, J=6.9 Hz), 3.30 (t, 2H, J=6.9 Hz), 5.87 (1H, s), 6.06 (1H, s), 6.93-6.97 (1H, m), 7.12-7.23 (2H, m), 7.49 (1H, m), 7.73 (1H, s), [M+H]$^+$ 326.16.

Example 4

Synthesis of 1-(3-chlorophenyl)-3-(2-hexylcarbonyloxyethyl)urea (761)

To a solution of 2-aminoethanol (2.98 g, 48.8 mmol) in DMF (30 mL) was added 3-chlorophenol isocyanate (2.50 g, 16.3 mmol) at 0° C. The reaction mixture was stirred for 5 hr at room temperature. The solvent was evaporated, and the residue was partitioned between ether (30 mL) and 1N hydrochloric acid (20 mL), and the ether layer was washed with brine, dried over Na$_2$SO$_4$, and evaporated. The residue was purified by column chromatography on silica gel eluting hexane and ethyl acetate (1:1) to provide 1.49 g (40%) of urea alcohol (viii) as a white solid.

To a solution of viii (1.00 g, 4.60 mmol) and TEA (0.97 mL, 6.90 mmol) in DMF (15 mL) was added a solution of heptanoic anhydride (2.23 g, 9.20 mmol) in DMF (5 mL) at room temperature. The reaction was stirred for 12 hr, and the solvent was evaporated. The residue was partitioned between ether (30 mL) and cold 1N hydrochloric acid (20 mL). The ether layer was washed with brine, dried over Na$_2$SO$_4$, and evaporated. The residual solid was purified using silica gel column chromatography (hexane:ethyl acetate=3:1) to afford 1.05 g (70%) of 761. δ(CDCl$_3$): 0.87 (t, 3H, J=6.9 Hz), 1.20-1.29 (6H, m), 1.60-1.62 (2H, m), 2.22-2.29 (2H, m), 3.50-3.55 (2H, m), 4.09-4.20 (2H, m), 5.32 (1H, s), 7.01-7.06 (2H, m), 7.16-7.22 (2H, m), 7.40 (1H, s), [M+H]$^+$ 327.15

Compounds 760 and 762 were prepared in the same manner as that used for compound 761 from chloroformic acid pentyl ester and pentyl isocyanate in place of heptanoic anhydride, respectively.

1-(3-chlorophenyl)-3-(2-pentoxycarbonyloxyethyl)urea (760)

δ(CDCl$_3$): 0.91 (t, 3H, J=6.9 Hz), 1.25-1.36 (4H, m), 1.63-1.67 (2H, m), 3.55-3.60 (2H, m), 4.14 (3H, t, J=6.9 Hz), 4.25-4.28 (2H, m), 5.11 (1H, s), 6.50 (1H, s), 7.02-7.05 (1H, m), 7.19-7.23 (2H, m), 7.42 (1H, s), [M+H]$^+$ 329.09

1-(3-chlorophenyl)-3-(2-pentylaminocarbonyloxyethyl)urea (762)

1δ(CDCl$_3$): 0.87 (3H, t, J=6.9 Hz), 1.30-1.33 (4H, m), 1.46-1.50 (2H, m), 3.12-3.19 (2H, m), 3.50-3.52 (2H, m), 4.17-4.20 (2H, m), 4.83 (1H, s), 5.47 (1H, s), 6.96 (1H, s), 6.98-7.02 (1H, m), 7.18-7.21 (2H, m), 7.44 (1H, s), [M+H]$^+$ 328.20.

Example 5

Synthesis of 1-(3-chlorophenyl)-3-(2-hexylcarbonylaminoethyl)urea (765)

A solution of di-t-butyl dicarbonate (0.50 g, 2.29 mmol) in dioxane (20 mL) was added over a period of 1 hr to a solution of 1,2-diaminoethane (1.10 g, 18.3 mmol) in dioxane (20 mL). The mixture was allowed to stir for 22 hr and the solvent was evaporated to dryness. Water (30 mL) was added to the residue and the insoluble bis-substituted product was removed by filtration. The filtrate was extracted with methylene chloride (3×30 mL) and the methylene chloride evaporated to yield ix as an oil (0.35 g, 95%).

A solution of heptanoic anhydride (0.91 g, 3.75 mmol; chloroformic acid pentyl ester for 777 and pentyl isocyanate for 766) and ix (0.50 g, 3.13 mmol) in DMF (20 mL) was stirred for 2 hr at room temperature. Then the solvent was evaporated. The residue was partitioned between ether (30 mL) and water (30 mL). The ether layer was dried over Na$_2$SO$_4$ and evaporated. The residue was purified by using column chromatography on silica gel eluting hexane and ethyl acetate (1:1) to get 0.57 g (67%) of alkylated N-t-butoxycarbonyl amine (x).

To a solution of x in dioxane (10 mL) was treated with 4M hydrochloric acid (2 mL) in dioxane, and the mixture was stirred for 1 hr at room temperature. Then the solvent was evaporated to dryness, and the residual solid was dissolved in DMF (10 mL) and treated with TEA (0.58 mL, 4.19 mmol) and 3-chlorophenyl isocyanate (0.32 g, 2.10 mmol) at room temperature. After stirring for 5 hr, the product was extracted with ether (30 mL), and the ether was washed with water (30 mL), dried over Na$_2$SO$_4$, and evaporated to dryness. The residue was purified by column chromatography on silica gel eluting hexane and ethyl acetate (1:1) to afford 0.68 g (100%) of 765. δ(CDCl$_3$): 0.84 (t, 3H, J=6.9 Hz), 1.16-1.25 (6H, m), 1.55-5.61 (2H, m), 2.21-2.24 (2H, m), 3.31-3.40 (4H, m), 6.27 (1H, s), 6.90-6.95 (2H, m), 7.18-7.20 (2H, m), 7.56 (1H, s), 8.07 (1H, s), [M+H]$^+$ 326.25

The following compounds were prepared in a similar manner:

1-(3-chlorophenyl)-3-(2-pentoxycarbonylaminoethyl)urea (777)

δ(CDCl$_3$): 0.88 (3H, t, J=6.9 Hz), 1.28-1.32 (4H, m), 1.44-1.49 (2H, m), 3.23-3.33 (4H, m), 3.95-3.97 (2H, m), 6.01 (1H, s), 6.34 (1H, s), 6.87-6.91 (1H, m), 7.18-7.26 (2H, m), 7.78 (1H, s), 8.21 (1H, s), [M+H]$^+$ 328.22

1-(3-chlorophenyl)-3-(2-pentylaminocarbonylaminoethyl)urea (766)

δ(Acetone): 0.87 (3H, t, J=6.9 Hz), 1.27-1.30 (4H, m), 2.04-2.06 (2H, m), 3.02-3.05 (2H, m), 3.20-3.22 (2H, m), 5.74 (2H, s), 6.22 (1H, s), 7.23-7.29 (2H, m), 7.82-7.87 (2H, m), 8.67 (1H, s), [M+H]$^+$ 327.10.

Example 6

Synthesis of 1-(1-adamantyl)-3-(12-dodecanoic acid)urea (687)

A mixture of 1-adamantyl isocyanate (1.30 g, 7.34 mmol) and 12-aminododecanoic acid (1.46 g, 6.77 mmol) in chloroform (30 mL) was refluxed for 10 hr. The solvent was removed by evaporation, and the residue was washed with ethyl acetate (20 mL) to provide 2.66 g (100%) of urea acid product as a white solid. δ(CDCl$_3$): 1.20-1.36 (16H, m), 1.42-1.48 (2H, m), 1.57-1.65 (6H, m), 1.82-1.90 (6H, m), 1.94-1.98 (3H, m), 2.18 (2H, t, J=6.9 Hz), 2.86-2.92 (2H, m), 3.45 (1H, bs), 5.43 (1H, s), 5.587 (1H, t, J=5.4 Hz), [M+H]$^+$ 393.28, mp 140° C.

Example 7

Synthesis of 1-(1-adamantyl)-3-(11-methoxycarbonylundecyl)urea (780)

To a mixture of compound 687 (0.15 g, 0.38 mmol), K$_2$CO$_3$ (64 mg, 0.46 mmol), and iodomethane (54 mg, 0.38 mmol) in acetonitrile (20 mL) was refluxed for 10 hr. Then the reaction mixture was filtered, and the filtrate was washed with brine (20 mL), dried over $Na_2SO_4$, and evaporated. The residue was purified using column chromatography on silica gel eluting hexane and ethyl acetate (3:1) to afford 0.14 g (92%) of 780 as a white solid. δ($CDCl_3$): 1.19-1.34 (12H, m), 1.41-1.48 (2H, m), 1.58-1.62 (4H, m), 1.63-1.75 (6H, m), 1.93-2.00 (6H, m), 2.04-2.07 (3H, m), 2.30 (2H, t, J=6.9 Hz), 3.06-3.12 (2H, m), 3.67 (3H, s), 4.00 (1H, s), 4.06 (1H, s), $[M+H]^+$ 407.22, mp 75° C.

Compounds 780, 784, 783, 781, 788, 800, 785, 801, 802, 803, 804, and 782 were prepared in the same manner using corresponding halides in a range of 30-95% yield.

1-(1-Adamantyl)-3-(11-ethoxycarbonylundecyl)urea (784)

δ($CDCl_3$): 1.21-1.38 (12H, m), 1.42-1.68 (15H, m), 1.96 (6H, bs), 2.06 (3H, m), 2.30 (2H, t, J=6.9 Hz), 3.06-3.12 (2H, m), 3.97-4.01 (2H, bs), 4.12 (2H, q), $[M+H]^+$ 421.46, mp 82° C.

1-(1-Adamantyl)-3-(11-propoxycarbonylundecyl) urea (783)

δ($CDCl_3$): 0.94 (3H, t, J=6.9 Hz), 1.19-1.34 (12H, m), 1.41-1.48 (2H, m), 1.58-1.62 (4H, m), 1.63-1.75 (8H, m), 1.93-2.00 (6H, m), 2.04-2.07 (3H, m), 2.30 (2H, t, J=6.9 Hz), 3.06-3.12 (2H, m), 3.95-4.05 (4H, m), $[M+H]^+$ 435.52, mp 86° C.

1-(1-Adamantyl)-3-(11-allyloxycarbonylundecyl) urea (781)

δ($CDCl_3$): 1.19-1.34 (12H, m), 1.41-1.48 (2H, m), 1.58-1.73 (13H, m), 1.93-2.00 (6H, m), 2.04-2.07 (3H, m), 2.33 (2H, t, J=6.9 Hz), 3.06-3.12 (2H, m), 3.99 (1H, s), 4.04 (1H, s), 4.57-4.59 (2H, m), $[M+H]^+$ 433.43, mp 81° C.

1-(1-Adamantyl)-3-(11-propagyloxycarbonylundecyl)urea (788)

δ($CDCl_3$): 1.24-1.31 (12H, m), 1.44-1.46 (2H, m), 1.58-1.67 (11H, m), 1.94-1.98 (6H, m), 2.05-2.07 (3H, m), 2.35 (2H, t, J=6.9 Hz), 3.05-3.12 (2H, m), 3.99 (1H, s), 4.04 (1H, s), 4.67 (2H, s), $[M+H]^+$ 431.67, mp 79° C.

1-(1-Adamantyl)-3-(11-butoxycarbonylundecyl)urea (800)

δ($CDCl_3$): 0.95 (3H, t, J=6.9 Hz), 1.23-1.35 (12H, m), 1.44-1.52 (4H, m), 1.57-1.61 (4H, m), 1.66-1.69 (6H, m), 1.96-2.00 (8H, m), 2.07-2.09 (3H, m), 2.30 (2H, t, J=6.9 Hz), 3.09-3.13 (2H, m), 4.02-4.10 (4H, m), $[M+H]^+$ 449.34

1-(1-Adamantyl)-3-(11-iso-propoxycarbonylundecyl)urea (785)

δ($CDCl_3$): 1.19-1.26 (18H, m), 1.41-1.48 (2H, m), 1.58-1.62 (4H, m), 1.63-1.75 (6H, m), 1.94-2.00 (6H, m), 2.03-2.07 (3H, m), 2.30 (2H, t, J=6.9 Hz), 3.06-3.12 (2H, m), 3.67 (3H, s), 4.00 (1H, s), 4.06 (1H, s), 4.94-5.04 (1H, m), $[M+H]^+$ 435.33, mp 90° C.

1-(1-Adamantyl)-3-(11-sec-butoxycarbonylundecyl) urea (802)

δ($CDCl_3$): 0.89 (3H, t, J=6.9 Hz), 1.19 (3H, d, J=6.9 Hz), 1.23-1.35 (12H, m), 1.44-1.50 (2H, m), 1.57-1.61 (4H, m), 1.66-1.72 (8H, m), 1.96-2.00 (6H, m), 2.07-2.09 (3H, m), 2.27 (2H, t, J=6.9 Hz), 3.09-3.13 (2H, m), 4.00 (1H, s), 4.05 (1H, s), 4.91-4.96 (1H, m); and $[M+H]^+$ 449.29, mp 65° C.

1-(1-Adamantyl)-3-(11-isobutoxycarbonylundecyl) urea (803)

δ($CDCl_3$): 0.93 (6H, d, J=6.9 Hz), 1.23-1.35 (12H, m), 1.45-1.47 (2H, m), 1.56-1.58 (4H, m), 1.65-1.68 (6H, m), 1.94-1.97 (7H, m), 2.06-2.08 (3H, m), 2.31 (2H, t, J=6.9 Hz), 3.07-3.11 (2H, m), 3.85 (2H, d, J=6.9 Hz), 3.99 (1H, s), 4.03 (1H, s), $[M+H]^+$ 449.32, mp 91° C.

1-(1-Adamantyl)-3-(11-benzyloxycarbonylundecyl) urea (804)

δ($CDCl_3$): 1.24-1.28 (12H, m), 1.44-1.48 (2H, m), 1.63-1.68 (10H, m), 1.94-1.97 (6H, m), 2.05-2.07 (3H, m), 2.34 (2H, t, J=6.9 Hz), 3.05-3.13 (2H, m), 4.04 (1H, s), 4.09 (1H, s), 5.12 (2H, s), 7.33-7.37 (5H, m), $[M+H]^+$ 483.33, mp 49° C.

1-(1-Adamantyl)-3-(11-(2-chlorobenzyl)oxycarbonylundecyl)urea (782)

δ($CDCl_3$): 1.24-1.28 (12H, m), 1.44-1.48 (2H, m), 1.63-1.68 (10H, m), 1.94-1.97 (6H, m), 2.05-2.07 (3H, m), 2.39 (2H, t, J=6.9 Hz), 3.07-3.13 (2H, m), 4.00 (1H, s), 4.06 (1H, s), 5.23 (2H, s), 7.27-7.30 (3H, m), 7.39-7.42 (1H, m), $[M+H]^+$ 517.05, mp 48° C.

Example 8

Synthesis of 1-(1-adamantyl)-3-(11-(1-adamantyl) methyloxycarbonylundecyl)urea (786)

A solution of 687 (0.15, 0.38 mmol) and TEA (96 mg, 0.96 mmol) in DMF (10 mL) was treated at room temperature with isobutyl chloroformate (52 mg, 0.38 mmol). After 30 min, a solution of adamantanemethanol (64 mg, 0.38 mmol) in DMF (2 mL) was added. The reaction mixture was stirred for 12 hr. The solvent was evaporated, and the residue was partitioned between ethyl acetate (25 mL) and water (25 mL). The ethyl acetate layer was washed with 5% $NaHCO_3$ (10 mL) and brine (20 mL) and dried over $Na_2SO_4$, and evaporated. The residue was chromatographed on silica gel eluting hexane and ethyl acetate (5:1) to give 72 mg (35%) of 786 as a white solid. δ($CDCl_3$): 1.23-1.33 (15H, m), 1.48-1.71 (21H, m), 1.90-1.96 (8H, m), 2.04-2.06 (3H, m), 2.31 (2H, t, J=6.9 Hz), 3.05-3.12 (2H, m), 3.67 (2H, s), 4.00 (1H, s), 4.05 (1H, s), $[M+H]^+$ 541.33, mp 68° C.

Compound 792, 793 and 787 were prepared in this manner using ethylamine, isopropylamine, and 1-naphthalenemethanol, respectively, instead of adamantanemethanol.

1-(1-Adamantyl)-3-(11-ethylaminocarbonylundecyl) urea (792)

δ($CDCl_3$): 1.14 (3H, t, J=6.9 Hz), 1.24-1.31 (12H, m), 1.43-1.46 (2H, m), 1.58-1.66 (10H, m), 1.94-1.98 (6H, m), 2.05-2.07 (3H, m), 2.15 (2H, t, J=6.9 Hz), 3.06-3.12 (2H, m), 3.25-3.13 (2H, m), 4.05 (1H, s), 4.12 (1H, s), 5.43 (1H, s), $[M+H]^+$ 420.48, mp 119° C.

1-(1-Adamantyl)-3-(11-isopropylaminocarbonylundecyl)urea (793)

δ($CDCl_3$): 1.14 (6H, d, J=6.9 Hz), 1.24-1.31 (12H, m), 1.43-1.46 (2H, m), 1.61-1.69 (10H, m), 1.94-1.98 (6H, m), 2.07-2.18 (5H, m), 3.07-3.13 (2H, m), 4.03-4.10 (2H, m), 4.14 (1H, s), 5.26 (1H, s), [M+H]$^+$ 434.50, mp 115° C.

1-(1-Adamantyl)-3-(11-(1-naphthyl)methoxycarbonylundecyl)urea (787)

δ(CDCl$_3$): 1.20-1.27 (12H, m), 1.43-1.46 (2H, m), 1.61-1.67 (10H, m), 1.96-2.06 (6H, m), 2.14-2.16 (2H, m), 2.35 (2H, t, J=6.9 Hz), 3.06-3.10 (2H, m), 4.02 (1H, s), 4.08 (1H, s), 5.57 (2H, s), 7.43-7.56 (4H, m), 7.84-7.87 (2H, m), 7.90 (8.02 (1H, m), [M+H]$^+$ 533.59.

Example 9

Synthesis of 1-(1-Adamantyl)-3-(11-t-butoxycarbonylundecyl)urea (801)

To a solution of compound 687 (0.10 g, 0.25 mmol), N,N-dimethylaminopyridine (DMAP, 10 mg, 0.13 mmol), and t-butanol (23 mg, 0.31 mmol) in methylene chloride (20 mL) was added 1-(3-(dimethylamino)propyl)-3-ethylcarbodiimide hydrochloride (EDCI, 50 mg, 0.25 mmol) at room temperature. The mixture was stirred for 20 hr. The solvent was evaporated, and the residue was partitioned between ether (30 mL) and water (30 mL). The ether layer was dried over Na$_2$SO$_4$ and evaporated. Purification of the residue by silica gel column chromatography eluting hexane and ethyl acetate (3:1) provided 21 mg (18%) of t-butyl ester as a white solid.
δ(CDCl$_3$): 1.23-1.35 (12H, m), 1.44-1.50 (2H, m), 1.57-1.61 (13H, m), 1.66-1.72 (6H, m), 1.96-2.00 (6H, m), 2.07-2.09 (3H, m), 2.27 (2H, t, J=6.9 Hz), 3.09-3.13 (2H, m), 3.96 (1H, s), 4.01 (1H, s), [M+H]$^+$ 449.36, mp 150° C.

Example 10

Synthesis of 4-(3-Cyclohexyl-ureido)-butyric acid (632)

To a cold solution of 4-aminobutyric acid (2.16 g, 21 mmol) and catalytic amount of DBU in 22 mL of 1.0 N NaOH, 2.5 g (20 mmol) of cyclohexyl isocyanate were added in one time. The mixture was strongly mixed at room temperature overnight. The reaction was then acidified with concentrated HCl. The formed white solid was collected by filtration. The mixture was purified by chromatography on a silica column (8×3 cm). Elution with a mixture 50:50:1 of hexane:ethyl acetate:acetic acid gave the pure targeted product. The resulting white crystal (3.46 g; yield: 76%) had a mp of 153.0-154.0° C. [M+H]$^+$ 281.18.

Example 11

Synthesis of 2-[4-(3-Cyclohexyl-ureido)-butyrylamino]-3-(4-hydroxy-phenyl)-propionic acid (632-Tyr)

To a solution of 632 (0.45 g, 2.0 mmol) and 1-ethyl-3-(3-(dimethylamino)-propyl) carbodiimide (0.5 g, 2.2 mmol) in 15 mL of DMF, 0.53 g (2.3 mmol) of tyrosine methyl ester and 2.4 mmol of diisopropylethylamine were added. The mixture was heated at 60° C. for 6 h. Then, 50 mL of 0.1 N NaOH were added and the mixture was left at room temperature overnight. The reaction mixture was then acidified with concentrated HCl and extracted twice with a 2:1 mixture of chloroform:methanol. The organic phases were pooled, dried and evaporated. The residue was purified by chromatography on a silica column (5×4 cm). Elution with a 75:25:1 mixture of ethyl acetate:methanol:acetic acid yielded 140 mg (yield: 18%) of the target product as a brown oily liquid. LC-MS-ES negative mode: 390.3 (100%, [M–H]–), 290.9 (10%, (M–C$_6$H10N]$^-$), 264.9 (5%, [M–C$_7$H$_{12}$NO]$^-$); positive mode: 392.5 (40%, [M+H]$^+$), 264.95 (100%, [M–C$_7$H$_{10}$NO]$^+$).

Example 12

Synthesis of 4-(3-Adamantan-1-yl-ureido) butyric Acid Methyl Ester (883)

The title compound was prepared by a procedure described in J. Med. Chem. 2004, 47, 2110. To a suspension of 4-aminobutyric acid (2.79 g, 27.1 mmol) in DMF (40 mL) was added 1-adamantyl isocyanate (1.20 g, 6.77 mmol) at room temperature. The reaction mixture was stirred for 24 h. Then 1 N HCl aqueous solution (40 mL) was added into the reaction, and the mixture was stirred for 30 min. The solid crystalline product was filtered and washed with water (20 mL) and ethyl acetate (20 mL). The resulting solid was dried in a vacuum oven to give 1.90 g (100%) of 4-(3-adamantan-1-yl-ureido)butyric acid 822 as a white solid: $^1$H NMR (CD$_3$OD): 1.66-1.75 (8H, m), 1.94-1.97 (6H, m), 2.05-2.07 (3H, m), 2.30 (2H, t, J=6.9 Hz), 3.08 (2H, q, J=6.9 Hz), 3.32 (2H, s); LC-MS (ESI) m/z calcd for C$_{15}$H$_{24}$N$_2$O$_3$ [M+H]$^+$ 281.18. found [M+H]$^+$ 281.25; mp 165 C. Anal. (C$_{15}$H$_{24}$N$_2$O$_3$) C, H, N.

A mixture of 4-(3-adamantan-1-yl-ureido)butyric acid 822 (0.15 g, 0.54 mmol), K$_2$CO$_3$ (0.09 g, 0.64 mmol), and iodomethane (0.04 mL, 0.59 mmol) in DMF (20 mL) was stirred at room temperature for 20 h. Then the product was extracted with ether (20 mL), and the ether was washed with 1 N NaOH aqueous solution (20 mL) and brine (20 mL), dried over Na$_2$SO$_4$, and evaporated to afford 0.15 g (95%) of 883: $^1$H NMR (CDCl$_3$) 1.66-1.68 (6H, m), 1.81 (2H, quint, J=6.9 Hz), 1.94-1.97 (6H, m), 2.05-2.07 (3H, m), 2.37 (2H, t, J=6.9 Hz), 3.16 (2H, q, J=6.9 Hz), 3.68 (3H, s), 4.09 (1H, s), 4.25 (1H, s); LC-MS (ESI) m/z calcd for C$_{16}$H$_{26}$N$_2$O$_3$ [M+H]$^+$ 295.19. found [M+H]$^+$ 295.24; mp 114 C. Anal. (C$_{16}$H$_{26}$N$_2$O$_3$) C, H, N.

Compounds 857, 876, 858, 877, and 878 were prepared in the same manner using the corresponding ethyl bromoalkanoates instead of iodomethane to yield 30-95%.

Example 13

Synthesis of 4-(3-Adamantan-1-yl-ureido) butyric Acid 3,7-Dimethyl-oct-6-enyl Ester (798)

To a solution of 4-(3-adamantan-1-yl-ureido)butyric acid 822 (0.10 g, 0.36 mmol), 4-(dimethylamino)pyridine (DMAP; 44 mg, 0.36 mmol), and 3,7-dimethyl-oct-6-en-1-ol (61 mg, 0.39 mmol) in methylene chloride (20 mL) was added 1-[3-(dimethylamino)propyl]-3-ethylcarbodiimide hydrochloride (EDCI; 75 mg, 0.39 mmol) at room temperature. After stirring for 12 h, the reaction mixture was washed with 1 N NaOH aqueous solution (15 mL) and water (30 mL), and the organic layer was dried over Na2SO4 and concentrated. The residue was purified by column chromatography on silica gel eluting with hexane and ethyl acetate (3:1) to give 798 (97 mg, 65%) as a solid: $^1$H NMR (CDCl$_3$) 0.91 (3H, d, J=6.9 Hz), 1.34-1.37 (2H, m), 1.56-1.60 (9H, m), 1.67-1.69 (8H, m), 1.81 (2H, quint, J=6.9 Hz), 1.94-1.97 (6H, m), 2.05-2.07 (3H, m), 2.35 (2H, t, J=6.9 Hz), 3.16 (2H, q, J=6.9 Hz), 4.05 (1H, s), 4.11 (2H, t, J=6.9 Hz), 4.21 (1H, s), 5.09 (1H, t, J=6.9 Hz); LC-MS (ESI) m/z calcd for C$_{25}$H$_{42}$N$_2$O$_3$ [M+H]$^+$ 419.32. found [M+H]⁺ 419.22; mp 49 C. Anal. Calcd for C$_{25}$H$_{42}$N$_2$O$_3$: C, 71.73; H, 10.11; N, 6.69. Found: C, 70.27; H, 9.83; N, 6.39.

Example 14

Synthesis of 8-[4-(3-Adamantan-1-yl-ureido)butyryloxy]octanoic Acid Ethyl Ester (879)

To a solution of 8-bromooctanoic acid (0.20 g, 0.89 mmol), DMAP (0.12 g, 0.99 mmol), and ethanol (0.05 g, 0.99 mmol) in methylene chloride (20 mL) was added EDCI (0.19 g, 0.99 mmol) at room temperature. After stirring for 12 h, the reaction mixture was washed with 1 N NaOH aqueous solution (15 mL) and water (30 mL), and the organic layer was dried over Na$_2$SO$_4$ and evaporated to give 8-bromooctanoic acid ethyl ester (0.17 g, 75%). This bromide reacted with 4-(3-adamantan-1-yl-ureido)butyric acid 822 in the same manner as that used for the preparation of 883 to provide 879 (0.19 g, 65%) as a solid: ¹H NMR (CDCl$_3$) 1.26 (3H, t, J=6.9 Hz), 1.32-1.35 (6H, m), 1.59-1.66 (10H, m), 1.82 (2H, quint, J=6.9 Hz), 1.94-1.97 (6H, m), 2.05-2.07 (3H, m), 2.28 (2H, t, J=6.9 Hz), 2.36 (2H, t, J=6.9 Hz), 3.16 (2H, q, J=6.9 Hz), 4.05-4.14 (5H, m), 4.31 (1H, s); LC-MS (ESI) m/z calcd for C$_{25}$H$_{42}$N$_2$O$_5$ [M+H]⁺ 451.31. found [M+H]⁺ 451.20; mp 58-59 C. Anal. (C$_{25}$H$_{42}$N$_2$O$_5$) C, H, N.

Example 15

Synthesis of 10-[4-(3-Adamantan-1-yl-ureido)butyryloxy]decanoic Acid Ethyl Ester (880)

A mixture of 10-hydroxydecanoic acid (0.25 g, 1.33 mmol; 11-hydroxyundecanoic acid for compound 881 and 12-hydroxydodecanoic acid for compound 882), ethyl bromide (0.16 g, 1.46 mmol), and lithium carbonate (0.11 g, 1.46 mmol) in DMF (25 mL) was stirred at 70 C for 6 h. Then the product was extracted with ether (30 mL), and the ether solution was washed with 1 N NaOH aqueous solution (20 mL) and water (30 mL), dried over Na$_2$SO$_4$, and concentrated. The residue was purified by column chromatography on silica gel eluting with hexane and ethyl acetate (3:1) to give 10-hydroxydecanoic acid ethyl ester (80 mg, 28%). This alcohol was coupled with 4-(3-adamantan-1-yl-ureido)butyric acid 822 by using EDCI/DMAP coupling reagent to give 880 (0.11 g, 60%) as a solid: ¹H NMR (CDCl$_3$) 1.24-1.32 (13H, m), 1.62-1.68 (10H, m), 1.80 (2H, quint, J=6.9 Hz), 1.94-1.97 (6H, m), 2.05-2.07 (3H, m), 2.28 (2H, t, J=6.9 Hz), 2.36 (2H, t, J=6.9 Hz), 3.16 (2H, q, J=6.9 Hz), 4.05-4.14 (5H, m), 4.25 (1H, s); LC-MS (ESI) m/z calcd for C$_{27}$H$_{46}$N$_2$O$_5$ [M+H]⁺ 479.34. found [M+H]⁺ 479.29; mp 60-61 C. Anal. Calcd for C$_{27}$H$_{46}$N$_2$O$_5$: C, 67.75; H, 9.69; N, 5.85. Found: C, 68.33; H, 9.92; N, 5.97.

Compound 4-(3-adamantan-1-yl-ureido)butyric acid 822 was coupled with 11-hydroxyundecanoic acid ethyl ester and 12-hydroxydodecanoic acid ethyl ester prepared from corresponding acids to get compounds 881 and 882, respectively.

Example 16

Synthesis of 4-[4-(3-Adamantan-1-yl-ureido)butyryloxymethyl]benzoic Acid Ethyl Ester (849)

A mixture of 4-formylbenzoic acid (1.00 g, 6.66 mmol), bromoethane (1.09 g, 9.99 mmol), and K$_2$CO$_3$ (1.10 g, 7.99 mmol) in acetonitrile (30 mL) was refluxed for 6 h. After evaporation of the solvent, 4-formylbenzoic acid ethyl ester was extracted with ether (30 mL), and the organic solution was washed with 1 N NaOH aqueous solution (20 mL) and water (30 mL), dried over Na$_2$SO$_4$, and concentrated to give the ethyl ester product (0.65 g, 55%). Without further purification, to a solution of the ester was added sodium borohydride (NaBH$_4$; 0.05 g, 3.65 mmol) in ethanol (20 mL) at 0 C. After stirring for 5 h at room temperature, the product was extracted with ether (30 mL), and the ether solution was washed with water (30 mL), dried over Na$_2$SO$_4$, and concentrated. The residue was purified by using column chromatography on silica gel eluting with hexane and ethyl acetate (3:1) to give 4-hydroxymethylbenzoic acid ethyl ester (0.30 g, 46%) as an oil.

To a solution of 4-(3-adamantan-1-yl-ureido)butyric acid 822 (1.23 g, 0.83 mmol), DMAP (0.05 g, 0.42 mmol), and the above alcohol (0.15 g, 0.83 mmol) in methylene chloride (30 mL) was added EDCI (0.16 g, 0.83 mmol) at room temperature. After stirring for 12 h, the reaction mixture was washed with 1 N NaOH aqueous solution (15 mL) and water (30 mL), and the organic layer was dried over Na$_2$SO$_4$ and concentrated. Then the residue was purified by column chromatography on silica gel eluting hexane and ethyl acetate (5:1) to provide 849 (0.28 g, 75%) as a white solid: ¹H NMR (CDCl$_3$) 1.40 (3H, t, J=6.9 Hz), 1.66-1.68 (6H, m), 1.84 (2H, quint, J=6.9 Hz), 1.94-1.96 (6H, m), 2.05-2.07 (3H, m), 2.44 (2H, t, J=6.9 Hz), 3.17 (2H, q, J=6.9 Hz), 4.02 (1H, s), 4.17 (1H, s), 4.38 (2H, q, J=6.9 Hz), 5.17 (2H, s), 7.40 (2H, d, J=7.8 Hz), 8.00 (2H, d, J=7.8 Hz); LC-MS (ESI) m/z calcd for C$_{25}$H$_{34}$N$_2$O$_5$ [M+H]⁺ 443.25. found [M+H]⁺ 443.25; mp 96-99 C. Anal. (C$_{25}$H$_{34}$N$_2$O$_5$) C, H, N.

Example 17

Synthesis of 4-(3-Adamantan-1-yl-ureido)butyric Acid 4-Ethoxycarbonylmethylphenyl Ester (852)

To a solution of 4-(3-adamantan-1-yl-ureido)butyric acid 822 (0.15 g, 0.54 mmol), DMAP (0.07 g, 0.54 mmol), and 4-hydroxyphenylacetic acid (0.09 g, 0.59 mmol) in methylene chloride (20 mL) was added EDCI (0.11 g, 0.59 mmol) at room temperature. After stirring for 12 h, the reaction mixture was washed with water (20 mL), and the methylene chloride solution dissolving the product was dried over Na$_2$SO$_4$ and concentrated to give conjugated product. This crude mixture in DMF (30 mL) was treated with bromoethane (0.15 g, 1.34 mmol) and K$_2$CO$_3$ (0.18 g, 1.34 mmol) at room temperature and stirred for 12 h at room temperature. The ethyl ester product was extracted with ether (30 mL), and the ether solution was washed with 1 N NaOH aqueous solution (20 mL) and water (30 mL), dried over Na$_2$SO$_4$, and concentrated. The residue was purified by column chromatography on silica gel eluting hexane and ethyl acetate (5:1) to give 852 (47 mg, 20%) as a white solid: ¹H NMR (CDCl$_3$) 1.40 (3H, t, J=6.9 Hz), 1.66-1.68 (6H, m), 1.89-1.95 (8H, m), 2.05-2.07 (3H, m), 2.62 (2H, t, J=6.9 Hz), 3.25 (2H, q, J=6.9 Hz), 3.60 (2H, s), 4.07 (1H, s), 4.16 (2H, q, J=6.9 Hz), 4.29 (1H, s), 7.08-7.10 (2H, m), 7.28-7.30 (2H, m); LC-MS (ESI) m/z calcd for C$_{25}$H$_{34}$N$_2$O$_5$ [M+H]⁺ 443.25. found [M+H]⁺ 443.25; mp 95-97 C. Anal. (C$_{25}$H$_{34}$N$_2$O$_5$) C, H, N.

Compound 851 was prepared in the same manner by using 4-hydroxyphenylacrylic acid instead of 4-hydroxyphenylacetic acid.

Example 18

Synthesis of N-[12-(3-Adamantan-1-yl-ureido)dodecanoyl]methanesulfonamide (848)

To a solution of compound 687 (0.2 g, 0.51 mmol) and N-hydroxysuccinimide (60 mg, 0.56 mmol) in THF (10 mL) was added 1,3-dicyclohexylcarbodiimide (0.12 g, 0.56 mmol) at room temperature. The reaction mixture was stirred for 12 hrs and filtered. And then, the filtrate was purified by column chromatography (hexane:ethyl acetate=1:1) to give 2,5-dioxopyrrolidinyl ester (I) (0.18 g, 0.37 mmol) in 72% yield. To this intermediate (I) dissolved in HMPA (10 mL) was added portionwise 4-dimethylaminopyridine (54 mg, 0.44 mmol; DMAP) and methanesulfonamide (0.35 g, 3.7 mmol). After stirring for 2 hrs at 90° C., the product was extracted with ether (30 mL) and washed with water (30 mL). The organic solution was dried over magnesium sulfate and evaporated, and then the residue was purified using column chromatography eluting with hexane and ethyl acetate (1:1) to afford compound 848 (0.16 g, 0.34 mmol) in 92% yield. $^1$H NMR δ (CDCl$_3$) 1.23-1.35 (12H, m), 1.44-1.52 (4H, m), 1.57-1.61 (2H, m), 1.65-1.69 (6H, m), 1.92-1.98 (6H, m), 2.07-2.09 (3H, m), 2.38 (2H, t, J=6.9 Hz), 3.11 (2H, q, J=6.9 Hz), 3.20 (3H, s), 4.40 (1H, s), 4.48 (1H, s), 10.52 (1H, s), LC-MS (ESI) m/z calcd for C$_{24}$H$_{43}$N$_3$O$_4$S [M+H]$^+$ 469.30. found [M+H]$^+$, mp 103° C., Anal. (C$_{24}$H$_{43}$N$_3$O$_4$S) C, H, N.

Compound 914 was synthesized with the same method used for the preparation of compound 687 using benzenesulfonamide instead of methanesulfonamide. $^1$H NMR δ (CDCl$_3$) 1.23-1.35 (12H, m), 1.44-1.52 (4H, m), 1.57-1.61 (2H, m), 1.65-1.69 (6H, m), 1.94-1.98 (6H, m), 2.06-2.09 (3H, m), 2.28 (2H, t, J=6.9 Hz), 3.10 (2H, q, J=6.9 Hz), 4.39 (1H, s), 4.93 (1H, s), 5.45 (1H, s), 7.50-7.55 (2H, m), 7.60-7.62 (1H, m), 7.80-7.83 (1H, m), 8.05-8.08 (1H, m), LC-MS (ESI) m/z calcd for C$_{29}$H$_{45}$N$_3$O$_4$S [M+H]$^+$ 532.31. found [M+H]$^+$ 532.34, mp 100° C., Anal. (C$_{29}$H$_{45}$N$_3$O$_4$S) C, H, N.

Example 19

Synthesis of 2-[12-3-(Adamantan-1-yl-ureido)dodecanoylamino]decanoic acid (1001)

Sodium metal (3.9 g, 0.17 mol) was dissolved in ethanol (100 mL) under an inert atmosphere in a round bottom flask fitted with a water condenser. Diethyl acetamido malonate (30.4 g, 0.14 mol) was then added followed by 1-bromooctane (36.7 g, 0.19 mol). The solution was refluxed overnight under an inert atmosphere. The reaction mixture was poured onto crushed ice (600 mL) and stirred. The aminodiester product precipitated and was collected by filtration. The crude product was then refluxed overnight in a solution HCl:DMF (9:1, 200 mL). The precipitated product was collected by filtration, washed with ice water, and air dried in a vacuum desiccator to afford the α-amino acid hydrochloride in >90% crude yield. The crude amino acid (3.0 g, 24.8 mmol) was then dissolved in methanol (100 mL) and cooled to 0° C. Thionyl chloride (5.0 mL, 25.8 mmol) was added dropwise, and the reaction was stirred at 0° C. for 10 minutes and then refluxed overnight. The reaction was cooled to room temperature and the volatiles removed under reduced pressure, and the crude product was triturated in methanol to afford racemic methyl 2-amino decanoate, 4.44 g, 89% yield.

Compound 687 (1.04 g, 2.65 mmol) and HBTU (1.0 g, 2.64 mmol) were dissolved in THF (60 mL). DIEA (0.5 mL, 2.87 mmol), DMF (~2 mL), and methyl 2-amino decanoate (1.26 g, 5.30 mmol) were added, and the solution was stirred under N$_2$ at room temperature overnight. The yellow oil produced was diluted with 5% citric acid (100 mL) and extracted with ethyl acetate (3×50 mL). Organic layers were combined and washed with 5% citric acid (2×50 mL), saturated sodium bicarbonate (NaHCO$_3$) (2×50 mL), and brine (1×50 mL). The organic layer was dried over magnesium sulfate and evaporated to yield an oil. The crude product was purified by column chromatography with 1-2% MeOH/DCM to yield a methyl ester as a yellow oil (0.77 g, 66% yield). The methyl ester (0.77 g, 1.34 mmol) was dissolved in DME (25 mL) and water (10 mL). Solid LiOH.H$_2$O (0.33 g, 7.86 mmol) was added, and the solution was stirred at room temperature overnight. Reaction mixture was acidified (pH=4) with 5% citric acid (~20 mL), and the product was extracted with ethyl acetate (3×30 mL). Combined organic layers were washed with brine (30 mL), dried over MgSO$_4$, filtered, and evaporated to yield compound 1001 as a yellow oil (0.34 g, 45% yield). $^1$H NMR δ (CDCl$_3$) 0.82 (3H, t, J=7 Hz), 1.16-1.23 (28H, bm), 1.41 (2H, m), 1.57 (2H, bm), 1.60 (6H, bs), 1.89 (6H, bs), 2.01 (3H, bs), 2.18 (2H, t, J=7 Hz), 2.98 (2H, m), 4.52 (1H, dd, J=7.3, 13.3 Hz), 6.46 (2H, d, J=7.6 Hz) 8.16 (1H, bs). $^{13}$C NMR δ (CDCl$_3$) 14.0, 22.5, 25.0, 25.6, 26.7, 28.85, 28.00, 29.06, 29.10, 29.13, 29.24, 29.31, 29.44, 29.56, 31.73, 32.22, 36.27, 36.41, 40.68, 42.29, 50.96, 52.31, 158.70, 173.65, 175.39. LC-MS (ESI) m/z calcd for C$_{33}$H$_{59}$N$_3$O$_4$ [M+H]$^+$ 562.45. found [M+H]$^+$ 562.51.

Example 20

Synthesis of 12-(3-Adamantan-1-yl-ureido)dodecanoic acid [1-(2,3,4-trihydroxy-5-hydroxymethyl-cyclohexylcarbamoyl)nonyl]amide (1002)

1,2,3,4,6-Penta-O-acetyl-α-D-glucopyranose (5.00 g, 12.8 mmol) was dissolved in 10-15 mL dry CH$_2$Cl$_2$ under an inert atmosphere. Trimethylsilyl azide (4.24 mL, 32.1 mmol) and tin (IV) chloride (0.75 mL, 6.41 mmol) were added, and the reaction was stirred for 18 hours at room temperature. The reaction mixture was diluted with CH$_2$Cl$_2$ (30 mL) and washed twice with saturated NaHCO$_3$ (20 mL) and with brine (20 mL). The organic phase was dried, filtered and concentrated to leave 2,3,4,6-tetra-O-acetyl-α-D-glucopyranosyl azide as a white solid (3.92 g, 82%). 2,3,4,6-tetra-O-acetyl-α-D-glucopyranosyl azide (0.30 g, 80 mmol) was then dissolved in dry THF (15 mL), and Pd/C was added (~5%) to this solution. The mixture was stirred under H$_2$ overnight. TLC revealed the reduction was completed (Rfazide=0.80, Rfamine=0.10). In a separate flask, compound 23 (0.17 g, 0.30 mmol) and 0.5 M HBTU in DMF (1.20 mL, 0.60 mmol) were combined, followed by the addition of DMF (~2 mL) and DIEA (104 μL, 0.60 mmol). This solution was then added to the reaction flask, and the reaction mixture was stirred under N$_2$ overnight. The resulting suspension was filtered through celite which was washed well with ethyl acetate (~100 mL), and the filtrate was washed with 5 M HCl (50 mL), saturated NaHCO3 (2×50 mL), and brine (1×50 mL). The organic solution was dried over magnesium sulfate, filtered, and concentrated. The residue was purified using a silica gel column chromatography with 10% MeOH/DCM to yield V (0.16 g, 59.33). 1H NMR δ (CDCl$_3$) 0.78 (3H, t, J=7 Hz), 1.16-1.23 (32H, brm), 1.35 (2H, m) 1.52 (2H, m) 1.57 (6H, brs), 1.86 (6H, brs), 1.91-2.00 (15H, m), 2.14 (2H, m), 2.99 (2H, t, J=7 Hz), 3.75 (2H, m), 3.95-4.07 (3H, m), 4.15-4.29 (4H, m), 4.43-4.38 (1H, m) 4.80 (1H, dd, J=5, 11 Hz), 4.84-4.89 (2H, m), 4.95-5.02 (3H, m), 5.12-5.24 (3H, m), 5.35 (1H, d, J=3 Hz), 5.47 (1H, t, J=9.8 Hz), 6.28 (1H, dd, J=7.6, 19 Hz), 6.60 (1H, d, J=9.3 Hz), 7.18 (1H, d, J=9.1 Hz), 7.34 (1H, d, J=9.1

Hz). LC-MS (ESI) m/z calcd for $C_{47}H_{78}N_4O_{12}$ [M+H]$^+$ 891.56. found [M+H]$^+$ 891.69.

To a solution of V (0.16 g, 0.18 mmol) in MeOH (15 mL) was added sodium metal (0.05 g), and the mixture was stirred at room temperature overnight. The reaction mixture was filtered through amberlite and washed with MeOH (~150 mL). The solvent was evaporated under vacuum to produce compound 1002 as a fine white powder (0.12 g, 95%). LC-MS (ESI) m/z calcd for $C_{39}H_{70}N_4O_8$ [M+H]$^+$ 724.50. found [M+H]$^+$ 724.6.

Compound 798 was prepared with the same method as that used for the preparation of compound 1002 from compound 687 instead of compound 1001.

Example 21

Synthesis of 5-(3-Chloro-phenylcarbamoyl)pentanoic Acid Pentyl Ester (987)

To a solution of adipic acid (0.5 g, 3.42 mmol) and DMAP (0.42 g, 3.42 mmol) in dichloromethane (30 mL) and DMF (3 mL) was added 3-chloroaniline (0.44 g, 3.42 mmol) at room temperature. After stirring 10 min, 1-[3-(dimethylamino)propyl]-3-ethylcarbodiimide hydrochloride (0.65 g, 3.42 mmol; EDCI) was added portionwise to the mixture at room temperature. The reaction was stirred for 12 h. A 1 N aqueous HCl solution (20 mL) was poured into the reaction mixture, and 5-(3-chlorophenylcarbomoyl)pentanoic acid was extracted with dichloromethane (30 mL). The organic solution was washed with water (50 mL), dried over $Na_2SO_4$, and concentrated. This residue was used for the next reaction without further purification.

To the solution of the above carbamoylpentanoic acid (0.72 g, 2.80 mmol) in DMF (15 mL) was added $K_2CO_3$ (0.58 g, 4.21 mmol) and 1-bromopentane (0.64 g, 4.21 mmol) at room temperature. After stirring for 12 h, the product was extracted with ether (30 mL), and the ether solution was washed with an aqueous solution of 1 N NaOH (15 mL) and water (40 mL), dried over $Na_2SO_4$, and concentrated. The residue was purified using silica gel column chromatography (hexane:ethyl acetate=5:1) to afford 987 (0.59 g, 65%): $^1$H NMR (CDCl$_3$) 0.91 (3H, t, J=6.9 Hz), 1.29-1.37 (4H, m), 1.60-1.66 (2H, m), 1.70-1.78 (4H, m), 2.35-2.43 (4H, m), 4.08 (H, t, J=6.9 Hz), 7.05-7.09 (1H, m), 7.21-7.23 (1H, m), 7.37-7.40 (1H, m), 7.52-7.55 (1H, s), 7.68 (1H, s); LC-MS (ESI) m/z calcd for $C_{17}H_{24}ClNO_3$ [M+H]$^+$ 326.14. found [M+H]$^+$ 326.16, mp 82 C. Anal. ($C_{17}H_{24}ClNO_3$) C, H, N.

Compound 13 was prepared with the same method used for the preparation of compound 987 using adamantylamine instead of 3-chloroaniline: $^1$H NMR (CDCl$_3$) 0.91 (3H, t, J=6.9 Hz), 1.29-1.43 (4H, m), 1.64-1.69 (12H, m), 1.94-1.98 (6H, m), 2.06-2.13 (5H, m), 2.32 (2H, t, J=6.9 Hz), 4.06 (H, t, J=6.9 Hz), 5.16 (1H, s); LC-MS (ESI) m/z calcd for $C_{21}H_{35}NO_3$ [M+H]$^+$ 350.26. found [M+H]$^+$ 350.30. Anal. ($C_{21}H_{35}NO_3$) C, H, N.

Example 22

Synthesis of 4-(2-Chloro-phenyl)acethylaminolbutyric Acid Pentyl Ester (988)

To a solution of 3-chlorophenylacetic acid (0.5 g, 2.93 mmol) and DMAP (0.36 g, 2.93 mmol) in dichloromethane (30 mL) was added ethyl 4-aminobutyrate hydrochloride (0.49 g, 2.93 mmol) at room temperature. After stirring for 10 min, EDCI (0.56 g, 2.93 mmol) was added portionwise to the mixture at room temperature. The reaction was stirred for 12 h. A 1 N aqueous HCl solution (20 mL) was poured into the reaction mixture, and 4-[2-(3-chlorophenyl)acetylamino]butyric acid ethyl ester was extracted with ether (30 mL). The ether solution was washed with water (50 mL), dried over Na2SO4, and concentrated. To the residue dissolved in ethanol (10 mL) was added 1 N aqueous NaOH solution (6 mL), and after 12 h of stirring at room temperature, the product was extracted with dichloromethane (30 mL). The organic solution was washed with water (30 mL), dried over $Na_2SO_4$, and concentrated to give 4-[2-(3-chlorophenyl)acetylamino]butyric acid (0.6 g, 80%). A mixture of this acid (0.6 g, 2.35 mmol), $K_2CO_3$ (0.49 g, 3.52 mmol), and 1-bromopentane (0.53 g, 3.52 mmol) in DMF (20 mL) was stirred overnight at room temperature. The product was extracted with ether (40 mL), and the ether solution was washed with water (50 mL), dried over $Na_2SO_4$, and concentrated. The residue was purified using silica gel column chromatography (hexane:ethyl acetate=3:1) to afford 988 as an oil (0.74 g, 97%): $^1$H NMR (CDCl$_3$) 0.91 (3H, t, J=6.9 Hz), 1.26-1.33 (4H, m), 1.59-1.63 (2H, m), 1.80 (2H, quint, J=6.9 Hz), 2.31 (2H, t, J=6.9 Hz), 3.27 (2H, q, J=6.9 Hz), 3.52 (2H, s), 4.04 (2H, t, J=6.9 Hz), 5.72 (1H, s), 7.13-7.17 (2H, m), 7.27-7.30 (2H, m); LC-MS (ESI) m/z calcd for $C_{17}H_{24}ClNO_3$ [M+H]$^+$ 326.14. found [M+H]$^+$ 326.15. Anal. ($C_{17}H_{24}ClNO_3$) C, H, N.

Compounds 837 and 1068 were prepared with the same method used for the preparation of compound 988 using 1-adamantylacetic acid or adamantane-1-carboxylic acid instead of 3-chlorophenylacetic acid. Compound 837: 1H NMR (CDCl3) 0.91 (3H, t, J=6.9 Hz), 1.29-1.35 (4H, m), 1.35-1.72 (14H, m), 1.84 (2H, quint, J=6.9 Hz), 1.91 (2H, s), 1.97 (3H, m), 2.37 (2H, t, J=6.9 Hz), 3.29 (2H, q, J=6.9 Hz), 4.07 (2H, t, J=6.9 Hz), 5.66 (1H, s); LC-MS (ESI) m/z calcd for $C_{21}H_{35}NO_3$ [M+H]$^+$ 350.26. found [M+H]$^+$ 350.29. Anal. ($C_{21}H_{35}NO_3$) C, H, N.

Compound 1068: $^1$H NMR (CDCl$_3$) 0.91 (3H, t, J=6.9 Hz), 1.29-1.35 (4H, m), 1.60-1.86 (16H, m), 2.03 (3H, m), 2.35 (2H, t, J=6.9 Hz), 3.29 (2H, q, J=6.9 Hz), 4.07 (2H, t, J=6.9 Hz), 5.85 (1H, s); LC-MS (ESI) m/z calcd for $C_{20}H_{33}NO_3$ [M+H]$^+$ 336.25. found [M+H]$^+$ 336.34. Anal. ($C_{20}H_{33}NO_3$) C, H, N.

Example 23

Synthesis of 4-(3-Chloro-phenylcarbamoyloxy)butyric Acid Pentyl Ester (825)

To a solution of succinic anhydride (3.58 g, 35.7 mmol) and DMAP (4.16 g, 34.0 mmol) in DMF (40 mL) was added pentanol (3.0 g, 34.0 mmol) at room temperature under nitrogen. After stirring for 12 h, succinic acid pentyl ester was extracted with ether (40 mL), and the ether solution was washed with 1 N aqueous HCl solution (20 mL) and water (40 mL), dried over sodium sulfate ($Na_2SO_4$), and concentrated. The residue was purified by column chromatography on silica gel eluting with hexane and ethyl acetate (3:1) to give the succinic acid pentyl ester (6.07 g, 95%) as an oil. To the solution of this acid in tetrahydrofuran (THF, 60 mL) was added 1 M BH$_3$-THF complex (64.53 mL, 64.5 mmol) at –10 C under nitrogen, and the reaction mixture was allowed to warm to room temperature with stirring. After stirring for 12 h at room temperature, 5% NaHCO$_3$ aqueous solution (50 mL) was added to the reaction and then the reduced alcohol (I) was extracted with ethyl acetate (50 mL). The ethyl acetate solution was dried over Na$_2$SO$_4$ and concentrated to give 4-Hydroxybutyric acid pentyl ester (5.06 g, 90%).

4-Hydroxybutyric acid pentyl ester (100 mg, 0.57 mmol) was added to a solution of 3-chlorophenyl isocyanate (88 mg, 0.57 mmol) and triethylamine (0.12 mL, 0.86 mmol; TEA) in DMF (15 mL) at room temperature. The mixture was allowed to stand at room temperature for 12 h, the product was extracted with ether (20 mL), and the ether solution was washed with 1 N aqueous HCl solution (20 mL) and water (30 mL), dried over Na$_2$SO$_4$, and concentrated. The residue was purified by column chromatography on silica gel eluting with hexane and ethyl acetate (5:1) to afford 9 (94 mg, 50%) as a solid: $^1$H NMR (CDCl$_3$) 0.90 (3H, t, J=6.9 Hz), 1.26-1.34 (4H, m), 1.62-1.65 (2H, m), 1.71 (2H, quint, J=6.9 Hz), 2.66 (2H, t, J=6.9 Hz), 2.74 (2H, q, J=6.9 Hz), 4.10 (2H, t, J=6.9 Hz), 7.05-7.08 (1H, m), 7.18-7.22 (3H, m), 7.35 (1H, s); LC-MS (ESI) m/z calcd for C$_{16}$H$_{22}$ClNO$_4$ [M+H]$^+$ 328.12. found [M+H]$^+$ 328.13; mp 82 C. Anal. (C$_{16}$H$_{22}$ClNO$_4$) C, H, N.

Example 24

Synthesis of 1-(3-Chloro-phenyl)-3-(1-hydroxymethyl-pentyl)-urea (978)

2-aminohexanol hydrochloride (211 mg, 1.37 mmol), m-chlorophenyl isocyanate (211 mg, 1.37 mmol) were combined in THF (10 mL) with triethylamine (228 µL) and stirred over night. The solvent was removed and the residue chromatographed on silica gel to give 343 mg of the target product (93%). $^1$H NMR (300 MHz, CDCl$_3$/MeOH d4 1:1) δ=7.50-7.47 (m, 1H), 7.20-7.10 (m, 2H), 6.93 (dt, J=6.6, 1.6 Hz, 1H), 5.76 (d, J=8.2 Hz, 1H), 3.75 (br, 1H), 3.65-3.45 (m, 2H), 1.60-1.20 (m, 6H), 1.87 (m, 3H).

Compound 977 were prepared in the same manner using aminoalcohol and cyclohexylisocyanate.

Synthesis of 1-(3-Chloro-phenyl)-3-(1-hydroxymethyl-butyl)-urea (977)

$^1$H NMR (300 MHz, CDCl$_3$) δ=5.41 (m, 2H), 3.8-3.2 (m, 4H), 2.00-0.90 (m, 20H)

Example 25

Synthesis of (4-Butyl-4,5-dihydro-oxazol-2-yl)-(3-chloro-phenyl)-amine (980)

Compound 978 (50 mg) was treated with POCl$_3$ (1.0 mL). This was stirred overnight. The solvent was removed via reduced pressure distillation. The residue was washed with aqueous sodium bicarbonate and then dissolved in EtOAc. The solvent was dried, filtered and evaporated. The residue was dissolved in acetone (1 mL) and refluxed with water (2 mL) for 1.5 hrs. The solution was extracted with EtOAc, the organic layer evaporated and the residue chromatographed on silica to give the target compound. $^1$H NMR (300 MHz, CDCl$_3$) δ=7.38 (s, 1H), 7.15 (d, J=8.0 Hz, 1H), 7.05 (br, 1H), 7.00 (d, 7.5 Hz, 1H), 4.47 (m, 1H), 3.95 (m, 2H), 1.8-1.2 (m, 6H), 0.95 (m, 3H). ESIMS=224.9 m/z (M+H)

Example 26

Synthesis of (994)

Methylaminopentanoate hydrochloride (720 mg, 4.3 mmol) and benzophenoneimine (722 mg, 4.3 mmol) were stirred together in dichloromethane for 18 hrs. At this point, the reaction was washed with aqueous sodium bicarbonate and the organic layer dried with MgSO4 and evaporated to leave 1.3 g of a thick oil. The product (530 mg, 1.8 mmol) was then dissolved in THF (15 mL) and cooled (under N$_2$) to −78° C. DIBAL (2.0 mL, 1 M solution) was added dropwise and the reaction stirred for 1 hr. When TLC indicated the absence of the ester starting material and the presence of a aldehyde (via DNP stain), 1.3 eq of butyl magnesium bromide was added to the reaction. This was allowed to warm to room temperature over 2.5 hrs. The reaction was quenched with bicarbonate solution and the organic layer was dried and evaporated to give the imino alcohol (350 mg) as an oil. The imino alcohol (150 mg) was stirred with aqueous HCl (1M, 1 mL) and diethyl ether (5 mL) overnight. The aqueous layer was evaporated and 1 equivalent of 1-adamantylisocyanate was added as a solution in dichloromethane (5 ml) and triethylamine (0.5 mL). This was stirred overnight. The crude reaction was chromatographed on silica gel (1:1 EtOAc:hexanes) to give the product as an oil (35 mg). $^1$H NMR (300 MHz, CDCl$_3$) δ=4.22 (br, 1H), 4.08 (br, 1H), 3.91 (br, 1H), 3.10 (m, 1H), 2.30 (br, 2H), 2.2-1.0 (br m, 32H)

Example 27

Synthesis of (996)

Dodecylamine (500 mg, 2.7 mmol) was added to a biphasic system of dichloromethane (20 mL) and aqueous bicarbonate (20 mL, satd). The mixture was stirred while triphosgene (264 mg, 0.9 mmol) was added. The reaction was stirred for 2 hrs. The organic layer was removed and filtered through a plug of silica gel using EtOAc as the eluent. Evaporation of the solvent lead to 564 mg of the corresponding isocyanate. The isocyanate (1 eq) was combined with the amine (15 mg, 0.048 mmol) in dichloromethane. This was stirred overnight. The reaction was loaded onto silica gel and chromatographed using EtOAc to yield the product (22 mg, 89%) as an orange solid. $^1$H NMR (300 MHz, CDCl$_3$) δ=7.69 (d, J=8.3 Hz, 1H), 5.81 (d, J=8.3 Hz, 1H), 5.15 (d, J=6.72 Hz, 1H), 4.70 (m, 1H), 4.60 (m, 1H), 4.00-3.5 (br, 2H), 3.30 (t, J=6.7 Hz, 2H), 3.17 (q, J=6.6 Hz, 2H), 2.4-2.0 (m, 2H), 1.9-0.9 (br m, 32H). ESIMS=523 m/z (M+H)

Example 28

Synthesis of (997)

12-aminododecanol (50 mg) was stirred in dichloromethane with 1-adamantylisocyanate (44 mg) overnight. The reaction was evaporated and carbonyldiimidazole was added in 2 mL acetonitrile. This was refluxed 5 hrs. The solvent was removed in vacuo and the solid was partitioned between dichloromethane and water. The organic layer was washed repeatedly with water to yield the target compound (22 mg). $^1$H NMR (300 MHz, CDCl$_3$) δ=8.17 (s, 1H), 7.45 (s, 1H), 7.05 (s, 1H), 4.41 (t, J=7.5 Hz, 2H), 4.32 (br, 1H), 4.21 (br, 1H), 3.08 (q, J=6.7 Hz, 2H), 2.0-1.0 (m, 35H).

Example 29

General Procedure for the Synthesis of Trans-Benzyloxy Isomers

Synthesis of trans-1-(4-Benzyloxy-cyclohexyl)-3-tricyclo[3.3.1.1 3,7]decan-1-yl-urea 1032

Synthesis of trans-1-(4-Hydroxy-cyclohexyl)-3-tricyclo[3.3.1.1 3,7]decan-1-yl-urea 1039

To a solution of 1-adamantyl isocyanate (10 g, 56.4 mmol) and trans-4-aminocyclohexanol hydrochloride (10.3 g, 67.7 mmol) in DMF (300 mL) was added triethylamine (6.9 g, 67.7 mmol) at 0° C. The reaction mixture was stirred overnight. The reaction mixture was poured into water, and the resulting precipitates were collected and washed with water. The crude product was recrystallized from methanol/water. Yield: 15.5 g (94% of theory). M.P.: 254° C. $^1$H NMR (300 MHz, DMSO-$d_6$): δ 5.48 (d. J=9 Hz, 1H), 5.38 (s, 1H), 4.48 (d, J=4.7 Hz, 1H), 3.42-3.28 (m, 1H), 3.28-3.13 (m, 1H), 2.02-1.93 (m, 3H), 1.87-1.68 (m, 9H), 1.63-1.54 (m, 7H), 1.24-0.93 (4H).

Synthesis of trans-1-(4-Benzyloxy-cyclohexyl)-3-tricyclo[3.3.1.1$^{3,7}$]decan-1-yl-urea 1032

To a solution of compound 1 in DMF (10 mL) was added 60% sodium hydride in oil (60 mg, 1.5 mmol) at 0° C. After 10 min, benzyl bromide (0.20 g, 1.2 mmol) was introduced and then warmed up to room temperature and stirred overnight. The reaction was quenched by adding water and the resulting white precipitates were collected and washed with water. The solids were recrystallized from DCM/hexanes. Yield: 0.35 g (92% of theory). M.P.: 244° C. $^1$H NMR (300 MHz, CDCl$_3$): δ 7.40-7.23 (m, 5H), 4.52 (s, 2H), 4.10-3.92 (m, 2H), 3.58-3.41 (m, 1H), 3.37-3.24 (m, 1H), 2.11-1.81 (m, 13H), 1.50-1.33 (m, 6H), 1.50-1.33 (m, 2H), 1.17-0.99 (m, 2H).

Example 30

General Procedure for the Synthesis of Cis-Benzyloxy Isomers

Synthesis of cis-1-(4-Benzyloxy-cyclohexyl)-3-tricyclo[3.3.1.1$^{3,7}$]decan-1-yl-urea 1078

Synthesis of trans-4-Nitro-benzoic acid 4-(1,3-dioxo-1,3-dihydro-isoindol-2-yl)-cyclohexyl ester To a solution of trans-2-(4-Hydroxy-cyclohexyl)-isoindole-1,3-dione (38 g, 154.9 mmol), triphenylphosphine (65 g, 248 mmol), and 4-nitrobenzoic acid (41.4 g, 248 mmol) in 1500 mL of THF was added dropwise diisopropyl azodicarboxylate (50.1 g, 248 mmol) at room temperature. The reaction mixture was stirred overnight. The solvent was evaporated, and the resulting solid was recrystallized from methanol. Yield: 53 g (86.7% of theory). $^1$H NMR (300 MHz, CDCl$_3$): δ 8.40-8.36 (m, 4H), 7.79 (ddd, J=0.12, 0.02, and 0.02 Hz, 4H), 5.39 (s, 1H), 4.37-4.22 (m, 1H), 2.82-2.65 (m, 2H), 2.27-2.16 (m, 2H), 1.84-1.65 (m, 4H).

Synthesis of trans-4-Nitro-benzoic acid 4-amino-cyclohexyl ester 35 wt % Hydrazine hydrate (0.93 g, 10.1 mmol) was added to a solution of the above compound (2.0 g, 5.1 mmol) in DCM (50 mL) followed by MeOH (50 mL) at room temperature. The reaction mixture was allowed to stir overnight. The resulting white precipitates were filtered off and the solvent was removed in vacuo. The resulting white solids were dissolved in aqueous 1N HCl solution and washed with DCM. Aqueous layer was basified with excess 1N NaOH solution and then extracted with DCM. After drying with MgSO$_4$, the solvent was evaporated affording crude trans-4-Nitro-benzoic acid 4-amino-cyclohexyl ester as a solid, which was used in the next step without further purification. Yield: 1.1 g (89% of theory). $^1$H NMR (DMSO-$d_6$) δ 8.26 (dd, J=43.5 and 8.8 Hz, 4H), 6.72 (d, J=7.3 Hz, 2H), 5.08 (s, 1H), 2.00-1.36 (m, 9H).

Synthesis of trans-4-Nitro-benzoic acid 4-(3-tricyclo[3.3.1.1$^{3,7}$]decan-1-yl-ureido)-cyclohexyl ester 1076

To a solution the above compound (1.33 g, 5.1 mmol) in DMF was added 1-adamantyl isocyanate (0.82 g, 4.6 mmol) followed by triethylamine (0.47 g, 4.6 mmol) at 0° C. The reaction mixture was stirred overnight. The reaction mixture was poured into water, and the resulting precipitates were collected and washed with water. The crude product was recrystallized from DCM/hexanes. Yield: 1.83 g (90% of theory). M.P.: 124° C. $^1$H NMR (300 MHz, CDCl$_3$): δ 8.24 (dd, J=28.7 and 9.1 Hz, 4H), 5.23 (s, 1H), 4.13 (d, J=7.2 Hz, 1H), 4.05 (s, 1H), 3.75-3.61 (m, 1H), 2.17-1.41 (m, 23H).

Synthesis of cis-1-(4-Hydroxy-cyclohexyl)-3-tricyclo[3.3.1.1$^{3,7}$]decan-1-yl-urea 1077

To a solution of ester 1076 (1 g, 2.3 mmol) in THF (100 mL) was added 1N NaOH solution (4.6 mL, 4.6 mmol) at room temperature. The reaction mixture was stirred overnight, at which time the reaction was quenched by addition of 1N HCl solution (5.5 mL). The resulting white precipitate was collected by filtration and recrystallized from methanol/water. Yield: 0.63 g (95% of theory). M.P.: 205° C. $^1$H NMR (300 MHz, DMSO-$d_6$): δ 5.67 (d, J=8.2 Hz, 1H), 5.45 (s, 1H), 4.41 (s, 1H), 3.63-3.51 (m, 1H), 3.46-3.36 (m, 1H), 2.00-1.92 (m, 3H), 1.87-1.72 (m, 6H), 1.66-1.28 (m, 14H).

Synthesis of cis-1-(4-Benzyloxy-cyclohexyl)-3-tricyclo[3.3.1.1$^{3,7}$]decan-1-yl-urea 1078

Compound 1078 (2.22 g, 60%) was synthesized from compound 1077 (0.29 g, 1 mmol) by the same method) as that described for compound 1032 with benzyl bromide (0.20 g, 1.2 mmol) and 60% sodium hydride (0.06 g, 1.5 mmol). Yield: 0.35 g (92% of theory). M.P.: 181° C. 1H NMR (300 MHz, CDCl3): δ 7.43-7.24 (m, 5H), 4.49 (s, 2H), 4.11 (d, J=8.3 Hz, 1H), 4.02 (s, 1H), 3.66-3.51 (m, 2H), 2.23-1.07 (m, 23H).

Example 31

General Procedure for the Synthesis of Cis-Phenoxy Isomers

Synthesis of cis-1-[4-(4-Fluoro-phenoxy)-cyclohexyl]-3-tricyclo[3.3.1.1$^{3,7}$]decan-1-yl-urea 1135

Synthesis of cis-2-[4-(4-Fluoro-phenoxy)-cyclohexyl]isoindole-1,3-dione

To a solution of trans-2-(4-Hydroxy-cyclohexyl)-isoindole-1,3-dione 3 (1.0 g, 4.1 mmol), triphenylphosphine (1.3 g, 4.9 mmol), and 4-fluorophenol (0.55 g, 4.9 mmol) in 40 mL of THF was added dropwise at room temperature diisopropyl azodicarboxylate (0.99 g, 4.9 mmol). The reaction mixture was stirred overnight. The solvent was evaporated after 12 h, and the resulting solid was purified by recrystallization from methanol. Yield: 1.1 g (80% of theory). $^1$H NMR (300 MHz, CDCl$_3$): δ 7.84-7.80 (m, 2H), 7.71-7.67 (m, 2H), 6.98-6.94 (m, 4H), 4.51 (s, 1H), 4.26-4.12 (m, 1H), 2.76-2.60 (m, 2H), 2.18 (d, J=13 Hz, 2H), 1.79-1.49 (m, 4H).

Synthesis of cis-1-[4-(4-Fluoro-phenoxy)-cyclohexyl]-3-tricyclo[3.3.1.1 3,7]decan-1-yl-urea 1135

35 wt % Hydrazine hydrate (0.27 g, 2.9 mmol) was added to a solution of the above compound (0.5 g, 1.5 mmol) in DCM (15 mL) followed by MeOH (15 mL) at room temperature. The reaction mixture was allowed to stir overnight. The resulting white precipitates were filtered off and the solvent was removed in vacuo. The resulting white solids were dissolved in aqueous 1N HCl solution and washed with DCM. Aqueous layer was basified with excess 1N NaOH solution and then extracted with DCM. After drying with $MgSO_4$, the solvent was evaporated affording crude cis-4-(4-Fluoro-phenoxy)-cyclohexylamine 10 as a solid, which was used in the next step without further purification.

To a solution compound 10 in DMF was added 1-adamantyl isocyanate (0.16 g, 0.91 mmol) followed by triethylamine (0.10 g, 1.0 mmol) at 0° C. The reaction mixture was stirred overnight. The reaction mixture was poured into water, and the resulting precipitates were collected and washed with water. The crude product was recrystallized from DCM/hexanes. Yield: 0.31 g (88% of theory). M.P.: 207° C. $^1$H NMR (300 MHz, $CDCl_3$): δ 6.98-6.91 (m, 2H), 6.84-6.78 (m, 2H), 4.34 (s, 1H), 4.30 (d, J=9.8 Hz, 1H), 4.20 (s, 1H), 3.71-3.56 (m, 1H), 2.13-1.44 (m, 23H).

Example 32

General Procedure for the Synthesis of Trans-Phenoxy Isomers

Synthesis of trans-1-[4-(4-Fluoro-phenoxy)-cyclohexyl]-3-tricyclo[3.3.1.1 3,7]decan-1-yl-urea 1136

Synthesis of cis-2-(4-Hydroxy-cyclohexyl)-isoindole-1,3-dione

1N NaOH solution (19 mL, 19 mmol) was added at room temperature to a solution of ester 4 (5 g, 12.7 mmol) in THF (100 mL). The mixture was stirred overnight at room temperature, at which time the reaction was quenched by addition of 1N HCl solution (40 mL). The solvent was removed under reduced pressure, and the resulting white precipitate formed was collected by filtration and dissolved in DMF. After adding triethylamine (6.5 g, 64 mmol) at room temperature, the reaction mixture heated at 150° C. for 30 min in the microwave. After cooling to r.t., the reaction mixture was poured into water and then extracted with ether. The organic layer was washed with water thoroughly. After drying with MgSO4, the solvent was removed in vacuo. The resulting white solids were recrystallized from DCM/hexanes. Yield: 1.9 g (60% of theory). $^1$H NMR (300 MHz, $CDCl_3$): δ 7.76 (ddd, J=37.6, 5.4 and 3.1 Hz, 4H), 4.21-4.07 (m, 2H), 2.72-2.55 (m, 2H), 1.96 (d, J=13.9 Hz, 2H), 1.73-1.50 (m, 4H).

Synthesis of trans-2-[4-(4-Fluoro-phenoxy)-cyclohexyl]-isoindole-1,3-dione

Synthesis of trans-2-[4-(4-Fluoro-phenoxy)-cyclohexyl]-isoindole-1,3-dione was synthesized from the above compound (1 g, 4.1 mmol) by the same method as that described with DIAD (0.99 g, 4.9 mmol), PPh3 (1.3 g, 4.9 mmol), and 4-fluorophenol (0.55 g, 4.9 mmol). Yield: 0.56 g (40% of theory). $^1$H NMR (300 MHz, $CDCl_3$): δ 7.77 (ddd, J=37.6, 5.4 and 3.1 Hz, 4H), 7.00-6.84 (m, 4H), 4.30-4.15 (m, 2H), 2.48-2.31 (m, 2H), 2.26 (d, J=11.4 Hz, 2H), 1.89-1.77 (m, 2H), 1.65-1.49 (m, 4H).

Synthesis of trans-1-[4-(4-Fluoro-phenoxy)-cyclohexyl]-3-tricyclo[3.3.1.1 3,7]decan-1-yl-urea 1136

Compound 1136 was synthesized (0.5 g, 1.5 mmol) by the same method as that described above with 35 wt % hydrazine (0.27 g, 2.95 mmol) in 15 mL of DCM and 15 mL of MeOH followed by the reaction with 1-adamantyl isocyanate (0.12 g, 0.67 mmol) and triethylamine (0.07 g, 0.74 mmol) in DMF (5 mL). Yield: 0.24 g (93% of theory). M.P.: 243° C. $^1$H NMR (300 MHz, $CDCl_3$): δ 6.98-6.91 (m, 2H), 6.85-6.79 (m, 2H), 4.12-3.94 (m, 3H), 3.66-3.51 (m, 1H), 2.17-1.88 (m, 12H), 1.73-1.45 (m, 9H), 1.28-1.11 (m, 2H).

Example 33

Combinatorial Synthesis of Urea Inhibitors

A mixture of PS-Indole-CHO resin (0.5 g, 0.46 mmol), THF (3 mL), TEOF (3 mL) and the primary amine (1.0 mmol) was agitated at ambient temperature for 4 h. Then, a solution of $NaBH_3CN$ (1.0 mL, 1 M) in THF and acetic acid (0.1 mL) were added. The resulting mixture was stirred for 2 h. The supernatant liquid was drained off and the resin washed with THF (8 mL×2), MeOH (8 mL×3) and DCM (8 mL×2).

To a suspension of the resin-bound secondary amine (0.1 g) in DCM (2 mL) was added an isocyanate (0.5 mmol). The resulting mixture was agitated overnight at ambient temperature. The supernatant liquid is drained off and the resin washed with DMF, MeOH and DCM.

The resin-bound product was suspended in 1% (v/v) TFA (3 mL, ca. 4 mol equiv.) and the mixture agitated at ambient temperature for 4 h. The color of the resin became deep purple. The supernatant liquid was collected and the resin was washed with DCM (2×2 mL). The combined solution was concentrated to afford pure products in excellent yields.

Example 34

This example provides assays and illustrates the inhibition of mouse and human soluble epoxide hydrolases by compounds of the invention having a secondary pharmacophore that is a carboxylic acid or carboxylic methyl ester functional group.

Enzyme Preparation

Recombinant mouse sEH and human sEH were produced in a baculovirus expression system and purified by affinity chromatography. The preparations were at least 97% pure as judged by SDS-PAGE and scanning densitometry. No detectable esterase or glutathione transferase activity, which can interfere with this sEH assay, was observed. Protein concentration was quantified by using the Pierce BCA assay using Fraction V bovine serum albumin as the calibrating standard.

$IC_{50}$ Assay Conditions $IC_{50}$ values were determined in one of two method. One method uses racemic 4-nitrophenyl-trans-2,3-epoxy-3-phenylpropyl carbonate as substrate. Enzymes (0.12 μM mouse sEH or 0.24 μM human sEH) were incubated with inhibitors for 5 min in sodium phosphate buffer, 0.1 M pH 7.4, at 30° C. before substrate introduction ([S]=40 μM). Activity was assessed by measuring the appearance of the 4-nitrophenolate anion at 405 nm at 30° C. during 1 min (Spectramax 200; Molecular Devices). Assays were performed in triplicate. $IC_{50}$ is a concentration of inhibitor, which reduces enzyme activity by 50%, and was determined by regression of at least five datum points with a minimum of two points in the linear region of the curve on either side of the $IC_{50}$. The curve was generated from at least three separate runs, each in triplicate, to obtain the standard deviation (SD) given in Table 1 thru Table 4.

Other $IC_{50}$ values were determined using the procedure described in *Analytical Biochemistry* 343 66-75 (2005) using cyano(6-methoxy-naphthalen-2-yl)methyl trans-[(3-phenyloxiran-2-yl)methyl]carbonate as a substrate (see Table 18b). Enzymes (0.88 nM for murine and 0.96 nM for human sEH) were incubated with inhibitors ([I]=0.5-10,000 nM) for 5 min in BisTris-HCl buffer (25 mM, pH 7.0, containing 0.1 mg/ml of BSA) at 30° C. prior to substrate introduction ([S]=5 lM). Enzyme activity was measured by monitoring the appearance of 6-methoxy-2-naphthaldehyde. Assays were performed in triplicate. By definition, $IC_{50}$ values are concentrations of inhibitor that reduce enzyme activity by 50%. $IC_{50}$ values were determined by regression of at least five datum points, with a minimum of two datum points in the linear region of the curve on either side of the $IC_{50}$ values. The curve was generated from at least three separate runs, each in triplicate.

Assays were conducted with the compounds indicated in Table 1, as described above.

TABLE 1

Inhibition of mouse and human sEH by 1-cyclohexyl-3-n-(substituted)alkylureas

| No. | n | Z | $IC_{50}$ (μM) Mouse sEH | $IC_{50}$ (μM) Human sEH |
|---|---|---|---|---|
| 625 | 1 | H | >500 | >500 |
| 549 | 1 | $CH_3$ | 33 ± 2 | 70 ± 6 |
| 109 | 2 | H | 122 ± 2 | 358 ± 2 |
| 635 | 2 | $CH_3$ | 2.5 ± 0.1 | 78 ± 4 |
| 632 | 3 | H | >500 | >500 |
| 774 | 3 | $CH_3$ | 0.33 ± 0.03 | 6.2 ± 0.5 |
| 884 | 4 | H | 0.25 ± 0.02 | 2.4 ± 0.1 |

TABLE 1-continued

Inhibition of mouse and human sEH by 1-cyclohexyl-3-n-(substituted)alkylureas

| No. | n | Z | $IC_{50}$ (μM) Mouse sEH | $IC_{50}$ (μM) Human sEH |
|---|---|---|---|---|
| 854 | 4 | $CH_3$ | 0.13 ± 0.03 | 5.0 ± 0.6 |
| 56 | 5 | H | 90 ± 3 | 253 ± 8 |

[a]Enzymes (0.12 μM mouse sEH and 0.24 μM human sEH) were incubated with inhibitors for 5 min in sodium phosphate buffer (pH 7.4) at 30° C. before substrate introduction ([S] = 40 μM). Results are means ± SD of three separate experiments.

As can be seen from the above table, the conversion of a carboxylic acid function to its methyl ester (549, 635, and 774) increased inhibition potency for both mouse and human sEHs. Moreover, the methyl ester of butanoic acid (774) showed 8-100 fold higher activity than the esters of acetic and propanoic acids (549 and 635) for both enzymes, indicating that a polar functional group located three carbon units (carbonyl on the fourth carbon, about 7.5 angstroms from the urea carbonyl) from the carbonyl of the primary urea pharmacophore can be effective for making potent sEH inhibitors of improved water solubility. In addition, the distance from the carbonyl of the primary urea pharmacophore to the secondary ester pharmacophore in compound 854 is about 8.9 Å showing that the secondary pharmacophore may be located about 7 Å to about 9 Å from the carbonyl of the primary urea pharmacophore group.

Example 35

This example illustrates the inhibition of mouse and human soluble epoxide hydrolases by compounds of the invention having a secondary pharmacophore, with comparison to compounds having only a primary pharmacophore. As can be seen from the results in Table 2, the activity is relatively consistent.

Assays were conducted with the compounds indicated in Table 2, according to established protocols (see, above).

TABLE 2

Inhibition of mouse and human sEH by 1-cycloalkyl-3-alkylureas[a]

| No. | Structure | $IC_{50}$ (μM) Mouse sEH | $IC_{50}$ (μM) Human sEH |
|---|---|---|---|
| 772 | 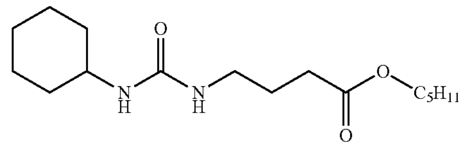 | 0.05 ± 0.01 | 1.02 ± 0.05 |

TABLE 2-continued

Inhibition of mouse and human sEH by 1-cycloalkyl-3-alkylureas[a]

| | | IC$_{50}$ (μM) | |
|---|---|---|---|
| No. | Structure | Mouse sEH | Human sEH |
| 789 | [1-adamantyl-NH-C(=O)-NH-CH$_2$CH$_2$CH$_2$-C(=O)-O-C$_5$H$_{11}$] | 0.05 ± 0.01 | 0.17 ± 0.01 |
| 791 | [cyclohexyl-NH-C(=O)-NH-(CH$_2$)$_5$-C$_5$H$_{11}$] | 0.05 ± 0.01 | 0.14 ± 0.01 |
| 790 | [1-adamantyl-NH-C(=O)-NH-(CH$_2$)$_5$-C$_5$H$_{11}$] | 0.05 ± 0.01 | 0.10 ± 0.01 |
| 297 | [cyclohexyl-NH-C(=O)-NH-(CH$_2$)$_5$-C$_7$H$_{15}$] | 0.05 ± 0.01 | 0.14 ± 0.01 |
| 686 | [1-adamantyl-NH-C(=O)-NH-(CH$_2$)$_5$-C$_7$H$_{15}$] | 0.05 ± 0.01 | 0.10 ± 0.01 |

[a]Enzymes (0.12 μM mouse sEH and 0.24 μM human sEH) were incubated with inhibitors for 5 min in sodium phosphate buffer (pH 7.4) at 30° C. before substrate introduction ([S]= 40 μM). Results are means ± SD of three separate experiments.

As shown in the above table, the substitution at R with a cyclohexyl (772) or adamantyl (789) increased inhibitor potency 10-fold over the 3-chlorophenyl analog (767, see Table 3 below). Furthermore, these compounds functionalized with a polar group were as active and potent as non-functionalized lipophilic inhibitors (for example, 791, 790, 297, and 686) for both murine and human enzymes. Adding polar groups to compounds generally increases their water solubility, and this was the case when one compares compounds 772 or 789 to 791 and 790. In addition, stripping water of hydration out of the enzyme catalytic site requires about the same amount of energy that is gained by forming a new hydrogen bond between the inhibitor and the enzyme. Thus addition of polar groups which hydrogen bond to a target enzyme does not dramatically increase potency if the inhibitor is already potent. However, the presence of an additional polar group can be expected to dramatically increase specificity by decreasing hydrophobic binding to biological molecules other than the primary target (sEH). In this way combining several active pharmacophores into a single molecule often has a massive increase in specificity and biological activity in complex biological systems.

Example 36

This example illustrates the inhibition of mouse and human soluble epoxide hydrolases by compounds of the invention having a secondary pharmacophore that is a ketone, amide, alcohol, carbonate, carbamate, urea, carboxylate ester functional group.

Based on the initial activity shown in Table 1, urea compounds were prepared having a polar carbonyl group located approximately 7.5 angstroms from the carbonyl of the primary urea pharmacophore to improve water solubility of lipophilic sEH inhibitors (192 and 686). The table below shows various functionalities such as ketone, ester, amide, carbonate, carbamate, and urea which contribute a carbonyl group, and are termed as the secondary pharmacophores. To determine the effect for each of the secondary pharmacophores, a 3-chlorophenyl group was held constant as one of substituents of the urea pharmacophore. The 3-chlorophenyl group is also particularly useful for monitoring chemical reactions quickly via chromatography. After optimizing the secondary pharmacophore, the aryl substituent can be replaced by a cyclohexyl, adamantyl or other group leading to more potent inhibitors.

Assays were conducted with the compounds indicated in Table 3, according to established protocols (see, above).

TABLE 3

Inhibition of mouse and human sEH by 1-(3-chlorophenyl)-3-(2-alkylated ethyl)ureas[a]

Structure: 3-chlorophenyl-NH-C(=O)-NH-CH$_2$CH$_2$-X-C(=O)-Y-C$_5$H$_{11}$

| No. | X | Y | IC$_{50}$ (μM) Mouse sEH | IC$_{50}$ (μM) Human sEH |
|---|---|---|---|---|
| 794 | CH$_2$ | CH$_2$ | 0.41 ± 0.05 | 2.1 ± 0.2 |
| 767 | CH$_2$ | O | 0.37 ± 0.04 | 2.1 ± 0.07 |
| 768 | CH$_2$ | NH | 7.2 ± 0.9 | 32 ± 0.8 |
| 761 | O | CH$_2$ | 7.7 ± 0.6 | 26 ± 1 |
| 760 | O | O | 7.6 ± 0.3 | 22 ± 1 |
| 762 | O | NH | 5.3 ± 0.1 | 18 ± 0.9 |
| 765 | NH | CH$_2$ | 100 ± 10 | >100 |
| 777 | NH | O | 78 ± 6 | >100 |
| 766 | NH | NH | 110 ± 20 | >100 |

[a] Enzymes (0.12 μM mouse sEH and 0.24 μM human sEH) were incubated with inhibitors for 5 min in sodium phosphate buffer (pH 7.4) at 30° C. before substrate introduction ([S]= 40 μM). Results are means ± SD of three separate experiments.

When the left of the carbonyl (X) is a methylene carbon, the best inhibition was obtained if a methylene carbon (ketone, 794) or oxygen (ester, 767) is present in the right position (Y). The ester bond can be stabilized by stearic hindrance of the alcohol or acid moiety or both (805). The presence of nitrogen (amide, 768) reduced the activity. In compounds with an oxygen in the left of the carbonyl group, a >10-fold drop in activity was observed and there was not any change in the activity even if the right position, Y, was modified with a methylene carbon (ester, 761), oxygen (carbonate, 760), or nitrogen (carbamate, 762), respectively. All compounds (765, 777, and 766) with nitrogen in the left position had lower activities than 794 or 767. Comparing compounds 767 and 761, the presence of a methylene carbon around the carbonyl showed a very different effect on the inhibition activity. The compound with a methylene carbon in the left of the carbonyl (767) showed a 20-fold better inhibition than that in the right (761). While the rank-order potency of this inhibitor series was equivalent with mouse and human sEH, a 3-5-fold higher inhibition potency was observed for the murine enzyme.

Example 37

This example illustrates the inhibition of mouse and human soluble epoxide hydrolases by compounds of the invention having no secondary pharmacophore, but having a tertiary pharmacophore that is an amide or a carboxylate ester functional group (with alkyl, alkenyl, alkynyl, cycloalkyl and arylalkyl ester groups).

Compound 687, having a carboxylic acid group at the end of twelve carbon chain, was found to be an excellent inhibitor of both the mouse and human enzymes. Additionally, an ester found to be a suitable secondary pharmacophore. As a result, a variety of ester derivatives having a carbonyl group located eleven carbon units from the urea pharmacophore were synthesized and evaluated to examine contributions of a tertiary pharmacophore.

Assays were conducted with the compounds indicated in Table 4, according to established protocols (see, above).

TABLE 4

Inhibition of mouse and human sEH by 1-(1-adamantyl)-3-(11-alkylated undecyl)-ureas[a]

Structure: 1-adamantyl-NH-C(=O)-NH-(CH$_2$)$_{10}$-C(=O)-X-R

| No. | X | R | IC$_{50}$ (μM) Mouse sEH | IC$_{50}$ (μM) Human sEH |
|---|---|---|---|---|
| 687 | O | H | 0.05 ± 0.01 | 0.10 ± 0.01 |
| 780 | O | methyl | 0.05 ± 0.01 | 0.10 ± 0.01 |
| 784 | O | ethyl | 0.05 ± 0.01 | 0.10 ± 0.01 |
| 792 | NH | ethyl | 0.05 ± 0.01 | 0.10 ± 0.01 |
| 783 | O | propyl | 0.05 ± 0.01 | 0.10 ± 0.01 |
| 781 | O | allyl (CH$_2$CH=CH$_2$) | 0.05 ± 0.01 | 0.10 ± 0.01 |
| 788 | O | propargyl (CH$_2$C≡CH) | 0.05 ± 0.01 | 0.10 ± 0.01 |
| 800 | O | butyl | 0.05 ± 0.01 | 0.10 ± 0.01 |

TABLE 4-continued

Inhibition of mouse and human sEH by 1-(1-adamantyl)-3-(11-alkylated undecyl)-ureas[a]

| No. | X | R | IC$_{50}$ ($\mu$M) Mouse sEH | IC$_{50}$ ($\mu$M) Human sEH |
|---|---|---|---|---|
| 785 | O |  | 0.05 ± 0.01 | 0.10 ± 0.01 |
| 793 | NH |  | 0.05 ± 0.01 | 0.10 ± 0.01 |
| 801 | O |  | 0.05 ± 0.01 | 0.10 ± 0.01 |
| 802 | O |  | 0.05 ± 0.01 | 0.10 ± 0.01 |
| 803 | O |  | 0.05 ± 0.01 | 0.10 ± 0.01 |
| 786 | O | 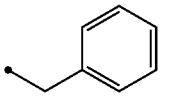 | 0.07 ± 0.01 | 0.23 ± 0.02 |
| 804 | O | 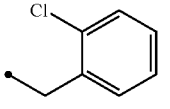 | 0.07 ± 0.01 | 0.13 ± 0.01 |
| 782 | O | 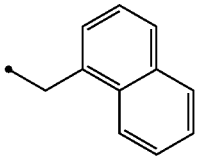 | 0.10 ± 0.01 | 0.29 ± 0.01 |
| 787 | O |  | 0.09 ± 0.01 | 0.21 ± 0.01 |

[a]Enzymes (0.12 µM mouse sEH and 0.24 µM human sEH) were incubated with inhibitors for 5 min in sodium phosphate buffer (pH 7.4) at 30° C. before substrate introduction ([S]=40 µM). Results are means ± SD of three separate experiments.

While the presence of a polar group at the end of a shorter chain reduced inhibition potency for both enzymes (see Table 1), when the carboxylic acid was modified to esters with various aliphatic groups (780, 784, 783, 781, 788, 800, 785, 801, 802, and 803) inhibition potencies were as high as that of the acid (687) for both enzymes. Ethyl (792) and isopropyl (793) amide derivatives were also potent inhibitors. Compounds with methyl-branched aliphatic chains were also potent (785, 801, 802, 803, and 793). Still further, larger bulky group such as 1-adamantylmethyl (786), benzyl (804), 2-chlorobenzyl (782) or 2-naphthylmethyl (787) provided good levels of activity, although slightly reduced (1.5-3-fold) for both enzymes. These results identified an additional site within the sEH inhibitor structure which allows the inclusion of a third polar function, i.e. a tertiary pharmacophore.

Example 38

In order to further explore the effects of functional groups which improve water solubility on the bioavailability and potency of the inhibitors, seven amide derivatives of compound 687 with various functionalities were synthesized. As shown in Table 5, alkyl, sulfonyl, lipoamino acid, and glucosylamide derivatives were prepared, and their inhibition potency on sEHs, melting point, and solubility in water and oil were examined. For mouse sEH, there was no change in the inhibition activity when the acid function of compound 687 was substituted by an alkyl (792 and 793), sulfonyl (848 and 914), lipoamino acid (1001), or glucosyl (1002 and 798) groups. Interestingly, for human sEH, significant differences in inhibition potencies, which were measured by the spectrometric and fluorescent based assays, were observed when replacing the acid function of compound 687 by the substituents. While introduction of the ethyl amide group (792) resulted in a 1.5-fold decrease in potency, the isopropyl analogue (793) exhibited very similar potency to ADUA (687). The corresponding ester derivatives 784 and 785 in Table 5 exhibited a 2-3-fold improvement in inhibition of the human enzyme. Two sulfonylamides with a methyl (848) or phenyl (914) group improved the inhibition potency of compound 4 about 1.5-fold. On the other hand, a 25-fold and 3-fold decrease in potency was observed when the sulfonylamide was replaced by a lipoamino acid (1001) or glucosyl groups (1002 and 798), respectively. This suggests that such bulky, and in the case of glucose, highly polar functional groups are not effective in retaining the inhibition potency on human sEH. Comparing compounds 1002 and 798, similar inhibition on the human enzyme was shown in these two compounds although an octyl group is present between the ADUA and sugar moieties of compound 1002, suggesting that relatively lipophilic alkyl groups located around the amide function do not alter the binding activity of inhibitors to the enzyme. Melting points of most of the amides in Table 5 were measured in a range of 100-140° C., which was similar to 114° C. of the acid compound 687, while the ester derivates of compound 687 in Table 5 showed 23-66° C. lower melting points than that of compound 687. An exception was compound 1001 for which we were unable to obtain a crystalline solid at room temperature. These results imply that the amide function is not as useful in reducing the melting point of AUDA derives as the esters. As with the esters prepared for this study, the amides failed to result in a large increase in potency on the target enzyme. Thus any advantage of these amides would result from improvements in ease of formulation, oral availability and pharmacokinetics. When water solubility of three compounds (848, 1001, and 1002) was compared to that of compound 4, a 3-fold lower or similar solubility was shown in compounds with a methanesulfonyl (848) or glucosyl (1002) group, respectively. Compound 1001, the lipoamino acid conjugate, surprisingly had a 2.5-fold better water solubility than compound 687. The 25-fold decrease in the inhibitory potency of compound 1001 compared to 687 indicates that with compound 1001 the biological activity will be attributed largely to the production of AUDA rather than being due to both AUDA and its ester or amide. In addition, no valuable improvement in oil solubility was obtained in the amides. Although significant improvements in the properties of the compounds were not observed in the seven amide derivatives, their relative stability and inhibition potency is sufficient to encourage the further exploration of other amide compounds to develop bioavailable inhibitors with improved physical properties. We have reported that modification of the urea pharmacophore of potent sEH inhibitors to an amide functionality does not dramatically alter the inhibition potency and that at least a 10-fold improvement in water solubility and a decrease in the melting points of these amide inhibitors is observed. (Kim, et al. *J. Med. Chem.* 2005, 48, 3621-3629). This suggests that the inhibition potency and physical properties of the amide derivatives in Table 5 might be improved with the modification of the urea function to the corresponding amide pharmacophore.

TABLE 5

Inhibition of mouse and human sEH 12-(3-adamantan-1-yl-ureido)dodecanoic acid alkyl or sulfonylamide derivatives

| No. | R | Mouse sEH[a] IC50 (µM) | Human sEH[a] | Human sEH[b] IC$_{50}$ (nM) | Mp[c] (° C.) | Solubility in water (µg/mL) | Solubility in oil (µg/mL) |
|---|---|---|---|---|---|---|---|
| 792 |  | 0.05 ± 0.01 | 0.1 ± 0.01 | 4.3 | 119 | — | — |
| 793 |  | 0.05 ± 0.01 | 0.1 ± 0.01 | 2.9 | 115 | — | — |
| 848 |  | 0.05 ± 0.01 | 0.1 ± 0.01 | 2.1 | 103 | 10 | 4,000 |
| 914 | 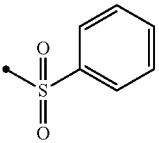 | 0.05 ± 0.01 | 0.1 ± 0.01 | 1.9 | 100 | — | 5,000 |

TABLE 5-continued

Inhibition of mouse and human sEH 12-(3-adamantan-1-yl-ureido)dodecanoic acid alkyl or sulfonylamide derivatives

| No. | R | Mouse sEH[a] IC50 (μM) | Human sEH[a] IC50 (μM) | Human sEH[b] IC$_{50}$ (nM) | Mp[c] (° C.) | Solubility in water (μg/mL) | Solubility in oil (μg/mL) |
|---|---|---|---|---|---|---|---|
| 1001 | (structure with C$_8$H$_{17}$, C(O)OH) | 0.05 ± 0.01 | 0.21 ± 0.01 | 55 | oil | 63 | — |
| 1002 | (structure with C$_8$H$_{17}$, sugar ester) | 0.05 ± 0.01 | 0.1 ± 0.01 | 7.5 | 130-140 | 38 | 2,000 |
| 798 | (sugar structure with OH groups) | 0.05 ± 0.01 | 0.22 ± 0.01 | 7.6 | — | — | — |

[a]Spectrometric-based assay: enzymes (0.12 μM mouse sEH or 0.24 μM human sEH) were incubated with inhibitors for 5 min in sodium phosphate buffer (200 μL; pH 7.4) at 30° C. before substrate introduction ([S] = 40 μM), results are means ± SD of three separate experiments.
[b]Fluorescent-based assay: enzymes (0.88 nM mouse sEH or 0.96 nM human sEH) were incubated with inhibitors for 5 min in Bis-Tris/HCl buffer (25 mM; pH 7.0) at 30° C. before substrate introduction ([S] = 5 μM), results are means ± SD of three separate experiments
[c]Melting point

Example 39

This example provides assays and illustrates the inhibition of mouse and human soluble epoxide hydrolases by compounds of the invention having a both a secondary and tertiary pharmacophore that is a carboxylic ester functional group.

Assays were conducted with the compounds indicated in Table 6, according to established protocols (see, above).

TABLE 6

Inhibition of mouse and human sEH by 4-(3-adamantan-1-yl-ureido)-butyryloxy compounds

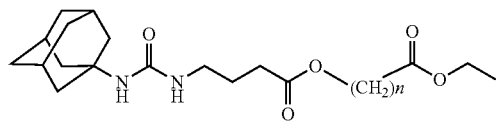

| No. | n | T$_A$[a] | Mouse sEH[b] IC$_{50}$ (μM) | Mouse sEH[b] IC$_{90}$ (μM) | Human sEH[b] IC$_{50}$ (μM) | Human sEH[b] IC$_{90}$ (μM) | MP (° C.) | cLog P[c] |
|---|---|---|---|---|---|---|---|---|
| 857 | 1 | 8 | 0.05 ± 0.01 | 0.11 ± 0.01 | 0.39 ± 0.01 | 9 ± 2 | 123 | 0.98 ± 0.47 |
| 876 | 2 | 9 | 0.05 ± 0.01 | 0.63 ± 0.02 | 0.54 ± 0.05 | 9 ± 2 | 95-97 | 1.27 ± 0.47 |
| 858 | 3 | 10 | 0.05 ± 0.01 | 0.16 ± 0.01 | 0.12 ± 0.01 | 5.0 ± 0.1 | 89-91 | 1.55 ± 0.47 |
| 877 | 4 | 11 | 0.05 ± 0.01 | 0.10 ± 0.01 | 0.13 ± 0.01 | 1.5 ± 0.1 | 84-86 | 1.97 ± 0.47 |
| 878 | 6 | 13 | 0.05 ± 0.01 | 0.13 ± 0.01 | 0.12 ± 0.01 | 0.81 ± 0.01 | 65-67 | 2.81 ± 0.47 |
| 879 | 7 | 14 | 0.05 ± 0.01 | 0.16 ± 0.02 | 0.11 ± 0.01 | 0.72 ± 0.01 | 58-59 | 3.22 ± 0.47 |
| 880 | 9 | 16 | 0.05 ± 0.01 | 0.26 ± 0.03 | 0.10 ± 0.01 | 0.68 ± 0.01 | 60-61 | 4.06 ± 0.47 |
| 881 | 10 | 17 | 0.05 ± 0.01 | 0.35 ± 0.05 | 0.10 ± 0.01 | 1.2 ± 0.1 | 54-55 | 4.48 ± 0.47 |
| 882 | 11 | 18 | 0.05 ± 0.01 | 0.63 ± 0.04 | 0.10 ± 0.01 | 1.8 ± 0.2 | 64-65 | 4.89 ± 0.47 |

[a]The total number of atoms extending from the carbonyl group of the primary urea pharmacophore, T$_A$ = n + 7
[b]Enzymes (0.12 μM mouse sEH and 0.24 μM human sEH) were incubated with inhibitors for 5 min in sodium phosphate buffer (pH 7.4) at 30° C. before substrate introduction ([S] = 40 μM). Results are means ± SD of three separate experiments.
[c]cLog P: calculated log P by Crippen's method by using CS ChemDraw 6.0 version As can be seen from the above table, in increasing the distance between the secondary ester pharmacophore and the tertiary ester pharmacophore (549, 635, and 774) increased inhibition potency for human sEHs but mouse EH activity remained relatively consistent.

Example 40

This example illustrates the inhibition of mouse and human soluble epoxide hydrolases by compounds of the invention (formula (I)) having a secondary ether pharmacophore.

Adamantyl-urea compounds were prepared having a polar ether group located various distances from the carbonyl of the primary urea pharmacophore. These compounds were prepared to improve water solubility of lipophilic sEH inhibitors (192 and 686). As can be seen from the results in Table 7, the activity is relatively consistent.

Assays were conducted with the compounds indicated in Table 7, according to established protocols (see, above).

TABLE 7

Inhibition of mouse and human sEH by alkyl ether derivatives

| No. | Structure | IC$_{50}$ (µM) | |
| --- | --- | --- | --- |
| | | Mouse sEH | Human sEH |
| 866 | 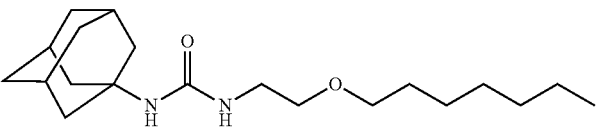 [SMILES: CCCCCCCOCCNC(=O)NC12CC3CC(CC(C3)C1)C2] | 0.06 ± 0.01 | 1.5 ± 0.2 |
| 867 | 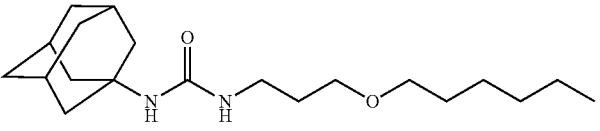 [SMILES: CCCCCCOCCCNC(=O)NC12CC3CC(CC(C3)C1)C2] | 0.05 ± 0.01 | 0.22 ± 0.02 |
| 868 | 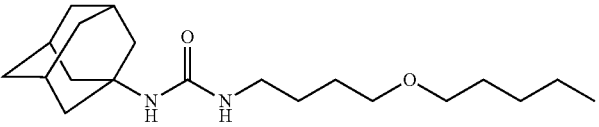 [SMILES: CCCCCOCCCCNC(=O)NC12CC3CC(CC(C3)C1)C2] | 0.05 ± 0.01 | 0.17 ± 0.01 |
| 869 | 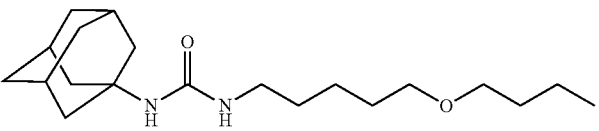 | 0.05 ± 0.01 | 0.12 ± 0.01 |
| 870 | 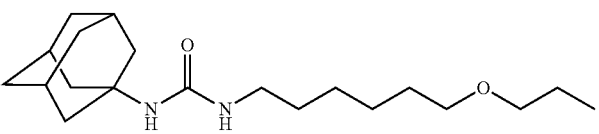 [SMILES: CCCOCCCCCCNC(=O)NC12CC3CC(CC(C3)C1)C2] | 0.05 ± 0.01 | 0.10 ± 0.01 |

As shown in the above table, these compounds functionalized with a single ether group could be as active and potent as non-functionalized lipophilic inhibitors (790, see Table 2 above) for both murine and human enzymes. Adding a polar ether group to these compounds increased their water solubility (compare compound 866-870 with 790). The distance from the carbonyl of the primary urea pharmacophore to the secondary ether pharmacophore in compound 869 is about 8.9 Å showing that the secondary pharmacophore may be located about 7 Å to about 9 Å from the carbonyl of the primary urea pharmacophore group.

Example 41

This example illustrates the inhibition of mouse and human soluble epoxide hydrolases by compounds of the invention (formula (I)) having a secondary ether or polyether pharmacophore, with comparison to compounds further including a tertiary pharmacophore.

Because compounds having a ether secondary pharmacophore were found to be suitable inhibitors of both the mouse and human enzymes, a variety of polyether derivatives were synthesized and evaluated along with contributions of a tertiary pharmacophore. As can be seen from the results in Table 8, the activity is relatively consistent.

Assays were conducted with the compounds indicated in Table 8, according to established protocols (see, above).

TABLE 8

Inhibition of mouse and human sEH by substituted ether derivatives

| No. | Structure | IC$_{50}$ (μM)$^a$ Mouse sEH | Human sEH |
|---|---|---|---|
| 908 | 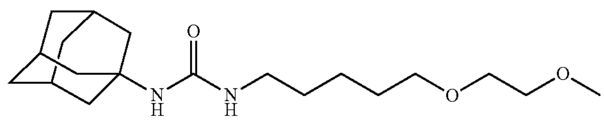 [SMILES: COCCOCCCCCNC(=O)NC12CC3CC(CC(C3)C1)C2] | 0.05 ± 0.01 | 0.16 ± 0.01 |
| 913 | 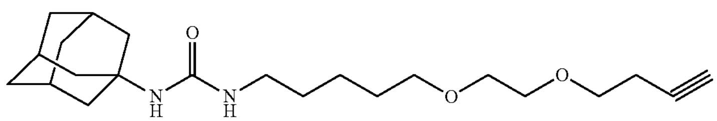 [SMILES: C#CCCOCCOCCCCCNC(=O)NC12CC3CC(CC(C3)C1)C2] | 0.05 ± 0.01 | 0.10 ± 0.01 |
| 940 | 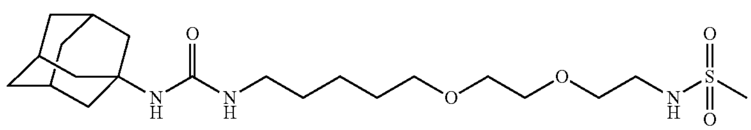 [SMILES: CS(=O)(=O)NCCOCCOCCCCCNC(=O)NC12CC3CC(CC(C3)C1)C2] | 0.05 ± 0.01 | 0.10 ± 0.01 |
| 941 | 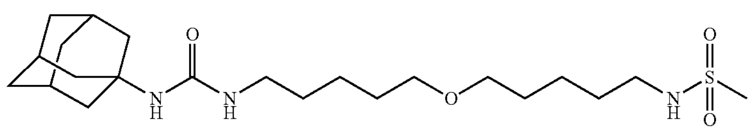 [SMILES: CS(=O)(=O)NCCCCCOCCCCCNC(=O)NC12CC3CC(CC(C3)C1)C2] | 0.05 ± 0.01 | 0.10 ± 0.01 |
| 950 | 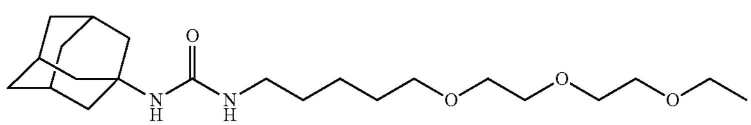 [SMILES: CCOCCOCCOCCCCCNC(=O)NC12CC3CC(CC(C3)C1)C2] | 0.05 ± 0.01 | 0.10 ± 0.01 |
| 951 | 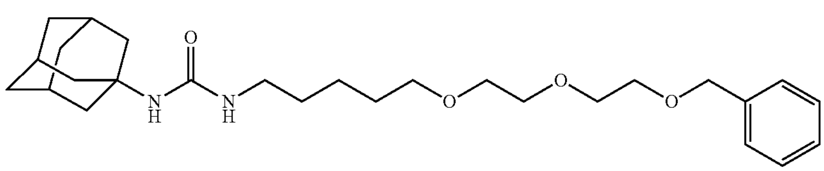 [SMILES: O=C(NCCCCCOCCOCCOCc1ccccc1)NC12CC3CC(CC(C3)C1)C2] | 0.05 0.01 | 0.10 ± 0.01 |
| 952 | 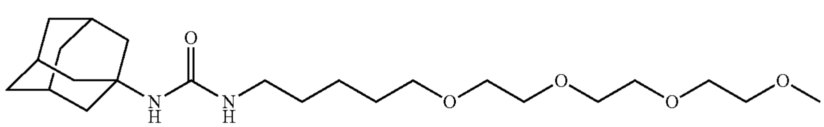 [SMILES: COCCOCCOCCOCCCCCNC(=O)NC12CC3CC(CC(C3)C1)C2] | 0.05 ± 0.01 | 0.10 ± 0.01 |
| 972 | 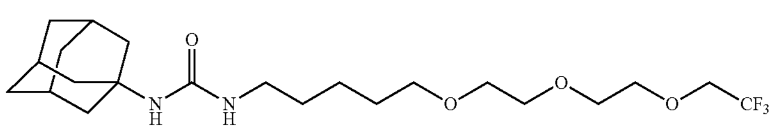 [SMILES: O=C(NCCCCCOCCOCCOCC(F)(F)F)NC12CC3CC(CC(C3)C1)C2] | 0.05 ± 0.01 | 0.10 ± 0.01 |

TABLE 8-continued
Inhibition of mouse and human sEH by substituted ether derivatives
| No. | Structure | IC$_{50}$ (μM)$^a$ Mouse sEH | Human sEH |
|---|---|---|---|
| 973 | 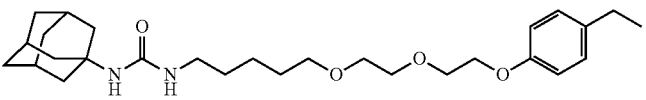 [SMILES: CCc1ccc(OCCOCCOCCCCCNC(=O)NC23CC4CC(CC(C4)C2)C3)cc1] | 0.05 ± 0.01 | 0.10 ± 0.01 |
| 975 | 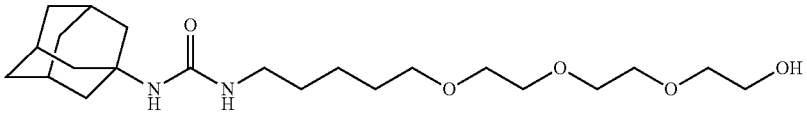 [SMILES: O=C(NCCCCCOCCOCCOCCO)NC12CC3CC(CC(C3)C1)C2] | 0.05 ± 0.01 | 0.10 ± 0.01 |
| 1003 | 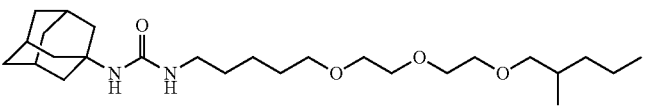 [SMILES: CCCC(C)COCCOCCOCCCCCNC(=O)NC12CC3CC(CC(C3)C1)C2] | 0.05 ± 0.01 | 0.13 ± 0.01 |
| 1004 | 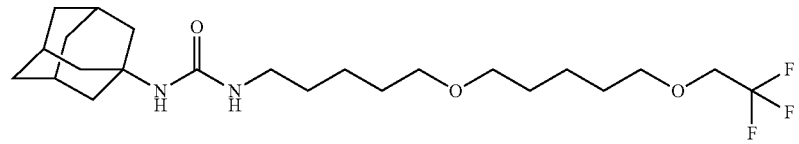 [SMILES: O=C(NCCCCCOCCCCCOCC(F)(F)F)NC12CC3CC(CC(C3)C1)C2] | 0.05 ± 0.01 | 0.16 ± 0.01 |
| 1005 | 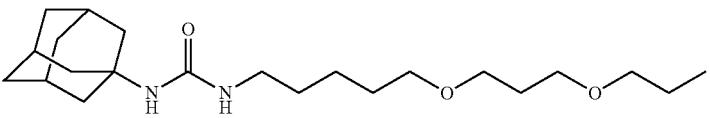 [SMILES: CCCOCCCOCCCCCNC(=O)NC12CC3CC(CC(C3)C1)C2] | 0.05 ± 0.01 | 0.10 ± 0.01 |
| 1006 | 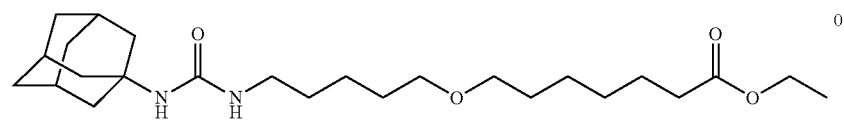 | 0.05 ± 0.01 | 0.11 ± 0.01 |
| 1011 | 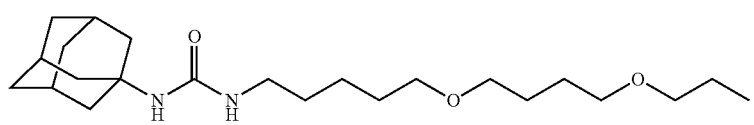 [SMILES: CCCOCCCCOCCCCCNC(=O)NC12CC3CC(CC(C3)C1)C2] | 0.05 ± 0.01 | 0.10 ± 0.01 |

Compounds with from two to four ether groups (908, 950, and 952) had inhibition potencies that were as high as non-functionalized lipophilic inhibitors (790, see Table 2 above) for both murine and human enzymes, as well as increased water solubility and improved pharmacokinetics (See FIGS. 14-24). Including a tertiary pharmacophore were also potent inhibitors but did not further increase their activity (compare compounds 913 and 940 with 908 and compound 951 with 950).

Example 42

This example illustrates the inhibition of mouse and human soluble epoxide hydrolases by compounds of the invention (formula (I)) having a primary amide pharmacophore.

Adamantyl-amide compounds were prepared having a polar secondary pharmacophore group located various distances from the carbonyl of the primary amide pharmacophore.

Assays were conducted with the compounds indicated in Table 9, according to established protocols (see, above).

TABLE 9

Inhibition of mouse and human sEH by adamantyl-amide derivatives

| No. | Structure | $IC_{50}$ ($\mu M$)$^a$ | |
|---|---|---|---|
| | | Mouse sEH | Human sEH |
| 834 | 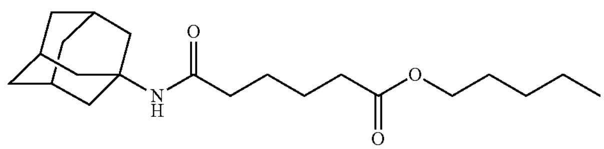 [SMILES: CCCCCOC(=O)CCCCC(=O)NC12CC3CC(CC(C3)C1)C2] | $0.34 \pm 0.01$ | $2.4 \pm 0.2$ |
| 959 | 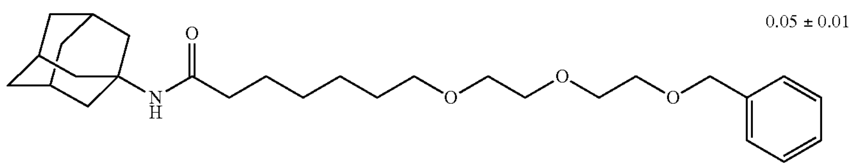 | $0.05 \pm 0.01$ | $0.11 \pm 0.02$ |
| 989 | 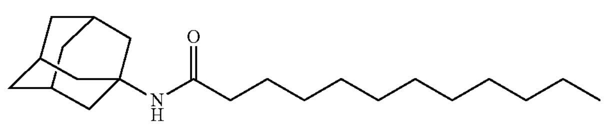 [SMILES: CCCCCCCCCCCC(=O)NC12CC3CC(CC(C3)C1)C2] | $0.05 \pm 0.01$ | $5.0 \pm 0.3$ |
| 1007 | 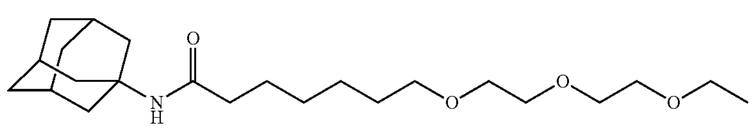 [SMILES: CCOCCOCCOCCCCCCC(=O)NC12CC3CC(CC(C3)C1)C2] | $0.05 \pm 0.01$ | $2.0 \pm 0.2$ |
| 1017 | 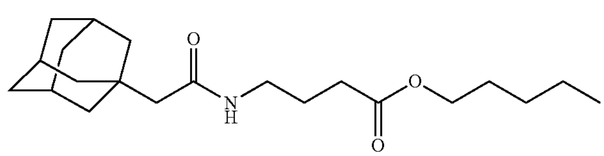 [SMILES: CCCCCOC(=O)CCCNC(=O)CC12CC3CC(CC(C3)C1)C2] | $0.05 \pm 0.01$ | $0.43 \pm 0.02$ |
| 1018 | 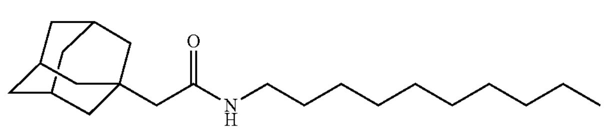 [SMILES: CCCCCCCCCCNC(=O)CC12CC3CC(CC(C3)C1)C2] | $0.05 \pm 0.01$ | $0.10 \pm 0.01$ |

As shown in the above table, these compounds functionalized with a amide group could be as active and potent as urea inhibitors for both murine and human enzymes. The nitrogen to the right of the amide carbonyl group is important for activity.

Example 43

This example illustrates the inhibition of mouse and human soluble epoxide hydrolases by compounds of the invention (formula (I)) having an arylene or cycloalkylene linker.

Because compounds having an alkylene linker between the primary and secondary pharmacophore were found to be excellent inhibitors of both the mouse and human enzymes, a variety of admantyl-urea derivatives having a phenyl or cyclohexyl spacer between a primary urea and secondary pharmacophore were synthesized and evaluated to examine the contributions of the linker.

Assays were conducted with the compounds indicated in Table 10, according to established protocols (see, above).

TABLE 10

Inhibition of mouse and human sEH by substituted phenyl and cyclohexyl derivatives

| No. | Structure | $IC_{50}$ (μM)[a] | |
| --- | --- | --- | --- |
| | | Mouse sEH | Human sEH |
| 859 | 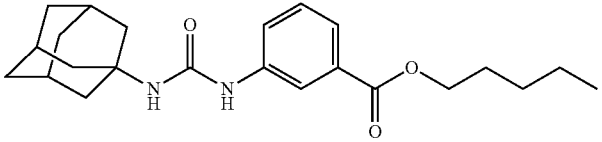 [SMILES: CCCCCOC(=O)c1cccc(NC(=O)NC23CC4CC(CC(C4)C2)C3)c1] | 0.05 ± 0.01 | 0.10 ± 0.01 |
| 860 | 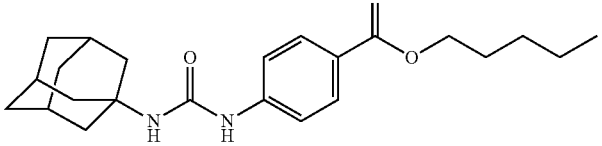 | 0.05 ± 0.01 | 0.10 ± 0.01 |
| 861 | 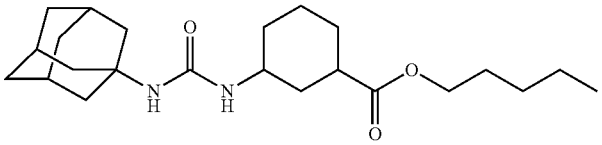 [SMILES: CCCCCOC(=O)C1CCCC(NC(=O)NC23CC4CC(CC(C4)C2)C3)C1] | 0.05 ± 0.01 | 0.10 ± 0.01 |
| 863 | 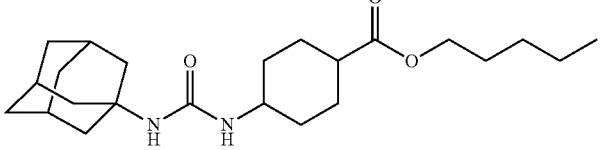 | 0.05 ± 0.01 | 0.12 ± 0.01 |
| 904 | 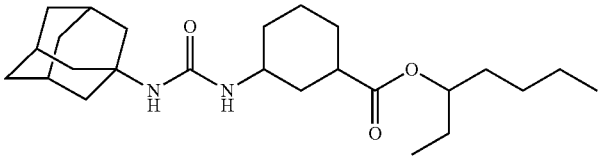 [SMILES: CCCCC(CC)OC(=O)C1CCCC(NC(=O)NC23CC4CC(CC(C4)C2)C3)C1] | 0.05 ± 0.01 | 0.10 ± 0.01 |
| 909 | 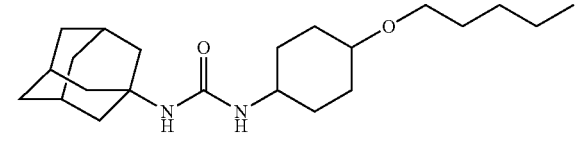 [SMILES: CCCCCOC1CCC(NC(=O)NC23CC4CC(CC(C4)C2)C3)CC1] | 0.05 ± 0.01 | 0.11 ± 0.01 |

TABLE 10-continued

Inhibition of mouse and human sEH by substituted phenyl and cyclohexyl derivatives

| No. | Structure | IC$_{50}$ (μM)$^a$ | |
| --- | --- | --- | --- |
| | | Mouse sEH | Human sEH |
| 960 | 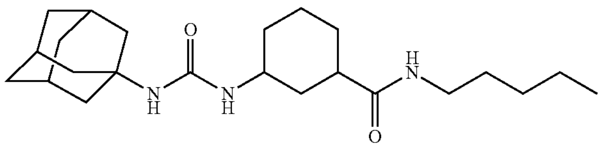 [SMILES: CCCCCNC(=O)C1CCCC(NC(=O)NC23CC4CC(CC(C4)C2)C3)C1] | 0.05 ± 0.01 | 0.10 ± 0.01 |
| 961 | 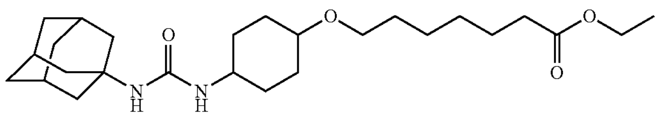 [SMILES: CCOC(=O)CCCCCCOC1CCC(NC(=O)NC23CC4CC(CC(C4)C2)C3)CC1] | 0.05 ± 0.01 | 0.10 ± 0.01 |
| 981 | 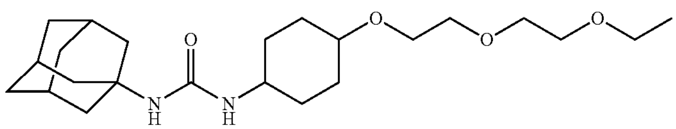 [SMILES: CCOCCOCCOC1CCC(NC(=O)NC23CC4CC(CC(C4)C2)C3)CC1] | 0.05 ± 0.01 | 0.10 ± 0.01 |
| 982 | 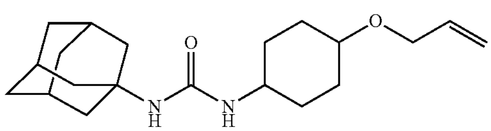 [SMILES: C=CCOC1CCC(NC(=O)NC23CC4CC(CC(C4)C2)C3)CC1] | 0.05 ± 0.01 | 0.10 ± 0.01 |
| 983 | 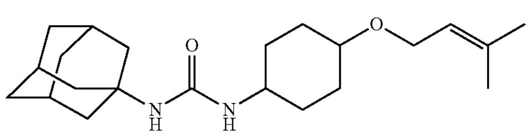 [SMILES: CC(C)=CCOC1CCC(NC(=O)NC23CC4CC(CC(C4)C2)C3)CC1] | 0.05 ± 0.01 | 0.10 ± 0.01 |
| 984 | 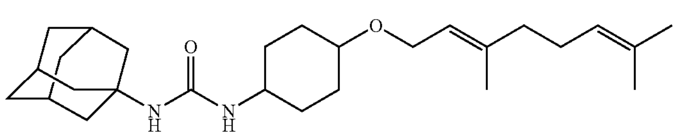 [SMILES: CC(C)=CCC/C(C)=C/COC1CCC(NC(=O)NC23CC4CC(CC(C4)C2)C3)CC1] | 0.05 ± 0.01 | 0.10 ± 0.01 |
| 985 | 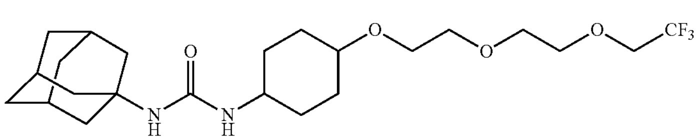 [SMILES: O=C(NC1CCC(OCCOCCOCC(F)(F)F)CC1)NC12CC3CC(CC(C3)C1)C2] | 0.05 ± 0.01 | 0.10 ± 0.01 |

TABLE 10-continued

Inhibition of mouse and human sEH by substituted phenyl and cyclohexyl derivatives

| No. | Structure | IC$_{50}$ (μM)$^a$ | |
|---|---|---|---|
| | | Mouse sEH | Human sEH |
| 1009 trans | 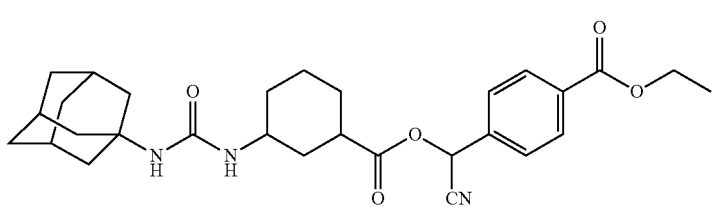 [SMILES: CCOC(=O)c1ccc(C(C#N)OC(=O)C2CCCC(NC(=O)NC34CC5CC(CC(C5)C3)C4)C2)cc1] | 0.05 ± 0.01 | 0.10 ± 0.01 |
| 1014-cis | 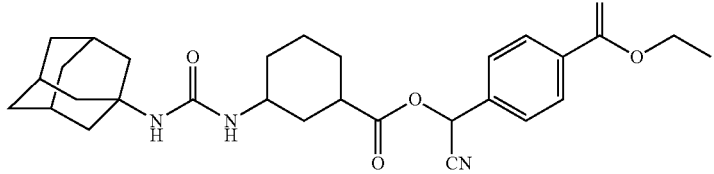 | 0.05 ± 0.01 | 0.14 ± 0.01 |

Compounds with alkylene and arylene linker groups (859 and 861) had inhibition potencies that were higher than compounds with alkylene linkers (789, see Table 2 above, and 868, see Table 7 above) for both murine and human enzymes, independent of the topography (compare compound 859 with 860 and compound 861 with 863) or type of the secondary pharmacophore (compare compounds 860 and 863 with 909).

Example 44

This example illustrates the inhibition of mouse soluble epoxide hydrolases by compounds of the invention (formula (I)) having a secondary pharmacophore, and further including a mono amino acid moiety. This example further illustrates the use of a combinatorial approach toward compound preparation and evaluation.

The utility of a combinatorial approach is illustrated by using the butanoic acid derivatives from Table 11 and Table 12 to form amide bonds with one or more natural or synthetic amino acids. This approach rapidly leads to a large number of compounds that are highly active and can be recognized by the intestinal peptide uptake system. As shown above, polar groups could be incorporated into one of the alkyl groups of the dialkyl-urea sEH inhibitors without loss of activity, when placed at an appropriate distance from the urea function. These modifications give the new inhibitors better solubility and availability. To expand this assessment of inhibitor structure refinement a semi-combinatorial approach was used with amino acids. Because amino acids are simple bifunctional synthons with a wide variety of side chains, mono and di-peptidic derivatives of 4-(3-cyclohexyl-ureido)-butyric acid 625 were synthesized. This parent compound (acid 625) was selected due to its low inhibition of sEH. Furthermore, to make the peptidic bond, reactants were used, such as 1-ethyl-3-(3-(dimethylamino)-propyl) carbodiimide, that themselves or their reaction product, such as 1-ethyl-3-(3-dimethylamino)-propyl urea, are not inhibitors of sEH. Therefore, any inhibition observed was derived from the targeted peptidic derivatives. This approach allows the preparation of compounds on an analytical scale (10 μmol) without purification of the products. The presence of the desired products was confirmed by LC-MS and the ratio of the LC-MS peak of the desire compounds with the starting material was used to estimate the reaction yield. Because each inhibitor presents a single carboxyl group for negative mode ionization, the estimation of yield is reasonably quantitative.

Syntheses of amino acid derivatives of 4-(3-cyclohexyl-ureido)-butyric acid (632) were performed at analytical scale. Reactions were performed in 2 mL glass vials for each amino acid. To 100 μL of a solution of 632 in DMF at 100 mM (10 μmol), 200 μL of a solution of 1-ethyl-3-(3-(dimethylamino)-propyl) carbodiimide in DMF at 100 mM (20 mmol) was added. After 15 minutes reaction at room temperature, 400 μL of amino acid methyl ester solution at 100 mM (40 μmol) in 90:10 DMF:1 N NaOH was added. The reaction was strongly mixed at 40° C. overnight. Three hundred microliters of 1 N NaOH was then added and allowed to react overnight at 40° C. Product formation was confirmed for each amino acid using electrospray-ionization mass spectrometry (ESI-MS). Reaction solutions were used directly for inhibitor potency measurement with a theoretical concentration of 10 mM.

Assays were conducted with the compounds indicated in Table 11, according to established protocols (see, above).

TABLE 11

Inhibition of mouse sEH by mono-amino acid derivatives of 4-(3-cyclohexyl-ureido)-butyric acid (632).

| | MS m/z (Da) | | Mouse sEH IC$_{50}$ (μM) |
|---|---|---|---|
| R: | M$_{th}$ | (M + H)$^{+-}$ | |
| OH | 228.1 | Control | >50 |
| Alanine | 299.2 | 229.5 | >50 |
| Arginine | 384.3 | 385.8 | >50 |
| Aspartate | 344.2 | 344.7 | >50 |
| Cysteine | 331.2 | 332.8 | >50 |

TABLE 11-continued

Inhibition of mouse sEH by mono-amino acid derivatives of 4-(3-cyclohexyl-ureido)-butyric acid (632).

| R: | MS m/z (Da) | | Mouse sEH IC$_{50}$ (µM) |
|---|---|---|---|
| | M$_{th}$ | (M + H)$^{+-}$ | |
| Glutamate | 357.2 | 358.7 | >50 |
| Glycine | 285.2 | 286.6 | >50 |
| Histidine | 365.2 | 366.6 | 1.9 ± 0.2 |
| Isoleucine | 341.2 | 342.7 | 18 ± 3 |
| Leucine | 341.2 | 342.7 | >50 |
| Lysine | 356.3 | 357.7 | 2.2 ± 0.5 |
| Methionine | 359.2 | 360.7 | >50 |
| Phenylalanine | 375.2 | 376.7 | 5.6 ± 0.4 |
| Proline | 325.2 | 326.7 | >50 |
| Serine | 315.2 | 316.7 | >50 |
| Threonine | 329.2 | 330.7 | >50 |
| Tryptophane | 414.2 | 415.8 | 1.6 ± 0.2 |
| Tyrosine | 391.2 | 392.8 | 0.59 ± 0.03 |
| Valine | 327.2 | 328.7 | >50 |

Results are means ± SD of three separate experiments.

Significant improvement of the inhibition potency was observed for the aromatic derivatives (phenylalanine, tryptophane and tyrosine), histidine and lysine. Again, without intending to be bound by theory, it is believed that the specificity of the interaction of the enzyme with the five peptidic inhibitors listed results from specific pi-pi stacking between tryptophane 334 (Trp$^{334}$) located in close proximity to the secondary pharmacophore, and the aromatic moieties with four of the five amino acids above. This interaction should alter the fluorescence spectrum of the enzyme. For the lysine derivative, because reaction can occur with the side chain amino group, the resulting product could resemble the alkyl derivatives synthesized above with the acid function playing the role of the third pharmacophore.

Example 45

This example illustrates the inhibition of mouse soluble epoxide hydrolases by compounds of the invention (formula (I)) having a secondary pharmacophore, and further including a dipeptide moiety.

Compounds in the amino acid derivative series, 625-Tyr, showed an inhibition potency in the hundreds of nanomolar range, prompting the evaluation of the effect of adding a second amino acid.

In a manner similar to that described above, syntheses of amino acid derivatives of 2-[4-(3-Cyclohexyl-ureido)-butyrylamino]-3-(4-hydroxy-phenyl)-propionic acid (632-Tyr) that are examples of dipeptide derivatives of 632 were done on an analytical scale. Synthesis was performed as described above for the derivatives of 632, simply substituting this compound by 632-Tyr. Product formation was confirmed by ESI-MS.

Assays were conducted with the compounds indicated in Table 12, according to established protocols (see, above).

TABLE 12

Inhibition of mouse sEH by mono-amino acid derivatives of 4-(3-cyclohexyl-ureido)-butyryl-tyrosine.

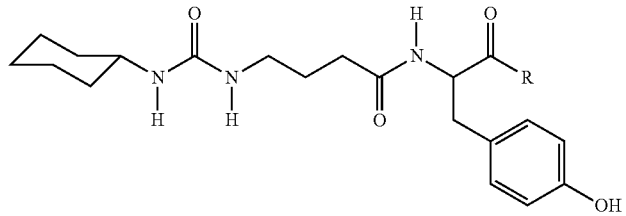

| R: | MS m/z (Da) | | | Mouse sEH | |
|---|---|---|---|---|---|
| | M$_{th}$ | (M − H)$^−$ | (M − H)$^−$: m/z$_{390.2}$ | IC$_{50}$ (µM) | IC$_{90}$ (µM) |
| OH | 391.5 | 390.2 | Control | 0.50 | 30 |
| Alanine | 462.6 | 461.4 | 3 | 0.22 | 25 |
| Arginine | 547.7 | 546.2 | 1 | 0.05 | 4.0 |
| Aspartate | 506.6 | 505.3 | 1 | 0.05 | 1.6 |
| Glycine | 448.5 | 447.3 | 1 | 0.06 | 6.5 |
| Isoleucine | 504.6 | 503.2 | 3 | 0.07 | 12.5 |
| Leucine | 504.6 | 503.5 | 6 | 0.07 | 16.0 |
| Lysine | 519.7 | 518.4 | 0.5 | 0.05 | 6.3 |
| Methionine | 522.8 | 521.2 | 2 | 0.05 | 2.0 |
| Phenylalanine | 538.7 | 537.5 | 1 | 0.05 | 1.6 |
| Proline | 488.6 | 487.4 | 1 | 0.06 | 6.3 |
| Serine | 478.6 | 477.3 | 1 | 0.07 | 3.3 |
| Threonine | 492.6 | 491.3 | 4 | 0.12 | 12.5 |
| Tryptophane | 577.7 | 576.4 | 1 | 0.05 | 1.0 |
| Tyrosine | 554.7 | 553.4 | 5 | 0.05 | 2.5 |
| Valine | 490.6 | 489.4 | 2 | 0.05 | 3.1 |

Results are means ± SD of three separate experiments.

Significant improvement of inhibition potency was observed for almost all the derivatives tested except for alanine, isoleucine, leucine and threonine. These results indicate that the enzyme has a narrower specificity close to the catalytic center than toward the end of the active site tunnel. The inhibition potency found for the best dipeptidic derivatives are similar to those found for the corresponding alkyl inhibitors (see, C. Morisseau, et al., *Biochem. Pharm.* 63: 1599-1608 (2002)), indicating that such peptide-mimics are excellent inhibitors of sEH. Because of the presence of the amino acid derivatives in their structure, these compounds have excellent water solubility. Furthermore, because of the presence of active small peptide transport system in the gut, the dipeptidic urea derivatives will be absorbed in the gut by such systems as observed for several peptide derivative drugs (see, E. Walter, et al., *Pharm. Res.* 12: 360-365 (1995) and K. Watanabe, et al., *Biol. Pharm. Bull.* 25: 1345-1350 (2002)), giving these compounds excellent bioavailability.

Example 46

This example provides studies directed to the metabolic stability of certain inhibitors of sEH.

Figure 7:
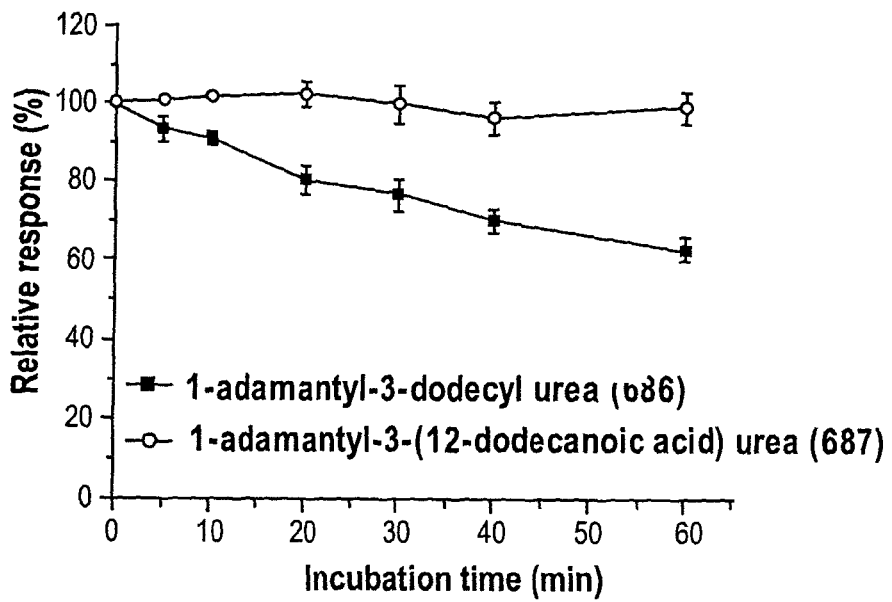
FIG. 7 is a graph illustrating the metabolic stabilities of 686 and 687 in rat hepatic microsomes as described above.
Figure 8:
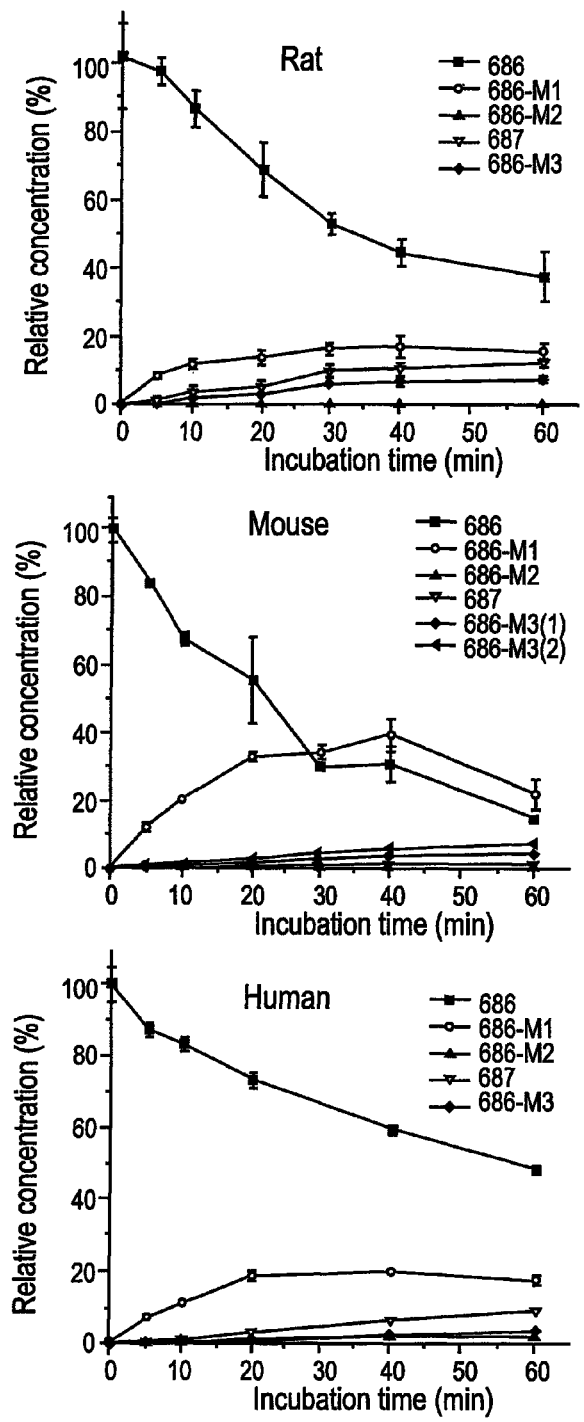
FIG. 8 is a series of graphs illustrating the metabolic conversion of 1-adamantyl-3-dodecyl urea (686) in microsomal preparations from rat, mouse, and human hepatic tissues. The metabolites identified are the omega hydroxyl (686-M1), the omega aldehyde (686-M2), the omega acid (687), and a mixture of monohydroxy adamantyl omega hydroxylated compounds (686-M3). These structures are shown in Table 13.
Figure 9:
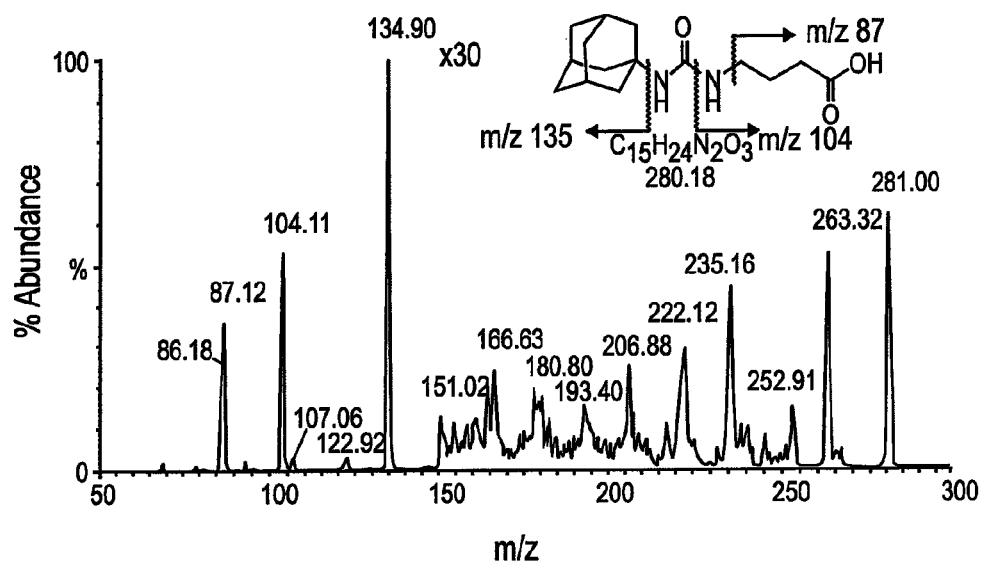
FIG. 9 provides a mass spectrum showing collision induced dissociation of a dominant urinary metabolite of 1-adamantyl-3-dodecyl urea (686) and the 3-dodecanoic acid analog (687) suggesting that these compounds can ultimately enter beta-oxidation to produce chain shortened inhibitors.

To evaluate the metabolic stability of these inhibitors, the microsomal and NADPH dependent metabolism of a number of potent sEH inhibitors was evaluated. The rates of metabolism among the compounds varied dramatically, however the appearance of an omega-terminal acid was observed for all inhibitors containing n-alkane substitutions. When tested, the potent alkyl derivatives (e.g. 686) are rapidly metabolized in microsomal preparations by P450 dependents processes (see FIG. 6), while the omega acid analogs (e.g. 687) were stable (see FIG. 7). The first step in the metabolic transformation of the n-alkyl to n-alkanoic acid derivatives is an NAPDH dependent process carried out by cytochrome P450 dependent omega hydroxylation in rodent and human hepatic tissue preparations (see FIG. 8). The metabolites identified along this metabolic route are provided in Table 13. When in vivo metabolism was evaluated, evidence for the beta-oxidation of the alkanoic acid derivatives was also found (see FIG. 9).

Together, these data indicate that P450 omega hydroxylation can result in the rapid in vivo metabolic inactivation and excretion of these inhibitors.

TABLE 13

Structure of metabolites formed from compound 686.

| No | X | Y |
|---|---|---|
| 686 | H | $CH_3$ |
| 686-M1 | H | $CH_2OH$ |
| 686-M2 | H | CHO |
| 687 | H | COOH |
| 686-M3 | OH | $CH_2OH$ |

Example 47

This example provides the structures of compounds of the invention designed to slow esterase dependent inactivation, block beta-oxidation, block cytochrome P450 dependent omega hydroxylation, or inhibit cytochrome P450 omega hydrolase.

Beta-oxidation can be blocked in a variety of ways, for example with an alpha halogen or alpha branched alkyl group (806), cyclopropane (807) or aromatic groups (808), or by replacing the acid or ester functional groups with alternate functionalities, such as sulfonamides (809 and 810), which mimic ester and acid functional groups yet provide metabolic stability in vivo. Similarly in pharmacology heterocyclic groups are used for hydrogen bond donors and acceptors to mimic carboxylic acids and esters (811). In addition, P450 omega hydroxylation can be blocked by including acetylene (812), trifluoromethyl (813), or aryl (814) groups at the terminus of the alkyl chain. This series of inhibitors also illustrates that with both the secondary and tertiary pharmacophore, replacement can be made for the carbonyl with other functionalities as hydrogen bond donors and acceptors.

TABLE 14

Structures of sEH inhibitors designed to prevent beta-oxidation and P450 omega hydroxylation.

| No. | Structure | Action |
|---|---|---|
| 809 | 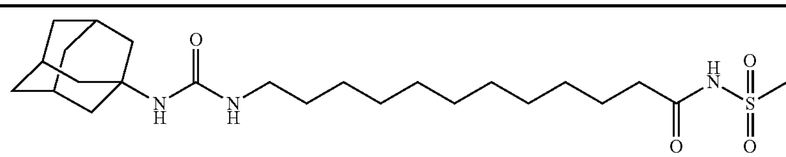 | Block beta-oxidation |
| 810 | 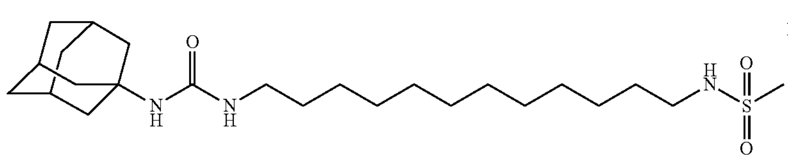 | Block beta-oxidation |
| 811 | 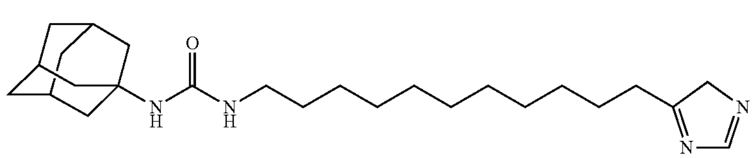 [SMILES: O=C(NCCCCCCCCCCCC1=NC=NC1)NC12CC3CC(CC(C3)C1)C2] | Block beta-oxidation Block P450 dependent omega hydroxylation |

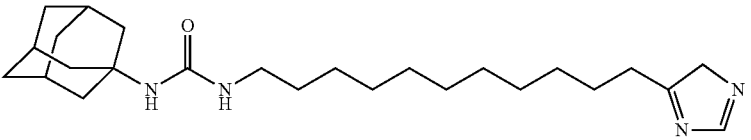

TABLE 14-continued

Structures of sEH inhibitors designed to prevent beta-oxidation and P450 omega hydroxylation.

| No. | Structure | Action |
|---|---|---|
| 812 | 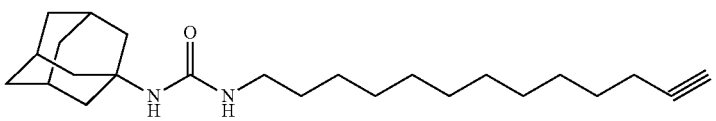 [SMILES: C#CCCCCCCCCCCCNC(=O)NC12CC3CC(CC(C3)C1)C2] | Block beta-oxidation Inhibit P450 omega hydroxylase |
| 813 | 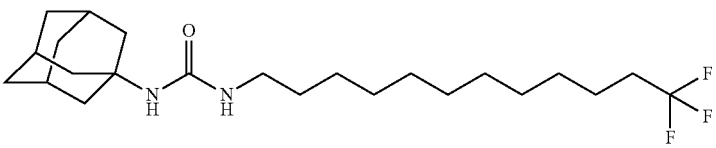 [SMILES: O=C(NCCCCCCCCCCCC(F)(F)F)NC12CC3CC(CC(C3)C1)C2] | Block P450 dependent omega hydroxylation |
| 814 | 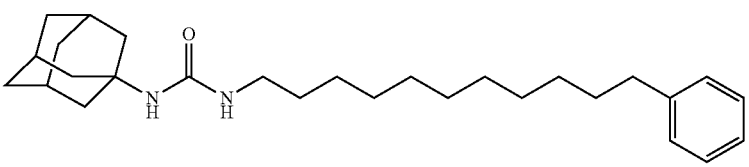 [SMILES: O=C(NCCCCCCCCCCCc1ccccc1)NC12CC3CC(CC(C3)C1)C2] | Block P450 dependent omega hydroxylation |

Example 48

This example illustrates a comparison of cyclohexyl and adamantyl groups in stability and solubility.

Figure 6:
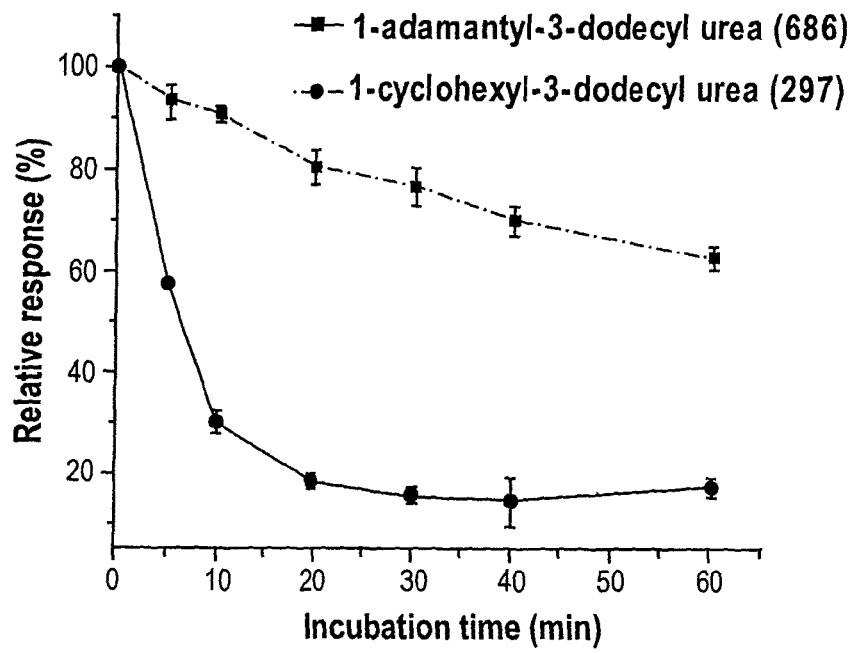
FIG. 6 is a graph illustrating the metabolic stabilities of 1-adamantyl-3-dodecyl urea (686) and 1-cyclohexyl-3-dodecyl urea (297) in rat hepatic microsomes. Microsomes were incubated with 1 μM 686 or 297 in the presence of an NADPH generating system. Data are expressed as mean±SD of triplicate experiments.

Another consistent observation during the metabolism studies was that the adamantyl substituent (both 192 and 686 substituted) provided compounds having improved stability (see FIG. 6). Surprisingly the adamantyl compounds were approximately 2× more soluble than the corresponding cyclohexyl derivatives (772 vs. 789, 791 vs. 790, and 297 vs. 686 see Table 2 for structures). Surprisingly, the LC-MS/MS analyses producing collision induced dissociation of compounds containing the adamantyl substituent provided extremely high abundance ions, which dramatically enhanced the analytical sensitivity for these inhibitors (see Table 15 below). This enhanced sensitivity is a distinct advantage for drug metabolism studies using either in vivo or in vitro systems. Moreover, adamantane represents the smallest diamond nucleus and the adamantyl substituents not only yield compounds of improved metabolic stability and pharmacokinetic parameters, but also compounds that are very easy to detect.

TABLE 15

Calibration curves and detections limit (DL) of inhibitors analyzed by HPLC-MS/MS.

| No. | Structure | Calibration curve | $r^2$ | DL (ng/mL) |
|---|---|---|---|---|
| 686 | 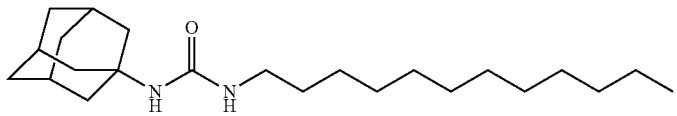 [SMILES: CCCCCCCCCCCCNC(=O)NC12CC3CC(CC(C3)C1)C2] | y = 0.067x − 0.003 | 0.999 | 0.05 |
| 687 | 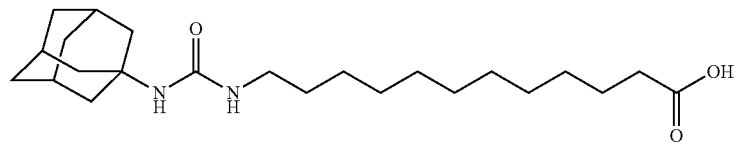 [SMILES: O=C(O)CCCCCCCCCCCNC(=O)NC12CC3CC(CC(C3)C1)C2] | y = 0.099x − 0.274 | 0.999 | 0.05 |
| 297 | 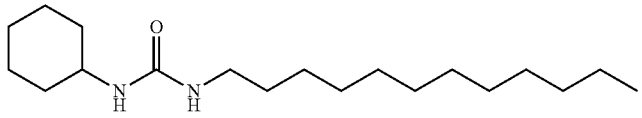 [SMILES: CCCCCCCCCCCCNC(=O)NC1CCCCC1] | y = 0.024x + 0.091 | 0.999 | 0.50 |
| 425 | 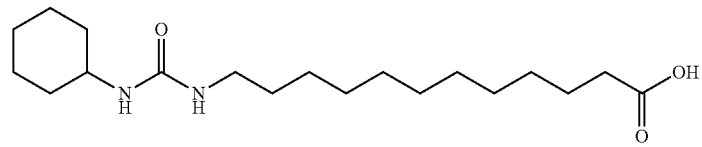 [SMILES: O=C(O)CCCCCCCCCCCNC(=O)NC1CCCCC1] | y = 0.009x − 0.003 | 0.999 | 0.50 |

Example 49

This example provides the pharmacokinetic studies carried out using compounds of the present invention.

The pharmacokinetic properties of some of the most potent sEH inhibitors was evaluated following oral gavage in mice. As noted above, the use of 1-adamantyl urea inhibitors afforded exquisite sensitivity, allowing the determination of the determined pharmacokinetic parameters from serial blood samples collected from individual mice (see Table 17).

Animals. Male Swiss Webster mice, 6 weeks-old, were obtained from Charles River (CA, USA). After 1-2 week acclimation period, healthy animals were assigned to study groups based on body-weight stratified randomization procedure. The body weight of animals used in all the experiments ranged from 28 g to 38 g. Mice were maintained on a 12 h light/12 h dark cycle under controlled temperature and humidity conditions, and food and water available ad libidum.

Administration and measurement. Pharmacokinetic studies in mice used a 5 mg/kg dose of sEH inhibitors dissolved in corn oil and 4% DMSO administered orally. Serial tail bled blood samples (5-10 μL) were collected in heparinized 1.5 mL tubes at various time points (0.5, 1, 2, 3, 4, 5, 6, and 24 hr) after the administration for measuring parent compounds and their metabolites by using LC-MS/MS: a Waters 2790 liquid chromatograph equipped with a 30×2.1 mm 3 μm C18 Xterra™ column (Waters) and a Micromass Quattro Ultima triple quadrupole tandem mass spectrometer (Micromass, Manchester, UK). To the collected samples were added 100 μL of distilled water, 25 μL of internal standard (500 ng/mL; 1-cyclohexyl-3-tetradecylurea, CTU), and 500 μL of ethyl acetate. Then the samples were centrifuged at 6000 rpm for 5 min, and the ethyl acetate layer was dried under nitrogen. The residue was reconstituted in 25 μL of methanol, and aliquots (5 μL) were injected onto the LC-MS/MS system.

Pharmacokinetic studies using a human subject employed doses of 0.1-1.0 mg/kg of sEH inhibitors (800) or a 0.3 mg/kg dose of 687 dissolved in olive oil administered orally. Serial bled blood samples (3-50 μL) were collected from finger tips into 50 μL heparinized capillary tube at various time points (0.5, 1, 2, 4, 6, 12 and 24 hr) after administration. These samples were used to measure parent compounds and their metabolites using LC-MS/MS as described above for experiments with mice. Blood samples were added 400 μL of distilled water and 25 μL of internal standard (500 ng/mL CTU), and vortexed. The blood samples were then extracted with 500 μL of ethyl acetate twice and the ethyl acetate layer was dried under nitrogen. The residue was reconstituted in 25 μL of methanol, and aliquots (10 μL) were injected onto the LC-MS/MS system as described above. Biological end points came from clinical chemistry samples run at The University of California Davis Clinical Laboratory and a series of 6 inflammatory markers including C reactive protein were run blind at the University of California Davis Department of Nephrology.

Analysis. Pharmacokinetics analysis was performed using SigmaPlot software system (SPSS science, Chicago, Ill.). A one-compartment model was used for blood concentration-time profiles for the oral gavage dosing and fits to the following equation (see, Gibson, G. G. and Skett, P.: INTRODUCTION TO DRUG METABOLISM, SECOND ED., Chapman and Hall, New York 1994, 199-210):

$$C = ae^{-bt}$$

The half-life ($t_{1/2}$) for the elimination phase was calculated by the following equation:

$$t_{1/2} = 0.693/b$$

The area under the concentration (AUC) was calculated by the following equation:

$$AUC = a/b$$

Where:
C = the total blood concentration at time t
a = the extrapolated zero intercept
b = the apparent first-order elimination rate constant

TABLE 17

Pharmacokinetic parameters of 1-(1-adamantyl)-3-(11-alkylated undecyl)ureas[a]

| No. | R | $C_{max}$[b] (ng/mL) | $tC_{max}$[c] (hr) | AUC[d] (ng·hr/mL) | $t_{1/2}$[e] (hr) |
|---|---|---|---|---|---|
| 686 | CH₃ | 19.8 | 1 | 47 | 2.3 |
| 687 | —C(=O)OH | 26.9 | 0.5 | 87 | 2.3 |
| 780 | —C(=O)O—CH₃ | 144.3 | 0.5 | 168 | 1.3 |
| 784 | —C(=O)O—CH₂CH₃ | 101.7 | 1 | 198 | 1.5 |

TABLE 17-continued

Pharmacokinetic parameters of 1-(1-adamantyl)-
3-(11-alkylated undecyl)ureas[a]

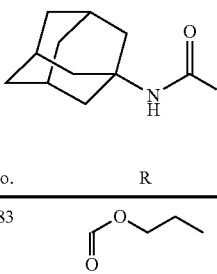

| No. | R | $C_{max}$[b] (ng/mL) | $tC_{max}$[c] (hr) | AUC[d] (ng·hr/mL) | $t_{1/2}$[e] (hr) |
|---|---|---|---|---|---|
| 783 | 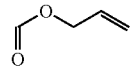 | 62.6 | 1 | 137 | 1.6 |
| 781 | 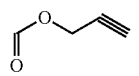 | 45.3 | 1 | 111 | 2 |
| 788 | 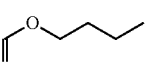 | 39.6 | 1 | 130 | 2.9 |
| 800 | 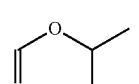 | 39.5 | 1 | 96 | 1.5 |
| 785 | 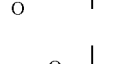 | 29.6 | 2 | 84 | 1.9 |
| 801 |  | 5.3 | 2 | 10 | 2.1 |
| 802 | 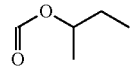 | 13.1 | 2 | 47 | 3.8 |
| 803 | 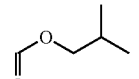 | 42.9 | 2 | 110 | 2.9 |
| 804 |  | 42.3 | 1 | 141 | 3 |

Figure 10:
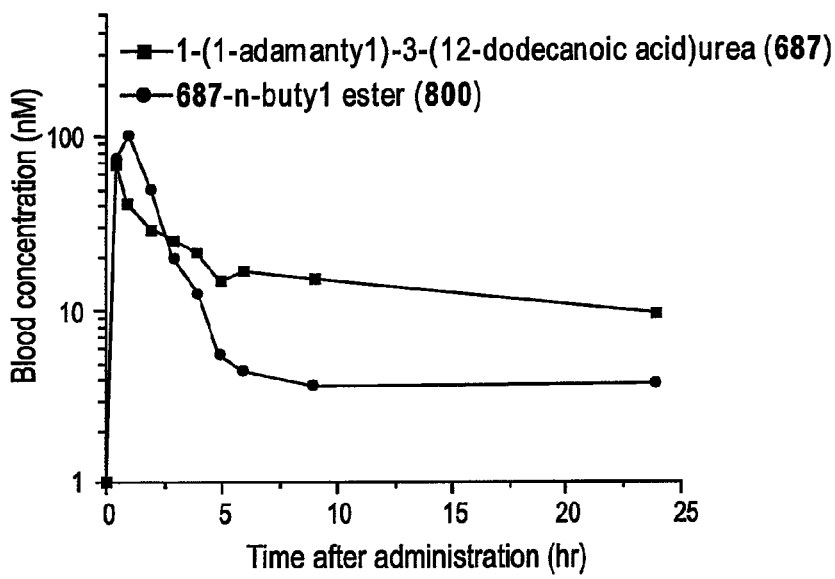
FIG. 10 is a graph illustrating the blood concentration vs. time profiles of 687 after oral administration of 5 mg/kg of either 687 or 800 to mice. The ester compound delays the time to achieve the maximum circulating dose, and increases the maximum circulating concentration of 687 observed. This translates into a longer half-life for the inhibitor.

[a]5 mg/kg dosing of compounds were administered orally to male Swill Webster mice, [b]maximum concentration, [c]time of maximum concentration, [d]area under concentration, [e]half-life The ester compounds were generally hydrolyzed to the acid compound (687) when administered orally. An example of the time course of free acid appearance is shown in FIG. 10. When compound 687 was administered orally, it reached the maximum concentration (2-fold higher than 686) in 30 min, while compound 686 reached its maximum concentration in 2 h. Furthermore, the area under the curve (AUC) for 687 was 2-fold higher, indicating an improvement in oral bioavailability. The maximum concentrations of primary esters (780, 784, 783, 781, 788, 800, 803 and 804) esters were 1.5-5-fold higher than 687, and the AUC increased 1.2-2.3-fold for the ester compounds indicating higher bioavailabilities. On the other hand, secondary esters (785 and 802) showed similar maximum concentrations and bioavailabilities to those of 687 in mice, while the tertiary ester (801) displayed a 4-8-fold decrease in maximum concentration and bioavailability. Accordingly, the alkylation of a potent acid inhibitor (687) to form primary esters improves the oral availability of these inhibitors.

Example 50

This example provides a table of structures for compounds of the invention having all three pharmacophores present. Tables 18a and b: Structures and inhibition of mouse and human sEH by other sEH inhibitors containing the primary, secondary, and tertiary pharmacophores.

TABLE 18a

| No. | Structure | IC$_{50}$ (μM)$^a$ | |
|---|---|---|---|
| | | Mouse sEH | Human sEH |
| 821 | 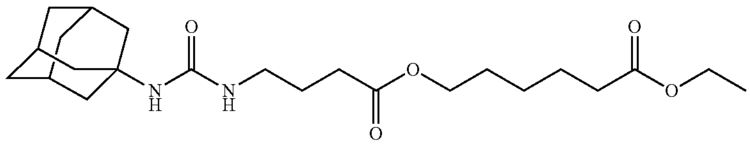 [SMILES: CCOC(=O)CCCCCOC(=O)CCCNC(=O)NC12CC3CC(CC(C3)C1)C2] | 0.06 ± 0.01 | |
| 836 | 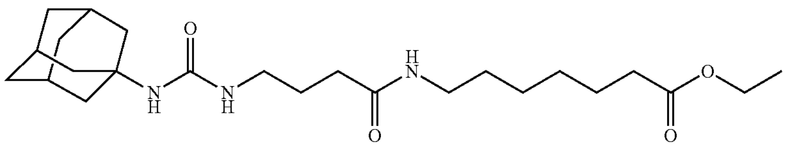 [SMILES: CCOC(=O)CCCCCCNC(=O)CCCNC(=O)NC12CC3CC(CC(C3)C1)C2] | 0.05 ± 0.01 | |
| 846 | 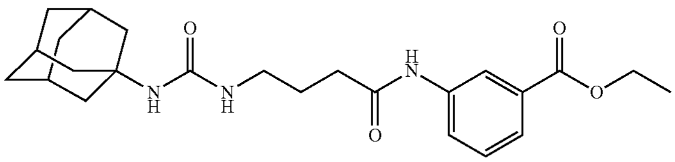 [SMILES: CCOC(=O)c1cccc(NC(=O)CCCNC(=O)NC23CC4CC(CC(C4)C2)C3)c1] | 0.04 ± 0.01 | |
| 849 | 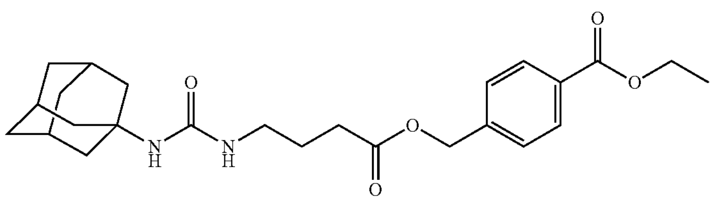 [SMILES: CCOC(=O)c1ccc(COC(=O)CCCNC(=O)NC23CC4CC(CC(C4)C2)C3)cc1] | 0.01 ± 0.01 | |
| 855 | 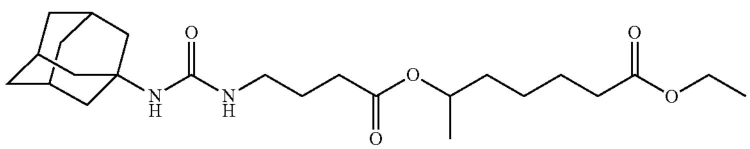 [SMILES: CCOC(=O)CCCCC(C)OC(=O)CCCNC(=O)NC12CC3CC(CC(C3)C1)C2] | 0.01 ± 0.01 | |
| 851 | 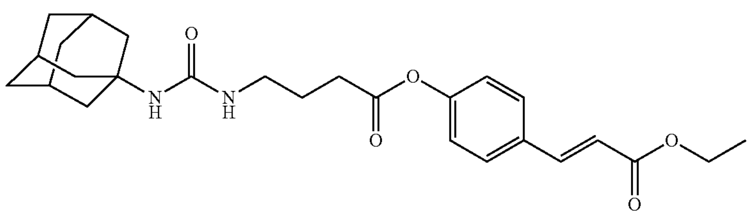 [SMILES: CCOC(=O)/C=C/c1ccc(OC(=O)CCCNC(=O)NC23CC4CC(CC(C4)C2)C3)cc1] | 0.01 ± 0.01 | |
| 900 | 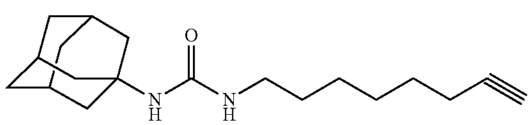 [SMILES: C#CCCCCCCNC(=O)NC12CC3CC(CC(C3)C1)C2] | 0.05 ± 0.01 | 0.1 ± 0.01 |
| 901 | 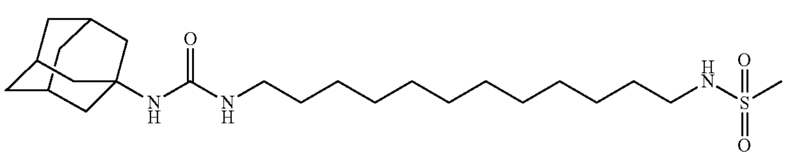 [SMILES: CS(=O)(=O)NCCCCCCCCCCCCNC(=O)NC12CC3CC(CC(C3)C1)C2] | 0.07 ± 0.01 | 0.1 ± 0.01 |
| 902 | 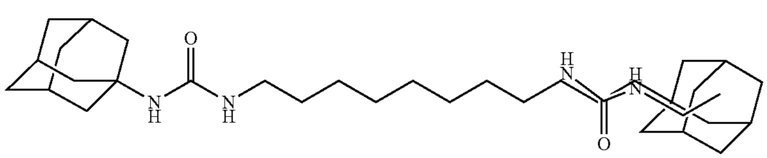 | 0.45 ± 0.01 | 0.44 ± 0.01 |

TABLE 18a-continued

| No. | Structure | IC$_{50}$ (µM)$^a$ | |
|---|---|---|---|
| | | Mouse sEH | Human sEH |
| 903 | 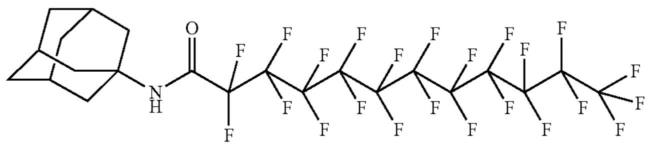 [SMILES: O=C(NC12CC3CC(CC(C3)C1)C2)C(F)(F)C(F)(F)C(F)(F)C(F)(F)C(F)(F)C(F)(F)C(F)(F)C(F)(F)C(F)(F)C(F)(F)C(F)(F)F] | 0.1 ± 0.01 | 0.01 ± 0.01 |
| 905 | 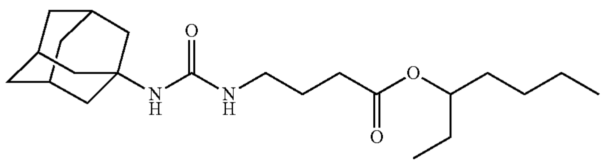 [SMILES: CCCCC(CC)OC(=O)CCCNC(=O)NC12CC3CC(CC(C3)C1)C2] | 0.13 ± 0.01 | 0.45 ± 0.01 |
| 906 | 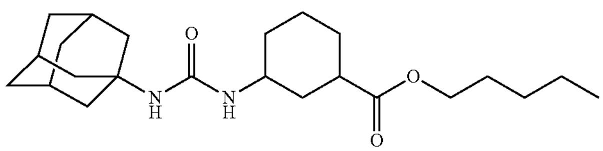 [SMILES: CCCCCOC(=O)C1CCCC(NC(=O)NC23CC4CC(CC(C4)C2)C3)C1] | 0.05 ± 0.01 | 0.1 ± 0.01 |
| 907 | 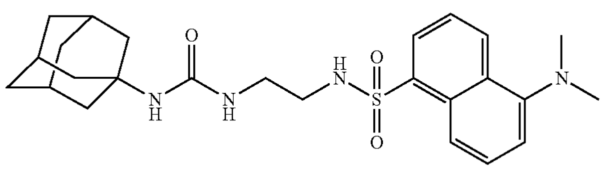 [SMILES: CN(C)c1cccc2c(S(=O)(=O)NCCNC(=O)NC34CC5CC(CC(C5)C3)C4)cccc12] | 0.4 ± 0.01 | 0.6 ± 0.01 |
| 910 | 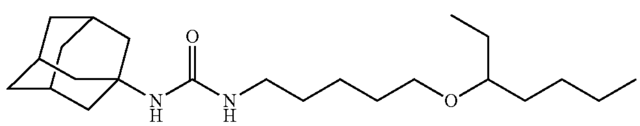 [SMILES: CCCCC(CC)OCCCCCNC(=O)NC12CC3CC(CC(C3)C1)C2] | 0.05 ± 0.01 | 0.24 ± 0.01 |
| 912 | 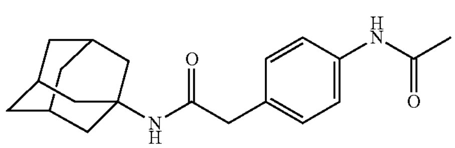 [SMILES: CC(=O)Nc1ccc(CC(=O)NC23CC4CC(CC(C4)C2)C3)cc1] | 4.1 ± 0.01 | 35 ± 0.01 |
| 914 | 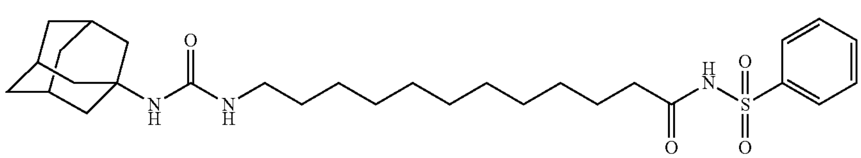 [SMILES: O=C(CCCCCCCCCCCNC(=O)NC12CC3CC(CC(C3)C1)C2)NS(=O)(=O)c1ccccc1] | 0.05 ± 0.01 | 0.1 ± 0.01 |
| 915 | 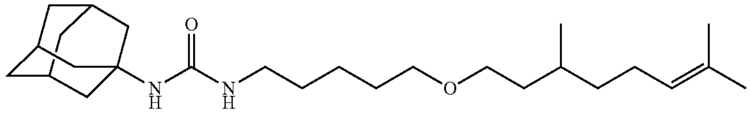 [SMILES: CC(C)=CCCC(C)CCOCCCCCNC(=O)NC12CC3CC(CC(C3)C1)C2] | 0.05 ± 0.01 | 0.12 ± 0.01 |

TABLE 18a-continued

| No. | Structure | IC$_{50}$ (μM)$^a$ | |
|---|---|---|---|
| | | Mouse sEH | Human sEH |
| 916 | 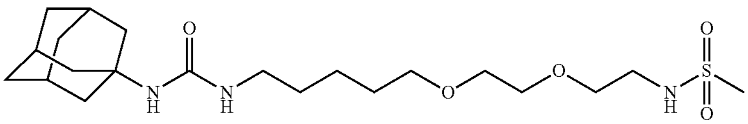 [SMILES: CS(=O)(=O)NCCOCCOCCCCCNC(=O)NC12CC3CC(CC(C3)C1)C2] | | |
| 942 | 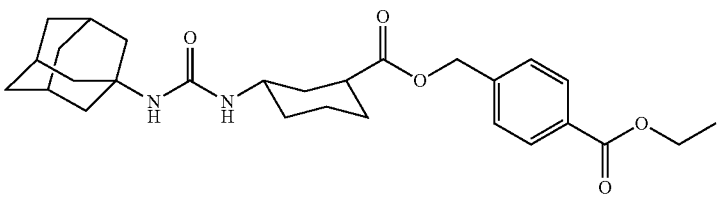 [SMILES: CCOC(=O)c1ccc(COC(=O)C2CCCC(NC(=O)NC34CC5CC(CC(C5)C3)C4)C2)cc1] | 0.05 ± 0.01 | 0.1 ± 0.01 |
| 943 | 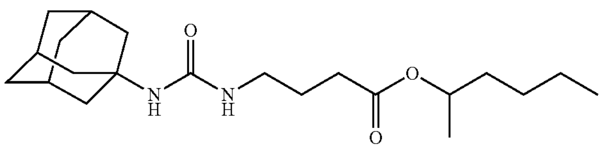 [SMILES: CCCCC(C)OC(=O)CCCNC(=O)NC12CC3CC(CC(C3)C1)C2] | 0.05 ± 0.01 | 0.13 ± 0.01 |
| 944 | 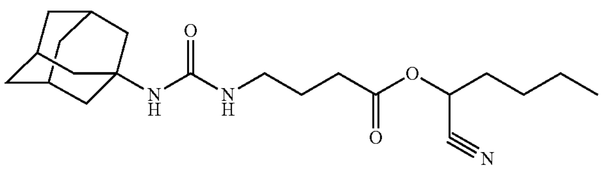 [SMILES: CCCCC(C#N)OC(=O)CCCNC(=O)NC12CC3CC(CC(C3)C1)C2] | 0.05 ± 0.01 | 0.2 ± 0.01 |
| 945 | 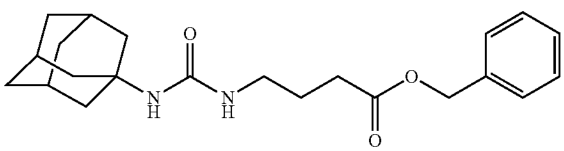 [SMILES: O=C(NCCCC(=O)OCc1ccccc1)NC12CC3CC(CC(C3)C1)C2] | 0.05 ± 0.01 | 0.19 ± 0.01 |
| 946 | 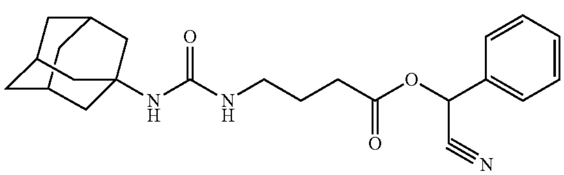 [SMILES: N#CC(OC(=O)CCCNC(=O)NC12CC3CC(CC(C3)C1)C2)c1ccccc1] | 0.05 ± 0.01 | 0.15 ± 0.01 |
| 947 | 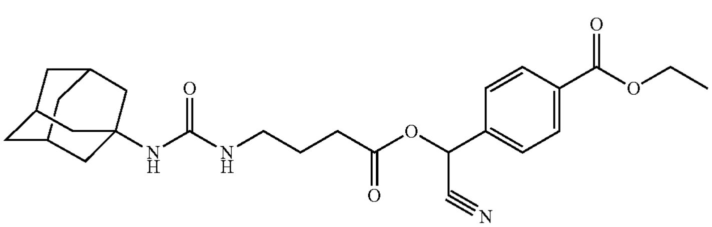 [SMILES: CCOC(=O)c1ccc(C(C#N)OC(=O)CCCNC(=O)NC23CC4CC(CC(C4)C2)C3)cc1] | 0.07 ± 0.01 | 0.11 ± 0.01 |
| 948 | 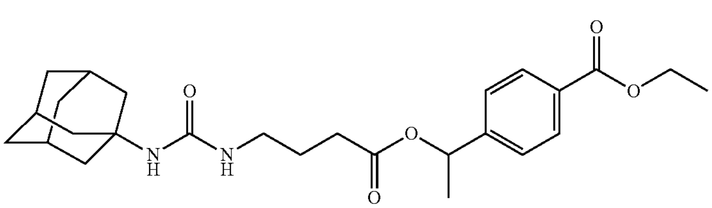 [SMILES: CCOC(=O)c1ccc(C(C)OC(=O)CCCNC(=O)NC23CC4CC(CC(C4)C2)C3)cc1] | 0.08 ± 0.01 | 0.12 ± 0.01 |

TABLE 18a-continued

| No. | Structure | IC$_{50}$ (μM)$^a$ | |
|---|---|---|---|
| | | Mouse sEH | Human sEH |
| 949 | 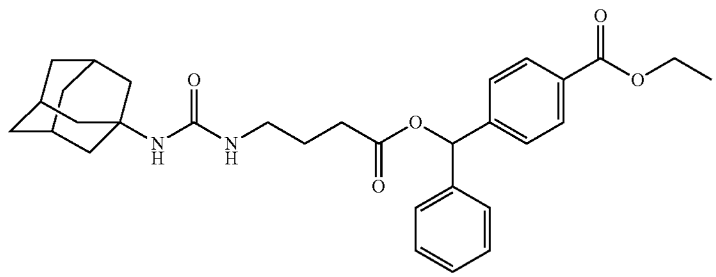 [SMILES: CCOC(=O)c1ccc(C(OC(=O)CCCNC(=O)NC23CC4CC(CC(C4)C2)C3)c2ccccc2)cc1] | 0.05 ± 0.01 | 0.1 ± 0.01 |
| 954 | 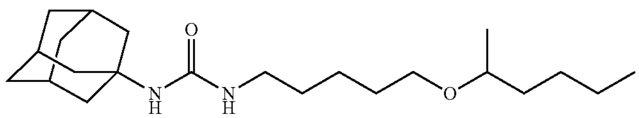 [SMILES: CCCCC(C)OCCCCCNC(=O)NC12CC3CC(CC(C3)C1)C2] | 0.05 ± 0.01 | 0.11 ± 0.01 |
| 955 | 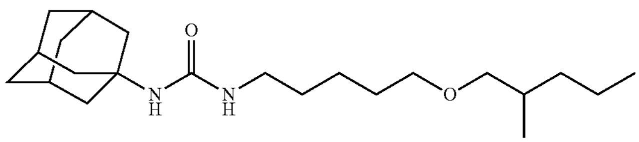 [SMILES: CCCC(C)COCCCCCNC(=O)NC12CC3CC(CC(C3)C1)C2] | 0.05 ± 0.01 | 0.11 ± 0.01 |
| 956 | 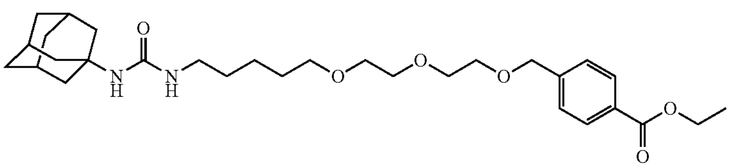 [SMILES: CCOC(=O)c1ccc(COCCOCCOCCCCCNC(=O)NC23CC4CC(CC(C4)C2)C3)cc1] | 0.05 ± 0.01 | 0.1 ± 0.01 |
| 957 | 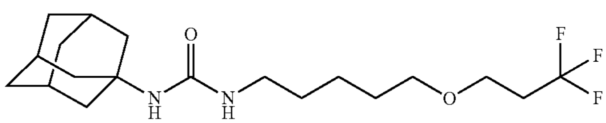 [SMILES: O=C(NCCCCCOCCC(F)(F)F)NC12CC3CC(CC(C3)C1)C2] | 0.05 ± 0.01 | 0.23 ± 0.01 |
| 958 | 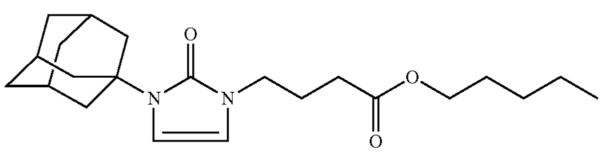 [SMILES: CCCCCOC(=O)CCCn1ccn(C23CC4CC(CC(C4)C2)C3)c1=O] | 0.7 ± 0.01 | 17 ± 0.01 |
| 964 | 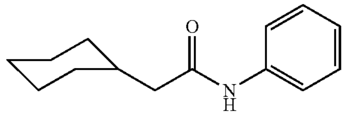 [SMILES: O=C(CC1CCCCC1)Nc1ccccc1] | 3.7 ± 0.01 | 16 ± 0.01 |
| 965 | 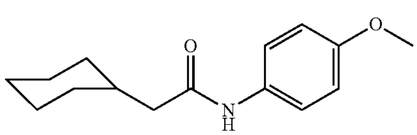 [SMILES: COc1ccc(NC(=O)CC2CCCCC2)cc1] | 0.15 ± 0.01 | 6.0 ± 0.01 |
| 966 | 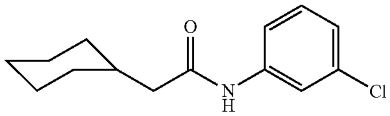 [SMILES: O=C(CC1CCCCC1)Nc1cccc(Cl)c1] | 0.58 ± 0.01 | 2.1 ± 0.01 |

TABLE 18a-continued
| No. | Structure | IC$_{50}$ (μM)$^a$ Mouse sEH | Human sEH |
|---|---|---|---|
| 967 | 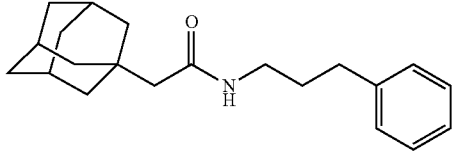 [SMILES: O=C(CC12CC3CC(CC(C3)C1)C2)NCCCc1ccccc1] | 0.07 ± 0.01 | 0.12 ± 0.01 |
| 968 | 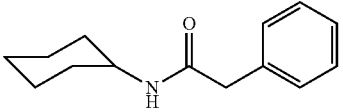 [SMILES: O=C(Cc1ccccc1)NC1CCCCC1] | 2.4 ± 0.01 | 14 ± 0.01 |
| 969 | 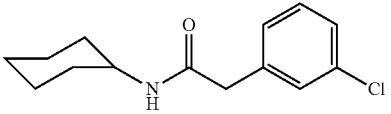 [SMILES: O=C(Cc1cccc(Cl)c1)NC1CCCCC1] | 0.56 ± 0.01 | 38 ± 0.01 |
| 970 | 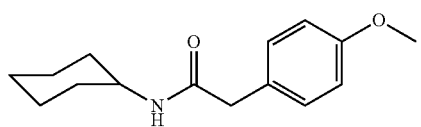 [SMILES: COc1ccc(CC(=O)NC2CCCCC2)cc1] | 1.4 ± 0.01 | 4.8 ± 0.01 |
| 971 | 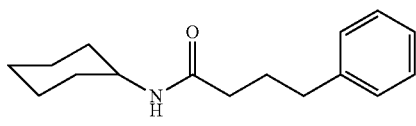 [SMILES: O=C(CCCc1ccccc1)NC1CCCCC1] | 0.11 ± 0.01 | 1.4 ± 0.01 |
| 974 | 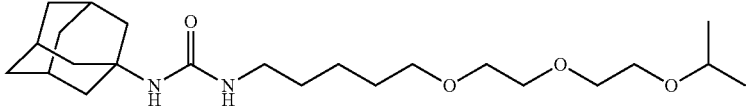 [SMILES: CC(C)OCCOCCOCCCCCNC(=O)NC12CC3CC(CC(C3)C1)C2] | 0.05 ± 0.01 | 0.1 ± 0.01 |
| 976 | 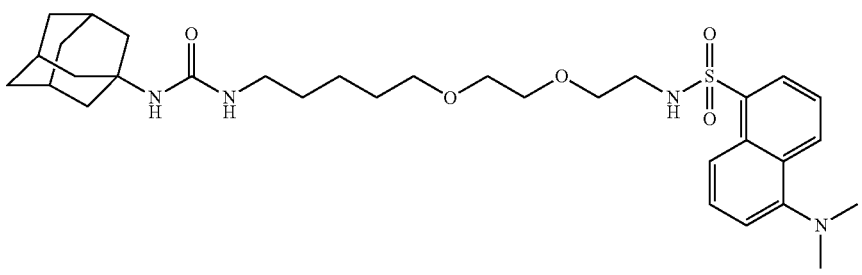 [SMILES: CN(C)c1cccc2c(S(=O)(=O)NCCOCCOCCCCCNC(=O)NC34CC5CC(CC(C5)C3)C4)cccc12] | 0.05 ± 0.01 | 0.1 ± 0.01 |
| 977 | 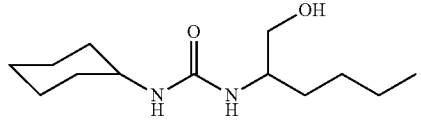 [SMILES: CCCCC(CO)NC(=O)NC1CCCCC1] | 0.1 ± 0.01 | 0.25 ± 0.01 |
| 978 | 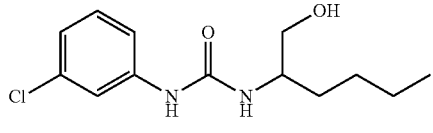 [SMILES: CCCCC(CO)NC(=O)Nc1cccc(Cl)c1] | 8.4 ± 0.01 | 1.9 ± 0.01 |
| 980 | 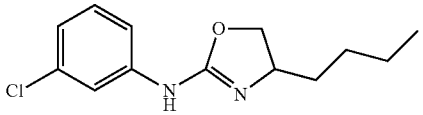 [SMILES: CCCCC1COC(Nc2cccc(Cl)c2)=N1] | 49 ± 0.01 | 60 ± 0.01 |

TABLE 18a-continued
| No. | Structure | IC$_{50}$ (μM)$^a$ | |
|---|---|---|---|
| | | Mouse sEH | Human sEH |
| 986 | 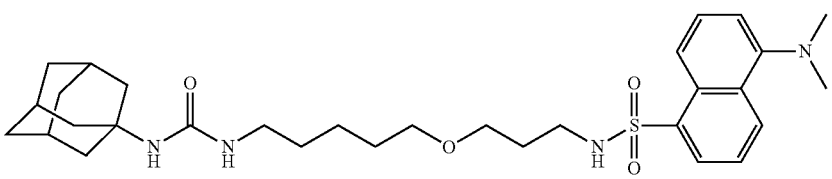 [SMILES: CN(C)c1cccc2c(S(=O)(=O)NCCCOCCCCCNC(=O)NC34CC5CC(CC(C5)C3)C4)cccc12] | 0.05 ± 0.01 | 0.29 ± 0.01 |
| 987 | 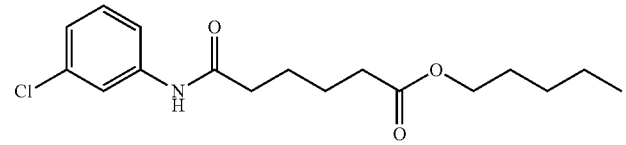 [SMILES: CCCCCOC(=O)CCCCC(=O)Nc1cccc(Cl)c1] | 1.7 ± 0.01 | 5.9 ± 0.01 |
| 988 | 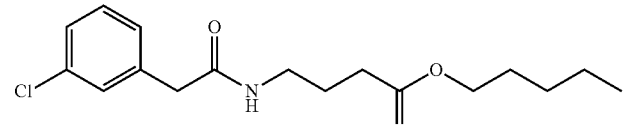 | 2.9 ± 0.01 | 5 ± 0.01 |
| 990 | 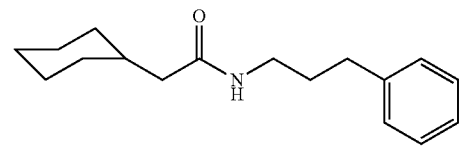 [SMILES: O=C(CC1CCCCC1)NCCCc1ccccc1] | 0.73 ± 0.01 | 1.1 ± 0.01 |
| 991 | 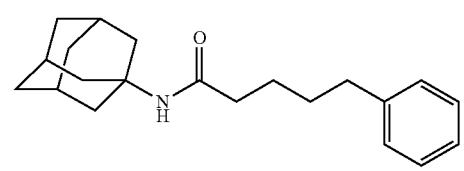 [SMILES: O=C(CCCCc1ccccc1)NC12CC3CC(CC(C3)C1)C2] | 0.06 ± 0.01 | 0.99 ± 0.01 |
| 992 | 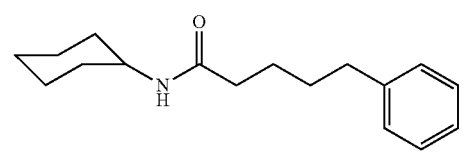 [SMILES: O=C(CCCCc1ccccc1)NC1CCCCC1] | 0.05 ± 0.01 | 1.6 ± 0.01 |
| 993 | 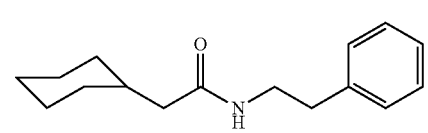 [SMILES: O=C(CC1CCCCC1)NCCc1ccccc1] | 2.1 ± 0.01 | 4.0 ± 0.01 |
| 994 | 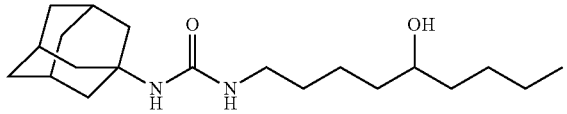 [SMILES: CCCCC(O)CCCCNC(=O)NC12CC3CC(CC(C3)C1)C2] | 0.05 ± 0.01 | 0.1 ± 0.01 |
| 995 | 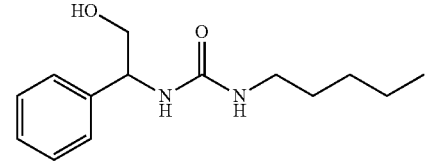 [SMILES: CCCCCNC(=O)NC(CO)c1ccccc1] | 11.0 ± 0.01 | 22.1 ± 0.01 |

TABLE 18a-continued

| No. | Structure | IC$_{50}$ (μM)$^a$ Mouse sEH | IC$_{50}$ (μM)$^a$ Human sEH |
|---|---|---|---|
| 996 | 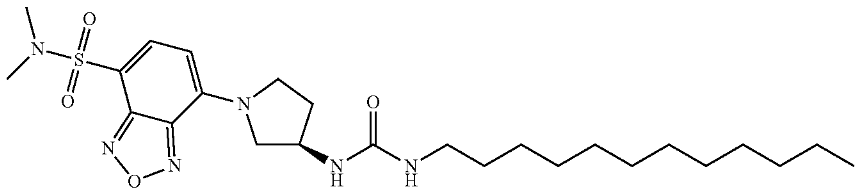 [SMILES: CCCCCCCCCCCCNC(=O)N[C@@H]1CCN(c2ccc(S(=O)(=O)N(C)C)c3nonc23)C1] | 0.17 ± 0.01 | 0.12 ± 0.01 |
| 997 | 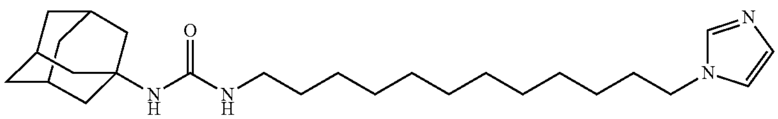 [SMILES: O=C(NCCCCCCCCCCCCn1ccnc1)NC12CC3CC(CC(C3)C1)C2] | 2.3 ± 0.01 | 63 ± 0.01 |
| 998 | 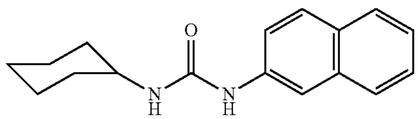 [SMILES: O=C(Nc1ccc2ccccc2c1)NC1CCCCC1] | 0.1 ± 0.01 | 3.7 ± 0.01 |
| 1001 | 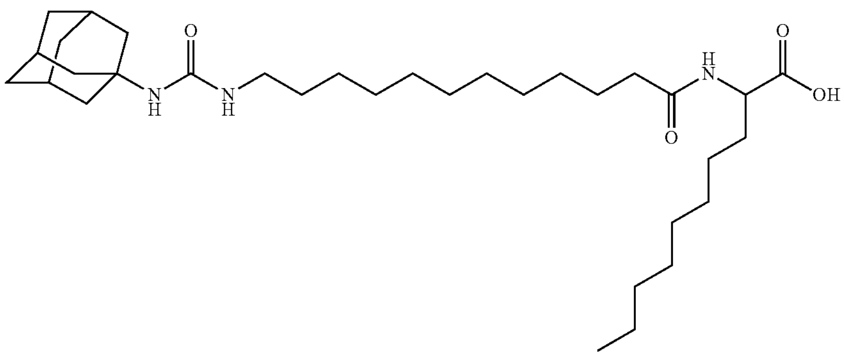 [SMILES: CCCCCCCCC(NC(=O)CCCCCCCCCCCNC(=O)NC12CC3CC(CC(C3)C1)C2)C(=O)O] | 0.05 ± 0.01 | 0.24 ± 0.01 |
| 1002 | 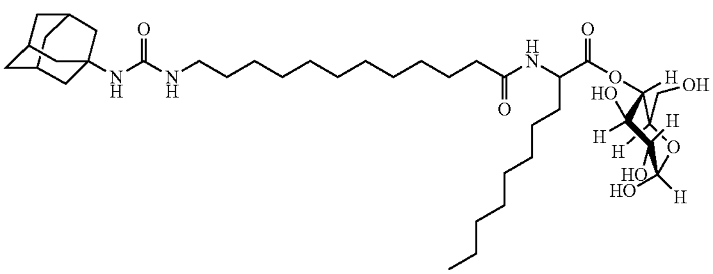 | 0.08 ± 0.01 | 0.05 ± 0.01 |
| 1003 | 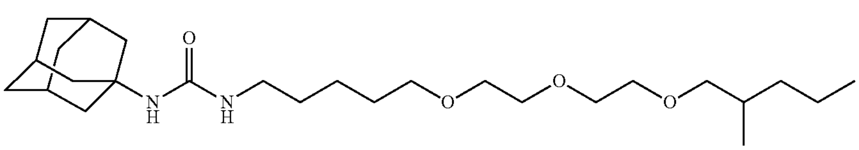 [SMILES: CCCC(C)COCCOCCOCCCCCNC(=O)NC12CC3CC(CC(C3)C1)C2] | 0.05 ± 0.01 | 0.13 ± 0.01 |
| 1004 | 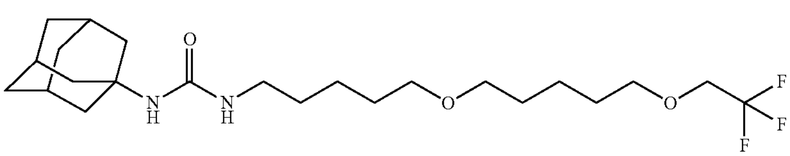 [SMILES: O=C(NCCCCCOCCCCCOCC(F)(F)F)NC12CC3CC(CC(C3)C1)C2] | 0.05 ± 0.01 | 0.16 ± 0.01 |
| 1005 | 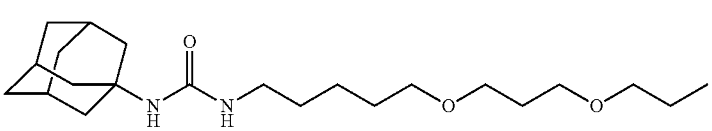 [SMILES: CCCOCCCOCCCCCNC(=O)NC12CC3CC(CC(C3)C1)C2] | 0.05 ± 0.01 | 0.1 ± 0.01 |

TABLE 18a-continued

| No. | Structure | IC$_{50}$ (μM)$^a$ Mouse sEH | IC$_{50}$ (μM)$^a$ Human sEH |
|---|---|---|---|
| 1006 | 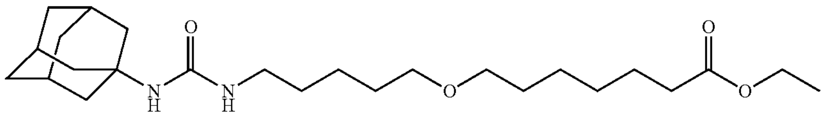 [SMILES: CCOC(=O)CCCCCCOCCCCCNC(=O)NC12CC3CC(CC(C3)C1)C2] | 0.05 ± 0.01 | 0.11 ± 0.01 |
| 1008 | 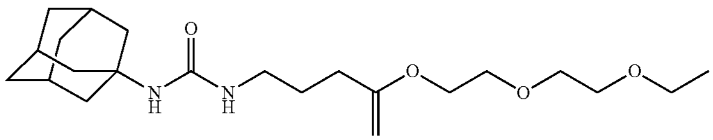 [SMILES: C=C(CCCNC(=O)NC12CC3CC(CC(C3)C1)C2)OCCOCCOCC] | 0.05 ± 0.01 | 0.17 ± 0.01 |
| 1010 | 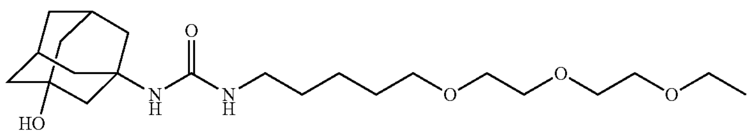 [SMILES: CCOCCOCCOCCCCCNC(=O)NC12CC3CC(CC(O)(C3)C1)C2] | 0.05 ± 0.01 | 14.4 ± 0.01 |
| 1011 | 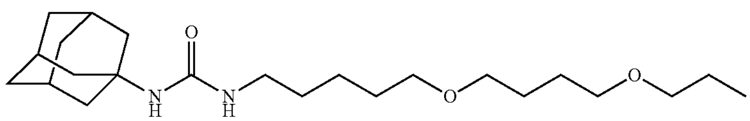 [SMILES: CCCOCCCCOCCCCCNC(=O)NC12CC3CC(CC(C3)C1)C2] | 0.05 ± 0.01 | 0.01 ± 0.01 |
| 1012 | 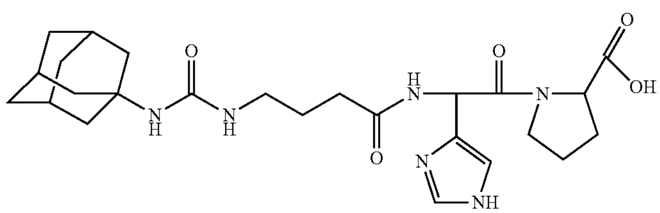 [SMILES: O=C(CCCNC(=O)NC12CC3CC(CC(C3)C1)C2)NC(C(=O)N1CCCC1C(=O)O)c1c[nH]cn1] | 0.09 ± 0.01 | 100 ± 0.01 |
| 1013 | 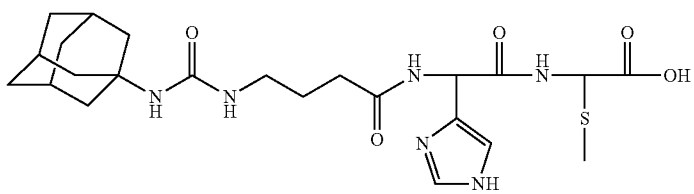 [SMILES: CSC(NC(=O)C(NC(=O)CCCNC(=O)NC12CC3CC(CC(C3)C1)C2)c1c[nH]cn1)C(=O)O] | 0.05 ± 0.01 | 1.5 ± 0.01 |
| 1015 | 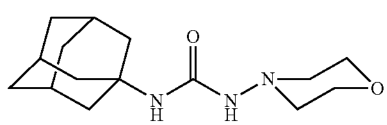 [SMILES: O=C(NN1CCOCC1)NC12CC3CC(CC(C3)C1)C2] | 1.3 ± 0.01 | 8.7 ± 0.01 |
| 1016 | 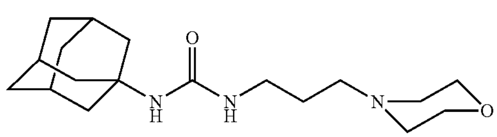 [SMILES: O=C(NCCCN1CCOCC1)NC12CC3CC(CC(C3)C1)C2] | 0.05 ± 0.01 | 6.0 ± 0.01 |

TABLE 18b

| No. | Structure | IC$_{50}$ (μM) |
|---|---|---|
| 1022 | 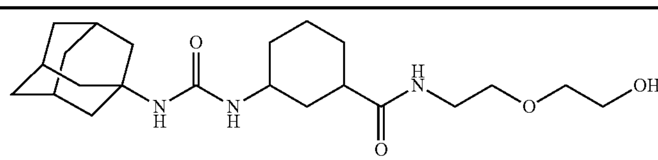 | 0.04 ± 0.01 |

TABLE 18b-continued

| No. | Structure | IC$_{50}$ (μM) |
|---|---|---|
| 1023 | 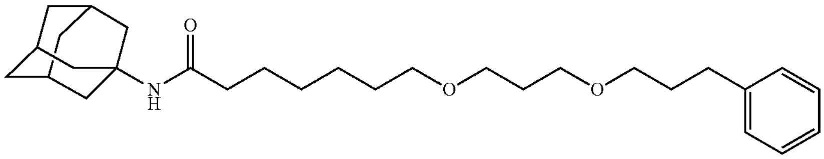 [SMILES: O=C(CCCCCCOCCCOCCCc1ccccc1)NC12CC3CC(CC(C3)C1)C2] | 0.07 ± 0.01 |
| 1025 | 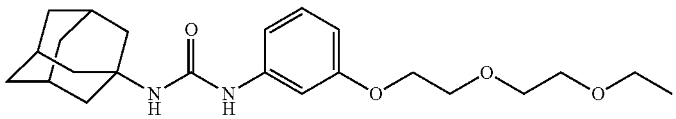 [SMILES: CCOCCOCCOc1cccc(NC(=O)NC23CC4CC(CC(C4)C2)C3)c1] | 0.01 ± 0.01 |
| 1026 | 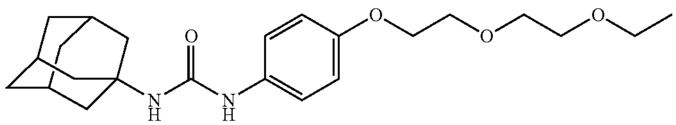 [SMILES: CCOCCOCCOc1ccc(NC(=O)NC23CC4CC(CC(C4)C2)C3)cc1] | 0.01 ± 0.01 |
| 1027 | 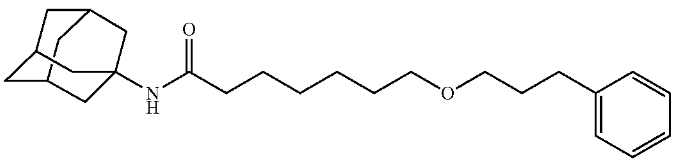 [SMILES: O=C(CCCCCCOCCCc1ccccc1)NC12CC3CC(CC(C3)C1)C2] | 0.02 ± 0.01 |
| 1028 | 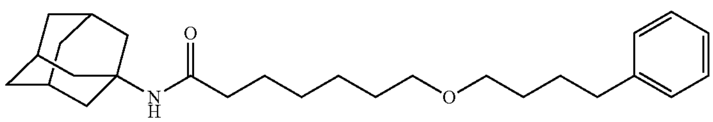 [SMILES: O=C(CCCCCCOCCCCc1ccccc1)NC12CC3CC(CC(C3)C1)C2] | 0.01 ± 0.01 |
| 1029 | 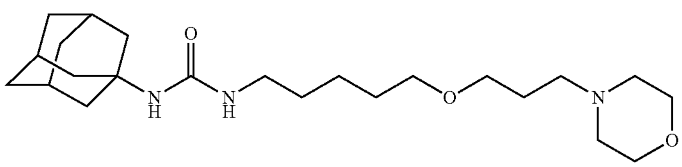 [SMILES: O=C(NCCCCCOCCCN1CCOCC1)NC12CC3CC(CC(C3)C1)C2] | 0.01 ± 0.01 |
| 1031 | 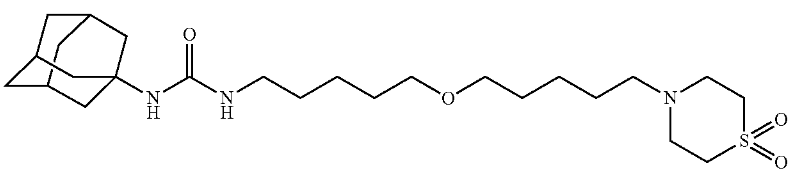 [SMILES: O=C(NCCCCCOCCCCCN1CCS(=O)(=O)CC1)NC12CC3CC(CC(C3)C1)C2] | 0.01 ± 0.01 |
| 1032 | 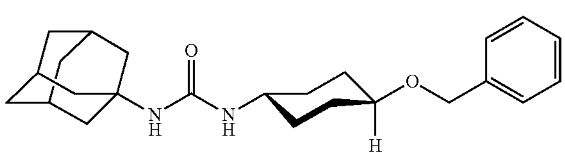 | 0.01 ± 0.01 |
| 1034 | 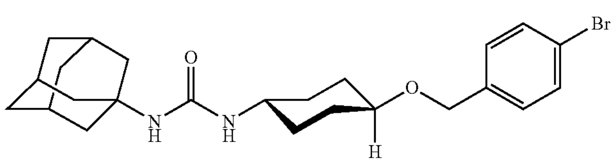 | 0.01 ± 0.01 |
| 1037 | 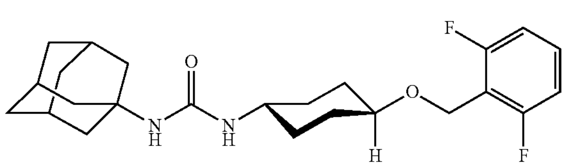 | 0.01 ± 0.01 |

TABLE 18b-continued

| No. | Structure | IC$_{50}$ (μM) |
|---|---|---|
| 1038 | 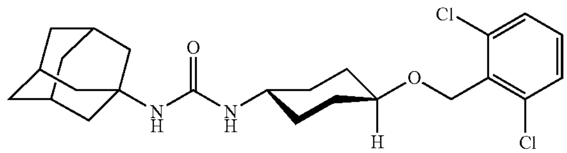 | 0.01 ± 0.01 |
| 1039 | 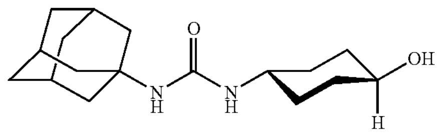 | 0.06 ± 0.01 |
| 1040 | 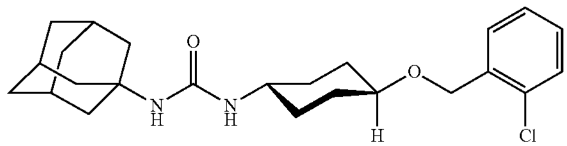 | 0.01 ± 0.01 |
| 1047 | 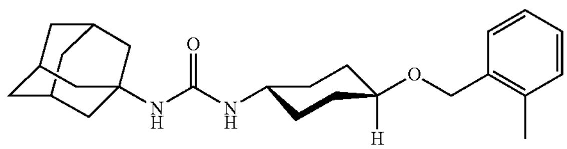 | 0.01 ± 0.01 |
| 1048 | 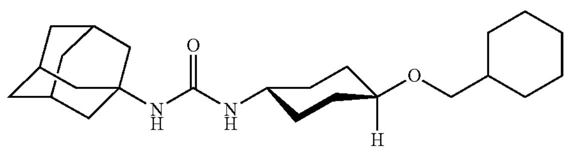 | 0.01 ± 0.01 |
| 1049 | 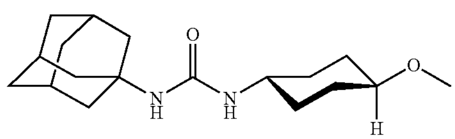 | 0.01 ± 0.01 |
| 1061 | 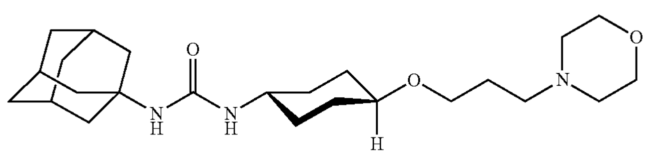 | 0.01 ± 0.01 |
| 1062 | 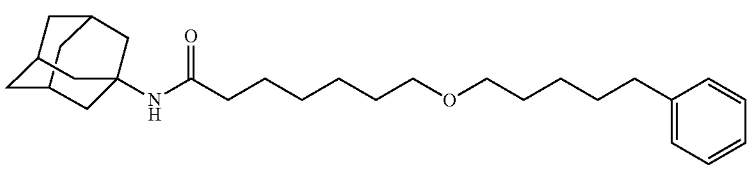 [SMILES: O=C(CCCCCCOCCCCCc1ccccc1)NC12CC3CC(CC(C3)C1)C2] | 0.01 ± 0.01 |
| 1063-1 | 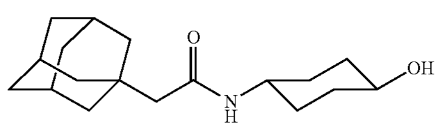 [SMILES: O=C(CC12CC3CC(CC(C3)C1)C2)NC1CCC(O)CC1] | 0.05 ± 0.01 |
| 1063-2 | 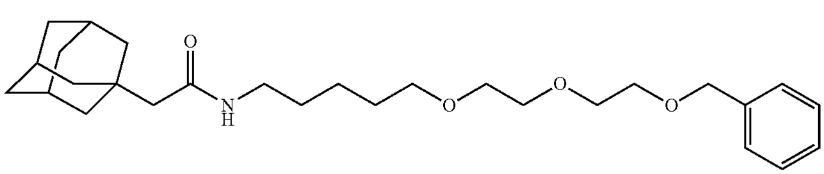 [SMILES: O=C(CC12CC3CC(CC(C3)C1)C2)NCCCCCOCCOCCOCc1ccccc1] | 0.01 ± 0.01 |

TABLE 18b-continued

| No. | Structure | IC$_{50}$ (μM) |
|---|---|---|
| 1064 | 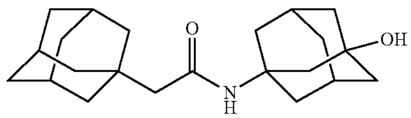 [SMILES: O=C(CC12CC3CC(CC(C3)C1)C2)NC12CC3CC(CC(O)(C3)C1)C2] | 0.04 ± 0.01 |
| 1066 | 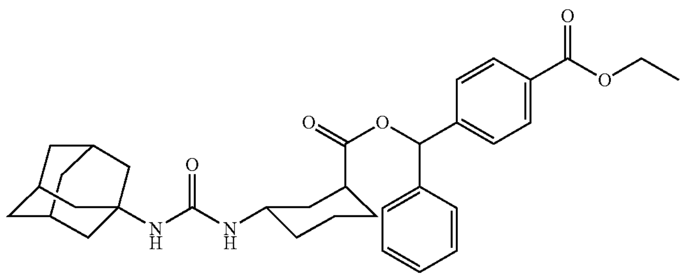 [SMILES: CCOC(=O)c1ccc(C(OC(=O)C2CCCC(NC(=O)NC34CC5CC(CC(C5)C3)C4)C2)c2ccccc2)cc1] | 0.01 ± 0.01 |
| 1067 | 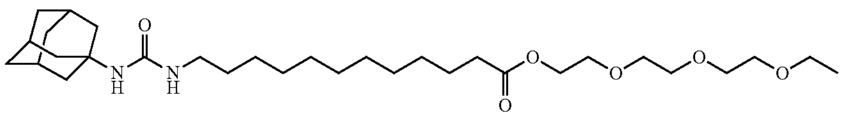 [SMILES: CCOCCOCCOCCOC(=O)CCCCCCCCCCCNC(=O)NC12CC3CC(CC(C3)C1)C2] | 0.01 ± 0.01 |
| 1068 | 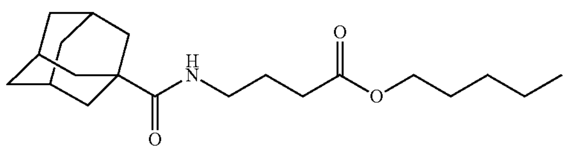 [SMILES: CCCCCOC(=O)CCCNC(=O)C12CC3CC(CC(C3)C1)C2] | 0.39 ± 0.01 |
| 1069 | 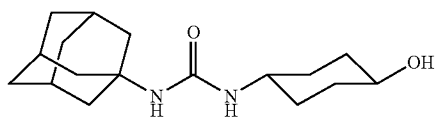 [SMILES: O=C(NC1CCC(O)CC1)NC12CC3CC(CC(C3)C1)C2] | 0.01 ± 0.01 |
| 1070 | 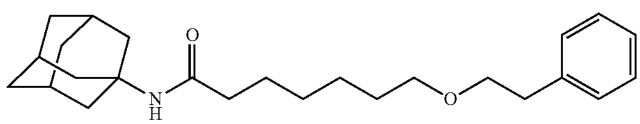 [SMILES: O=C(CCCCCCOCCc1ccccc1)NC12CC3CC(CC(C3)C1)C2] | 0.03 ± 0.01 |
| 1073 | 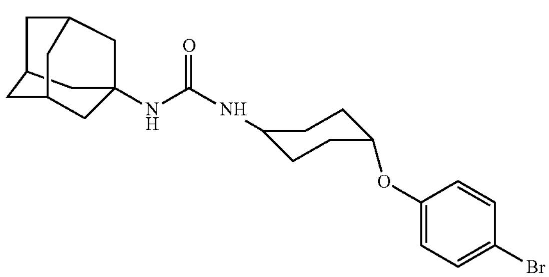 [SMILES: O=C(NC1CCC(Oc2ccc(Br)cc2)CC1)NC12CC3CC(CC(C3)C1)C2] | 0.01 ± 0.01 |
| 1074 | 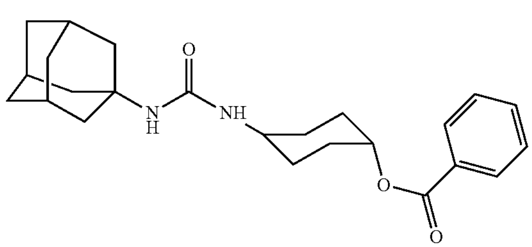 [SMILES: O=C(NC1CCC(OC(=O)c2ccccc2)CC1)NC12CC3CC(CC(C3)C1)C2] | 0.01 ± 0.01 |

TABLE 18b-continued

| No. | Structure | IC₅₀ (μM) |
|---|---|---|
| 1076 | 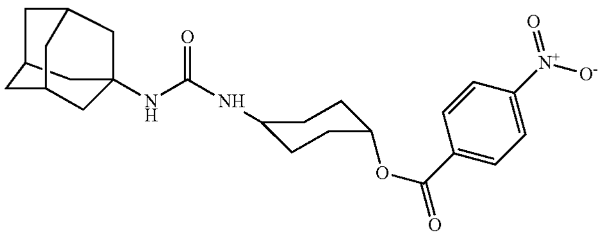 [SMILES: O=C(NC1CCC(OC(=O)c2ccc([N+](=O)[O-])cc2)CC1)NC12CC3CC(CC(C3)C1)C2] | 0.01 ± 0.01 |
| 1077 | 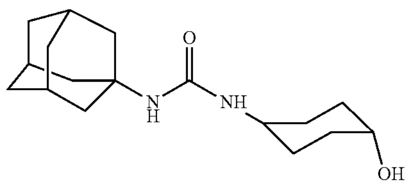 [SMILES: O=C(NC1CCC(O)CC1)NC12CC3CC(CC(C3)C1)C2] | 0.01 ± 0.01 |
| 1078 | 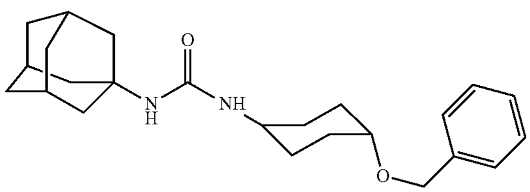 [SMILES: O=C(NC1CCC(OCc2ccccc2)CC1)NC12CC3CC(CC(C3)C1)C2] | 0.01 ± 0.01 |
| 1084 | 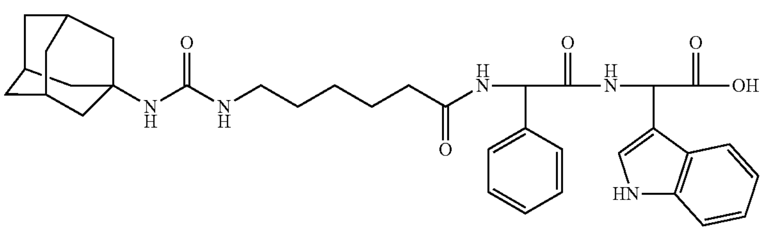 [SMILES: O=C(CCCCCNC(=O)NC12CC3CC(CC(C3)C1)C2)NC(C(=O)NC(C(=O)O)c1c[nH]c2ccccc12)c1ccccc1] | 0.01 ± 0.01 |
| 1096 | 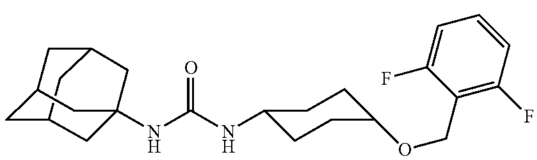 [SMILES: O=C(NC1CCC(OCc2c(F)cccc2F)CC1)NC12CC3CC(CC(C3)C1)C2] | 0.01 ± 0.01 |
| 1097 | 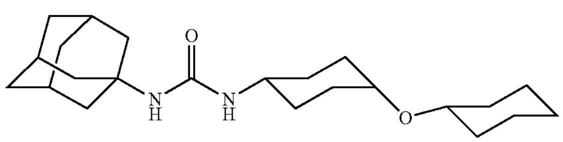 [SMILES: O=C(NC1CCC(OC2CCCCC2)CC1)NC12CC3CC(CC(C3)C1)C2] | 0.01 ± 0.01 |
| 1098 | 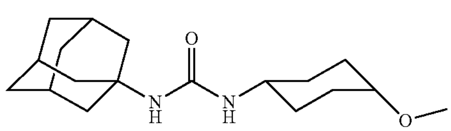 [SMILES: COC1CCC(NC(=O)NC23CC4CC(CC(C4)C2)C3)CC1] | 0.01 ± 0.01 |
| 1099 | 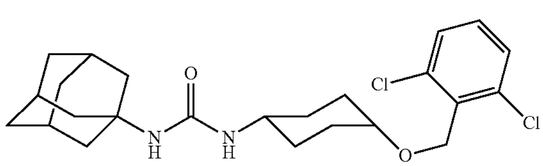 [SMILES: O=C(NC1CCC(OCc2c(Cl)cccc2Cl)CC1)NC12CC3CC(CC(C3)C1)C2] | 0.01 ± 0.01 |

TABLE 18b-continued
| No. | Structure | IC$_{50}$ (μM) |
|---|---|---|
| 1100 | 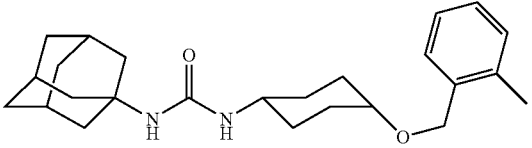 [SMILES: Cc1ccccc1COC1CCC(NC(=O)NC23CC4CC(CC(C4)C2)C3)CC1] | 0.01 ± 0.01 |
| 1101 | 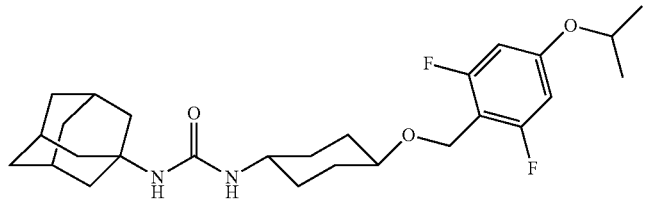 [SMILES: CC(C)Oc1cc(F)c(COC2CCC(NC(=O)NC34CC5CC(CC(C5)C3)C4)CC2)c(F)c1] | 0.01 ± 0.01 |
| 1102 | 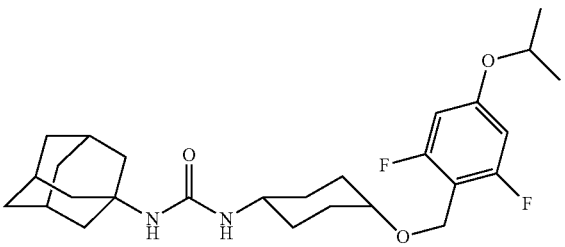 [SMILES: CC(C)Oc1cc(F)c(COC2CCC(NC(=O)NC34CC5CC(CC(C5)C3)C4)CC2)c(F)c1] | 0.01 ± 0.01 |
| 1103 | 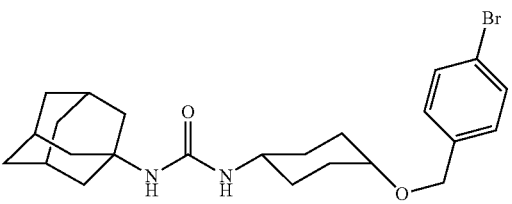 [SMILES: O=C(NC1CCC(OCc2ccc(Br)cc2)CC1)NC12CC3CC(CC(C3)C1)C2] | 0.01 ± 0.01 |
| 1104 | 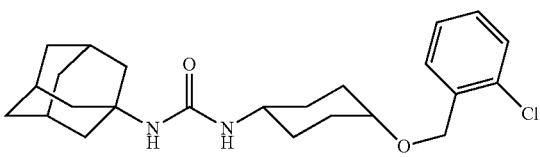 [SMILES: O=C(NC1CCC(OCc2ccccc2Cl)CC1)NC12CC3CC(CC(C3)C1)C2] | 0.01 ± 0.01 |
| 1105 | 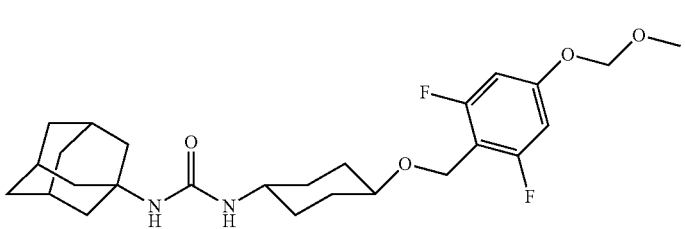 [SMILES: COCOc1cc(F)c(COC2CCC(NC(=O)NC34CC5CC(CC(C5)C3)C4)CC2)c(F)c1] | 0.01 ± 0.01 |
| 1106 | 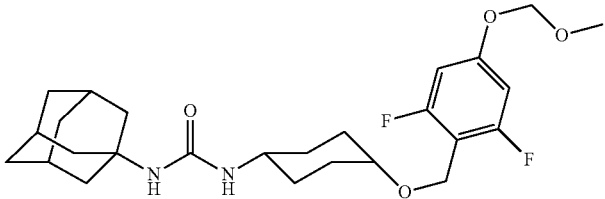 [SMILES: COCOc1cc(F)c(COC2CCC(NC(=O)NC34CC5CC(CC(C5)C3)C4)CC2)c(F)c1] | 0.01 ± 0.01 |

TABLE 18b-continued

| No. | Structure | IC$_{50}$ (μM) |
|---|---|---|
| 1107 | 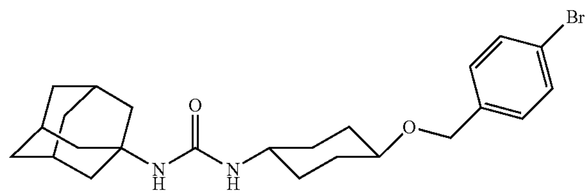 [SMILES: O=C(NC1CCC(OCc2ccc(Br)cc2)CC1)NC12CC3CC(CC(C3)C1)C2] | 0.01 ± 0.01 |
| 1116 | 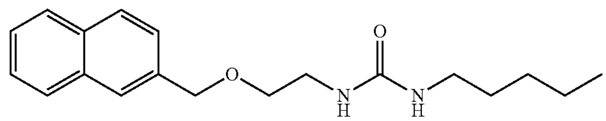 [SMILES: CCCCCNC(=O)NCCOCc1ccc2ccccc2c1] | 0.26 ± 0.01 |
| 1117 | 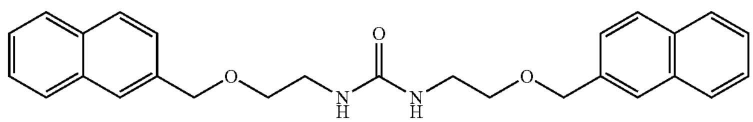 [SMILES: O=C(NCCOCc1ccc2ccccc2c1)NCCOCc1ccc2ccccc2c1] | 1.12 ± 0.01 |
| 1125 | 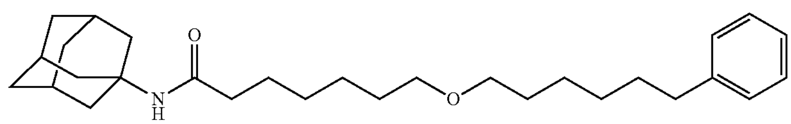 [SMILES: O=C(CCCCCCOCCCCCCc1ccccc1)NC12CC3CC(CC(C3)C1)C2] | 0.01 ± 0.01 |
| 1128 | 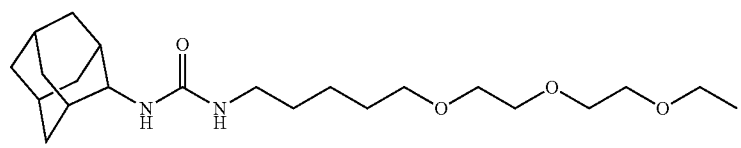 [SMILES: CCOCCOCCOCCCCCNC(=O)NC1C2CC3CC(C2)CC1C3] | 0.01 ± 0.01 |
| 1129 | 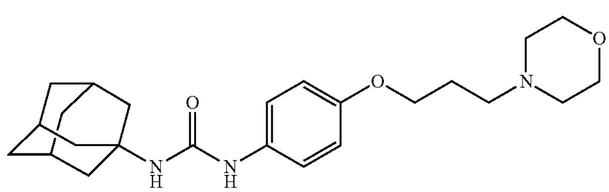 [SMILES: O=C(Nc1ccc(OCCCN2CCOCC2)cc1)NC12CC3CC(CC(C3)C1)C2] | 0.01 ± 0.01 |
| 1130 | 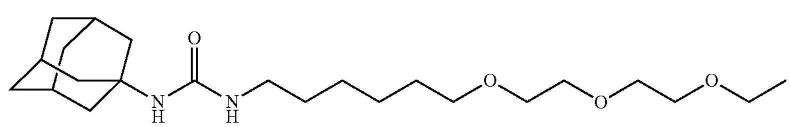 [SMILES: CCOCCOCCOCCCCCCNC(=O)NC12CC3CC(CC(C3)C1)C2] | 0.01 ± 0.01 |
| 1131 | 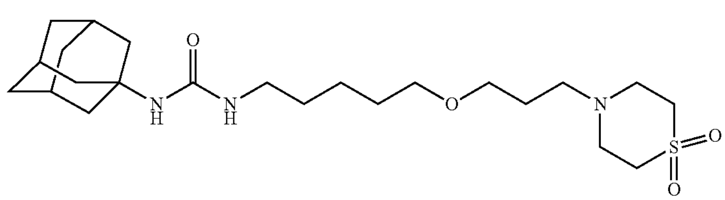 [SMILES: O=C(NCCCCCOCCCN1CCS(=O)(=O)CC1)NC12CC3CC(CC(C3)C1)C2] | 0.01 ± 0.01 |
| 1135 | 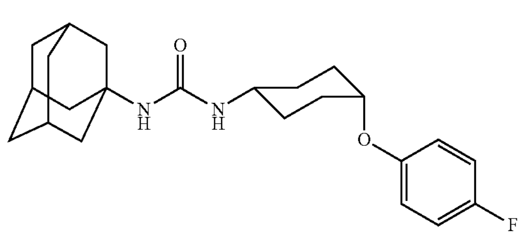 [SMILES: O=C(NC1CCC(Oc2ccc(F)cc2)CC1)NC12CC3CC(CC(C3)C1)C2] | 0.01 ± 0.01 |

TABLE 18b-continued

| No. | Structure | IC$_{50}$ (μM) |
|---|---|---|
| 1136 | 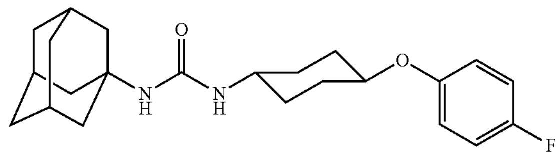 [SMILES: O=C(NC1CCC(Oc2ccc(F)cc2)CC1)NC12CC3CC(CC(C3)C1)C2] | 0.01 ± 0.01 |
| 1137 | 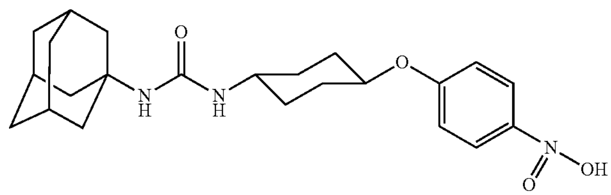 | 0.01 ± 0.01 |
| 1138 | 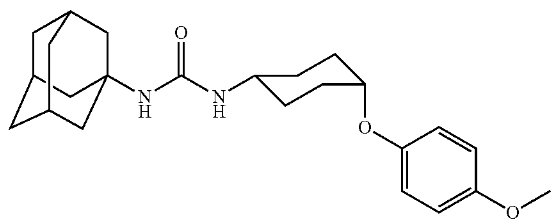 [SMILES: COc1ccc(OC2CCC(NC(=O)NC34CC5CC(CC(C5)C3)C4)CC2)cc1] | 0.01 ± 0.01 |
| 1139 | 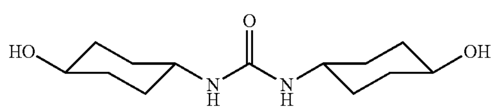 [SMILES: O=C(NC1CCC(O)CC1)NC1CCC(O)CC1] | 3.77 ± 0.01 |
| 1140 | 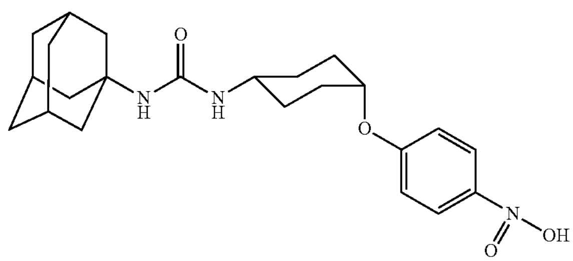 | 0.01 ± 0.01 |
| 1141 | 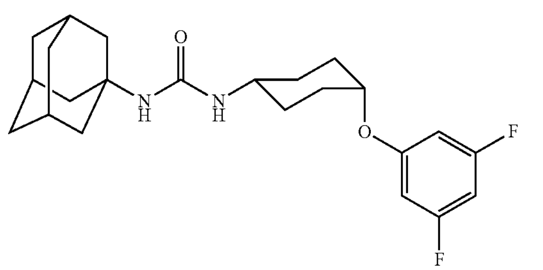 [SMILES: O=C(NC1CCC(Oc2cc(F)cc(F)c2)CC1)NC12CC3CC(CC(C3)C1)C2] | 0.01 ± 0.01 |
| 1142 | 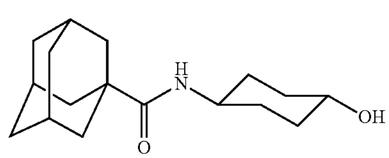 [SMILES: O=C(NC1CCC(O)CC1)C12CC3CC(CC(C3)C1)C2] | 0.01 ± 0.01 |

TABLE 18b-continued

| No. | Structure | IC$_{50}$ (μM) |
|---|---|---|
| 1143 | adamantyl-NH-C(O)-NH-cyclohexyl-O-CH$_2$-(2-CF$_3$-phenyl) | 0.01 ± 0.01 |
| 1144 | adamantyl-NH-C(O)-NH-cyclohexyl-O-CH$_2$-(2-OCF$_3$-phenyl) | 0.01 ± 0.01 |
| 1145 | adamantyl-NH-C(O)-NH-cyclohexyl-O-(4-methoxyphenyl) | 0.01 ± 0.01 |
| 1146 | adamantyl-NH-C(O)-NH-cyclohexyl-O-(3,5-difluorophenyl) | 0.01 ± 0.01 |
| 1147 | phenyl-NH-C(O)-NH-cyclohexyl-O-CH$_2$-(2,6-difluorophenyl) | 0.01 ± 0.01 |
| 1148 | phenyl-NH-C(O)-NH-cyclohexyl-O-CH$_2$-(2,6-difluorophenyl) | 0.01 ± 0.01 |
| 1149 | adamantyl-CH$_2$-C(O)-NH-cyclohexyl-O-CH$_2$-(2,6-difluorophenyl) | 0.01 ± 0.01 |
| 1150 | adamantyl-NH-C(O)-NH-cyclohexyl-O-CH$_2$-(2-fluorophenyl) | 0.01 ± 0.01 |

TABLE 18b-continued

| No. | Structure | IC$_{50}$ (μM) |
|---|---|---|
| 1164 | 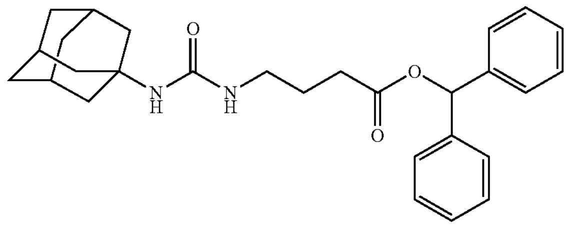 [SMILES: O=C(NCCCC(=O)OC(c1ccccc1)c1ccccc1)NC12CC3CC(CC(C3)C1)C2] | 0.01 ± 0.01 |
| 1165 | 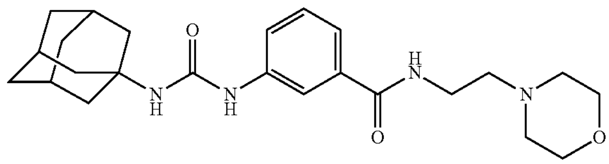 [SMILES: O=C(Nc1cccc(C(=O)NCCN2CCOCC2)c1)NC12CC3CC(CC(C3)C1)C2] | 0.06 ± 0.01 |
| 1166 | 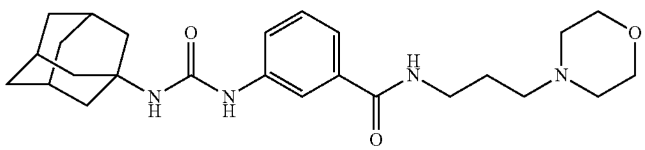 [SMILES: O=C(Nc1cccc(C(=O)NCCCN2CCOCC2)c1)NC12CC3CC(CC(C3)C1)C2] | 0.06 ± 0.01 |
| 1171 | 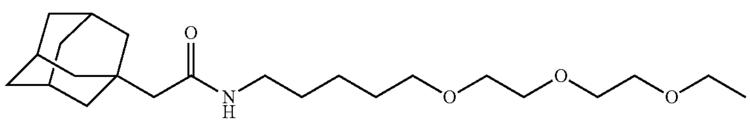 [SMILES: CCOCCOCCOCCCCCNC(=O)CC12CC3CC(CC(C3)C1)C2] | 0.01 ± 0.01 |
| 1172 | 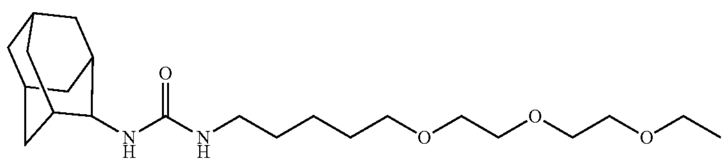 [SMILES: CCOCCOCCOCCCCCNC(=O)NC1C2CC3CC(C2)CC1C3] | 0.01 ± 0.01 |
| 1173 | 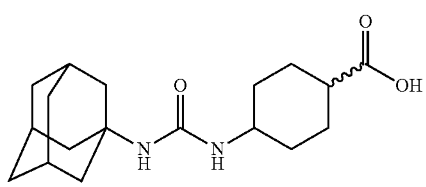 [SMILES: O=C(NC1CCC(C(=O)O)CC1)NC12CC3CC(CC(C3)C1)C2] | 0.01 ± 0.01 |
| 1176 | 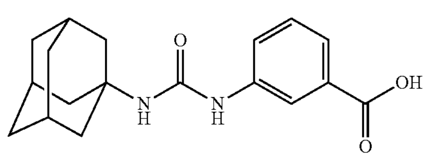 [SMILES: O=C(Nc1cccc(C(=O)O)c1)NC12CC3CC(CC(C3)C1)C2] | 0.01 ± 0.01 |
| 1177 | 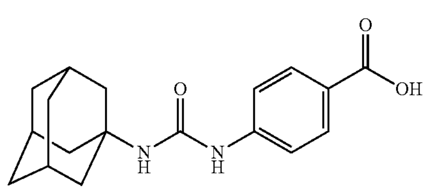 [SMILES: O=C(Nc1ccc(C(=O)O)cc1)NC12CC3CC(CC(C3)C1)C2] | 0.01 ± 0.01 |
| 1178 | 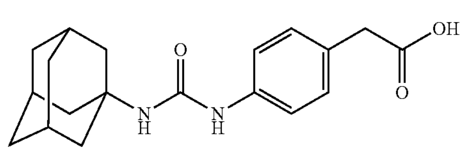 [SMILES: O=C(O)Cc1ccc(NC(=O)NC23CC4CC(CC(C4)C2)C3)cc1] | 0.01 ± 0.01 |

TABLE 18b-continued

| No. | Structure | IC$_{50}$ (μM) |
|---|---|---|
| 1181 | 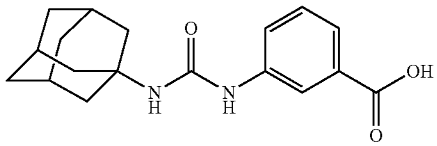 [SMILES: O=C(Nc1cccc(C(=O)O)c1)NC12CC3CC(CC(C3)C1)C2] | 0.21 ± 0.01 |
| 1182 | 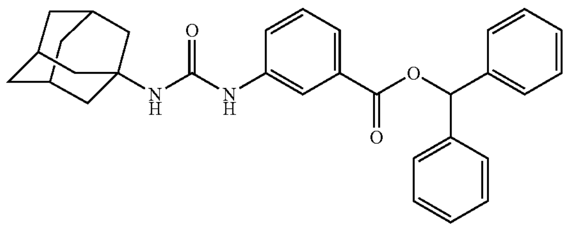 [SMILES: O=C(Nc1cccc(C(=O)OC(c2ccccc2)c2ccccc2)c1)NC12CC3CC(CC(C3)C1)C2] | 0.01 ± 0.01 |
| 1183 | 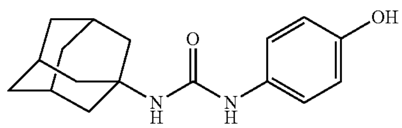 [SMILES: O=C(Nc1ccc(O)cc1)NC12CC3CC(CC(C3)C1)C2] | 0.02 ± 0.01 |
| 1184 | 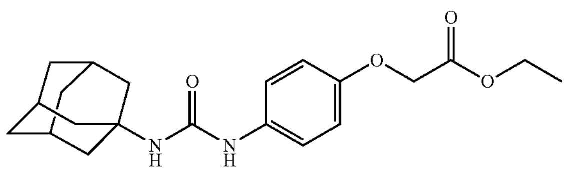 [SMILES: CCOC(=O)COc1ccc(NC(=O)NC23CC4CC(CC(C4)C2)C3)cc1] | 0.01 ± 0.01 |
| 1185 | 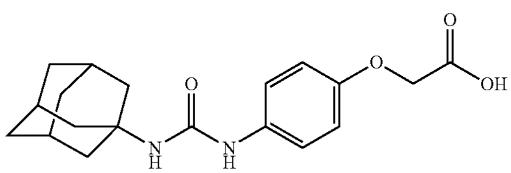 [SMILES: O=C(O)COc1ccc(NC(=O)NC23CC4CC(CC(C4)C2)C3)cc1] | 0.14 ± 0.01 |
| 1186 | 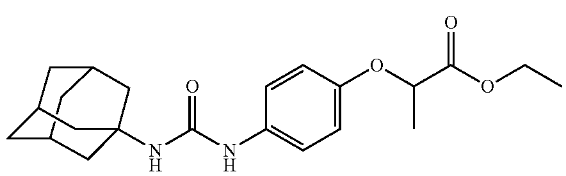 [SMILES: CCOC(=O)C(C)Oc1ccc(NC(=O)NC23CC4CC(CC(C4)C2)C3)cc1] | 0.01 ± 0.01 |
| 1187 | 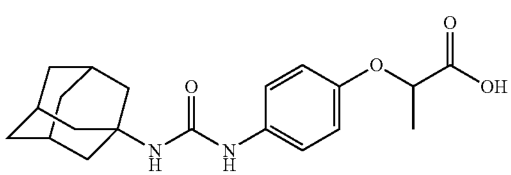 [SMILES: CC(Oc1ccc(NC(=O)NC23CC4CC(CC(C4)C2)C3)cc1)C(=O)O] | 0.01 ± 0.01 |
| 1189 | 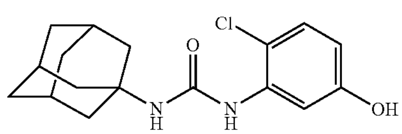 [SMILES: O=C(Nc1cc(O)ccc1Cl)NC12CC3CC(CC(C3)C1)C2] | 0.02 ± 0.01 |
| 1191 | 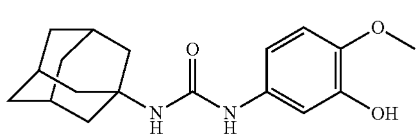 [SMILES: COc1ccc(NC(=O)NC23CC4CC(CC(C4)C2)C3)cc1O] | 0.01 ± 0.01 |

TABLE 18b-continued

| No. | Structure | IC$_{50}$ (μM) |
|---|---|---|
| 1192 | 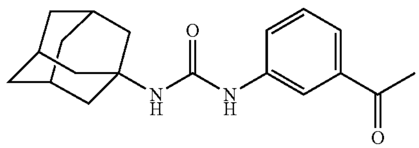 [SMILES: CC(=O)c1cccc(NC(=O)NC23CC4CC(CC(C4)C2)C3)c1] | 0.01 ± 0.01 |
| 1193 | 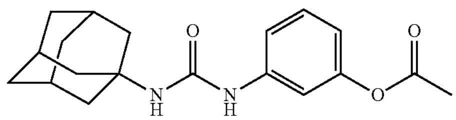 [SMILES: CC(=O)Oc1cccc(NC(=O)NC23CC4CC(CC(C4)C2)C3)c1] | 0.01 ± 0.01 |
| 1194 | 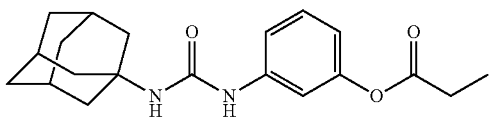 [SMILES: CCC(=O)Oc1cccc(NC(=O)NC23CC4CC(CC(C4)C2)C3)c1] | 0.01 ± 0.01 |
| 1195 | 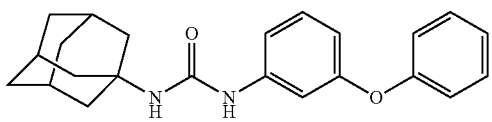 [SMILES: O=C(Nc1cccc(Oc2ccccc2)c1)NC12CC3CC(CC(C3)C1)C2] | 0.01 ± 0.01 |
| 1196 | 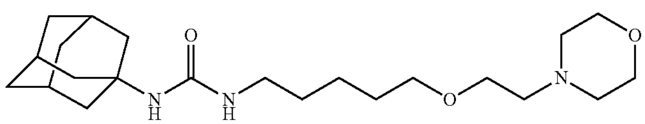 [SMILES: O=C(NCCCCCOCCN1CCOCC1)NC12CC3CC(CC(C3)C1)C2] | 0.01 ± 0.01 |
| 1197 | 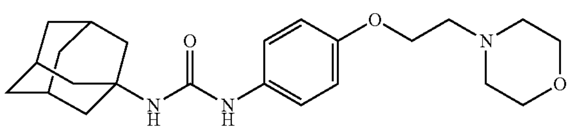 [SMILES: O=C(Nc1ccc(OCCN2CCOCC2)cc1)NC12CC3CC(CC(C3)C1)C2] | 0.01 ± 0.01 |
| 1198 | 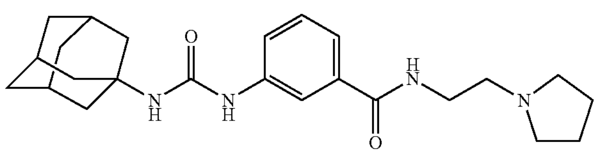 [SMILES: O=C(Nc1cccc(C(=O)NCCN2CCCC2)c1)NC12CC3CC(CC(C3)C1)C2] | 0.01 ± 0.01 |
| 1213 | 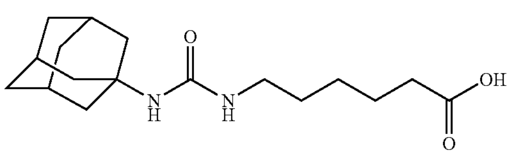 [SMILES: O=C(O)CCCCCNC(=O)NC12CC3CC(CC(C3)C1)C2] | 0.17 ± 0.01 |
| 1214 | 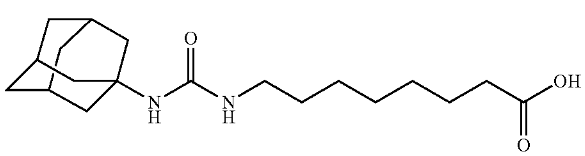 [SMILES: O=C(O)CCCCCCCNC(=O)NC12CC3CC(CC(C3)C1)C2] | 0.01 ± 0.01 |
| 1217 | 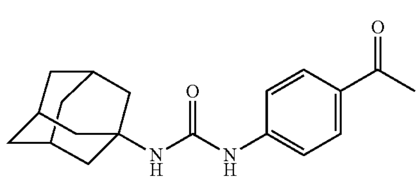 [SMILES: CC(=O)c1ccc(NC(=O)NC23CC4CC(CC(C4)C2)C3)cc1] | 0.01 ± 0.01 |

TABLE 18b-continued

| No. | Structure | IC$_{50}$ (μM) |
|---|---|---|
| 1218 | 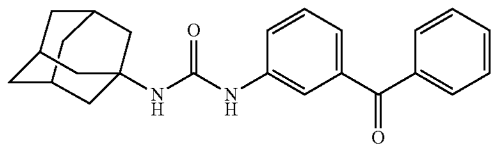 [SMILES: O=C(Nc1cccc(C(=O)c2ccccc2)c1)NC12CC3CC(CC(C3)C1)C2] | 0.01 ± 0.01 |
| 1219 | 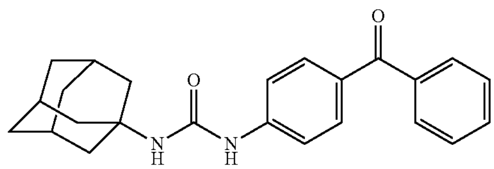 [SMILES: O=C(Nc1ccc(C(=O)c2ccccc2)cc1)NC12CC3CC(CC(C3)C1)C2] | 0.01 ± 0.01 |
| 1220 | 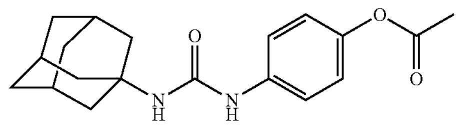 [SMILES: CC(=O)Oc1ccc(NC(=O)NC23CC4CC(CC(C4)C2)C3)cc1] | 0.01 ± 0.01 |
| 1221 | 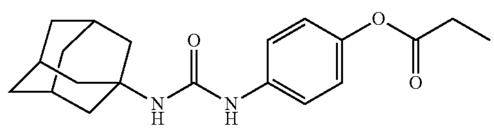 [SMILES: CCC(=O)Oc1ccc(NC(=O)NC23CC4CC(CC(C4)C2)C3)cc1] | 0.01 ± 0.01 |
| 1222 | 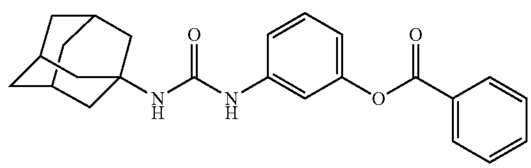 [SMILES: O=C(Nc1cccc(OC(=O)c2ccccc2)c1)NC12CC3CC(CC(C3)C1)C2] | 0.01 ± 0.01 |
| 1223 | 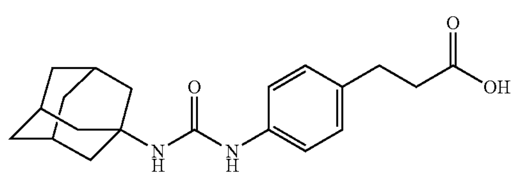 [SMILES: O=C(O)CCc1ccc(NC(=O)NC23CC4CC(CC(C4)C2)C3)cc1] | 0.01 ± 0.01 |
| 1224 | 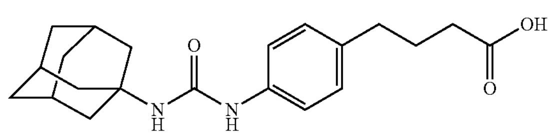 [SMILES: O=C(O)CCCc1ccc(NC(=O)NC23CC4CC(CC(C4)C2)C3)cc1] | 0.01 ± 0.01 |
| 1225 | 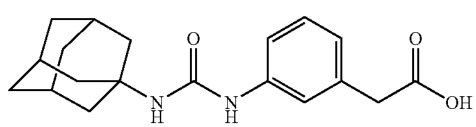 [SMILES: O=C(O)Cc1cccc(NC(=O)NC23CC4CC(CC(C4)C2)C3)c1] | 0.02 ± 0.01 |
| 1226 | 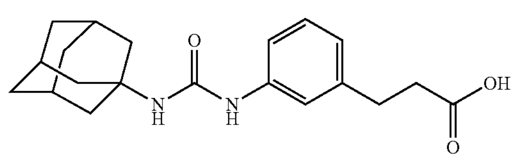 [SMILES: O=C(O)CCc1cccc(NC(=O)NC23CC4CC(CC(C4)C2)C3)c1] | 0.01 ± 0.01 |
| 1229 | 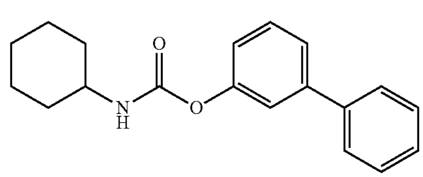 [SMILES: O=C(NC1CCCCC1)Oc1cccc(-c2ccccc2)c1] | 0.92 ± 0.01 |

TABLE 18b-continued

| No. | Structure | IC$_{50}$ (µM) |
|---|---|---|
| 1230 | 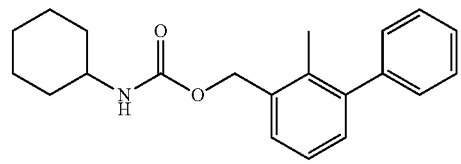 [SMILES: Cc1c(COC(=O)NC2CCCCC2)cccc1-c1ccccc1] | 0.66 ± 0.01 |
| 1233 | 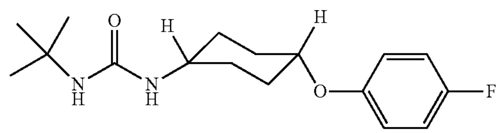 [SMILES: CC(C)(C)NC(=O)NC1CCC(Oc2ccc(F)cc2)CC1] | * |
| 1234 | 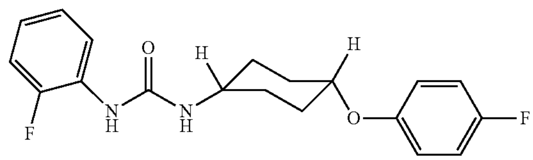 [SMILES: O=C(Nc1ccccc1F)NC1CCC(Oc2ccc(F)cc2)CC1] | * |
| 1235 | 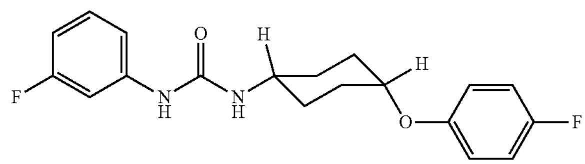 | * |
| 1236 | 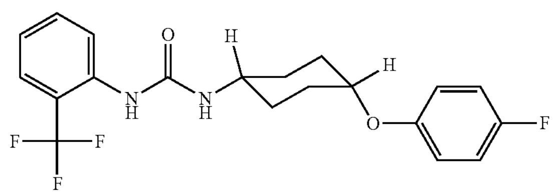 [SMILES: O=C(Nc1ccccc1C(F)(F)F)NC1CCC(Oc2ccc(F)cc2)CC1] | * |
| 1237 | 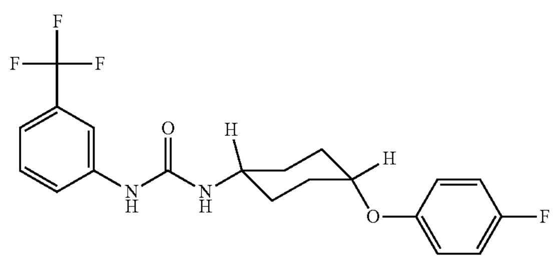 [SMILES: O=C(Nc1cccc(C(F)(F)F)c1)NC1CCC(Oc2ccc(F)cc2)CC1] | * |
| 1238 | 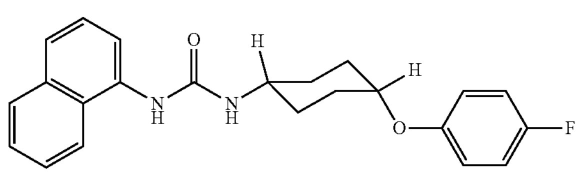 [SMILES: O=C(Nc1cccc2ccccc12)NC1CCC(Oc2ccc(F)cc2)CC1] | * |
| 1239 | 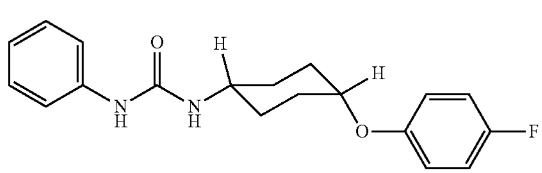 [SMILES: O=C(Nc1ccccc1)NC1CCC(Oc2ccc(F)cc2)CC1] | * |

TABLE 18b-continued

| No. | Structure | IC$_{50}$ (μM) |
|---|---|---|
| 1240 | 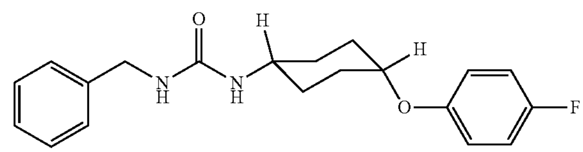 [SMILES: O=C(NCc1ccccc1)NC1CCC(Oc2ccc(F)cc2)CC1] | * |
| 1241 | 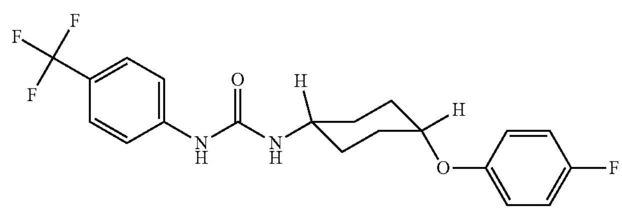 [SMILES: O=C(Nc1ccc(C(F)(F)F)cc1)NC1CCC(Oc2ccc(F)cc2)CC1] | * |
| 1242 | 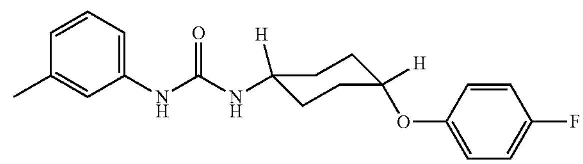 [SMILES: Cc1cccc(NC(=O)NC2CCC(Oc3ccc(F)cc3)CC2)c1] | * |
| 1243 | 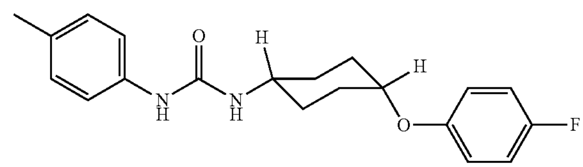 [SMILES: Cc1ccc(NC(=O)NC2CCC(Oc3ccc(F)cc3)CC2)cc1] | * |
| 1244 | 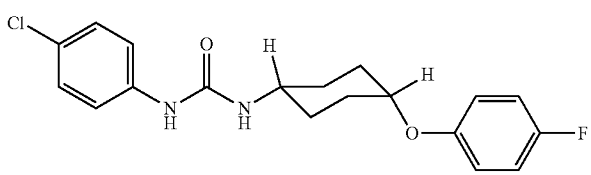 | * |
| 1245 | 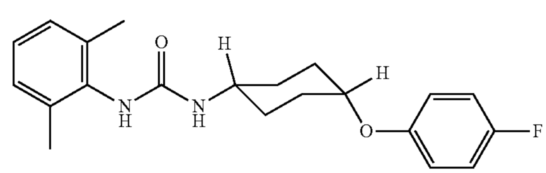 [SMILES: Cc1cccc(C)c1NC(=O)NC1CCC(Oc2ccc(F)cc2)CC1] | * |
| 1246 | 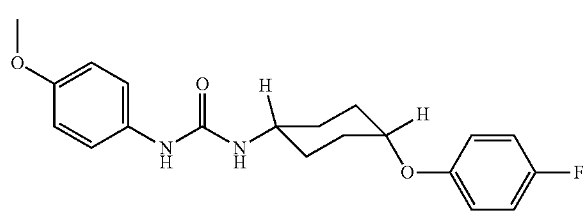 [SMILES: COc1ccc(NC(=O)NC2CCC(Oc3ccc(F)cc3)CC2)cc1] | * |
| 1247 | 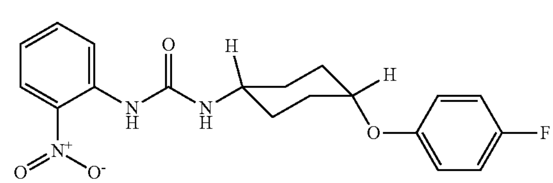 [SMILES: O=C(Nc1ccccc1[N+](=O)[O-])NC1CCC(Oc2ccc(F)cc2)CC1] | * |

TABLE 18b-continued

| No. | Structure | IC$_{50}$ (µM) |
|---|---|---|
| 1248 | 3-nitrophenyl-NH-C(O)-NH-cyclohexyl-O-(4-fluorophenyl) | * |
| 1249 | 4-nitrophenyl-NH-C(O)-NH-cyclohexyl-O-(4-fluorophenyl) | * |
| 1250 | 2,6-difluorophenyl-NH-C(O)-NH-cyclohexyl-O-(4-fluorophenyl) | * |
| 1251 | 4-bromophenyl-NH-C(O)-NH-cyclohexyl-O-(4-fluorophenyl) | * |
| 1252 | 2-methoxyphenyl-NH-C(O)-NH-cyclohexyl-O-(4-fluorophenyl) | * |
| 1253 | 3-methoxyphenyl-NH-C(O)-NH-cyclohexyl-O-(4-fluorophenyl) | * |
| 1254 | 3-chlorophenyl-NH-C(O)-NH-cyclohexyl-O-(4-fluorophenyl) | * |
| 1255 | 2-(trifluoromethoxy)phenyl-NH-C(O)-NH-cyclohexyl-O-(4-fluorophenyl) | * |

TABLE 18b-continued

| No. | Structure | IC$_{50}$ (µM) |
|---|---|---|
| 1256 | 4-(trifluoromethoxy)phenyl-NH-C(=O)-NH-cyclohexyl-O-(4-fluorophenyl) | * |
| 1257 | 2-bromophenyl-NH-C(=O)-NH-cyclohexyl-O-(4-fluorophenyl) | * |
| 1258 | 2-chlorophenyl-NH-C(=O)-NH-cyclohexyl-O-(4-fluorophenyl) | * |
| 1259 | 2-chlorophenyl-NH-C(=O)-NH-cyclohexyl-O-(4-fluorophenyl) | * |
| 1260 | 3-bromophenyl-NH-C(=O)-NH-cyclohexyl-O-(4-fluorophenyl) | * |
| 1261 | adamantyl-NH-C(=O)-NH-cyclohexyl-O-(4-fluorophenyl) | * |
| 1262 | 2,6-diisopropylphenyl-NH-C(=O)-NH-cyclohexyl-O-(4-fluorophenyl) | * |
| 1263 | phenethyl-NH-C(=O)-NH-cyclohexyl-O-(4-fluorophenyl) | * |

TABLE 18b-continued

| No. | Structure | IC$_{50}$ (μM) |
|---|---|---|
| 1264 | 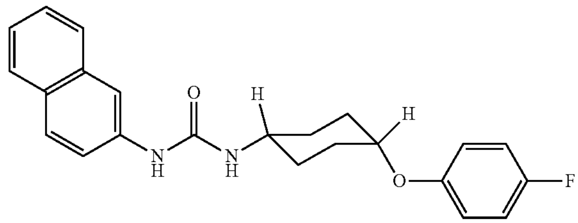 [SMILES: O=C(Nc1ccc2ccccc2c1)NC1CCC(Oc2ccc(F)cc2)CC1] | * |
| 1265 | 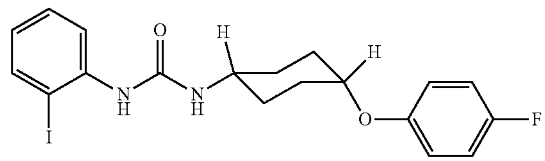 [SMILES: O=C(Nc1ccccc1I)NC1CCC(Oc2ccc(F)cc2)CC1] | * |
| 1266 | 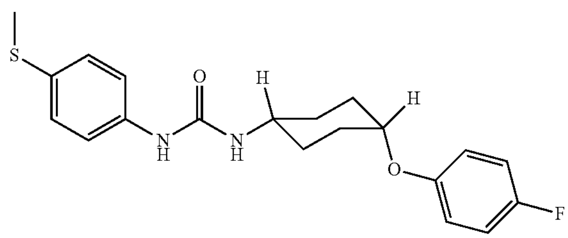 [SMILES: CSc1ccc(NC(=O)NC2CCC(Oc3ccc(F)cc3)CC2)cc1] | * |
| 1267 | 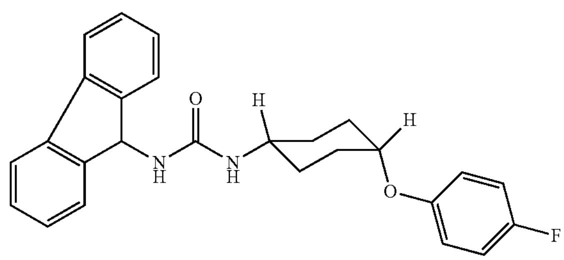 [SMILES: O=C(NC1CCC(Oc2ccc(F)cc2)CC1)NC1c2ccccc2-c2ccccc21] | * |
| 1268 | 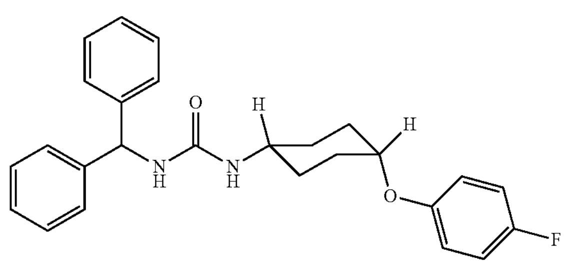 [SMILES: O=C(NC1CCC(Oc2ccc(F)cc2)CC1)NC(c1ccccc1)c1ccccc1] | * |
| 1269 | 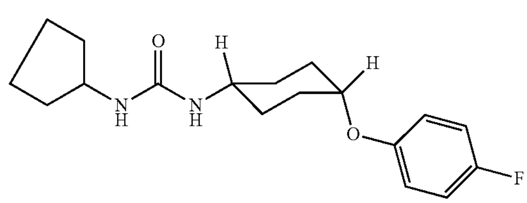 [SMILES: O=C(NC1CCCC1)NC1CCC(Oc2ccc(F)cc2)CC1] | * |

TABLE 18b-continued

| No. | Structure | IC$_{50}$ (µM) |
|---|---|---|
| 1270 | 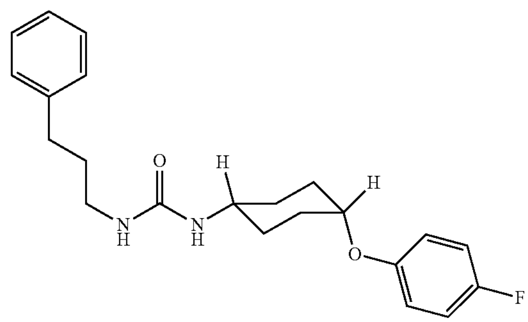 [SMILES: O=C(NCCCc1ccccc1)NC1CCC(Oc2ccc(F)cc2)CC1] | * |
| 1271 | 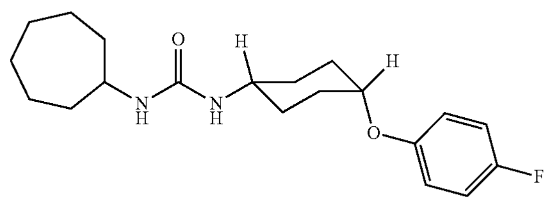 [SMILES: O=C(NC1CCCCCC1)NC1CCC(Oc2ccc(F)cc2)CC1] | * |
| 1272 | 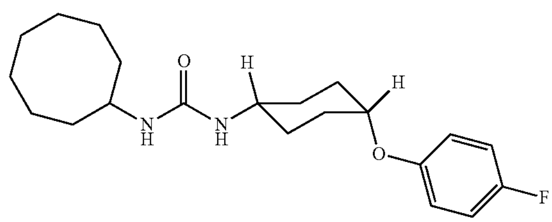 [SMILES: O=C(NC1CCCCCCC1)NC1CCC(Oc2ccc(F)cc2)CC1] | * |
| 1273 | 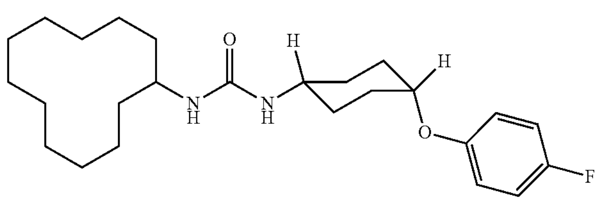 [SMILES: O=C(NC1CCCCCCCCCCC1)NC1CCC(Oc2ccc(F)cc2)CC1] | * |
| 1274 | 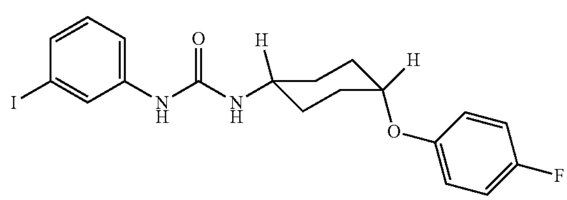 [SMILES: O=C(Nc1cccc(I)c1)NC1CCC(Oc2ccc(F)cc2)CC1] | * |
| 1275 | 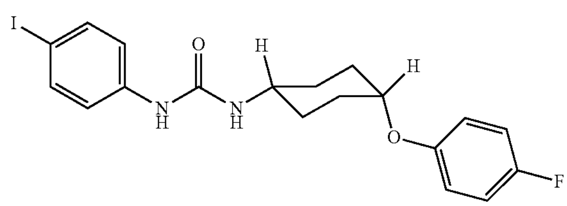 [SMILES: O=C(Nc1ccc(I)cc1)NC1CCC(Oc2ccc(F)cc2)CC1] | * |
| 1276 | 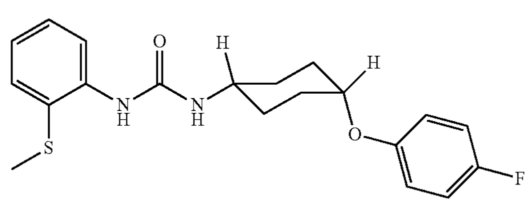 [SMILES: CSc1ccccc1NC(=O)NC1CCC(Oc2ccc(F)cc2)CC1] | * |

TABLE 18b-continued
| No. | Structure | IC$_{50}$ (μM) |
|---|---|---|
| 1277 | 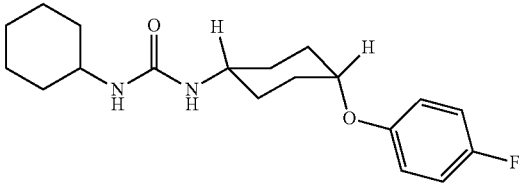 [SMILES: O=C(NC1CCCCC1)NC1CCC(Oc2ccc(F)cc2)CC1] | * |
| 1278 | 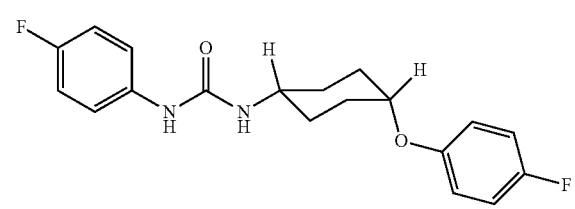 [SMILES: O=C(Nc1ccc(F)cc1)NC1CCC(Oc2ccc(F)cc2)CC1] | * |
| 1279 | 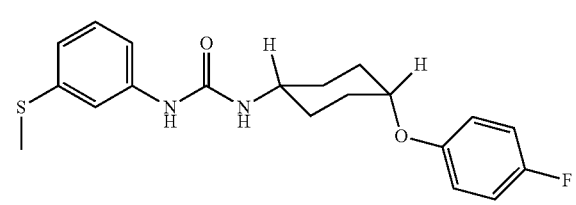 [SMILES: CSc1cccc(NC(=O)NC2CCC(Oc3ccc(F)cc3)CC2)c1] | * |
| 1280 | 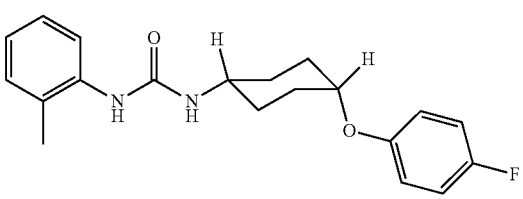 [SMILES: Cc1ccccc1NC(=O)NC1CCC(Oc2ccc(F)cc2)CC1] | * |
| 1281 | 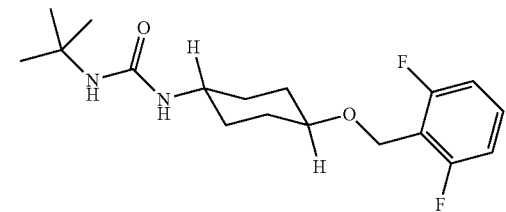 [SMILES: CC(C)(C)NC(=O)NC1CCC(OCc2c(F)cccc2F)CC1] | * |
| 1282 | 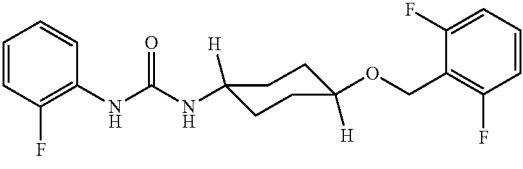 [SMILES: O=C(Nc1ccccc1F)NC1CCC(OCc2c(F)cccc2F)CC1] | * |
| 1283 | 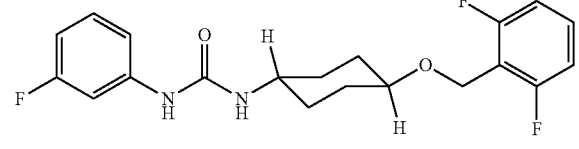 | * |

TABLE 18b-continued

| No. | Structure | IC$_{50}$ (μM) |
|---|---|---|
| 1284 | 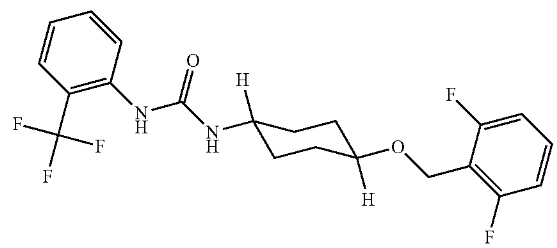 [SMILES: O=C(Nc1ccccc1C(F)(F)F)NC1CCC(OCc2c(F)cccc2F)CC1] | * |
| 1285 | 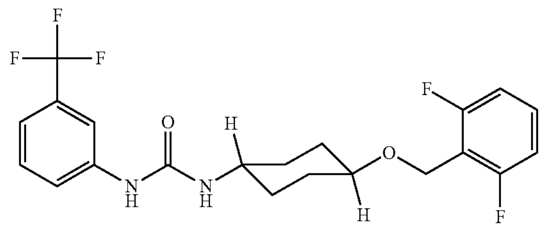 [SMILES: O=C(Nc1cccc(C(F)(F)F)c1)NC1CCC(OCc2c(F)cccc2F)CC1] | * |
| 1286 | 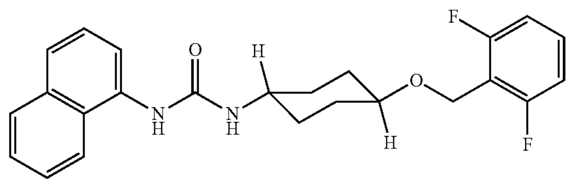 [SMILES: O=C(Nc1cccc2ccccc12)NC1CCC(OCc2c(F)cccc2F)CC1] | * |
| 1287 | 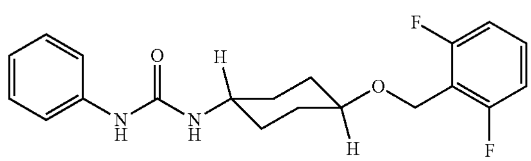 [SMILES: O=C(Nc1ccccc1)NC1CCC(OCc2c(F)cccc2F)CC1] | * |
| 1288 | 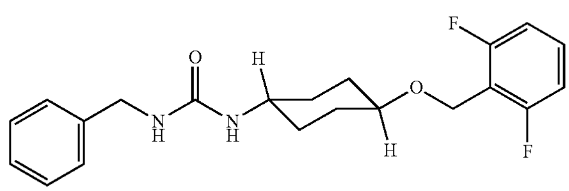 [SMILES: O=C(NCc1ccccc1)NC1CCC(OCc2c(F)cccc2F)CC1] | * |
| 1289 | 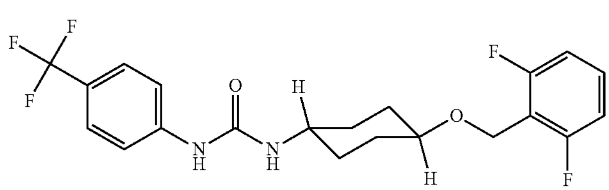 [SMILES: O=C(Nc1ccc(C(F)(F)F)cc1)NC1CCC(OCc2c(F)cccc2F)CC1] | * |
| 1290 | 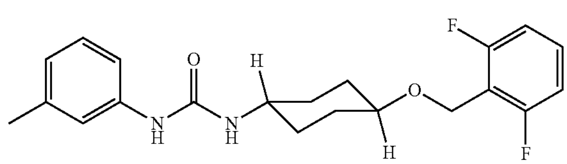 [SMILES: Cc1cccc(NC(=O)NC2CCC(OCc3c(F)cccc3F)CC2)c1] | * |
| 1291 | 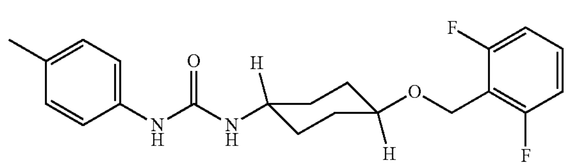 | * |

US 8,476,043 B2
TABLE 18b-continued
| No. | Structure | IC$_{50}$ (μM) |
|---|---|---|
| 1292 | 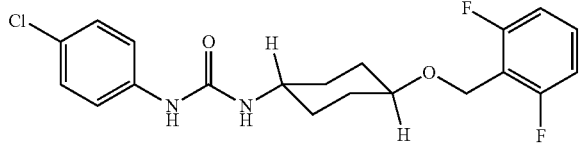 [SMILES: O=C(Nc1ccc(Cl)cc1)NC1CCC(OCc2c(F)cccc2F)CC1] | * |
| 1293 | 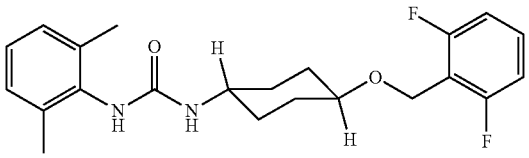 [SMILES: Cc1cccc(C)c1NC(=O)NC1CCC(OCc2c(F)cccc2F)CC1] | * |
| 1294 | 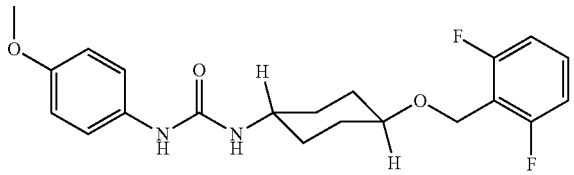 [SMILES: COc1ccc(NC(=O)NC2CCC(OCc3c(F)cccc3F)CC2)cc1] | * |
| 1295 | 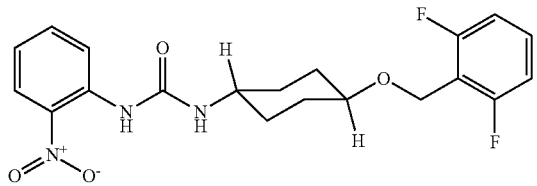 [SMILES: O=C(Nc1ccccc1[N+](=O)[O-])NC1CCC(OCc2c(F)cccc2F)CC1] | * |
| 1296 | 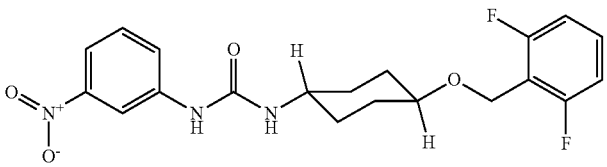 [SMILES: O=C(Nc1cccc([N+](=O)[O-])c1)NC1CCC(OCc2c(F)cccc2F)CC1] | * |
| 1297 | 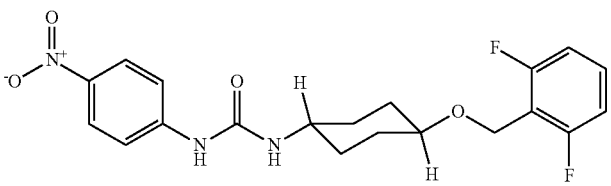 | * |
| 1298 | 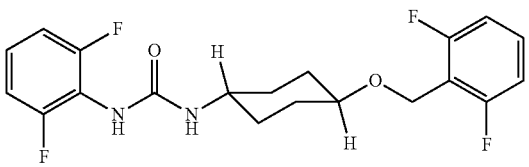 [SMILES: O=C(Nc1c(F)cccc1F)NC1CCC(OCc2c(F)cccc2F)CC1] | * |
| 1299 | 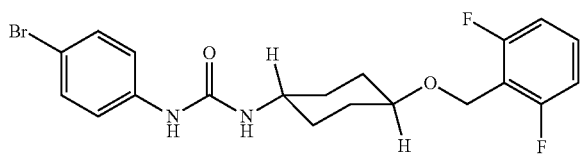 | * |

TABLE 18b-continued

| No. | Structure | IC$_{50}$ (μM) |
|---|---|---|
| 1300 | 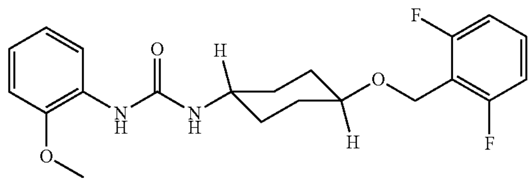 [SMILES: COc1ccccc1NC(=O)NC1CCC(OCc2c(F)cccc2F)CC1] | * |
| 1301 | 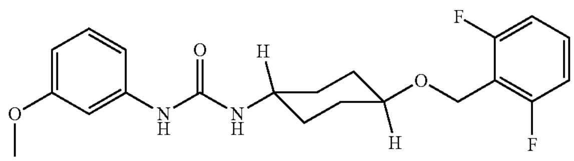 [SMILES: COc1cccc(NC(=O)NC2CCC(OCc3c(F)cccc3F)CC2)c1] | * |
| 1302 | 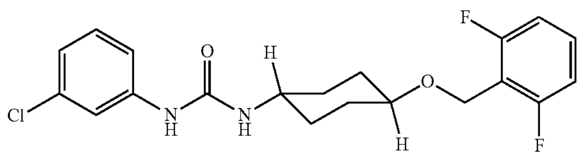 [SMILES: O=C(Nc1cccc(Cl)c1)NC1CCC(OCc2c(F)cccc2F)CC1] | * |
| 1303 | 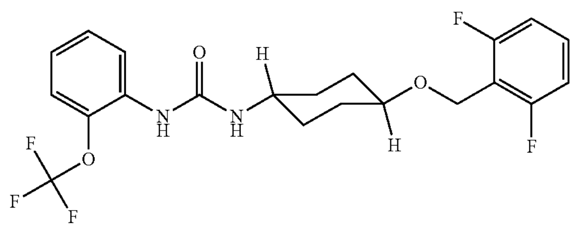 [SMILES: O=C(Nc1ccccc1OC(F)(F)F)NC1CCC(OCc2c(F)cccc2F)CC1] | * |
| 1304 | 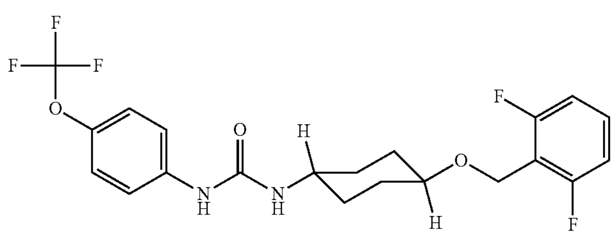 [SMILES: O=C(Nc1ccc(OC(F)(F)F)cc1)NC1CCC(OCc2c(F)cccc2F)CC1] | * |
| 1305 | 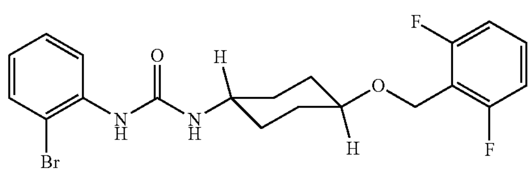 [SMILES: O=C(Nc1ccccc1Br)NC1CCC(OCc2c(F)cccc2F)CC1] | * |
| 1306 | 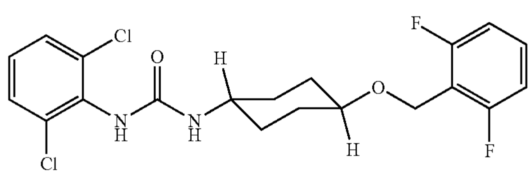 [SMILES: O=C(Nc1c(Cl)cccc1Cl)NC1CCC(OCc2c(F)cccc2F)CC1] | * |
| 1307 | 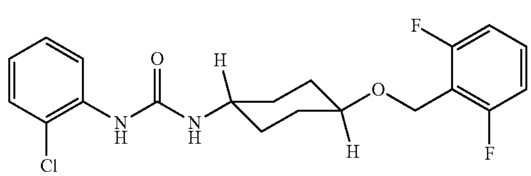 [SMILES: O=C(Nc1ccccc1Cl)NC1CCC(OCc2c(F)cccc2F)CC1] | * |

TABLE 18b-continued

| No. | Structure | IC$_{50}$ (μM) |
|---|---|---|
| 1308 | 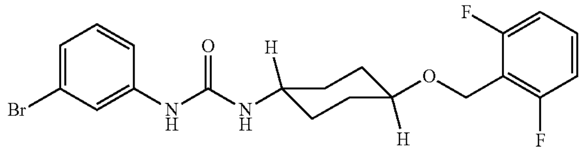 | * |
| 1309 | 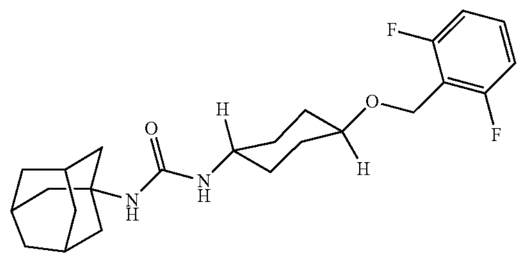 [SMILES: O=C(NC1CCC(OCc2c(F)cccc2F)CC1)NC12CC3CC(CC(C3)C1)C2] | * |
| 1310 | 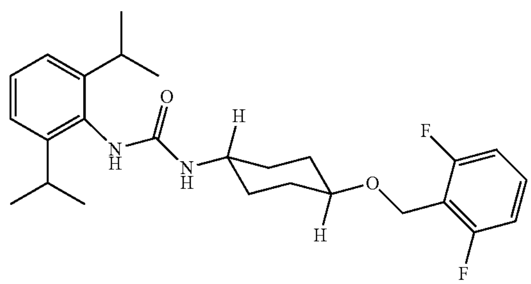 [SMILES: CC(C)c1cccc(C(C)C)c1NC(=O)NC1CCC(OCc2c(F)cccc2F)CC1] | * |
| 1311 | 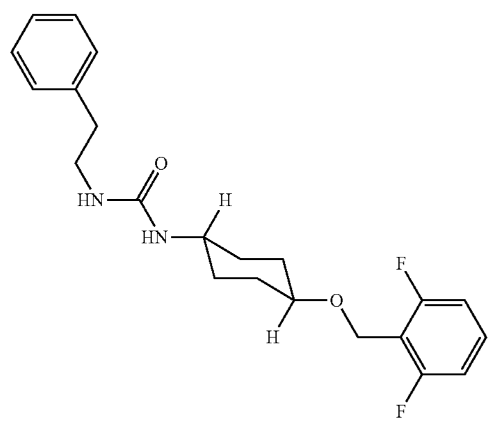 [SMILES: O=C(NCCc1ccccc1)NC1CCC(OCc2c(F)cccc2F)CC1] | * |
| 1312 | 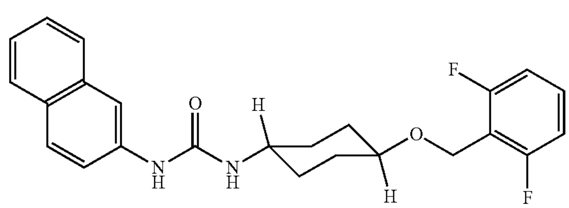 [SMILES: O=C(Nc1ccc2ccccc2c1)NC1CCC(OCc2c(F)cccc2F)CC1] | * |
| 1313 | 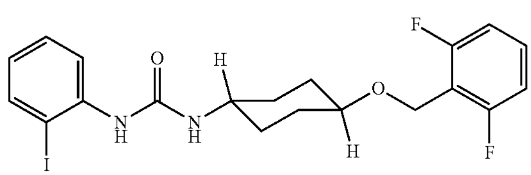 [SMILES: O=C(Nc1ccccc1I)NC1CCC(OCc2c(F)cccc2F)CC1] | * |

TABLE 18b-continued

| No. | Structure | IC$_{50}$ (µM) |
|---|---|---|
| 1314 | 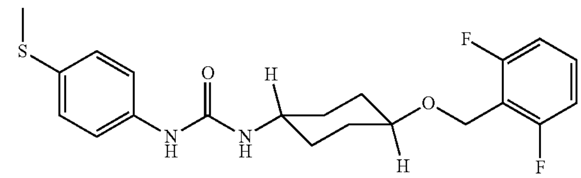 [SMILES: CSc1ccc(NC(=O)NC2CCC(OCc3c(F)cccc3F)CC2)cc1] | * |
| 1315 | 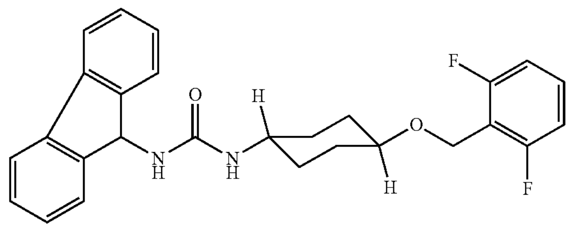 [SMILES: O=C(NC1CCC(OCc2c(F)cccc2F)CC1)NC1c2ccccc2-c2ccccc21] | * |
| 1316 | 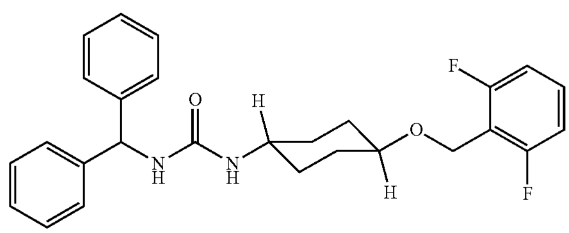 [SMILES: O=C(NC1CCC(OCc2c(F)cccc2F)CC1)NC(c1ccccc1)c1ccccc1] | * |
| 1317 | 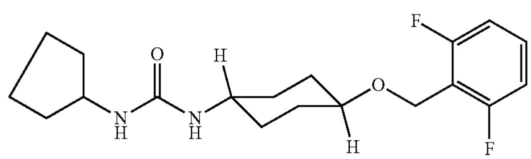 [SMILES: O=C(NC1CCCC1)NC1CCC(OCc2c(F)cccc2F)CC1] | * |
| 1318 | 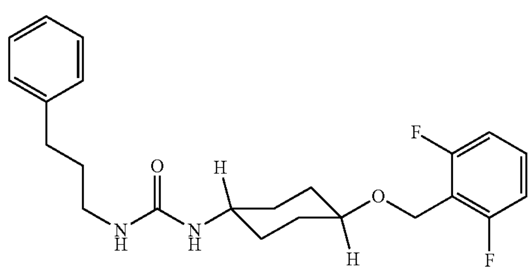 [SMILES: O=C(NCCCc1ccccc1)NC1CCC(OCc2c(F)cccc2F)CC1] | * |
| 1319 | 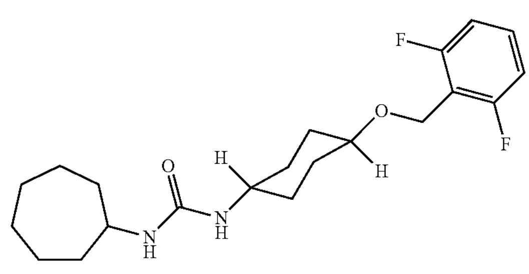 [SMILES: O=C(NC1CCCCCC1)NC1CCC(OCc2c(F)cccc2F)CC1] | * |

TABLE 18b-continued
| No. | Structure | IC$_{50}$ (μM) |
|---|---|---|
| 1320 | 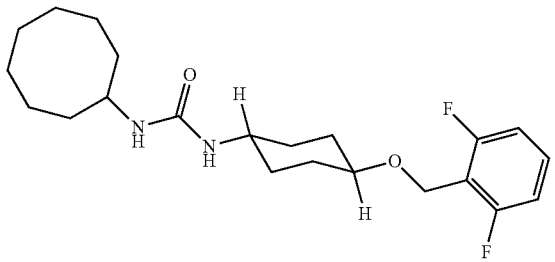 [SMILES: O=C(NC1CCCCCCC1)NC1CCC(OCc2c(F)cccc2F)CC1] | * |
| 1321 | 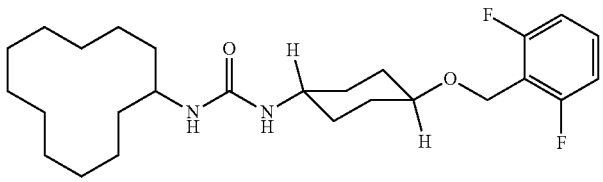 [SMILES: O=C(NC1CCCCCCCCCCC1)NC1CCC(OCc2c(F)cccc2F)CC1] | * |
| 1322 | 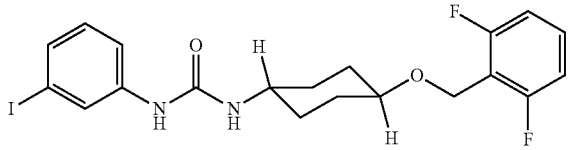 [SMILES: O=C(Nc1cccc(I)c1)NC1CCC(OCc2c(F)cccc2F)CC1] | * |
| 1323 | 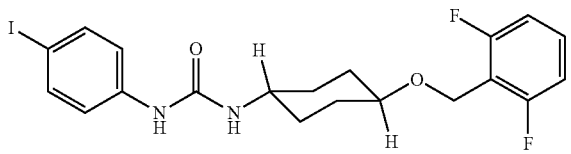 [SMILES: O=C(Nc1ccc(I)cc1)NC1CCC(OCc2c(F)cccc2F)CC1] | * |
| 1324 | 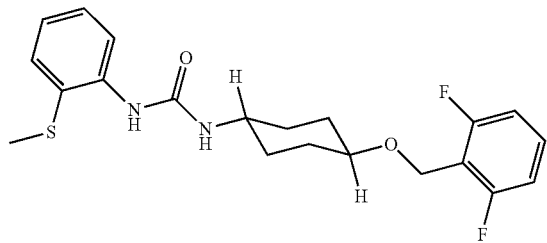 [SMILES: CSc1ccccc1NC(=O)NC1CCC(OCc2c(F)cccc2F)CC1] | * |
| 1325 | 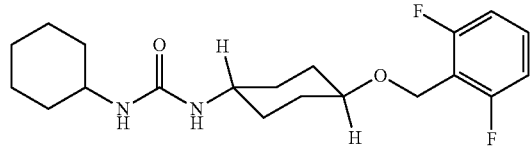 [SMILES: O=C(NC1CCCCC1)NC1CCC(OCc2c(F)cccc2F)CC1] | * |

TABLE 18b-continued

| No. | Structure | IC$_{50}$ (μM) |
|---|---|---|
| 1326 | 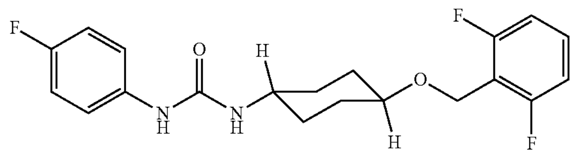 [SMILES: O=C(Nc1ccc(F)cc1)NC1CCC(OCc2c(F)cccc2F)CC1] | * |
| 1327 | 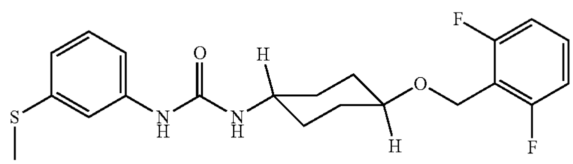 [SMILES: CSc1cccc(NC(=O)NC2CCC(OCc3c(F)cccc3F)CC2)c1] | * |
| 1328 | 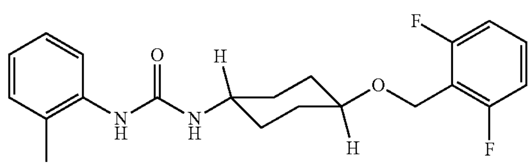 [SMILES: Cc1ccccc1NC(=O)NC1CCC(OCc2c(F)cccc2F)CC1] | * |
| 1329 | 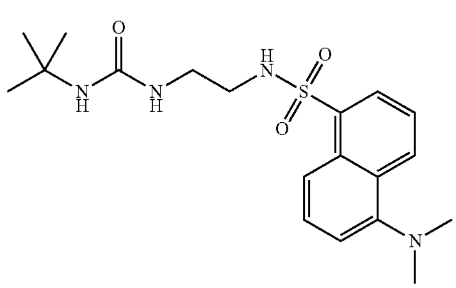 [SMILES: CN(C)c1cccc2c(S(=O)(=O)NCCNC(=O)NC(C)(C)C)cccc12] | * |

TABLE 18b-continued

| No. | Structure | IC$_{50}$ (μM) |
|---|---|---|
| 1330 | 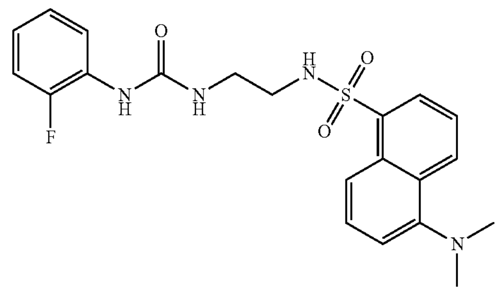 | * |
| 1331 | 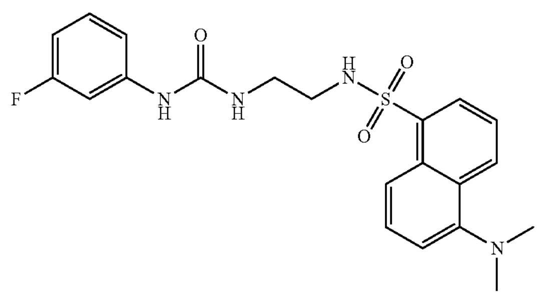 [SMILES: CN(C)c1cccc2c(S(=O)(=O)NCCNC(=O)Nc3cccc(F)c3)cccc12] | * |
| 1332 | 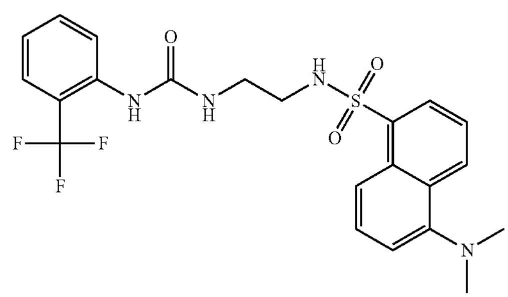 [SMILES: CN(C)c1cccc2c(S(=O)(=O)NCCNC(=O)Nc3ccccc3C(F)(F)F)cccc12] | * |
| 1333 | 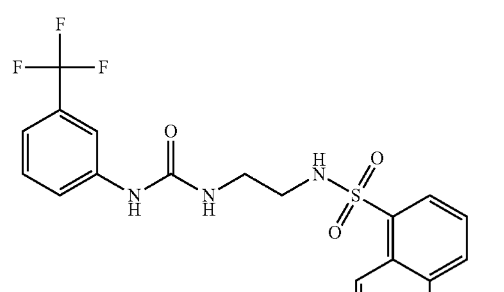 | ** |

TABLE 18b-continued

| No. | Structure | IC$_{50}$ (μM) |
|---|---|---|
| 1334 | 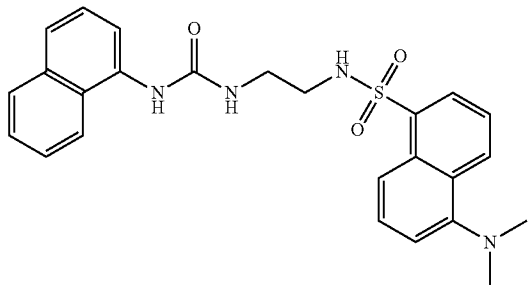 [SMILES: CN(C)c1cccc2c(S(=O)(=O)NCCNC(=O)Nc3cccc4ccccc34)cccc12] | * |
| 1335 | 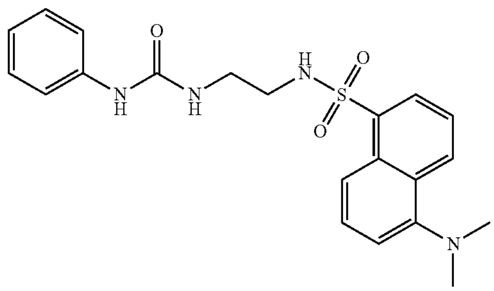 [SMILES: CN(C)c1cccc2c(S(=O)(=O)NCCNC(=O)Nc3ccccc3)cccc12] | * |
| 1336 | 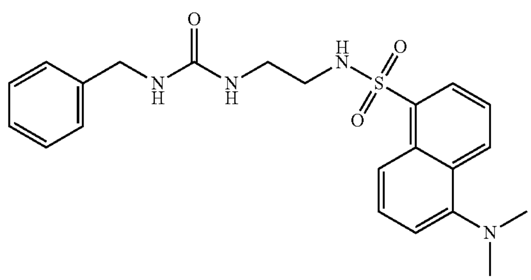 [SMILES: CN(C)c1cccc2c(S(=O)(=O)NCCNC(=O)NCc3ccccc3)cccc12] | * |
| 1337 | 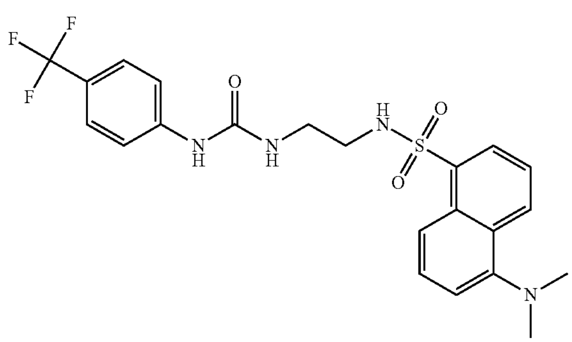 [SMILES: CN(C)c1cccc2c(S(=O)(=O)NCCNC(=O)Nc3ccc(C(F)(F)F)cc3)cccc12] | * |

TABLE 18b-continued

| No. | Structure | IC$_{50}$ (μM) |
|---|---|---|
| 1338 | 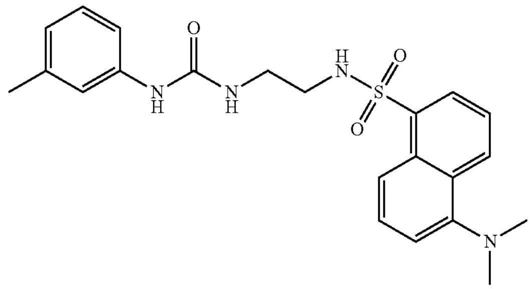 | * |
| 1339 | 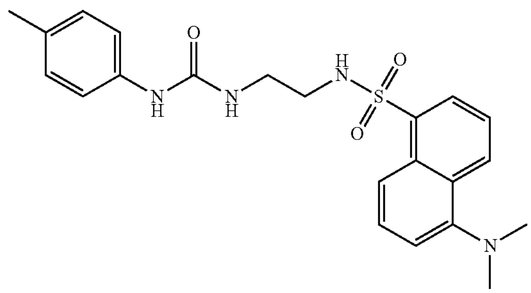 | * |
| 1340 | 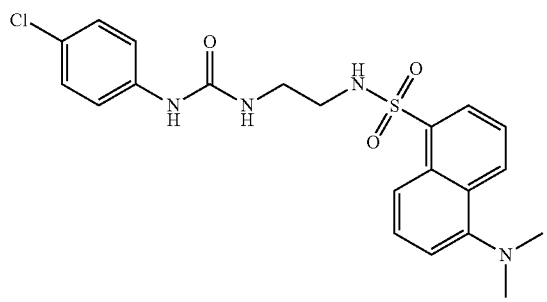 [SMILES: CN(C)c1cccc2c(S(=O)(=O)NCCNC(=O)Nc3ccc(Cl)cc3)cccc12] | * |
| 1341 | 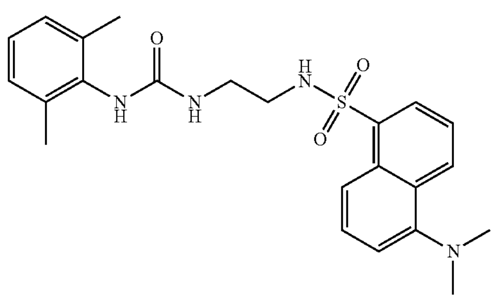 [SMILES: Cc1cccc(C)c1NC(=O)NCCNS(=O)(=O)c1cccc2c(N(C)C)cccc12] | * |
| 1342 | 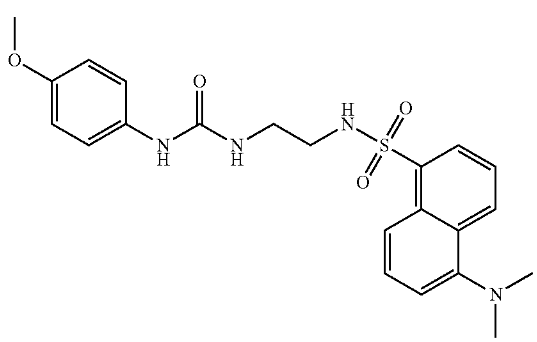 [SMILES: COc1ccc(NC(=O)NCCNS(=O)(=O)c2cccc3c(N(C)C)cccc23)cc1] | * |

TABLE 18b-continued

| No. | Structure | IC$_{50}$ (μM) |
|---|---|---|
| 1343 | 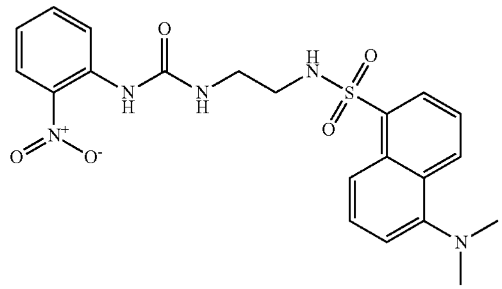 [SMILES: CN(C)c1cccc2c(S(=O)(=O)NCCNC(=O)Nc3ccccc3[N+](=O)[O-])cccc12] | * |
| 1344 | 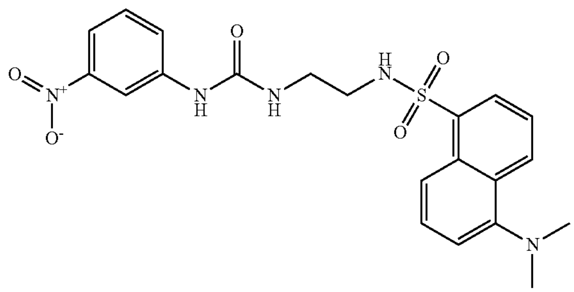 [SMILES: CN(C)c1cccc2c(S(=O)(=O)NCCNC(=O)Nc3cccc([N+](=O)[O-])c3)cccc12] | * |
| 1345 | 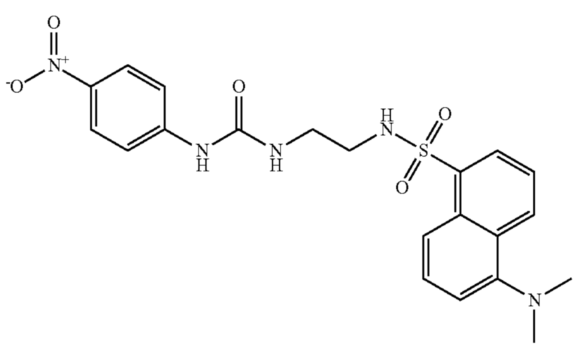 | * |
| 1346 | 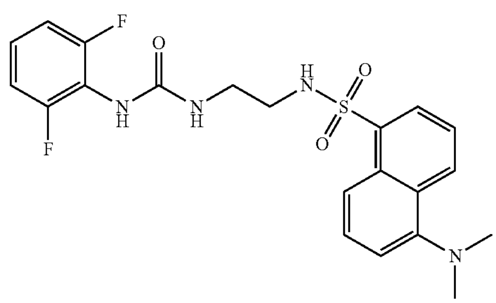 [SMILES: CN(C)c1cccc2c(S(=O)(=O)NCCNC(=O)Nc3c(F)cccc3F)cccc12] | * |

TABLE 18b-continued
| No. | Structure | IC$_{50}$ (μM) |
|---|---|---|
| 1347 | 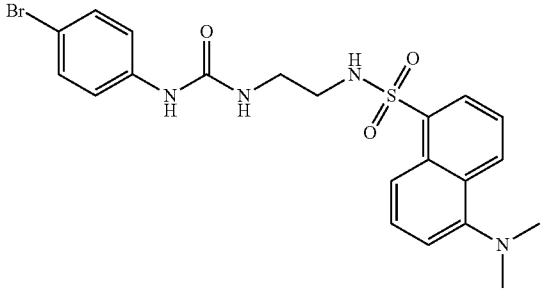 | * |
| 1348 | 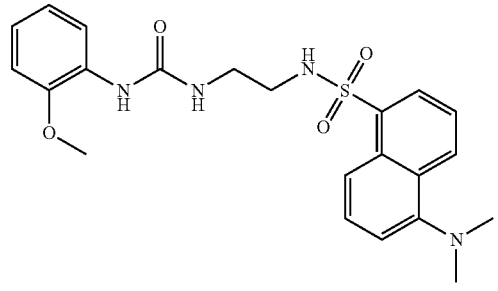 [SMILES: COc1ccccc1NC(=O)NCCNS(=O)(=O)c1cccc2c(N(C)C)cccc12] | * |
| 1349 | 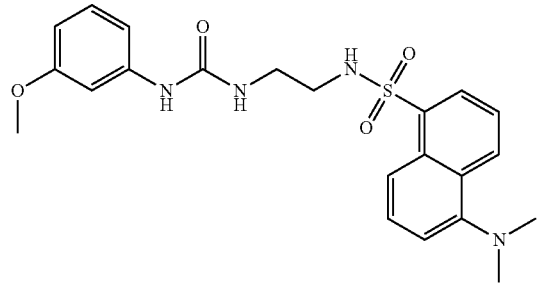 [SMILES: COc1cccc(NC(=O)NCCNS(=O)(=O)c2cccc3c(N(C)C)cccc23)c1] | * |
| 1350 | 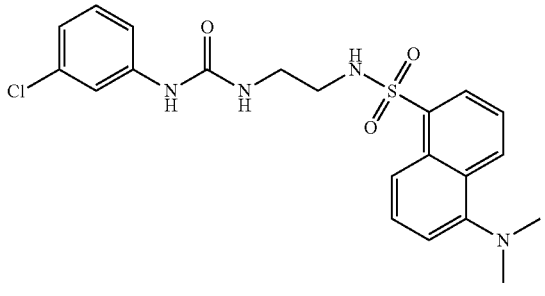 [SMILES: CN(C)c1cccc2c(S(=O)(=O)NCCNC(=O)Nc3cccc(Cl)c3)cccc12] | * |
| 1351 | 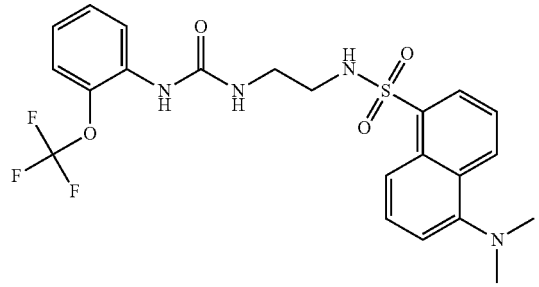 [SMILES: CN(C)c1cccc2c(S(=O)(=O)NCCNC(=O)Nc3ccccc3OC(F)(F)F)cccc12] | * |

TABLE 18b-continued
| No. | Structure | IC$_{50}$ (μM) |
|---|---|---|
| 1352 | 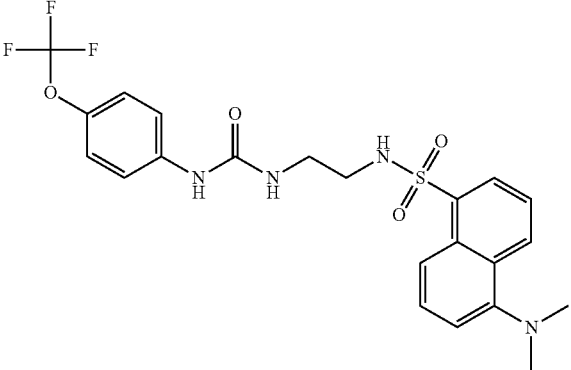 [SMILES: CN(C)c1cccc2c(S(=O)(=O)NCCNC(=O)Nc3ccc(OC(F)(F)F)cc3)cccc12] | * |
| 1353 | 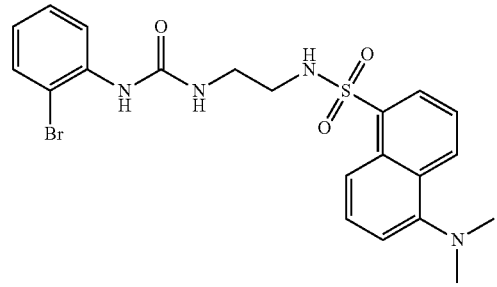 [SMILES: CN(C)c1cccc2c(S(=O)(=O)NCCNC(=O)Nc3ccccc3Br)cccc12] | * |
| 1354 | 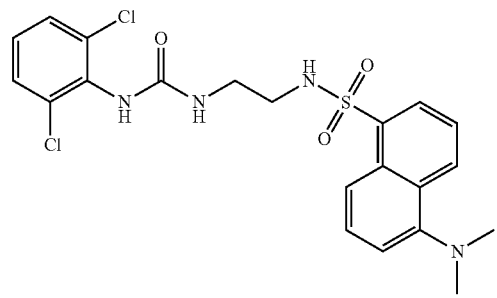 [SMILES: CN(C)c1cccc2c(S(=O)(=O)NCCNC(=O)Nc3c(Cl)cccc3Cl)cccc12] | * |
| 1355 | 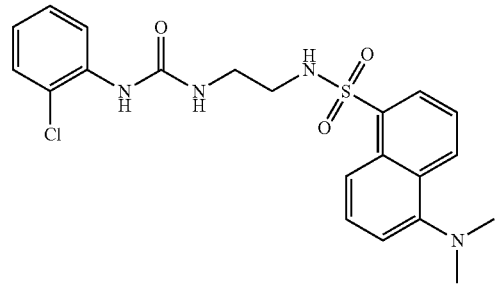 [SMILES: CN(C)c1cccc2c(S(=O)(=O)NCCNC(=O)Nc3ccccc3Cl)cccc12] | * |

TABLE 18b-continued

| No. | Structure | IC$_{50}$ (μM) |
|---|---|---|
| 1356 | 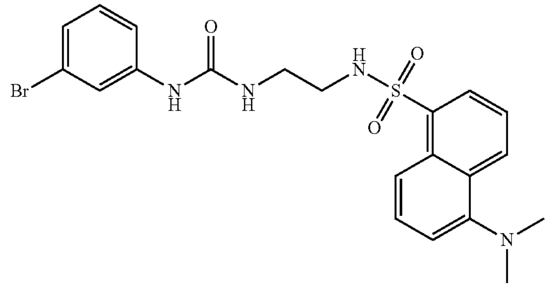 | * |
| 1357 | 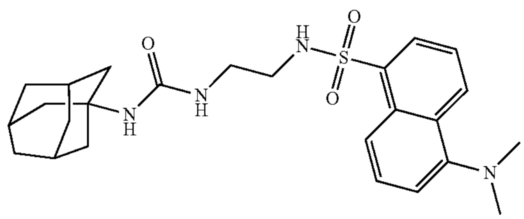 [SMILES: CN(C)c1cccc2c(S(=O)(=O)NCCNC(=O)NC34CC5CC(CC(C5)C3)C4)cccc12] | * |
| 1358 | 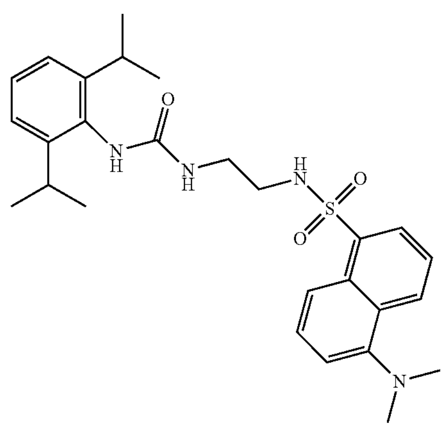 [SMILES: CC(C)c1cccc(C(C)C)c1NC(=O)NCCNS(=O)(=O)c1cccc2c(N(C)C)cccc12] | * |
| 1359 | 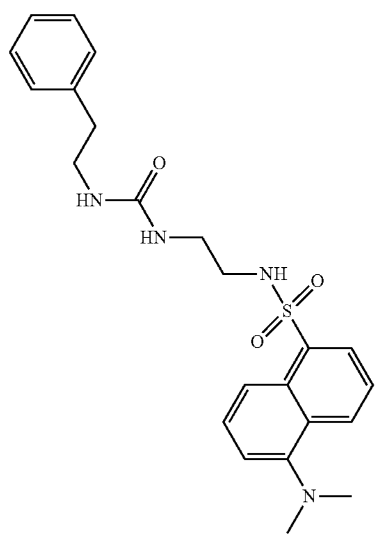 [SMILES: CN(C)c1cccc2c(S(=O)(=O)NCCNC(=O)NCCc3ccccc3)cccc12] | * |

TABLE 18b-continued

| No. | Structure | IC$_{50}$ (µM) |
|---|---|---|
| 1360 | 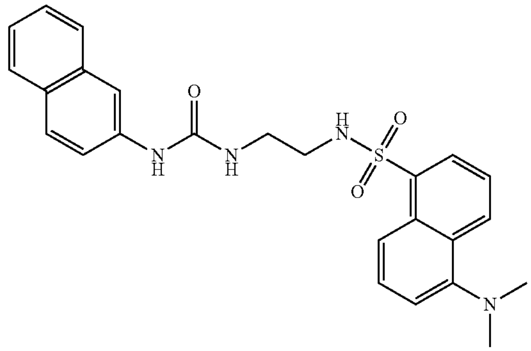 [SMILES: CN(C)c1cccc2c(S(=O)(=O)NCCNC(=O)Nc3ccc4ccccc4c3)cccc12] | * |
| 1361 | 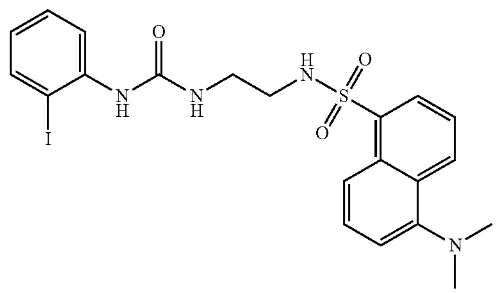 [SMILES: CN(C)c1cccc2c(S(=O)(=O)NCCNC(=O)Nc3ccccc3I)cccc12] | * |
| 1362 | 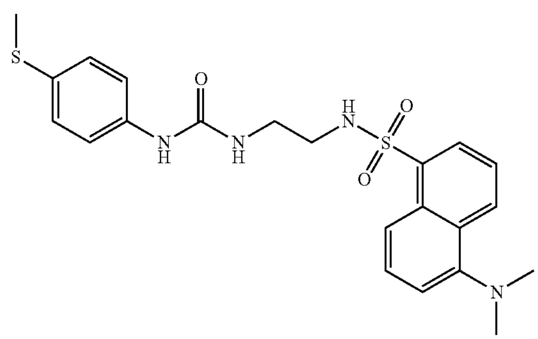 [SMILES: CSc1ccc(NC(=O)NCCNS(=O)(=O)c2cccc3c(N(C)C)cccc23)cc1] | * |
| 1363 | 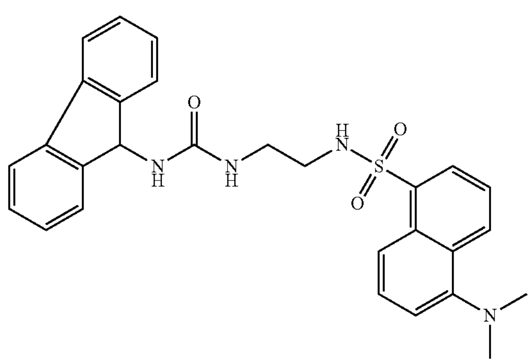 [SMILES: CN(C)c1cccc2c(S(=O)(=O)NCCNC(=O)NC3c4ccccc4-c4ccccc43)cccc12] | * |

TABLE 18b-continued

| No. | Structure | IC$_{50}$ (μM) |
|---|---|---|
| 1364 | 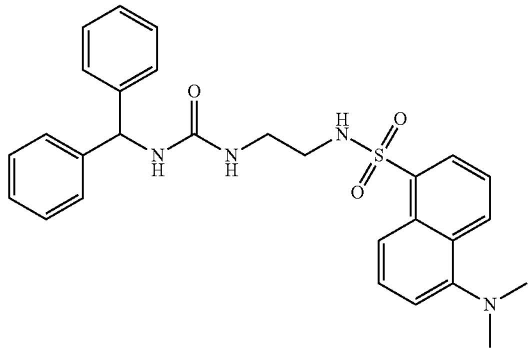 [SMILES: CN(C)c1cccc2c(S(=O)(=O)NCCNC(=O)NC(c3ccccc3)c3ccccc3)cccc12] | * |
| 1365 | 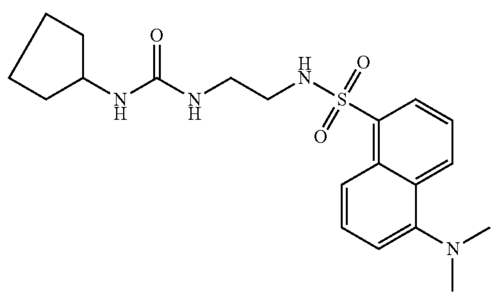 [SMILES: CN(C)c1cccc2c(S(=O)(=O)NCCNC(=O)NC3CCCC3)cccc12] | * |
| 1366 | 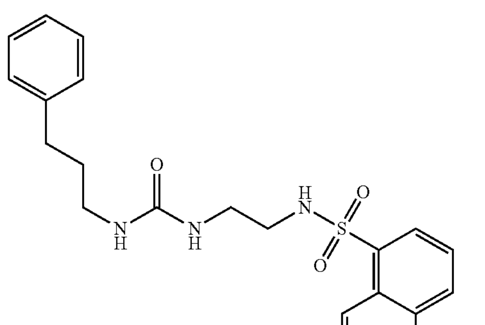 | * |
| 1367 | 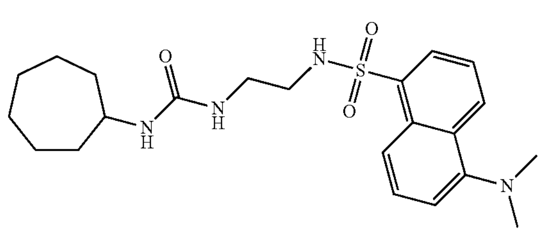 [SMILES: CN(C)c1cccc2c(S(=O)(=O)NCCNC(=O)NC3CCCCCC3)cccc12] | * |

TABLE 18b-continued

| No. | Structure | IC$_{50}$ (μM) |
|---|---|---|
| 1368 | 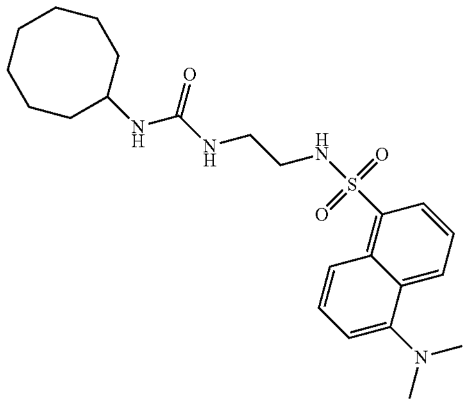 [SMILES: CN(C)c1cccc2c(S(=O)(=O)NCCNC(=O)NC3CCCCCCC3)cccc12] | * |
| 1369 | 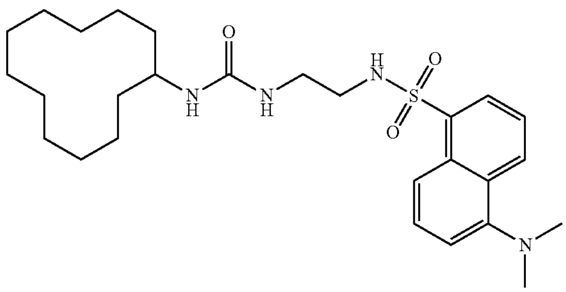 [SMILES: CN(C)c1cccc2c(S(=O)(=O)NCCNC(=O)NC3CCCCCCCCCCC3)cccc12] | * |
| 1370 | 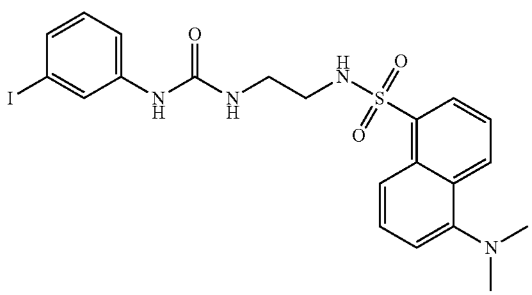 [SMILES: CN(C)c1cccc2c(S(=O)(=O)NCCNC(=O)Nc3cccc(I)c3)cccc12] | * |
| 1371 | 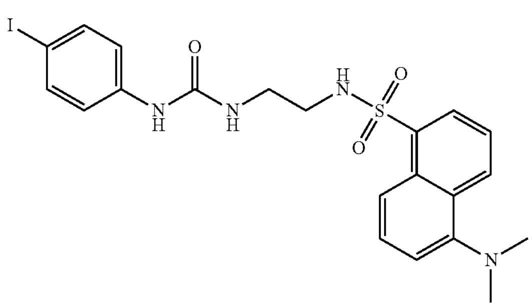 [SMILES: CN(C)c1cccc2c(S(=O)(=O)NCCNC(=O)Nc3ccc(I)cc3)cccc12] | * |

TABLE 18b-continued

| No. | Structure | IC$_{50}$ (μM) |
|---|---|---|
| 1372 | 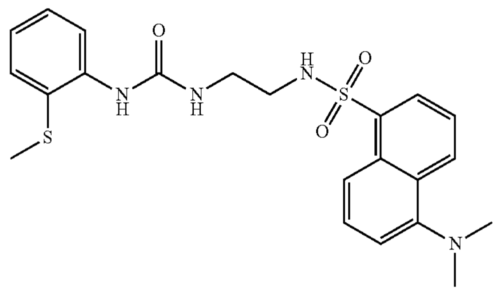 [SMILES: CSc1ccccc1NC(=O)NCCNS(=O)(=O)c1cccc2c(N(C)C)cccc12] | * |
| 1373 | 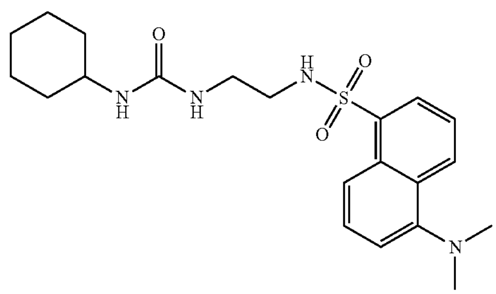 [SMILES: CN(C)c1cccc2c(S(=O)(=O)NCCNC(=O)NC3CCCCC3)cccc12] | * |
| 1374 | 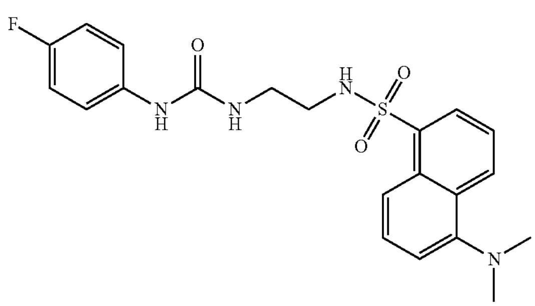 [SMILES: CN(C)c1cccc2c(S(=O)(=O)NCCNC(=O)Nc3ccc(F)cc3)cccc12] | * |
| 1375 | 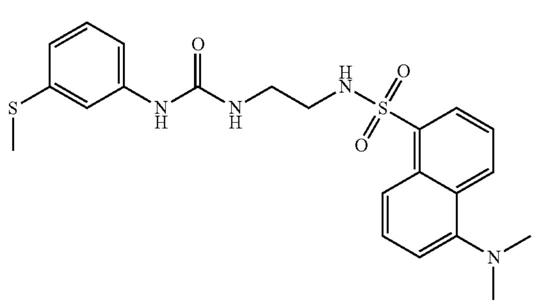 [SMILES: CSc1cccc(NC(=O)NCCNS(=O)(=O)c2cccc3c(N(C)C)cccc23)c1] | * |

TABLE 18b-continued
| No. | Structure | IC$_{50}$ (μM) |
|---|---|---|
| 1376 | 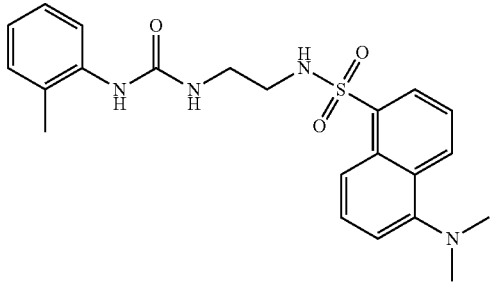 [SMILES: Cc1ccccc1NC(=O)NCCNS(=O)(=O)c1cccc2c(N(C)C)cccc12] | * |
| 1425 | 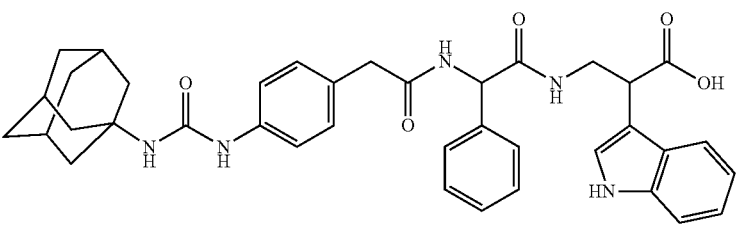 [SMILES: O=C(Cc1ccc(NC(=O)NC23CC4CC(CC(C4)C2)C3)cc1)NC(C(=O)NCC(C(=O)O)c1c[nH]c2ccccc12)c1ccccc1] | 0.01 ± 0.01 |
| 1437 | 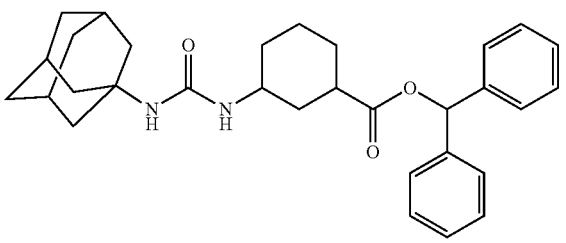 [SMILES: O=C(NC1CCCC(C(=O)OC(c2ccccc2)c2ccccc2)C1)NC12CC3CC(CC(C3)C1)C2] | 0.01 ± 0.01 |
| 1438 | 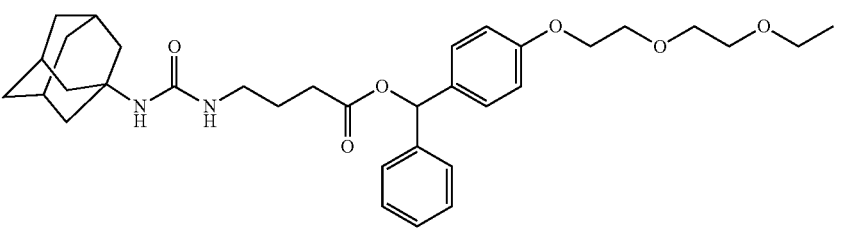 [SMILES: CCOCCOCCOc1ccc(C(OC(=O)CCCNC(=O)NC23CC4CC(CC(C4)C2)C3)c2ccccc2)cc1] | 0.01 ± 0.01 |
| 1439 | 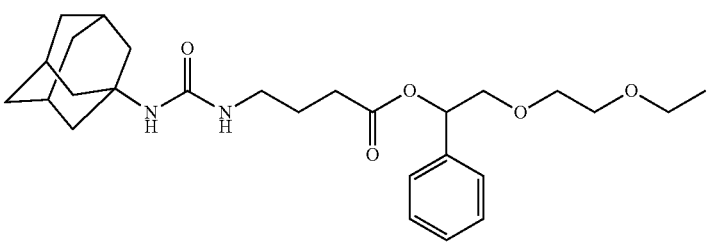 [SMILES: CCOCCOCC(OC(=O)CCCNC(=O)NC12CC3CC(CC(C3)C1)C2)c1ccccc1] | 0.01 ± 0.01 |

TABLE 18b-continued

| No. | Structure | IC$_{50}$ (μM) |
|---|---|---|
| 1440 | 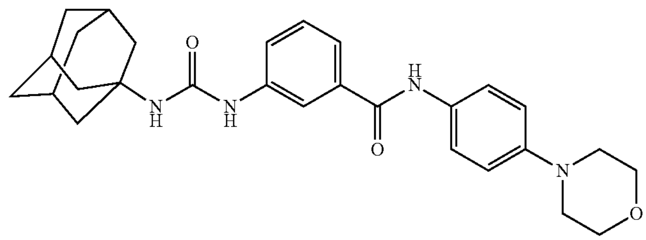 [SMILES: O=C(Nc1cccc(C(=O)Nc2ccc(N3CCOCC3)cc2)c1)NC12CC3CC(CC(C3)C1)C2] | 0.07 ± 0.01 |
| 1441 | 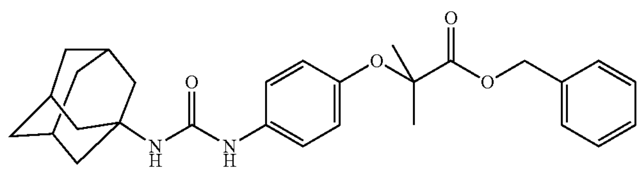 [SMILES: CC(C)(Oc1ccc(NC(=O)NC23CC4CC(CC(C4)C2)C3)cc1)C(=O)OCc1ccccc1] | 0.01 ± 0.01 |
| 1442 | 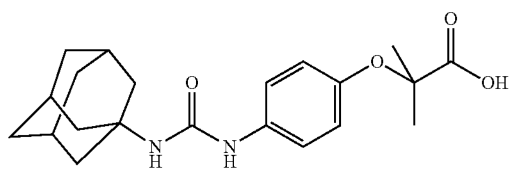 [SMILES: CC(C)(Oc1ccc(NC(=O)NC23CC4CC(CC(C4)C2)C3)cc1)C(=O)O] | 0.15 ± 0.01 |
| 1443 | 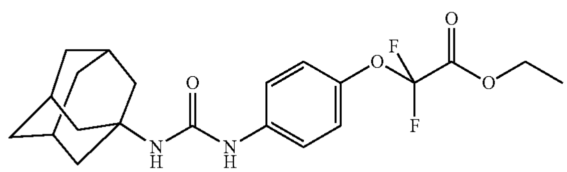 [SMILES: CCOC(=O)C(F)(F)Oc1ccc(NC(=O)NC23CC4CC(CC(C4)C2)C3)cc1] | 0.01 ± 0.01 |
| 1444 | 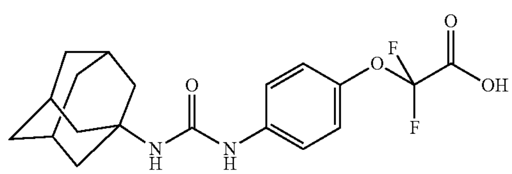 [SMILES: O=C(Nc1ccc(OC(F)(F)C(=O)O)cc1)NC12CC3CC(CC(C3)C1)C2] | 0.01 ± 0.01 |
| 1446 | 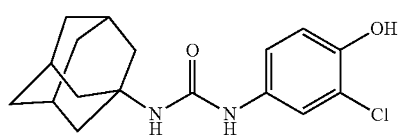 [SMILES: O=C(Nc1ccc(O)c(Cl)c1)NC12CC3CC(CC(C3)C1)C2] | 0.01 ± 0.01 |
| 1447 | 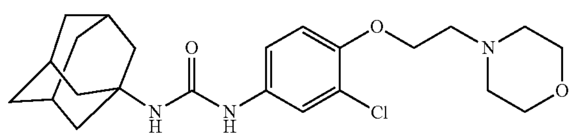 [SMILES: O=C(Nc1ccc(OCCN2CCOCC2)c(Cl)c1)NC12CC3CC(CC(C3)C1)C2] | 0.01 ± 0.01 |
| 1448 | 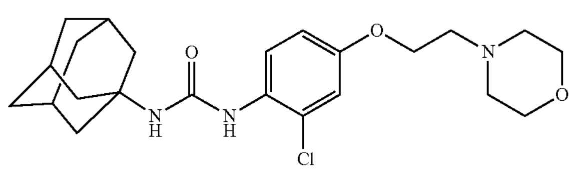 [SMILES: O=C(Nc1ccc(OCCN2CCOCC2)cc1Cl)NC12CC3CC(CC(C3)C1)C2] | 0.01 ± 0.01 |
| 1449 | 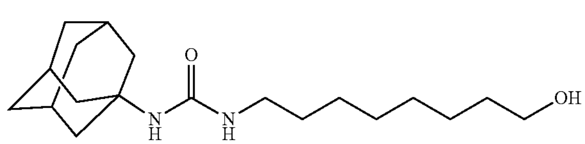 [SMILES: O=C(NCCCCCCCCO)NC12CC3CC(CC(C3)C1)C2] | 0.01 ± 0.01 |

TABLE 18b-continued

| No. | Structure | IC$_{50}$ (μM) |
|---|---|---|
| 1450 | 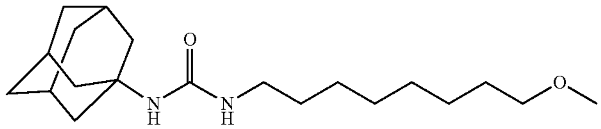 [SMILES: COCCCCCCCCNC(=O)NC12CC3CC(CC(C3)C1)C2] | 0.01 ± 0.01 |
| 1452 | 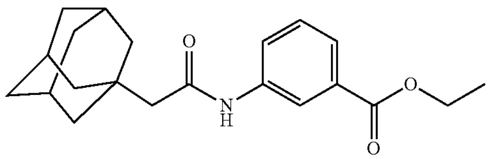 [SMILES: CCOC(=O)c1cccc(NC(=O)CC23CC4CC(CC(C4)C2)C3)c1] | 0.04 ± 0.01 |
| 1453 | 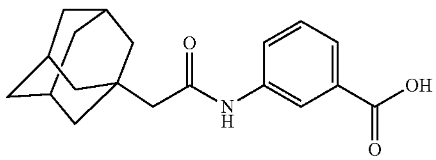 [SMILES: O=C(CC12CC3CC(CC(C3)C1)C2)Nc1cccc(C(=O)O)c1] | 0.03 ± 0.01 |
| 1454 | 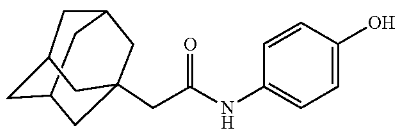 [SMILES: O=C(CC12CC3CC(CC(C3)C1)C2)Nc1ccc(O)cc1] | 0.03 ± 0.01 |
| 1455 | 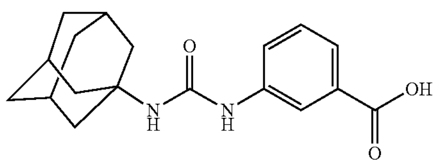 [SMILES: O=C(Nc1cccc(C(=O)O)c1)NC12CC3CC(CC(C3)C1)C2] | 0.92 ± 0.01 |
| 1458 | 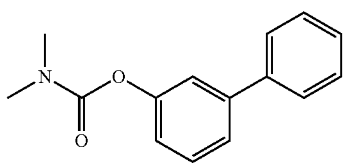 [SMILES: CN(C)C(=O)Oc1cccc(-c2ccccc2)c1] | * |
| 1459 | 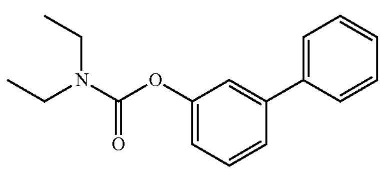 [SMILES: CCN(CC)C(=O)Oc1cccc(-c2ccccc2)c1] | * |
| 1460 | 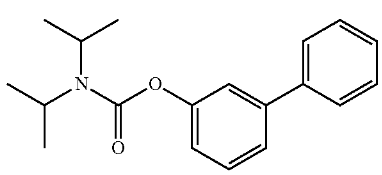 [SMILES: CC(C)N(C(=O)Oc1cccc(-c2ccccc2)c1)C(C)C] | 10.92 ± 0.01 |
| 1463 | 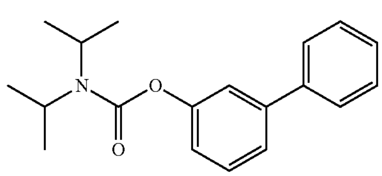 [SMILES: CC(C)N(C(=O)Oc1cccc(-c2ccccc2)c1)C(C)C] | 11.89 ± 0.01 |

TABLE 18b-continued

| No. | Structure | IC$_{50}$ (μM) |
|---|---|---|
| 1464 | 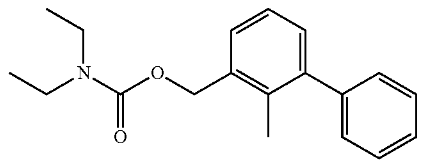 [SMILES: CCN(CC)C(=O)OCc1cccc(-c2ccccc2)c1C] | 7.19 ± 0.01 |
| 1465 | 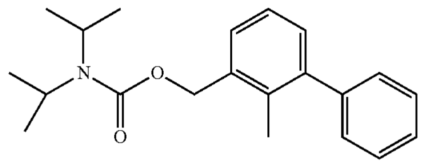 [SMILES: Cc1c(COC(=O)N(C(C)C)C(C)C)cccc1-c1ccccc1] | 1.23 ± 0.01 |
| 1469 | 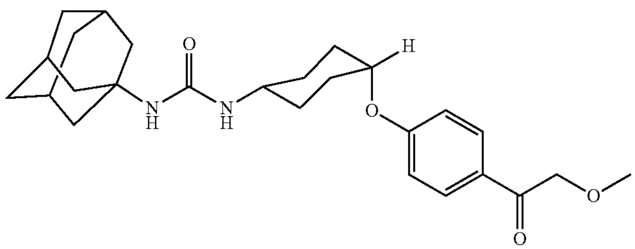 [SMILES: COCC(=O)c1ccc(OC2CCC(NC(=O)NC34CC5CC(CC(C5)C3)C4)CC2)cc1] | 0.01 ± 0.01 |
| 1470 | 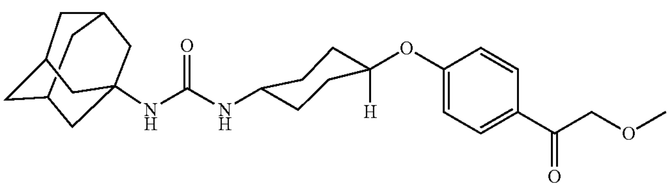 [SMILES: COCC(=O)c1ccc(OC2CCC(NC(=O)NC34CC5CC(CC(C5)C3)C4)CC2)cc1] | 0.01 ± 0.01 |
| 1471 | 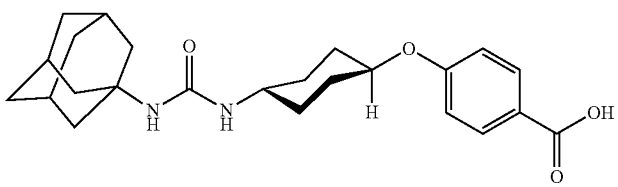 | * |
| 1498 | 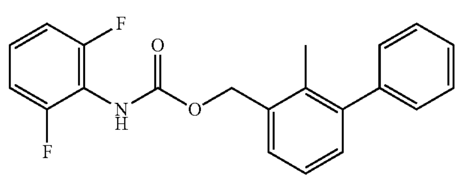 [SMILES: Cc1c(COC(=O)Nc2c(F)cccc2F)cccc1-c1ccccc1] | * |
| 1513 | 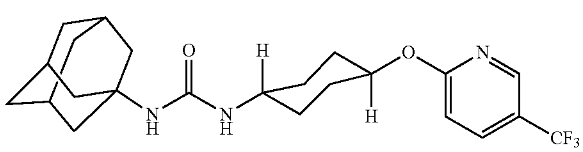 [SMILES: O=C(NC1CCC(Oc2ccc(C(F)(F)F)cn2)CC1)NC12CC3CC(CC(C3)C1)C2] | 0.05 ± 0.01 |
| 1514 | 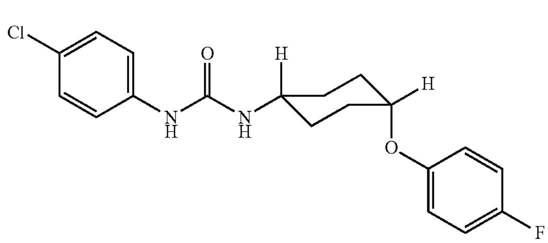 [SMILES: O=C(Nc1ccc(Cl)cc1)NC1CCC(Oc2ccc(F)cc2)CC1] | 0.01 ± 0.01 |

TABLE 18b-continued

| No. | Structure | IC$_{50}$ (μM) |
|---|---|---|
| 1515 | 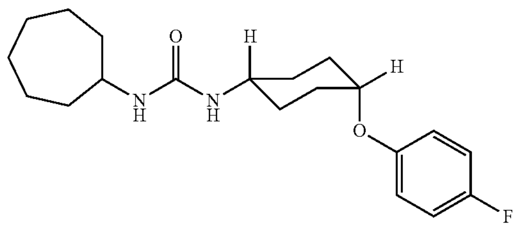 [SMILES: O=C(NC1CCCCCC1)NC1CCC(Oc2ccc(F)cc2)CC1] | 0.01 ± 0.01 |
| 1516 | 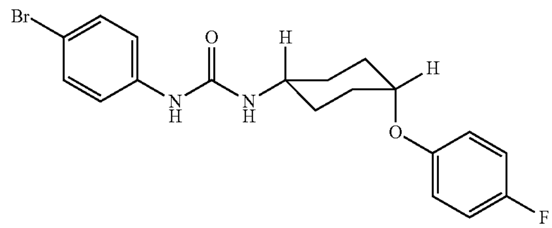 | 0.01 ± 0.01 |
| 1517 | 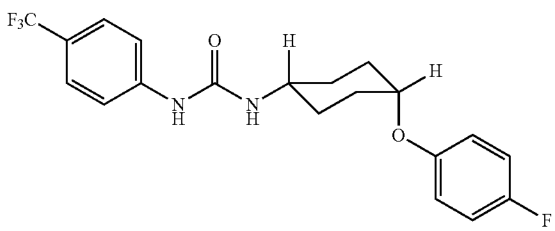 [SMILES: O=C(Nc1ccc(C(F)(F)F)cc1)NC1CCC(Oc2ccc(F)cc2)CC1] | 0.01 ± 0.01 |
| 1518 | 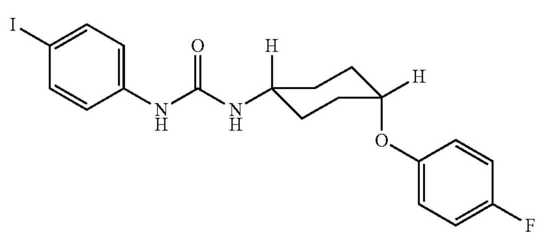 [SMILES: O=C(Nc1ccc(I)cc1)NC1CCC(Oc2ccc(F)cc2)CC1] | 0.01 ± 0.01 |
| 1519 | 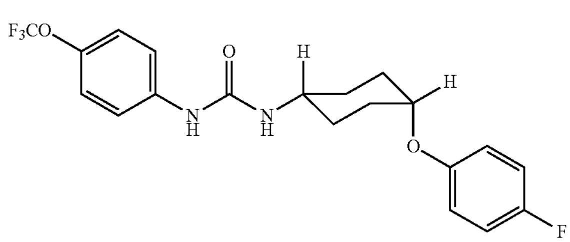 [SMILES: O=C(Nc1ccc(OC(F)(F)F)cc1)NC1CCC(Oc2ccc(F)cc2)CC1] | 0.01 ± 0.01 |

*Inhibition potencies were determined using a fluorescent based high-throughput assay. Inhibitors in solution at 10 mM in DMSO were serially diluted by 10-fold increment in Bis/Tris HCl buffer (25 mM PH 7.0) containing 0.1 mg/mL of BSA (Buffer A). In black 96-well plates, 20 μL of the inhibitor dilution or buffer were delivered in every well, and then 130 μL of Human sEH at ~0.4 μg/mL in solution in Buffer A were added to each well. The plate was then mixed and incubated at room temperature for 5 minutes. Fifty microliters of substrate ((3-Phenyl-oxiranyl)-acetic acid cyano-(6-methoxy-naphthalen-2-yl)-methyl ester; PHOME) at 200 μM in solution in 96:4 Buffer A:DMSO was then added to each well to give $[S]_{final}$ = 50 μM and $[E]_{final}$ = ~4 nM. The plate was then mixed and incubated in the dark at room temperature (~25° C.) for 90 min. Activity was measured by determining the relative quantity of 6-methoxy-2-naphthaldehyde formed with an excitation wavelength of 316 nm and an emission wavelength of 460 mn measured with a SpectraMax M-2 fluorometer (molecular Devices, Sunnyvale CA). Results are not reported.

The primary urea pharmacophore can be varied (compound #) with amide or carbamate functionality to improve physical properties of sEH inhibitors as well. The carbonyls can be replaced by heterocyclic or acyclic hydrogen bond acceptors and donators as shown in Table 14.

Example 51

This example shows the effect of sEH inhibitors on serum and urinary oxylipin profiles in rodents.

Figure 13A:
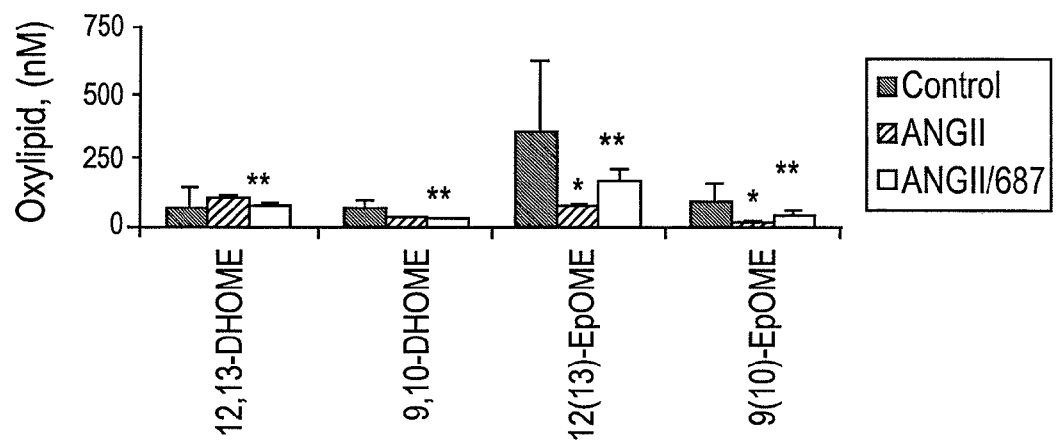
FIG. 13 is a bar graph showing the levels of urinary octadecanoids (A) and urinary eicosanoids (B) in rats treated with angiotensin II in the presence of absence of 687.
Figure 13B:
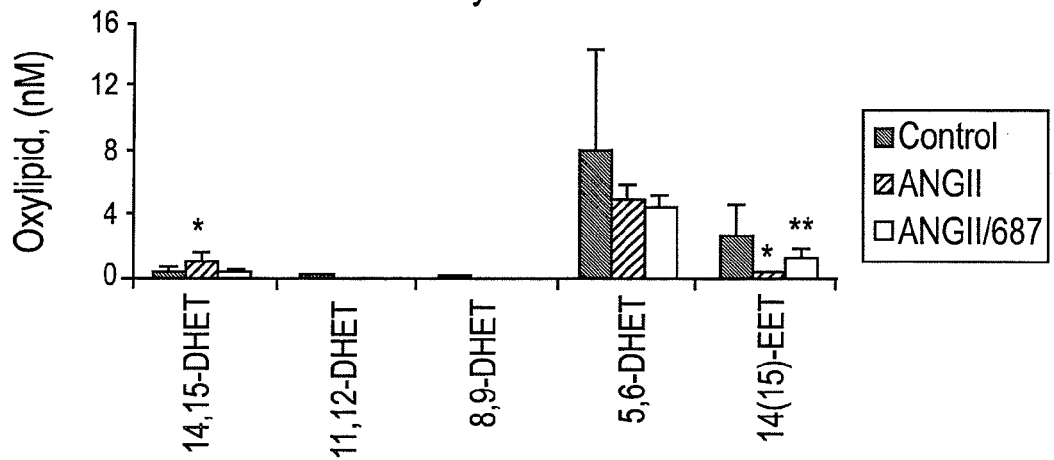
Figure 15:
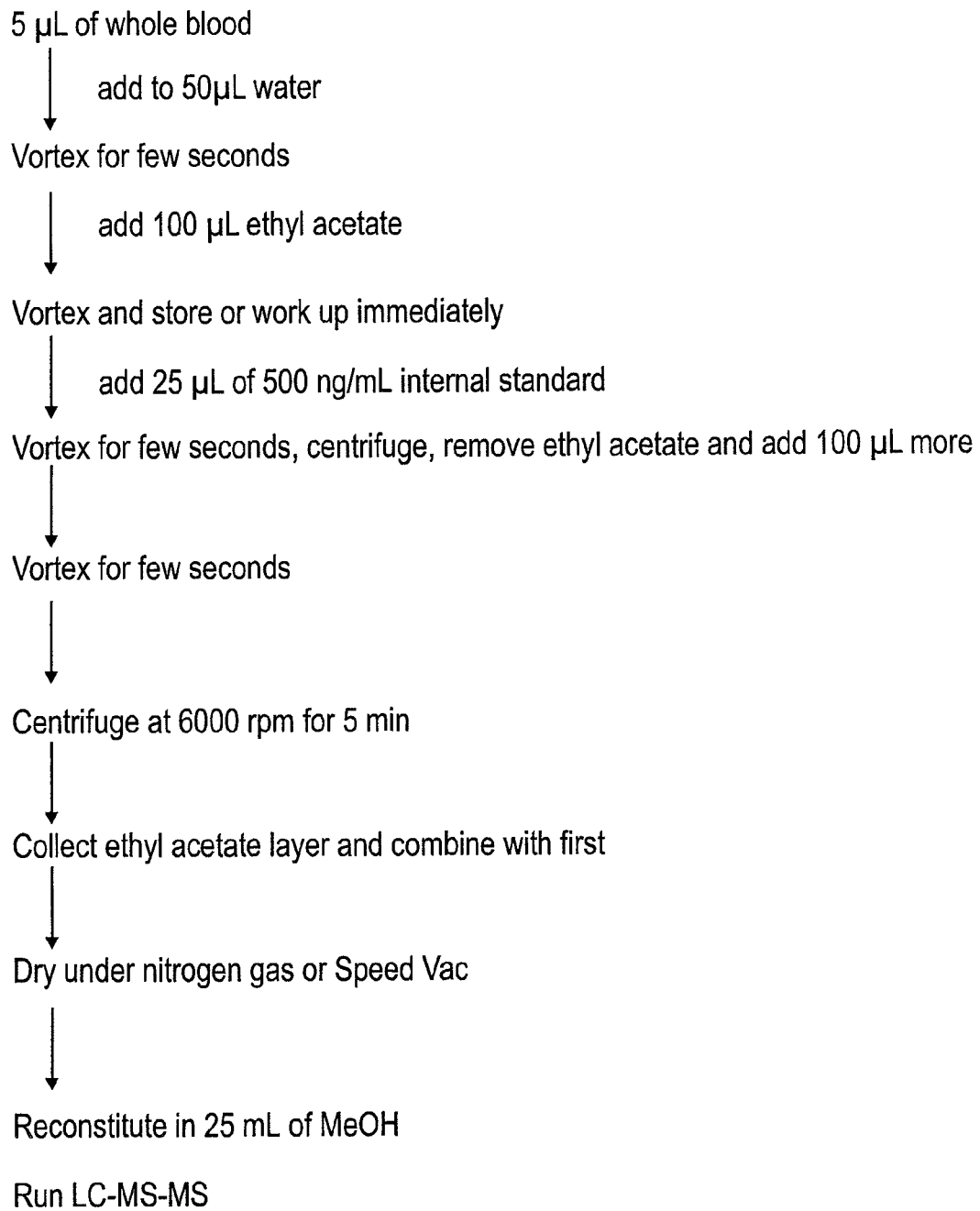
FIG. 15 provides a sample preparation procedure for a pharmacokinetic study. A 5 μl whole blood sample was drawn into a capillary at a specific time point, each sample was extracted and analyzed by LC/MS-MS.
Figure 16:
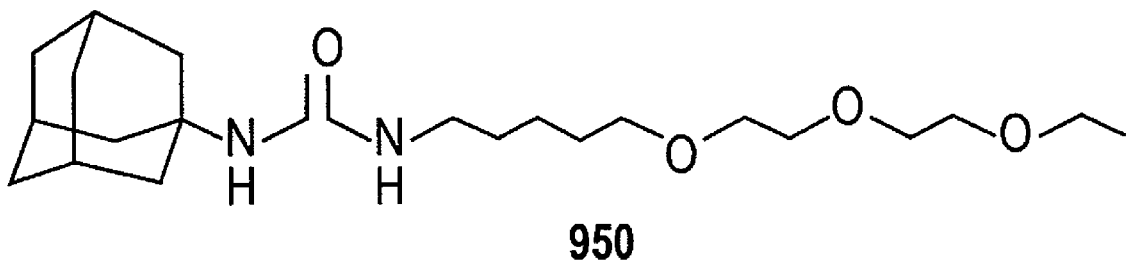
FIG. 16 shows the physical properties/parameters of compound 950.
Figure 17A:
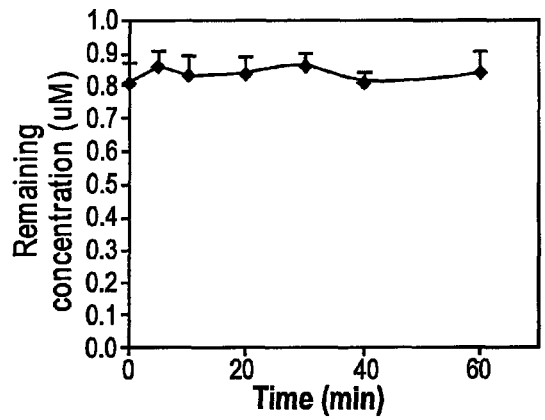
FIG. 17 shows graphs which illustrate the in vitro metabolism of 950 in (A) human liver microsome (no NADPH), (B) S9 fractions, and (C) Liver microsomes both with NADPH. Both rat and human microsomes were used for the 950 metabolism study. The hydroxy metabolite was the major metabolite.
Figure 17B:
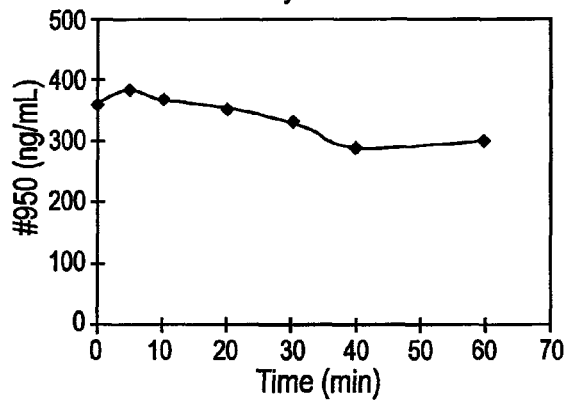
Figure 17C:
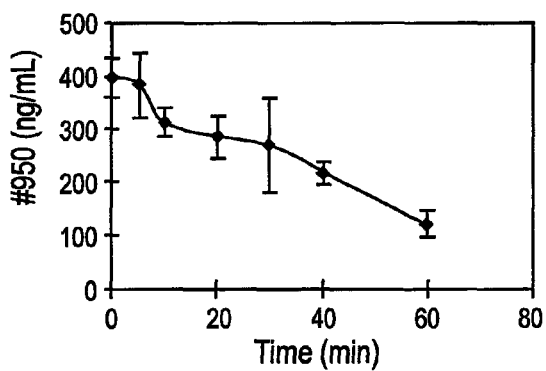

The described soluble epoxide inhibitors have been shown to modulate the relative abundance and amounts of epoxy and dihydroxy fatty acids formed in treated animals. One such example of this alteration is provided in FIG. 13. In this example, hypertension was induced in one group of Sprague-Dawley rats by the infusion of angiotensin II (ANGII). A second group of rats received both ANGII and a subcutaneous injection of the model sEH inhibitor 1-adamantyl-3-(dodecanoic acid) urea (i.e. compound 687). Urine samples were collected for 24 hr post exposure to compound 687 and analyzed for linoleate (Panel A) and arachidonate (Panel B) derived epoxides and diols using LC/MS/MS. As shown in FIG. 13, ANGII exposure decreased the concentration of both linoleate (EpOMEs) and arachidonate (EETs) derived epoxides and increased arachidonate derived diols (DHETs) but not linoleate derived diols (DHOMEs). In the case of both lipid classes, treating animals with compound 687 resulted in an increase in urinary epoxides, as well as a decrease in diol concentrations.

Example 52

This example illustrates the effect of certain compounds of the invention on members of the arachidonic acid cascade.

For epoxy fatty acid hydrolysis, the soluble epoxide hydrolase prefers substrates with epoxide moieties that are more distant from the carboxyl terminal. Specifically the substrate preference decreases in the order of 14,15-EET>11,12-EET>8,9-EET>>>5,6-EET for the epoxides of arachidonic acid. Independently, the relative substrate turnover of the epoxy arachidonates were calculated at 0.1:8.1:14.3 when a 1:1:2 mixture of 8,9-, 11,12-, and 14,15-EET fatty acid was hydrolyzed to 30% by rat renal cortex cytosol. By considering the primary pharmacophore of the urea to be a transition-state analog of epoxide hydrolysis, inhibitors have now been developed which incorporate long aliphatic acids. These compounds are better substrate and transition state mimics than those incorporating shorter aliphatic acids. Accordingly, optimal soluble epoxide hydrolase inhibitors can be obtained by producing compounds with aliphatic acid substituents (i.e. a tertiary pharmacophore) which are separated from the primary pharmacophore by an equivalent distance as the terminal acid is separated from the epoxide in optimal substrates. Within the enzyme active site, epoxy fatty acids have been predicted to exist in an extended or pseudo-linear confirmation. Therefore, both the epoxy fatty acids and the aliphatic acid containing urea structures were approximated as two dimensional linear representations and measurements were made on each species. The critical measurements taken were distances (in angstroms) from the carboxylate hydroxyl to the urea carbonyl and the urea nitrogens.

The distance of the carboxylate to the urea function of 1-cyclohexyl-3-octanoic acid is similar to the distance of the epoxide to the carboxylate in 8,9-EET. Therefore, the calculated inhibitor potencies were normalized to this compound, resulting in a ranked inhibitor potency. We then correlated epoxide to carbonyl distance with respect to relative substrate turnover rate to establish a correlative regression. By plotting the relative inhibitor potency on this graph we find that the distances of the carboxyl to the N'-nitrogen correlate best with the carboxyl to epoxide oxygen distance. These data further highlight the similarity between inhibitor and substrate interaction with the soluble epoxide hydrolase.

Programs:

All structures were drawn and exported as MDL MOL files using ACD/ChemSketch v 4.55 (May 6, 2000) Advanced Chemistry Development Inc., Toronto, Ontario, Canada). Distance measurements were made on the corresponding MOL file image using ACD/3D v 4.52 (Apr. 10, 2000). Structural optimizations were not used.

Figure 12:
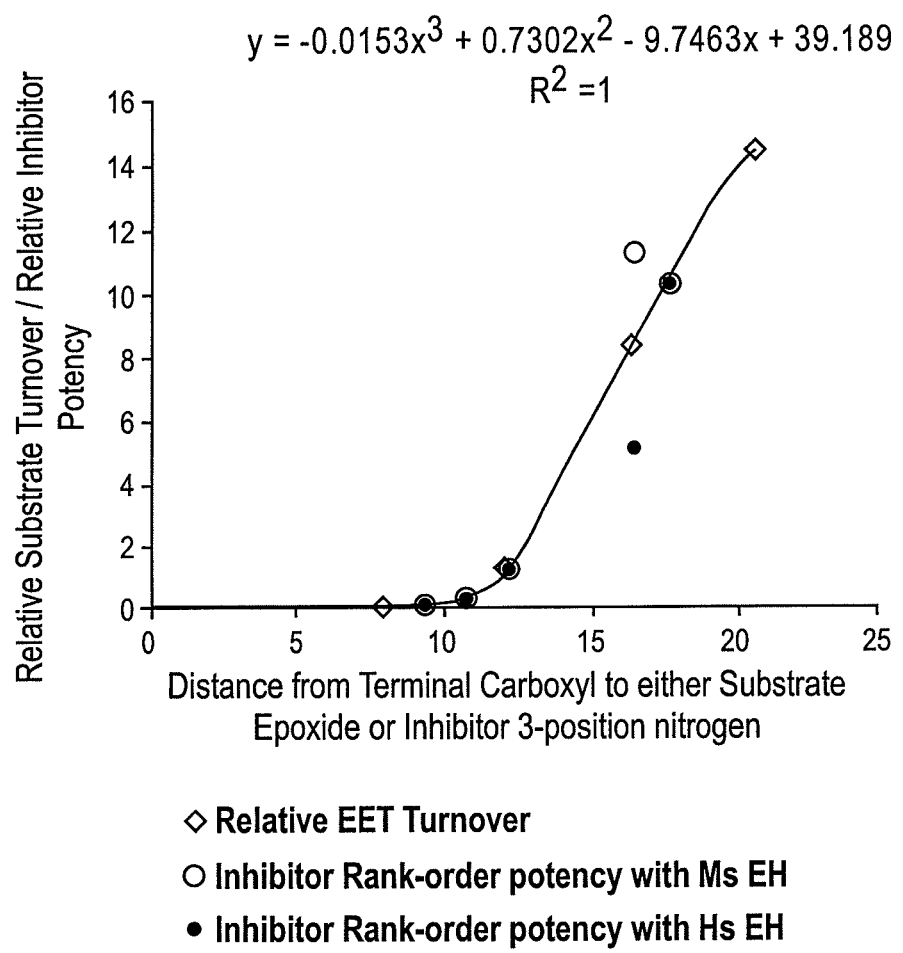
FIG. 12 is a graph illustrating the relative substrate turnover/relative inhibitor potency as a function of terminal carboxyl distance to either substrate epoxide of inhibitor 3-position nitrogen.

Table 19 provides results for this analysis (see also, FIG. 12).

TABLE 19

Linear distances between the primary and secondary pharmacophores of a series of sEH inhibitors and their rank order potencies with the mouse (MsEH) and human sEHs (HsEH) are shown in comparison with the epoxide to free acid distances and relative turnover rate of the four arachidonic acid epoxides with the rat sEH.

| | sEH Inhibitors | | | Endogenous sEH Substrates | | |
|---|---|---|---|---|---|---|
| R | N' to COOH (Å) | MsEH | HsEH | Substrates | $O_{Ep}$ to COOH (Å) | Relative EET Turnover |
| —(CH$_2$)$_5$COOH | 9.6 | 0.01 | 0.01 | 5,6-EET | 8 | 0.1 |
| —(CH$_2$)$_6$COOH | 10.9 | 0.1 | 0.1 | | | |
| —(CH$_2$)$_8$COOH | 12.4 | 1 | 1 | 8,9-EET | 12.1 | 1 |
| —(CH$_2$)$_{11}$COOH | 16.5 | 11 | 4.8 | 11,12-EET | 16.4 | 8.1 |
| —(CH$_2$)$_{12}$COOH | 17.8 | 10 | 10 | 14,15-EET | 20.7 | 14.3 |

What is claimed is:

1. A compound having a formula:

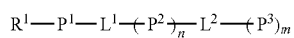

(I)

and its pharmaceutically acceptable salts, wherein $R^1$ is selected from the group consisting of cyclohexyl, cycloheptyl, cyclooctyl, norbornyl, adamantyl, noradamantyl, and phenyl, wherein the phenyl group is either unsubstituted or substituted with from one to three substituents selected from the group consisting of halogen, lower alkyl, lower halo alkyl, lower alkoxy, lower haloalkoxy, $C_3$-$C_5$ cycloalkyl and cyano;

$P^1$ is —NHC(O)NH—;

$P^2$ is selected from the group consisting of —C(O)—, —O(CH$_2$CH$_2$O)$_q$—, and —C(O)O—;

$P^3$ is —C(O)OR$^2$, wherein $R^2$ is a member selected from the group consisting of hydrogen, methyl and ethyl;

the subscripts n and m are each 1, and the subscript q is 0 to 6;

$L^1$ is cyclohexylene; and $L^2$ is a phenylene.

2. The compound in accordance with claim 1, wherein $R^1$ is phenyl substituted with from 1 to 3 substituents selected from the group consisting of halogen, methyl, isopropyl, methoxy, trifluoromethyl, and trifluoromethoxy.

3. The compound in accordance with claim 2, wherein $R^1$ is 4-substituted phenyl.

4. The compound in accordance with claim 3, wherein the $R^1$ is 4-trifluoromethoxyphenyl.

5. The compound in accordance with claim 1, wherein $P^2$ is —O(CH$_2$CH$_2$O)$_q$—; and wherein q is 0.

6. The compound in accordance with claim 1, wherein $L^1$ is trans-substituted.

7. The compound in accordance with claim 1, wherein $L^2$ is a 1,2-, 1,3-, or 1,4-linked phenylene.

8. The compound in accordance with claim 7, wherein $L^2$ is a 1,3- or 1,4-linked phenylene.

9. The compound in accordance with claim 1,
$R^1$ is 4-trifluoromethoxyphenyl;
$P^2$ is —O—;
$L^1$ is 1,3- or 1,4-cyclohexylene; and
$L^2$ is a 1,3- or 1,4-linked phenylene.

* * * * *

SEQUENCE LISTING

<160> NUMBER OF SEQ ID NOS: 4

<210> SEQ ID NO 1
<211> LENGTH: 555
<212> TYPE: PRT
<213> ORGANISM: Homo sapiens
<220> FEATURE:
<223> OTHER INFORMATION: human soluble epoxide hydrolase (sEH)

<400> SEQUENCE: 1

```
Met Thr Leu Arg Ala Ala Val Phe Asp Leu Asp Gly Val Leu Ala Leu
 1               5                  10                  15

Pro Ala Val Phe Gly Val Leu Gly Arg Thr Glu Glu Ala Leu Ala Leu
             20                  25                  30

Pro Arg Gly Leu Leu Asn Asp Ala Phe Gln Lys Gly Gly Pro Glu Gly
         35                  40                  45

Ala Thr Thr Arg Leu Met Lys Gly Glu Ile Thr Leu Ser Gln Trp Ile
     50                  55                  60

Pro Leu Met Glu Glu Asn Cys Arg Lys Cys Ser Glu Thr Ala Lys Val
 65                  70                  75                  80

Cys Leu Pro Lys Asn Phe Ser Ile Lys Glu Ile Phe Asp Lys Ala Ile
                 85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Ser Gly Pro Ala Val Cys Leu Cys His Gly Phe Pro Glu Ser Trp Tyr
            260                 265                 270

Ser Trp Arg Tyr Gln Ile Pro Ala Leu Ala Gln Ala Gly Tyr Arg Val
        275                 280                 285

Leu Ala Met Asp Met Lys Gly Tyr Gly Glu Ser Ser Ala Pro Pro Glu
    290                 295                 300

Ile Glu Glu Tyr Cys Met Glu Val Leu Cys Lys Glu Met Val Thr Phe
305                 310                 315                 320

Leu Asp Lys Leu Gly Leu Ser Gln Ala Val Phe Ile Gly His Asp Trp
                325                 330                 335

Gly Gly Met Leu Val Trp Tyr Met Ala Leu Phe Tyr Pro Glu Arg Val
            340                 345                 350
```

```
Arg Ala Val Ala Ser Leu Asn Thr Pro Phe Ile Pro Ala Asn Pro Asn
        355                 360                 365

Met Ser Pro Leu Glu Ser Ile Lys Ala Asn Pro Val Phe Asp Tyr Gln
370                 375                 380

Leu Tyr Phe Gln Glu Pro Gly Val Ala Glu Ala Glu Leu Glu Gln Asn
385                 390                 395                 400

Leu Ser Arg Thr Phe Lys Ser Leu Phe Arg Ala Ser Asp Glu Ser Val
            405                 410                 415

Leu Ser Met His Lys Val Cys Glu Ala Gly Gly Leu Phe Val Asn Ser
            420                 425                 430

Pro Glu Glu Pro Ser Leu Ser Arg Met Val Thr Glu Glu Ile Gln
        435                 440                 445

Phe Tyr Val Gln Gln Phe Lys Lys Ser Gly Phe Arg Gly Pro Leu Asn
450                 455                 460

Trp Tyr Arg Asn Met Glu Arg Asn Trp Lys Trp Ala Cys Lys Ser Leu
465                 470                 475                 480

Gly Arg Lys Ile Leu Ile Pro Ala Leu Met Val Thr Ala Glu Lys Asp
            485                 490                 495

Phe Val Leu Val Pro Gln Met Ser Gln His Met Glu Asp Trp Ile Pro
                500                 505                 510

His Leu Lys Arg Gly His Ile Glu Asp Cys Gly His Trp Thr Gln Met
        515                 520                 525

Asp Lys Pro Thr Glu Val Asn Gln Ile Leu Ile Lys Trp Leu Asp Ser
530                 535                 540

Asp Ala Arg Asn Pro Pro Val Val Ser Lys Met
545                 550                 555

<210> SEQ ID NO 2
<211> LENGTH: 554
<212> TYPE: PRT
<213> ORGANISM: Rattus norvegicus
<220> FEATURE:
<223> OTHER INFORMATION: rat soluble epoxide hydrolase (sEH)

<400> SEQUENCE: 2

Met Ala Leu Arg Val Ala Ala Phe Asp Leu Asp Gly Val Leu Ala Leu
  1               5                  10                  15

Pro Ser Ile Ala Gly Val Leu Arg His Thr Glu Glu Ala Leu Ala Leu
             20                  25                  30

Pro Arg Asp Phe Leu Leu Gly Ala Phe Gln Met Lys Phe Pro Glu Gly
         35                  40                  45

Pro Thr Glu Gln Leu Met Lys Gly Lys Ile Thr Phe Ser Gln Trp Val
     50                  55                  60

Pro Leu Met Asp Glu Ser Cys Arg Lys Ser Ser Lys Ala Cys Gly Ala
 65                  70                  75                  80

Ser Leu Pro Glu Asn Phe Ser Ile Ser Glu Ile Phe Ser Gln Ala Met
                 85                  90                  95

Ala Ala Arg Ser Ile Asn Arg Pro Met Leu Gln Ala Ala Ala Ala Leu
            100                 105                 110

Lys Lys Lys Gly Phe Thr Thr Cys Ile Val Thr Asn Asn Trp Leu Asp
        115                 120                 125

Asp Ser Asp Lys Arg Asp Ile Leu Ala Gln Met Met Cys Glu Leu Ser
130                 135                 140

Gln His Phe Asp Phe Leu Ile Glu Ser Cys Gln Val Gly Met Ile Lys
145                 150                 155                 160

Pro Glu Pro Gln Ile Tyr Lys Phe Val Leu Asp Thr Leu Lys Ala Lys
```

```
                         165                 170                 175
Pro Asn Glu Val Val Phe Leu Asp Asp Phe Gly Ser Asn Leu Lys Pro
            180                 185                 190
Ala Arg Asp Met Gly Met Val Thr Ile Leu Val Arg Asp Thr Ala Ser
            195                 200                 205
Ala Leu Arg Glu Leu Glu Lys Val Thr Gly Thr Gln Phe Pro Glu Ala
            210                 215                 220
Pro Leu Pro Val Pro Cys Ser Pro Asn Asp Val Ser His Gly Tyr Val
225                 230                 235                 240
Thr Val Lys Pro Gly Ile Arg Leu His Phe Val Glu Met Gly Ser Gly
                245                 250                 255
Pro Ala Ile Cys Leu Cys His Gly Phe Pro Glu Ser Trp Phe Ser Trp
            260                 265                 270
Arg Tyr Gln Ile Pro Ala Leu Ala Gln Ala Gly Phe Arg Val Leu Ala
            275                 280                 285
Ile Asp Met Lys Gly Tyr Gly Asp Ser Ser Pro Pro Glu Ile Glu
            290                 295                 300
Glu Tyr Ala Met Glu Leu Leu Cys Glu Glu Met Val Thr Phe Leu Asn
305                 310                 315                 320
Lys Leu Gly Ile Pro Gln Ala Val Phe Ile Gly His Asp Trp Ala Gly
                325                 330                 335
Val Leu Val Trp Asn Met Ala Leu Phe His Pro Glu Arg Val Arg Ala
            340                 345                 350
Val Ala Ser Leu Asn Thr Pro Leu Met Pro Pro Asn Pro Glu Val Ser
            355                 360                 365
Pro Met Glu Val Ile Arg Ser Ile Pro Val Phe Asn Tyr Gln Leu Tyr
            370                 375                 380
Phe Gln Glu Pro Gly Val Ala Glu Ala Glu Leu Glu Lys Asn Met Ser
385                 390                 395                 400
Arg Thr Phe Lys Ser Phe Phe Arg Thr Ser Asp Asp Met Gly Leu Leu
                405                 410                 415
Thr Val Asn Lys Ala Thr Glu Met Gly Gly Ile Leu Val Gly Thr Pro
            420                 425                 430
Glu Asp Pro Lys Val Ser Lys Ile Thr Thr Glu Glu Ile Glu Tyr
            435                 440                 445
Tyr Ile Gln Gln Phe Lys Lys Ser Gly Phe Arg Gly Pro Leu Asn Trp
            450                 455                 460
Tyr Arg Asn Thr Glu Arg Asn Trp Lys Trp Ser Cys Lys Ala Leu Gly
465                 470                 475                 480
Arg Lys Ile Leu Val Pro Ala Leu Met Val Thr Ala Glu Lys Asp Ile
                485                 490                 495
Val Leu Arg Pro Glu Met Ser Lys Asn Met Glu Asn Trp Ile Pro Phe
            500                 505                 510
Leu Lys Arg Gly His Ile Glu Asp Cys Gly His Trp Thr Gln Ile Glu
            515                 520                 525
Lys Pro Ala Glu Val Asn Gln Ile Leu Ile Lys Trp Leu Lys Thr Glu
            530                 535                 540
Ile Gln Asn Pro Ser Val Thr Ser Lys Ile
545                 550

<210> SEQ ID NO 3
<211> LENGTH: 554
<212> TYPE: PRT
<213> ORGANISM: Mus musculus
<220> FEATURE:
```

<223> OTHER INFORMATION: mouse liver soluble epoxide hydrolase (sEH)

<400> SEQUENCE: 3

```
Met Ala Leu Arg Val Ala Ala Phe Asp Leu Asp Gly Val Leu Ala Leu
  1               5                  10                  15
Pro Ser Ile Ala Gly Ala Phe Arg Arg Ser Glu Glu Ala Leu Ala Leu
                 20                  25                  30
Pro Arg Asp Phe Leu Leu Gly Ala Tyr Gln Thr Glu Phe Pro Glu Gly
             35                  40                  45
Pro Thr Glu Gln Leu Met Lys Gly Lys Ile Thr Phe Ser Gln Trp Val
         50                  55                  60
Pro Leu Met Asp Glu Ser Tyr Arg Lys Ser Lys Ala Cys Gly Ala
 65                  70                  75                  80
Asn Leu Pro Glu Asn Phe Ser Ile Ser Gln Ile Phe Ser Gln Ala Met
                 85                  90                  95
Ala Ala Arg Ser Ile Asn Arg Pro Met Leu Gln Ala Ala Ile Ala Leu
            100                 105                 110
Lys Lys Lys Gly Phe Thr Thr Cys Ile Val Thr Asn Asn Trp Leu Asp
            115                 120                 125
Asp Gly Asp Lys Arg Asp Ser Leu Ala Gln Met Met Cys Glu Leu Ser
        130                 135                 140
Gln His Phe Asp Phe Leu Ile Glu Ser Cys Gln Val Gly Met Ile Lys
145                 150                 155                 160
Pro Glu Pro Gln Ile Tyr Asn Phe Leu Leu Asp Thr Leu Lys Ala Lys
                165                 170                 175
Pro Asn Glu Val Val Phe Leu Asp Asp Phe Gly Ser Asn Leu Lys Pro
            180                 185                 190
Ala Arg Asp Met Gly Met Val Thr Ile Leu Val His Asn Thr Ala Ser
        195                 200                 205
Ala Leu Arg Glu Leu Glu Lys Val Thr Gly Thr Gln Phe Pro Glu Ala
    210                 215                 220
Pro Leu Pro Val Pro Cys Asn Pro Asn Asp Val Ser His Gly Tyr Val
225                 230                 235                 240
Thr Val Lys Pro Gly Ile Arg Leu His Phe Val Glu Met Gly Ser Gly
                245                 250                 255
Pro Ala Leu Cys Leu Cys His Gly Phe Pro Glu Ser Trp Phe Ser Trp
            260                 265                 270
Arg Tyr Gln Ile Pro Ala Leu Ala Gln Ala Gly Phe Arg Val Leu Ala
        275                 280                 285
Ile Asp Met Lys Gly Tyr Gly Asp Ser Ser Ser Pro Pro Glu Ile Glu
    290                 295                 300
Glu Tyr Ala Met Glu Leu Leu Cys Lys Glu Met Val Thr Phe Leu Asp
305                 310                 315                 320
Lys Leu Gly Ile Pro Gln Ala Val Phe Ile Gly His Asp Trp Ala Gly
                325                 330                 335
Val Met Val Trp Asn Met Ala Leu Phe Tyr Pro Glu Arg Val Arg Ala
            340                 345                 350
Val Ala Ser Leu Asn Thr Pro Phe Met Pro Asp Pro Asp Val Ser
        355                 360                 365
Pro Met Lys Val Ile Arg Ser Ile Pro Val Phe Asn Tyr Gln Leu Tyr
    370                 375                 380
Phe Gln Glu Pro Gly Val Ala Glu Ala Glu Leu Glu Lys Asn Met Ser
385                 390                 395                 400
Arg Thr Phe Lys Ser Phe Phe Arg Ala Ser Asp Glu Thr Gly Phe Ile
```

```
                    405                 410                 415
Ala Val His Lys Ala Thr Glu Ile Gly Gly Ile Leu Val Asn Thr Pro
                420                 425                 430

Glu Asp Pro Asn Leu Ser Lys Ile Thr Thr Glu Glu Ile Glu Phe
            435                 440                 445

Tyr Ile Gln Gln Phe Lys Lys Thr Gly Phe Arg Gly Pro Leu Asn Trp
        450                 455                 460

Tyr Arg Asn Thr Glu Arg Asn Trp Lys Trp Ser Cys Lys Gly Leu Gly
465                 470                 475                 480

Arg Lys Ile Leu Val Pro Ala Leu Met Val Thr Ala Glu Lys Asp Ile
                485                 490                 495

Val Leu Arg Pro Glu Met Ser Lys Asn Met Glu Lys Trp Ile Pro Phe
                500                 505                 510

Leu Lys Arg Gly His Ile Glu Asp Cys Gly His Trp Thr Gln Ile Glu
            515                 520                 525

Lys Pro Thr Glu Val Asn Gln Ile Leu Ile Lys Trp Leu Gln Thr Glu
        530                 535                 540

Val Gln Asn Pro Ser Val Thr Ser Lys Ile
545                 550

<210> SEQ ID NO 4
<211> LENGTH: 536
<212> TYPE: PRT
<213> ORGANISM: Mus musculus
<220> FEATURE:
<223> OTHER INFORMATION: mouse ovary soluble epoxide hydrolase (sEH)

<400> SEQUENCE: 4

Met Arg Phe Ala Ala Met Ala Ala Phe Ser Val Phe Phe Val Ser Lys
  1               5                  10                  15

Gly Leu Leu Met Asn Ser Asn Ile Trp Cys Val Gly Gln Glu Gly Pro
                20                  25                  30

Ser Gln Glu Asp Thr Asp Thr Ile His Thr Ser Glu Trp Val Pro Leu
            35                  40                  45

Met Asp Glu Ser Tyr Arg Lys Ser Ser Lys Ala Cys Gly Ala Asn Leu
        50                  55                  60

Pro Glu Asn Phe Ser Ile Ser Gln Ile Phe Ser Gln Ala Met Ala Ala
65                  70                  75                  80

Arg Ser Ile Asn Arg Pro Met Leu Gln Ala Ala Ile Ala Leu Lys Lys
                85                  90                  95

Lys Gly Phe Thr Thr Cys Ile Val Thr Asn Asn Trp Leu Asp Asp Gly
            100                 105                 110

Asp Lys Arg Asp Ser Leu Ala Gln Met Met Cys Glu Leu Ser Gln His
        115                 120                 125

Phe Asp Phe Leu Ile Glu Ser Cys Gln Val Gly Met Ile Lys Pro Glu
130                 135                 140

Pro Gln Ile Tyr Asn Phe Leu Leu Asp Thr Leu Lys Ala Lys Pro Asn
145                 150                 155                 160

Glu Val Val Phe Leu Asp Asp Phe Gly Ser Asn Leu Lys Pro Ala Arg
                165                 170                 175

Asp Met Gly Met Val Thr Ile Leu Val His Asn Thr Ala Ser Ala Leu
            180                 185                 190

Arg Glu Leu Glu Lys Val Thr Gly Thr Gln Phe Pro Glu Ala Pro Leu
        195                 200                 205

Pro Val Pro Cys Asn Pro Asn Asp Val Ser His Gly Tyr Val Thr Val
210                 215                 220
```

```
Lys Pro Gly Ile Arg Leu His Phe Val Glu Met Gly Ser Gly Pro Ala
225                 230                 235                 240

Leu Cys Leu Cys His Gly Phe Pro Glu Ser Trp Phe Ser Trp Arg Tyr
            245                 250                 255

Gln Ile Pro Ala Leu Ala Gln Ala Gly Phe Arg Val Leu Ala Ile Asp
            260                 265                 270

Met Lys Gly Tyr Gly Asp Ser Ser Ser Pro Pro Glu Ile Glu Glu Tyr
            275                 280                 285

Ala Met Glu Leu Leu Cys Lys Glu Met Val Thr Phe Leu Asp Lys Leu
    290                 295                 300

Gly Ile Pro Gln Ala Val Phe Ile Gly His Asp Trp Ala Gly Val Met
305                 310                 315                 320

Val Trp Asn Met Ala Leu Phe Tyr Pro Glu Arg Val Arg Ala Val Ala
            325                 330                 335

Ser Leu Asn Thr Pro Phe Met Pro Pro Asp Pro Asp Val Ser Pro Met
            340                 345                 350

Lys Val Ile Arg Ser Ile Pro Val Phe Asn Tyr Gln Leu Tyr Phe Gln
            355                 360                 365

Glu Pro Gly Val Ala Glu Ala Glu Leu Glu Lys Asn Met Ser Arg Thr
            370                 375                 380

Phe Lys Ser Phe Phe Arg Ala Ser Asp Glu Thr Gly Phe Ile Ala Val
385                 390                 395                 400

His Lys Ala Thr Glu Ile Gly Gly Ile Leu Val Asn Thr Pro Glu Asp
                405                 410                 415

Pro Asn Leu Ser Lys Ile Thr Thr Glu Glu Glu Ile Glu Phe Tyr Ile
            420                 425                 430

Gln Gln Phe Lys Lys Thr Gly Phe Arg Gly Pro Leu Asn Trp Tyr Arg
        435                 440                 445

Asn Thr Glu Arg Asn Trp Lys Trp Ser Cys Lys Gly Leu Gly Arg Lys
450                 455                 460

Ile Leu Val Pro Ala Leu Met Val Thr Ala Glu Lys Asp Ile Val Leu
465                 470                 475                 480

Arg Pro Glu Met Ser Lys Asn Met Glu Lys Trp Ile Pro Phe Leu Lys
                485                 490                 495

Arg Gly His Ile Glu Asp Cys Gly His Trp Thr Gln Ile Glu Lys Pro
            500                 505                 510

Thr Glu Val Asn Gln Ile Leu Ile Lys Trp Leu Gln Thr Glu Val Gln
            515                 520                 525

Asn Pro Ser Val Thr Ser Lys Ile
530                 535
```